US012016561B2

(12) United States Patent
Dell et al.

(10) Patent No.: US 12,016,561 B2
(45) Date of Patent: *Jun. 25, 2024

(54) SYSTEM FOR FIXATION OF LEAFLETS OF A HEART VALVE

(71) Applicant: ABBOTT CARDIOVASCULAR SYSTEMS INC., Santa Clara, CA (US)

(72) Inventors: Kent Dell, Redwood City, CA (US); Theodore Ketai, San Francisco, CA (US); Tanmay Mishra, Mountain View, CA (US); Stephanie Jones, Naperville, IL (US); Jacob Greenberg, Mountain View, CA (US); Michael Hong, Emeryville, CA (US); Daniel Hale, Belmont, CA (US); Francisco Valencia, East Palo Alto, CA (US); Steven Tyler, Portola Valley, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 477 days.

This patent is subject to a terminal disclaimer.

(21) Appl. No.: 16/987,582

(22) Filed: Aug. 7, 2020

(65) Prior Publication Data

US 2020/0360018 A1 Nov. 19, 2020

Related U.S. Application Data

(63) Continuation of application No. 16/540,285, filed on Aug. 14, 2019, now Pat. No. 10,743,876, which is a (Continued)

(51) Int. Cl.
*A61B 17/08* (2006.01)
*A61B 17/00* (2006.01)
(Continued)

(52) U.S. Cl.
CPC ............. *A61B 17/083* (2013.01); *A61B 17/08* (2013.01); *A61B 17/10* (2013.01); *A61F 2/2454* (2013.01);
(Continued)

(58) Field of Classification Search
None
See application file for complete search history.

(56) References Cited

U.S. PATENT DOCUMENTS 2,097,018 A 10/1937 Chamberlain
2,108,206 A 2/1938 Meeker
(Continued)

FOREIGN PATENT DOCUMENTS

CA 2296317 C 1/2009
CN 1142351 A 2/1997
(Continued)

OTHER PUBLICATIONS

U.S. Appl. No. 60/051,078, filed Jun. 27, 1997.
(Continued)

*Primary Examiner* — Shaun L David
(74) *Attorney, Agent, or Firm* — SLEMAN & LUND LLP

(57) ABSTRACT

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, where the instru-
(Continued)

ments utilized must negotiate long, narrow, and tortuous pathways to the treatment site. In addition, many of the devices and systems of the invention are adapted to be reversible and removable from the patient at any point without interference with or trauma to internal tissues.

26 Claims, 77 Drawing Sheets

Related U.S. Application Data continuation of application No. 14/575,024, filed on Dec. 18, 2014, now Pat. No. 10,624,640, which is a continuation of application No. 13/231,586, filed on Sep. 13, 2011, now Pat. No. 8,945,177.

(51) Int. Cl.
*A61B 17/10* (2006.01)
*A61F 2/24* (2006.01)

(52) U.S. Cl.
CPC .. *A61F 2/2466* (2013.01); *A61B 2017/00243* (2013.01)

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King et al. |
| 4,007,743 A | 2/1977 | Blake |
| 4,055,861 A | 11/1977 | Carpentier et al. |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,327,736 A | 5/1982 | Inoue |
| 4,340,091 A | 7/1982 | Skelton et al. |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,657,024 A | 4/1987 | Coneys |
| 4,686,965 A | 8/1987 | Bonnet et al. |
| 4,693,248 A | 9/1987 | Failla |
| 4,716,886 A | 1/1988 | Schulman et al. |
| 4,777,951 A | 10/1988 | Cribier et al. |
| 4,795,458 A | 1/1989 | Regan |
| 4,809,695 A | 3/1989 | Gwathmey et al. |
| 4,917,089 A | 4/1990 | Sideris |
| 4,930,674 A | 6/1990 | Barak |
| 4,944,295 A | 7/1990 | Gwathmey et al. |
| 4,969,890 A | 11/1990 | Sugita et al. |
| 4,994,077 A | 2/1991 | Dobben |
| 5,002,562 A | 3/1991 | Oberlander |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,098,440 A | 3/1992 | Hillstead |
| 5,108,368 A | 4/1992 | Hammerslag et al. |
| 5,125,758 A | 6/1992 | DeWan |
| 5,125,895 A | 6/1992 | Buchbinder et al. |
| 5,147,370 A | 9/1992 | McNamara et al. |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,222,963 A | 6/1993 | Brinkerhoff et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,271,544 A | 12/1993 | Fox et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,327,905 A | 7/1994 | Avitall |
| 5,330,442 A | 7/1994 | Green et al. |
| 5,330,501 A | 7/1994 | Tovey et al. |
| 5,332,402 A | 7/1994 | Teitelbaum |
| 5,334,217 A | 8/1994 | Das |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,363,861 A | 11/1994 | Edwards et al. |
| 5,368,564 A | 11/1994 | Savage |
| 5,368,601 A | 11/1994 | Sauer et al. |
| 5,383,886 A | 1/1995 | Kensey et al. |
| 5,389,077 A | 2/1995 | Melinyshyn et al. |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,413,584 A | 5/1995 | Schulze |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,425,744 A | 6/1995 | Fagan et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |

(56) References Cited

U.S. PATENT DOCUMENTS

| | | |
|---|---|---|
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,716,417 A | 2/1998 | Girard et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,741,297 A | 4/1998 | Simon |
| 5,749,828 A | 5/1998 | Solomon et al. |
| 5,755,778 A | 5/1998 | Kleshinski |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,239 A | 7/1998 | Webster, Jr. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,814,097 A | 9/1998 | Sterman et al. |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,178 A | 12/1998 | Vanney et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,601 A | 1/1999 | Bessler et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,258 A | 3/1999 | Sachdeva et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,976,159 A | 11/1999 | Bolduc et al. |
| 5,980,455 A | 11/1999 | Daniel et al. |
| 5,989,284 A | 11/1999 | Laufer |
| 6,007,552 A | 12/1999 | Fogarty et al. |
| 6,015,417 A | 1/2000 | Reynolds, Jr. |
| 6,017,358 A | 1/2000 | Yoon et al. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,079,414 A | 6/2000 | Roth |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,120,496 A | 9/2000 | Whayne et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,149,658 A | 11/2000 | Gardiner et al. |
| 6,156,055 A | 12/2000 | Ravenscroft |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,193,734 B1 | 2/2001 | Bolduc et al. |
| 6,200,315 B1 | 3/2001 | Gaiser et al. |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |

(56) References Cited

U.S. PATENT DOCUMENTS

| | | |
|---|---|---|
| 6,217,528 B1 | 4/2001 | Koblish et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,290,674 B1 | 9/2001 | Roue et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,880 B1 | 12/2001 | Yang et al. |
| 6,332,893 B1 | 12/2001 | Mortier et al. |
| 6,346,074 B1 | 2/2002 | Roth |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,419,696 B1 | 7/2002 | Ortiz et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,496,420 B2 | 12/2002 | Manning |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,544,215 B1 | 4/2003 | Bencini et al. |
| 6,551,303 B1 | 4/2003 | Van Tassel et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,837,867 B2 | 1/2005 | Kortelling |
| 6,855,137 B2 | 2/2005 | Bon |
| 6,860,179 B2 | 3/2005 | Hopper et al. |
| 6,875,224 B2 | 4/2005 | Grimes |
| 6,908,481 B2 | 6/2005 | Cribier |
| 6,926,715 B1 | 8/2005 | Hauck et al. |
| 6,926,730 B1 | 8/2005 | Nguyen et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,125,421 B2 | 10/2006 | Tremulis |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,513,908 B2 | 4/2009 | Lattouf |
| 7,533,790 B1 | 5/2009 | Knodel et al. |
| 7,556,632 B2 | 7/2009 | Zadno |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,655,040 B2 | 2/2010 | Douk et al. |
| 7,666,204 B2 | 2/2010 | Thornton et al. |
| 7,682,319 B2 | 3/2010 | Martin |
| 7,704,269 B2 | 4/2010 | St. Goar et al. |
| 7,736,388 B2 | 6/2010 | Goldfarb |
| 7,798,953 B1 | 9/2010 | Wilk |
| 7,811,296 B2 | 10/2010 | Goldfarb et al. |
| 7,914,544 B2 | 3/2011 | Nguyen et al. |
| 7,972,323 B1 | 7/2011 | Bencini et al. |
| 7,972,330 B2 | 7/2011 | Alejandro et al. |
| 7,981,139 B2 | 7/2011 | Martin |
| 8,029,565 B2 | 10/2011 | Lattouf |
| 8,057,493 B2 | 11/2011 | Goldfarb |
| 8,062,313 B2 | 11/2011 | Kimblad |
| 8,118,822 B2 | 2/2012 | Schaller et al. |
| 8,216,230 B2 | 7/2012 | Hauck |
| 8,216,256 B2 | 7/2012 | Raschdorf, Jr. et al. |
| 8,303,608 B2 | 11/2012 | Goldfarb |
| 8,348,963 B2 | 1/2013 | Wilson et al. |
| 8,500,761 B2 | 8/2013 | Goldfarb |
| 8,734,505 B2 | 5/2014 | Goldfarb |
| 8,740,920 B2 | 6/2014 | Goldfarb |
| 8,852,272 B2 | 10/2014 | Gross |
| 9,011,468 B2 | 4/2015 | Ketai et al. |
| 9,510,829 B2 | 12/2016 | Goldfarb |
| 10,076,415 B1 | 9/2018 | Metchik |
| 10,105,222 B1 | 10/2018 | Metchik |
| 10,123,873 B1 | 11/2018 | Metchik |
| 10,130,475 B1 | 11/2018 | Metchik |
| 10,136,993 B1 | 11/2018 | Metchik |
| 10,159,570 B1 | 12/2018 | Metchik |
| 10,231,837 B1 | 3/2019 | Metchik |
| 10,238,493 B1 | 3/2019 | Metchik |
| 10,245,144 B1 | 4/2019 | Metchik |
| D847,983 S | 5/2019 | Ho |
| 10,314,586 B2 | 6/2019 | Greenberg |
| 10,413,408 B2 | 9/2019 | Krone |
| 10,507,109 B2 | 12/2019 | Metchik |
| 10,517,726 B2 | 12/2019 | Chau |
| 10,524,792 B2 | 1/2020 | Hernandez |
| 10,595,997 B2 | 3/2020 | Metchik |
| 10,646,342 B1 | 5/2020 | Marr |
| 10,779,837 B2 | 9/2020 | Lee |
| D902,403 S | 11/2020 | Marsot |
| 10,856,988 B2 | 12/2020 | McNiven |
| 2001/0004715 A1 | 6/2001 | Duran et al. |
| 2001/0005787 A1 | 6/2001 | Oz et al. |
| 2001/0010005 A1 | 7/2001 | Kammerer et al. |

(56) References Cited

U.S. PATENT DOCUMENTS

| | | |
|---|---|---|
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0082621 A1 | 6/2002 | Schurr et al. |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0133178 A1 | 9/2002 | Muramatsu et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0018358 A1 | 1/2003 | Saadat |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0225423 A1 | 12/2003 | Huitema |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0034365 A1 | 2/2004 | Lentz et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thornton et al. |
| 2004/0093023 A1 | 5/2004 | Allen et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0181238 A1 | 9/2004 | Zarbatany |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0137693 A1 | 6/2005 | Haug |
| 2005/0149014 A1 | 7/2005 | Hauck et al. |
| 2005/0159810 A1 | 7/2005 | Filsoufi |
| 2005/0187616 A1 | 8/2005 | Realyvasquez |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0190036 A1 | 8/2006 | Wendel et al. |
| 2006/0195012 A1 | 8/2006 | Mortier et al. |
| 2006/0229708 A1 | 10/2006 | Powell et al. |

(56) References Cited

U.S. PATENT DOCUMENTS

| | | |
|---|---|---|
| 2006/0252984 A1 | 11/2006 | Randert et al. |
| 2006/0293701 A1 | 12/2006 | Ainsworth et al. |
| 2007/0038293 A1 | 2/2007 | St. Goar et al. |
| 2007/0100356 A1 | 5/2007 | Lucatero et al. |
| 2007/0112355 A1 | 5/2007 | Salahieh |
| 2007/0118155 A1 | 5/2007 | Goldfarb et al. |
| 2007/0129737 A1 | 6/2007 | Goldfarb et al. |
| 2007/0197858 A1 | 8/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thornton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0121433 A1 | 5/2010 | Bolling et al. |
| 2010/0324585 A1 | 12/2010 | Miles et al. |
| 2013/0138121 A1 | 5/2013 | Allen et al. |
| 2015/0223793 A1 | 8/2015 | Goldfarb et al. |
| 2015/0272734 A1 | 10/2015 | Sheps |
| 2017/0042546 A1 | 2/2017 | Goldfarb |
| 2017/0049455 A1 | 2/2017 | Seguin |
| 2017/0239048 A1 | 8/2017 | Goldfarb |
| 2017/0265994 A1 | 9/2017 | Krone |
| 2018/0021133 A1 | 1/2018 | Barbarino |
| 2018/0036119 A1 | 2/2018 | Wei |
| 2018/0092661 A1 | 4/2018 | Prabhu |
| 2018/0146964 A1 | 5/2018 | Garcia |
| 2018/0235657 A1 | 8/2018 | Abunassar |
| 2018/0242976 A1 | 8/2018 | Kizuka |
| 2018/0243086 A1 | 8/2018 | Barbarino |
| 2018/0325661 A1 | 11/2018 | Delgado |
| 2018/0325671 A1 | 11/2018 | Abunassar |
| 2018/0344460 A1 | 12/2018 | Wei |
| 2018/0353181 A1 | 12/2018 | Wei |
| 2018/0360457 A1 | 12/2018 | Ellis |
| 2019/0053803 A1 | 2/2019 | Ketai |
| 2019/0125536 A1 | 5/2019 | Prabhu |
| 2019/0151041 A1 | 5/2019 | Ho |
| 2019/0151089 A1 | 5/2019 | Wei |
| 2019/0159899 A1 | 5/2019 | Marsot |
| 2019/0167197 A1 | 6/2019 | Abunassar |
| 2019/0183571 A1 | 6/2019 | De Marchena |
| 2019/0209293 A1 | 7/2019 | Metchik |
| 2019/0247187 A1 | 8/2019 | Kizuka |
| 2019/0274831 A1 | 9/2019 | Prabhu |
| 2019/0321597 A1 | 10/2019 | Van Hoven |
| 2019/0343630 A1 | 11/2019 | Kizuka |
| 2019/0350702 A1 | 11/2019 | Hernandez |
| 2019/0350710 A1 | 11/2019 | Ketai |
| 2019/0365536 A1 | 12/2019 | Prabhu |
| 2020/0000473 A1 | 1/2020 | Dell |
| 2020/0060687 A1 | 2/2020 | Hernández |
| 2020/0078173 A1 | 3/2020 | McNiven |
| 2020/0113678 A1 | 4/2020 | McCann |
| 2020/0121460 A1 | 4/2020 | Dale |
| 2020/0121894 A1 | 4/2020 | Prabhu |
| 2020/0187942 A1 | 6/2020 | Wei |
| 2020/0205829 A1 | 7/2020 | Wei |
| 2020/0245998 A1 | 8/2020 | Basude |
| 2020/0261107 A1 | 8/2020 | Cohen |
| 2020/0281591 A1 | 9/2020 | Krone |
| 2020/0323528 A1 | 10/2020 | Khairkhahan |
| 2020/0323549 A1 | 10/2020 | Goldfarb |
| 2020/0323634 A1 | 10/2020 | Von Oepen |
| 2020/0360018 A1 | 11/2020 | Dell |
| 2020/0367871 A1 | 11/2020 | Van Hoven |

FOREIGN PATENT DOCUMENTS

| | | |
|---|---|---|
| CN | 101056596 | 10/2007 |
| DE | 3504292 C1 | 7/1986 |
| DE | 19810696 C1 | 5/1999 |
| DE | 101 16 168 A1 | 11/2001 |
| EP | 0 179 562 B1 | 7/1989 |
| EP | 0 558 031 B1 | 2/1993 |
| EP | 0 558 031 A2 | 9/1993 |
| EP | 0 684 012 A2 | 11/1995 |
| EP | 0 727 239 A2 | 8/1996 |
| EP | 0 782 836 A1 | 7/1997 |
| EP | 1 199 037 A2 | 4/2002 |
| EP | 1 230 899 A1 | 8/2002 |
| EP | 1383448 A2 | 1/2004 |
| EP | 1 674 040 A2 | 6/2006 |
| FR | 2 768 324 A1 | 3/1999 |
| FR | 2768325 B1 | 11/1999 |
| GB | 1 598 111 A | 9/1981 |
| GB | 2 151 142 A | 7/1985 |
| JP | 9-192137 A | 7/1997 |
| JP | 09-253030 A | 9/1997 |
| JP | 11-089937 A | 4/1999 |
| JP | 2000-283130 A | 10/2000 |
| JP | 2002-540878 A | 12/2002 |
| JP | 2006-528911 A | 12/2006 |
| JP | 2008-514307 A | 5/2008 |
| JP | 2010515488 | 5/2010 |
| JP | 59-85653 B2 | 9/2016 |
| WO | WO 81/00668 A1 | 3/1981 |
| WO | WO 91/01689 A1 | 2/1991 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/11620 A2 | 5/1995 |
| WO | WO 95/15715 A1 | 6/1995 |
| WO | WO 96/14032 A1 | 5/1996 |
| WO | WO 96/20655 A1 | 7/1996 |
| WO | WO 96/22735 A1 | 8/1996 |
| WO | WO 96/30072 A1 | 10/1996 |
| WO | WO 96/32882 A1 | 10/1996 |
| WO | WO 97/18746 A2 | 5/1997 |
| WO | WO 97/25927 A1 | 7/1997 |
| WO | WO 97/26034 A1 | 7/1997 |
| WO | WO 97/27807 A1 | 8/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 98/35638 A1 | 8/1998 |
| WO | WO 99/00059 A1 | 1/1999 |
| WO | WO 99/01377 A1 | 1/1999 |
| WO | WO 99/07354 A2 | 2/1999 |
| WO | WO 99/13777 A1 | 3/1999 |
| WO | WO 99/15223 A1 | 4/1999 |
| WO | WO 99/66967 A1 | 12/1999 |
| WO | WO 00/02489 A1 | 1/2000 |
| WO | WO 00/03651 A1 | 1/2000 |
| WO | WO 00/03759 A2 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 A2 | 10/2000 |
| WO | WO 01/00111 A1 | 1/2001 |
| WO | WO 01/00114 A1 | 1/2001 |
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/35832 A2 | 5/2001 |
| WO | WO 01/47438 A1 | 7/2001 |

(56) References Cited

FOREIGN PATENT DOCUMENTS

| | | |
|---|---|---|
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |
| WO | WO 02/34167 A2 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/082129 A2 | 10/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | WO 2004/030570 A2 | 4/2004 |
| WO | WO 2004/037317 A2 | 5/2004 |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 04/103162 A2 | 12/2004 |
| WO | WO 2004/103162 A2 | 12/2004 |
| WO | WO 2004/112585 A2 | 12/2004 |
| WO | WO 2004/112651 A2 | 12/2004 |
| WO | WO 2005/002424 A2 | 1/2005 |
| WO | WO 2005/018507 A2 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 A2 | 12/2005 |
| WO | WO 2006/037073 A2 | 4/2006 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |
| WO | 2007046955 | 4/2007 |
| WO | WO 2008/089044 A2 | 7/2008 |
| WO | 2010098804 | 9/2010 |
| WO | WO 2010/128502 A1 | 11/2010 |
| WO | 2015057289 A1 | 4/2015 |
| WO | 2016178722 A1 | 11/2016 |
| WO | 2018013856 A1 | 1/2018 |
| WO | 2018093663 A1 | 5/2018 |

OTHER PUBLICATIONS

U.S. Appl. No. 60/128,690, filed Apr. 9, 1999.
U.S. Appl. No. 16/540,285 (U.S. Pat. No. 10,743,876), filed Aug. 14, 2019 (Aug. 18, 2020).
U.S. Appl. No. 14/575,024 (U.S. Pat. No. 10,624,640), filed Dec. 18, 2014 (Apr. 21, 2020).
U.S. Appl. No. 13/231,586 (U.S. Pat. No. 8,945,177), filed Sep. 13, 2011 (Feb. 3, 2015).
U.S. Appl. No. 16/540,285, Jun. 17, 2020 Issue Fee Payment.
U.S. Appl. No. 16/540,285, May 27, 2020 Supplemental Notice of Allowance.
U.S. Appl. No. 16/540,285, May 11, 2020 Notice of Allowance.
U.S. Appl. No. 16/540,285, Feb. 21, 2020 Response to Non-Final Office Action.
U.S. Appl. No. 16/540,285, Nov. 21, 2019 Non-Final Office Action.
U.S. Appl. No. 14/575,024, Mar. 10, 2020 Issue Fee Payment.
U.S. Appl. No. 14/575,024, Dec. 12, 2019 Notice of Allowance.
U.S. Appl. No. 14/575,024, Nov. 18, 2019 Response to Non-Final Office Action.
U.S. Appl. No. 14/575,024, Aug. 22, 2019 Non-Final Office Action.
U.S. Appl. No. 14/575,024, Apr. 11, 2019 Amendment with RCE.
U.S. Appl. No. 14/575,024, Feb. 28, 2019 Advisory Action.
U.S. Appl. No. 14/575,024, Feb. 11, 2019 Response to Final Office Action.
U.S. Appl. No. 14/575,024, Oct. 11, 2018 Final Office Action.
U.S. Appl. No. 14/575,024, Sep. 6, 2018 Amendment with RCE.
U.S. Appl. No. 14/575,024, Mar. 9, 2018 Advisory Action.
U.S. Appl. No. 14/575,024, Feb. 7, 2018 Notice of Appeal.
U.S. Appl. No. 14/575,024, Aug. 8, 2017 Final Office Action.
U.S. Appl. No. 14/575,024, May 4, 2017 Response to Non-Final Office Action.
U.S. Appl. No. 14/575,024, Feb. 7, 2017 Non-Final Office Action.
U.S. Appl. No. 13/231,586, Dec. 18, 2014 Issue Fee Payment.
U.S. Appl. No. 13/231,586, Sep. 19, 2014 Notice of Allowance.
U.S. Appl. No. 13/231,586, Sep. 11, 2014 Response to Final Office Action.
U.S. Appl. No. 13/231,586, Jun. 11, 2014 Final Office Action.
U.S. Appl. No. 13/231,586, Feb. 27, 2014 Response to Non-Final Office Action.
U.S. Appl. No. 13/231,586, Feb. 21, 2014 Notice of Non-Compliant Amendment.
U.S. Appl. No. 13/231,586, Nov. 22, 2013 Response to Non-Final Office Action.
U.S. Appl. No. 13/231,586, Aug. 28, 2013 Non-Final Office Action.
U.S. Appl. No. 13/231,586, Jun. 18, 2013 Response to Restriction Requirement.
U.S. Appl. No. 13/231,586, Apr. 19, 2013 Restriction Requirement.
Abe et al., "De Vega's Annuloplasty for Acquired Tricuspid Disease: Early and Late Results in 110 Patients," Ann. Thorac. Surg., Jan. 1989, pp. 670-676, vol. 48.
Abe et al., "Updated: De Vega's Annuloplasty for Acquired Tricuspid Disease: Early and Late Results in 110 Patients," Ann. Thorac. Surg. 62:1876-1877 (1996).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association for Cardio-Thoracic Surgery, 14th Annual Meeting, Frankfurt / Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Alvarez et al., "Repairing the Degenerative Mitral Valve: Ten to Fifteen-year Follow-up," J. Thorac. Cardiovasc. Surg., Aug. 1996, pp. 238-247, vol. 112.
Arisi et al., "Mitral Valve Repair with Alfieri Technique in Mitral Regurgitation of Diverse Etiology: Early Echocardiographic Results," Circulation Supplement II, 104(17):3240 (2001).

(56) References Cited

OTHER PUBLICATIONS

Arthur C. Beall et al., Clinical Experience with a Dacron Velour-Covered Teflon-Disc Mitral Valve Prosthesis, 5 Ann. Thorac. Surg. 402-10 (1968).
Bach et al., "Early Improvement in Congestive Heart Failure After Correction of Secondary Mitral Regurgitation in End-stage Cardiomyopathy," Am. Heart J., Jun. 1995, pp. 1165-1170, vol. 129.
Bach et al., "Improvement Following Correction of Secondary Mitral Regurgitation in End-stage Cardiomyopathy with Mitral Annuloplasty," Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia et al., "Edge-to-edge Mitral Repair: A Versatile Mitral Repair," http://www.sts.org/doc/7007 accessed on Sep. 24, 2008.
Bolling et al., "Surgery for Acquired Heart Disease: Early Outcome of Mitral Valve Reconstruction in Patients with End-stage Cardiomyopathy," J. Thor. and Cardiovasc. Surg., Apr. 1995, pp. 676-683, vol. 109.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action dated Sep. 9, 2013 in Application No. 200980158707.2 (with English translation).
Communication dated Mar. 11, 2015 from the Japanese Patent Office in counterpart application No. 2014-529933.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Communication dated Jul. 9, 2018 from the Japanese Patent Office in counterpart application No. 2017-196998.
Copelan, "How Dr. Oz Kick-Started a Groundbreaking Device for Patients with Heart Failure," Parade (Sep. 26, 2018).
Cribier, A., et al., "Percutaneous Mitral Valvotomy with a Metal Dilatator," The Lancet 349:1667 (1997).
Cribier et al., "Percutaneous Mechanical Mitral Commissurotomy With a Newly Designed Metallic Valvulotome: Immediate Results of the Initial Experience in 153 Patients," Circulation 99:793-799 (1999).
Dec et al., "Idiopathic Dilated Cardiomyopathy," N. Engl. J. Med., Dec. 8, 1994, pp. 1564-1575, vol. 331.
Derwent citing German language patent, EP 684012 published Nov. 12, 1995, for: "Thread for constructing surgical seam—has flexible section with two ends, with lower fastening part on thread first end having hollow cylinder with continuous hole through which surgical needle threads".
Derwent citing Japanese language patent, JP 11089937 published Jun. 4, 1999, for: "Catheter for mitral regurgitation test—includes jet nozzles provided on rear side of large diametered spindle shaped portion attached to end of narrow diametered tube".
Dias de Azeredo Bastos et al., "Percutaneous Mechanical Mitral Commissurotomy Performed With a Cribier's Metallic Valvulotome. Initial Results," Arq Bras Cardiol, 77:126-131 (2001).
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report dated Mar. 5, 2020 in Application No. EP 19188678.
Extended European Search Report dated Jul. 19, 2018 in EP 18177999.2.
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Feldman, T., et al., "Technique of Percutaneous Transvenous Mitral Commissurotomy Using the Inoue Balloon Catheter," Catheterization and Cardiovascular Diagnosis Supplement 2:26-34 (1994).
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., "Early Clinical Experience with an Implantable, Intracardiac Circulatory Support Device: Operative Considerations and Physiologic Implications," http://www.sts.org/doc/7007 accessed on Sep. 24, 2008.
Freeny et al., "Subselective Diagnostic and Interventional Arteriography Using a Simple Coaxial Catheter System," Cardiovasc. Intervent. Radiol. 7:209-213 (1984).
Fucci et al., "Improved Results with Mitral Valve Repair Using New Surgical Techniques," Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Glazier, J. and Turi, Z., "Percutaneous Balloon Mitral Valvuloplasty," Progress in Cardiovascular Diseases 40(1):5-26 (1997).
Gregg W. Stone et al., Clinical Trial Design Principles and Endpoint Definitions for Transcatheter Mitral Valve Repair and Replacement: Part 1: Clinical Trial Design Principles: A Consensus Document from the Mitral Valve Academic Research Consortium, 66 J. Am. Coll. Cardiol. 278-307 (2015).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Hung et al., "Atrial Septal Puncture Technique in Percutaneous Transvenous Mitral Commissurotomy : Mitral Valvuloplasty Using the Inoue Balloon Catheter Technique," Catheterization and Cardiovascular Diagnosis 26: 275-284 (1992).
Hung et al., "Pitfalls and Tips in Inoue Balloon Mitral Commissurotomy," Catheterization and Cardiovascular Diagnosis, 37:188-199 (1996).
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).

(56) References Cited

OTHER PUBLICATIONS

Ing et al., "The Snare-Assisted Technique for Transcatheter Coil Occlusion of Moderate to Large Patent Ductus Arteriosus: Immediate and Intermediate Results," J. Am. Col. Cardiol. 33(6):1710-1718 (1999).
Inoue, K. and Feldman, T., "Percutaneous Transvenous Mitral Commissurotomy Using the Inoue Balloon Catheter," Catheterization and Cardiovascular Diagnosis 28:119-125 (1993).
Inoue, K., et al., "Clinical Application of Transvenous Mitral Commissurotomy by a New Balloon Catheter," J Thorac Cardiovasc Surg 87:394-402 (1984).
International Search Report and Written Opinion of PCT Application No. PCT/US2009/068023, dated Mar. 2, 2010, 10 pages total.
International Search Report and Written Opinion issued in International Application No. PCT/US12/54363 dated Nov. 13, 2012.
International Search Report and Written Opinion issued in International Application No. PCT/US12/54381 dated Dec. 21, 2012.
Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).
Kameda et al., "Annuloplasty for Severe Mitral Regurgitation Due to Dilated Cardiomyopathy," Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy: Experience with the First 50 Procedures," Cathet. Cardiovasc. Diagn., Aug. 1991, pp. 257-262, vol. 23.
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lau, K. and Hung, J., "'Balloon Impasse'; A Marker for Severe Mitral Subvalvular Disease and a Predictor of Mitral Regurgitation in Inoue-Balloon Percutaneous Transvenous Mitral Commissurotomy," Catheterization and Cardiovascular Diagnosis 35:310-319 (1995).
Lock et al., "Transcatheter Closure of Atrial Septal Defects: Experimental Studies," Circulation 79:1091-1099 (1989).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The Double Orifice Repair for Barlow Disease: A Simple Solution for Complex Repair," Circulation 100(18):I-94 (1999).
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The Edge-to-edge Technique: A Simplified Method to Correct Mitral Insufficiency," Eur. J. Cardiothorac. Surg., Jan. 14, 1998, pp. 240-246, vol. 13.
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair with the Cosgrove-Edwards Annuloplasty System," Ann. Thorac. Surg., Jan. 16, 1997, pp. 267-268, vol. 64.
McCarthy, P., et al., "Early Results with Partial Left Ventriculectomy," J Thorac Cardiovasc Surg 114(5):755-765 (1997).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37:263-266 (2001) [Abstract in English; Article in Japanese].
Netter, F. H., et al., "The Ciba Collection of Medical Illustrations," vol. 5. Royal Victorian Institute for the Blind Tertiary Resource Service, Melbourne (1969).
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
O'Rourke, R. and Crawford, M., "Mitral Valve Regurgitation," Year Book Medical Publishers, Inc. 1-52 (1984).
Osawa et al., "Partial Left Ventriculectomy in a 3-Year Old Boy with Dilated Cardiomyopathy," Japanese Journal of Thoracic and Cardiovascular Surg, 48:590-593 (2000).
Otto, Catherine M., "Timing of Surgery in Mitral Regurgitation," Heart 89:100-105 (2003).
Park et al., "Clinical Use of Blade Atrial Septostomy," Circulation, 1978, pp. 600-608, vol. 58.
Patel et al., "Epicardial Atrial Defibrillation: Novel Treatment of Postoperative Atrial Fibrillation," http://www.sts.org/doc/7007 accessed on Sep. 23, 2008.
Privitera et al., "Alfieri Mitral Valve Repair: Clinical Outcome and Pathology," Circulation, 106:e173-e174 (2002).
Rahhal, "Tiny device to 'zip up' leaky hearts invented by Dr Oz 20 years ago could save millions, study finds," Daily Mail (Sep. 26, 2018).
Randas J. V. Batista et al., Partial Left Ventriculectomy to Treat End-Stage Heart Disease, 64 Ann. Thorac. Surg. 634-38 (1997).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al., "Linear Segmental Annuloplasty for Mitral Valve Repair," Ann. Thorac. Surg., Jan. 7, 1997, pp. 1805-1806, vol. 63.
Robicsek et al., "The Bicuspid Aortic Valve. How Does It Function? Why Does It Fail," http://www.sts.org/doc/7007 accessed on Sep. 24, 2008.
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al., "Long-Term Follow-Up of Rheumatic Patients Undergoing Left-Sided Valve Replacement with Tricuspid Annuloplasty—Validity of Preoperative Echocardiographic Criteria in the Decision to Perform Tricuspid Annuloplasty," Am. J. Cardiol., Apr. 15, 1998, pp. 1013-1016, vol. 81.

(56) References Cited

OTHER PUBLICATIONS

Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).

Tibayan et al., "Annular Geometric Remodeling in Chronic Ischemic Mitral Regurgitation," http://www.sts.org/doc/7007 accessed on Sep. 24, 2008.

Timek et al., "Edge-to-edge mitral repair: gradients and three-dimensional annular dynamics in vivo during inotropic stimulation," Eur J. of Cardiothoracic Surg., 19:431-437 (2001).

Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).

Totaro, "Mitral valve repair for isolated prolapse of the anterior leaflet: an 11-year follow-up," European Journal of Cardio-thoracic Surgery, 15:119-126 (1999).

Uchida et al., "Percutaneous Cardiomyotomy and Valvulotomy with Angioscopic Guidance," Am. Heart J., Apr. 1991, pp. 1221-1224, vol. 121.

Umana et al., "'Bow-tie' Mitral Valve Repair Successfully Addresses Subvalvular Dysfunction in Ischemic Mitral Regurgitation," Surgical Forum, XLVIII:279-280 (1997).

Umana et al., "Bow-Tie Mitral Valve Repair: An Adjuvant Technique for Ischemic Mitral Regurgitation," Ann. Thorac. Surg., May 12, 1998, pp. 1640-1646, vol. 66.

U.S. Appl. No. 60/316,892 to Tremulis et al., filed Aug. 31, 2001.

Vismara et al., "Transcatheter Edge-to-Edge Treatment of Functional Tricuspid Regurgitation in an Ex Vivo Pulsatile Heart Model," JACC 68(10):1024-1033 (2016).

Votta et al., "3-D Computational Analysis of the Stress Distribution on the Leaflets after Edge-to-Edge Repair of Mitral Regurgitation," Journal of Heart Valve Disease, 11:810-822 (2002).

Waller et al., "Anatomic Basis for and Morphologic Results from Catheter Balloon Valvuloplasty of Stenotic Mitral Valves," Clin. Cardiol. 13:655-661 (1990).

Werker, P. and Kon M., "Review of Facilitated Approaches to Vascular Anastomosis Surgery," Ann Thorac Surg 63:122-7 (1997).

U.S. Appl. No. 14/575,024 (US 2015/0105804), filed Dec. 18, 2014 (Apr. 16, 2015).

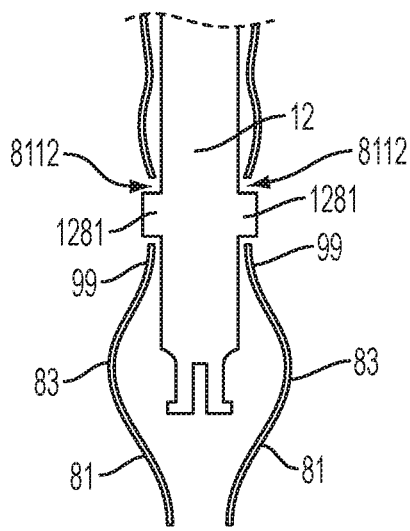
FIG. 15E1
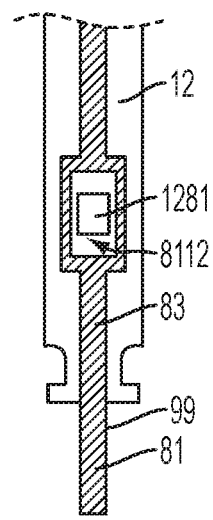
FIG. 15E2
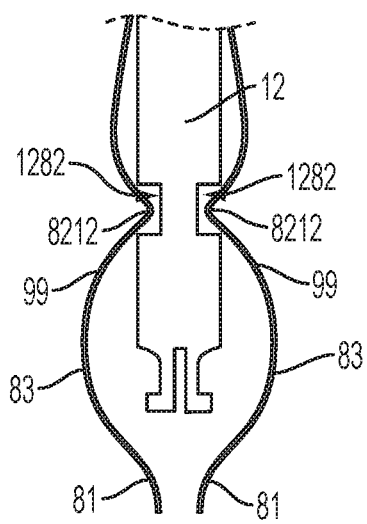
FIG. 15E3
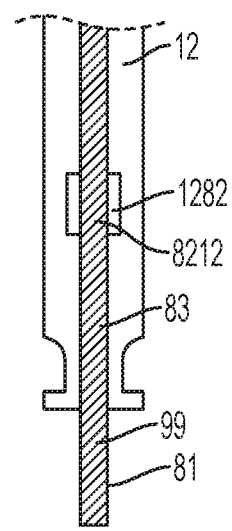
FIG. 15E4

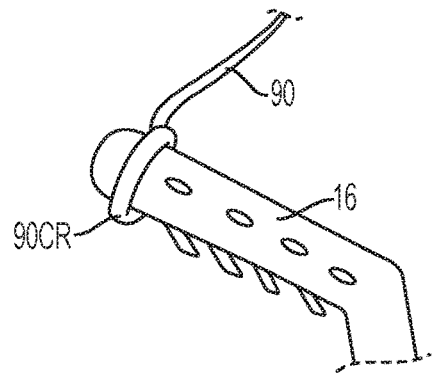
FIG. 15W1
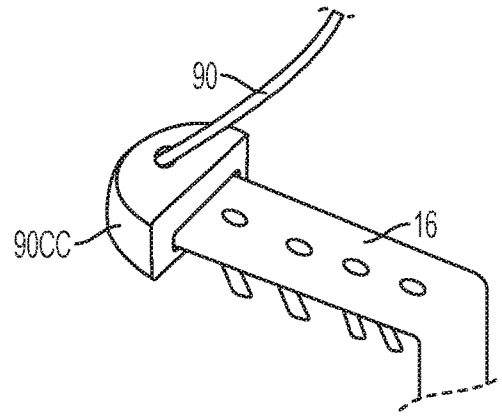
FIG. 15W2
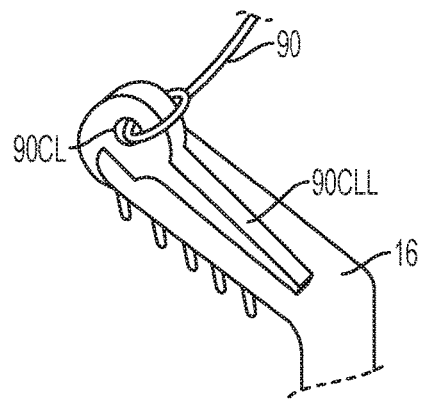
FIG. 15W3
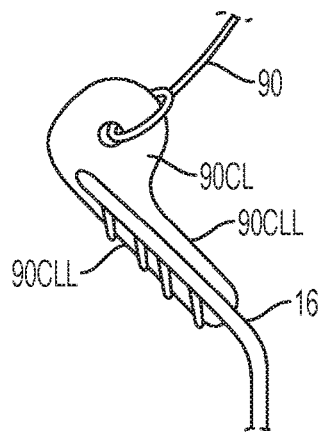
FIG. 15W4
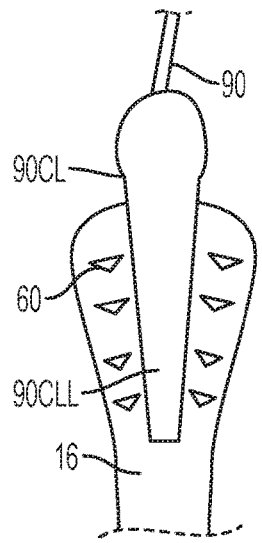
FIG. 15W5

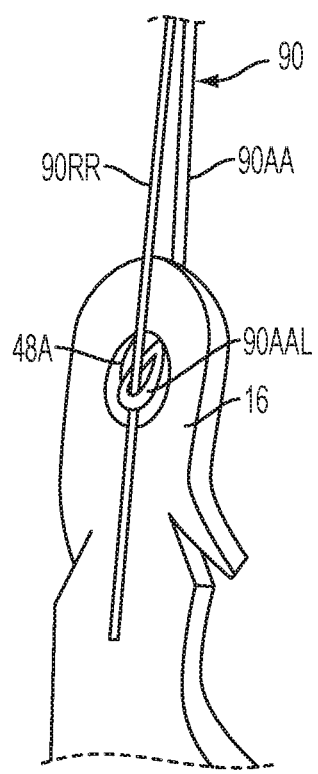
FIG. 15X1
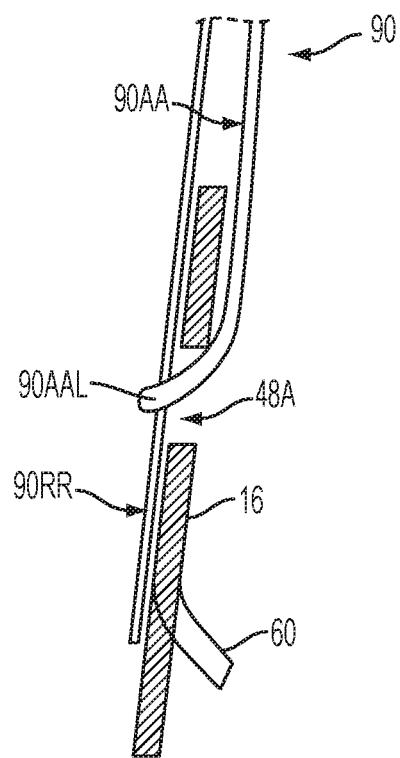
FIG. 15X2
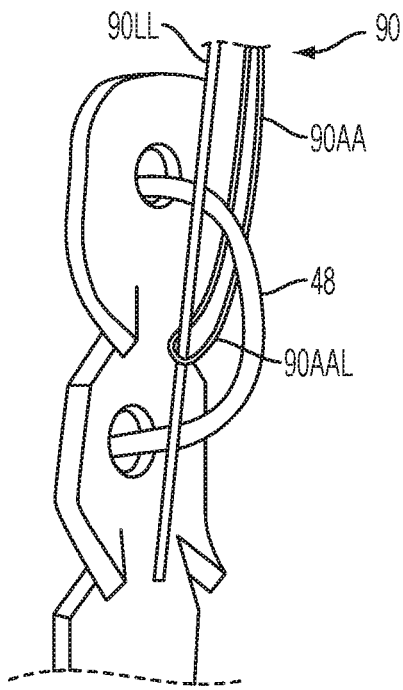
FIG. 15X3

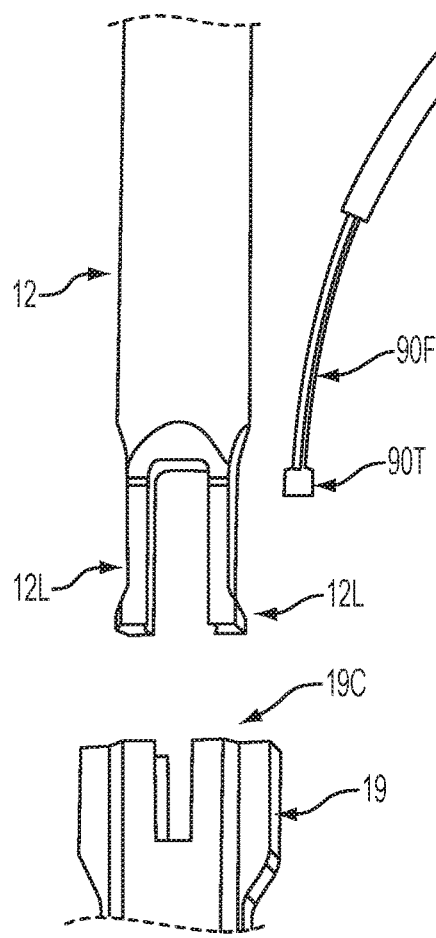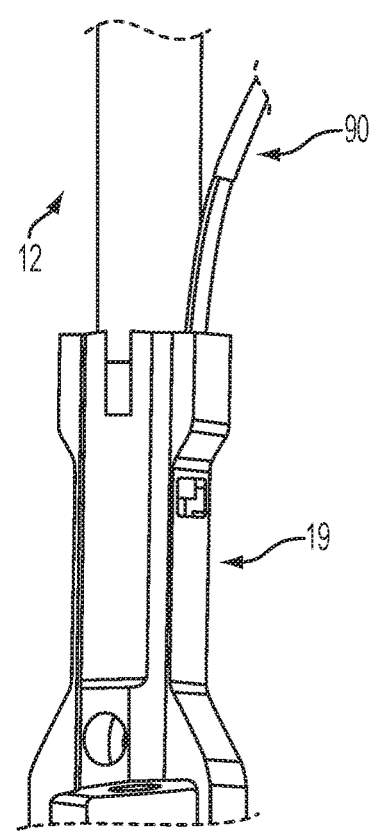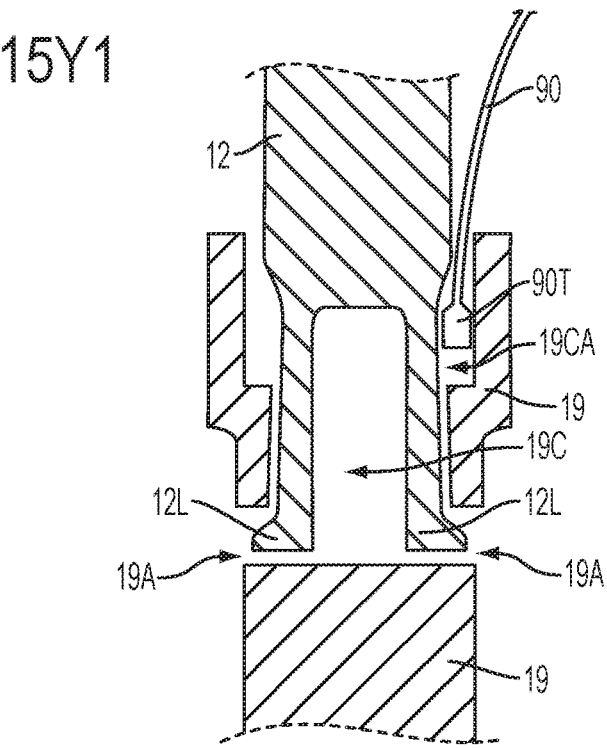
FIG. 15Y1
FIG. 15Y2
FIG. 15Y3

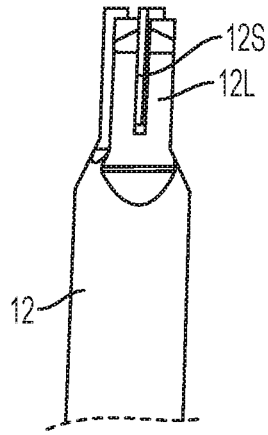
FIG. 15Z1
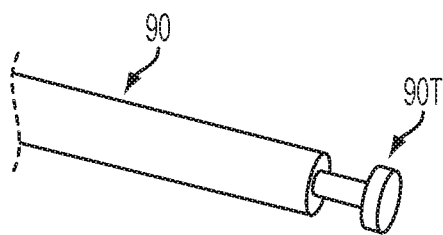
FIG. 15Z2
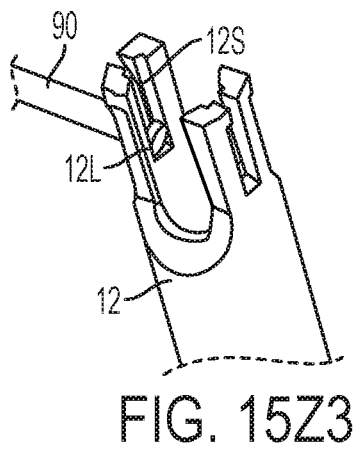
FIG. 15Z3
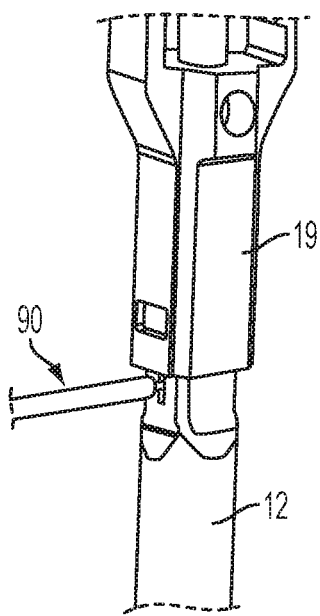
FIG. 15Z4
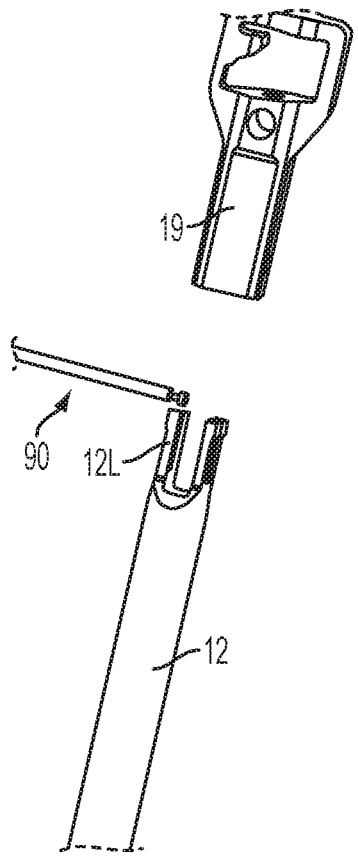
FIG. 15Z5

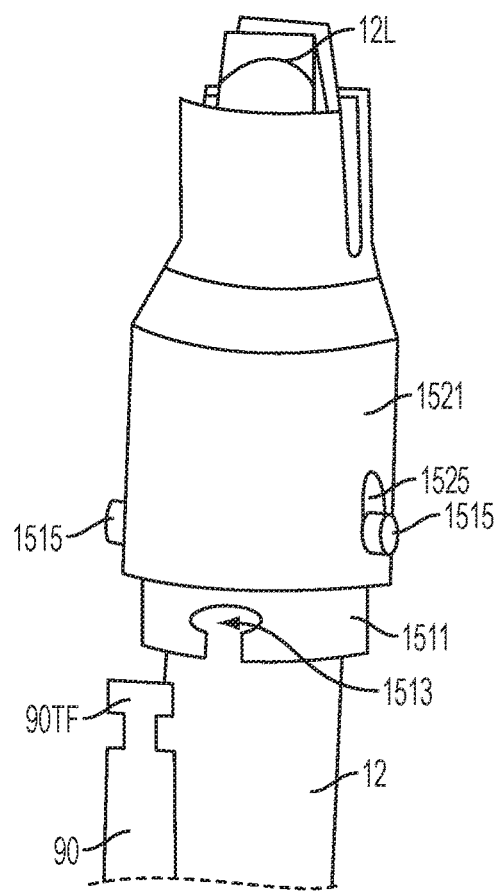
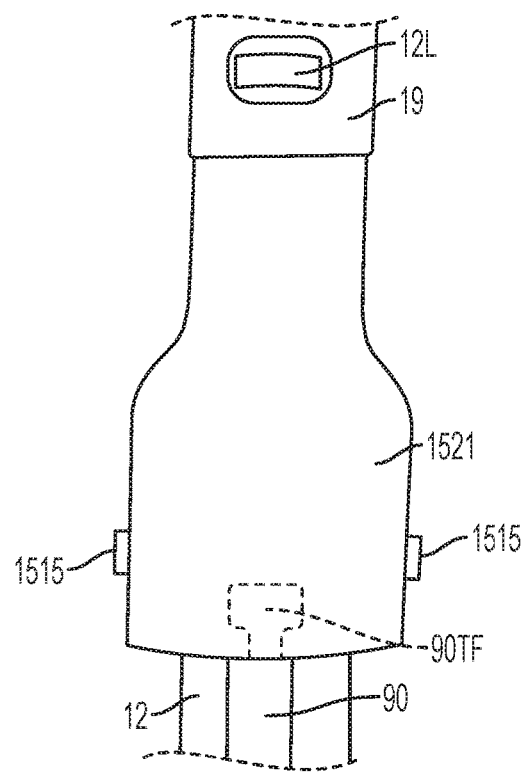
FIG. 15AA1
FIG. 15AA2

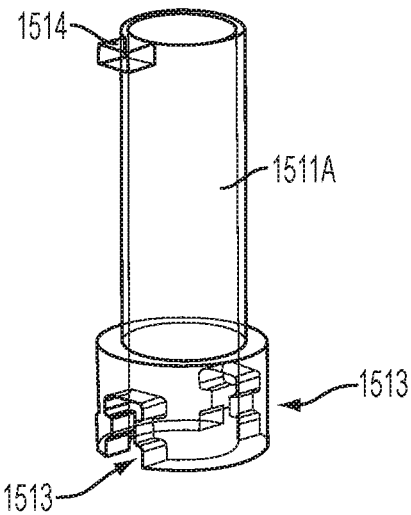
FIG. 15AB1
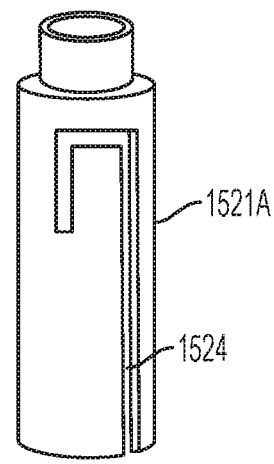
FIG. 15AB2
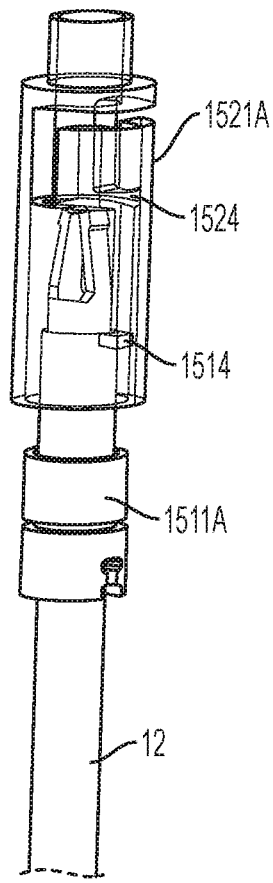
FIG. 15AB3
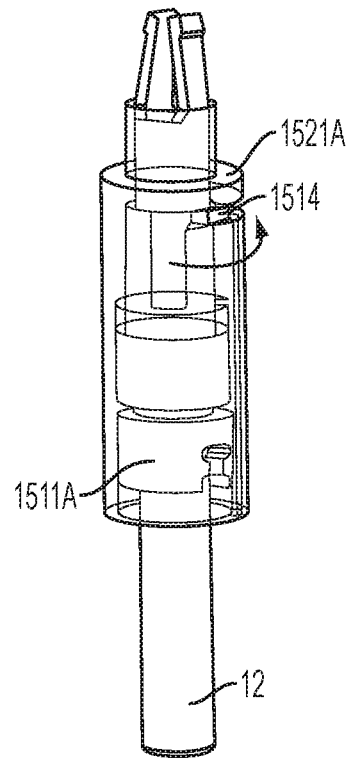
FIG. 15AB4

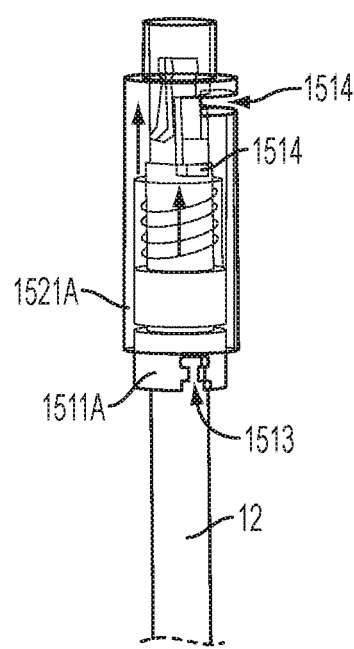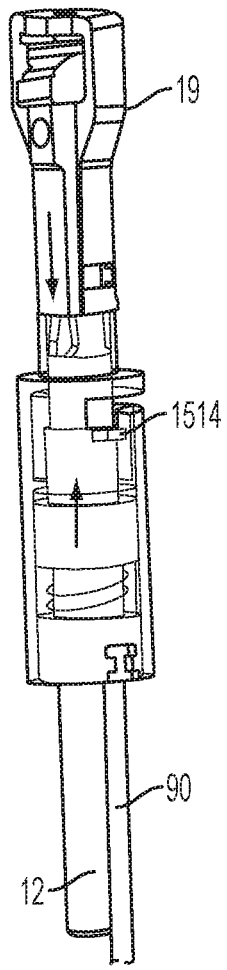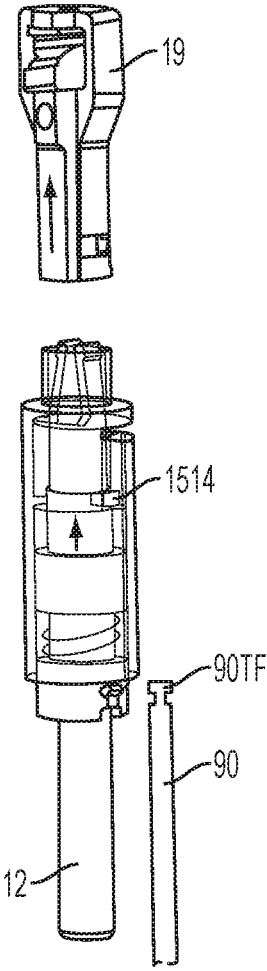
FIG. 15AB5
FIG. 15AB6
FIG. 15AB7

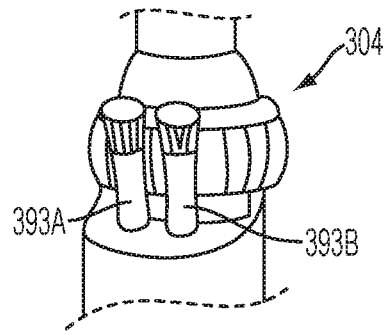
FIG. 15AC1
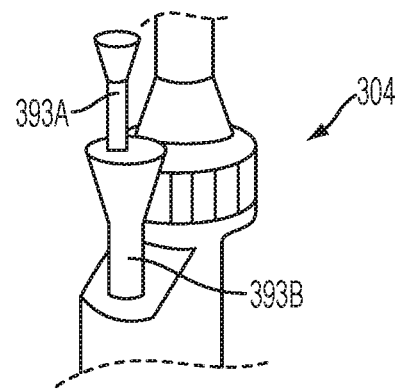
FIG. 15AC2
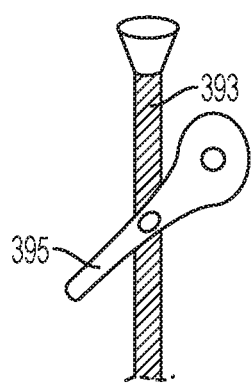
FIG. 15AC3
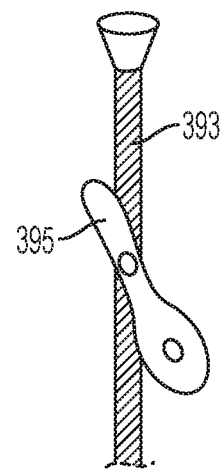
FIG. 15AC4

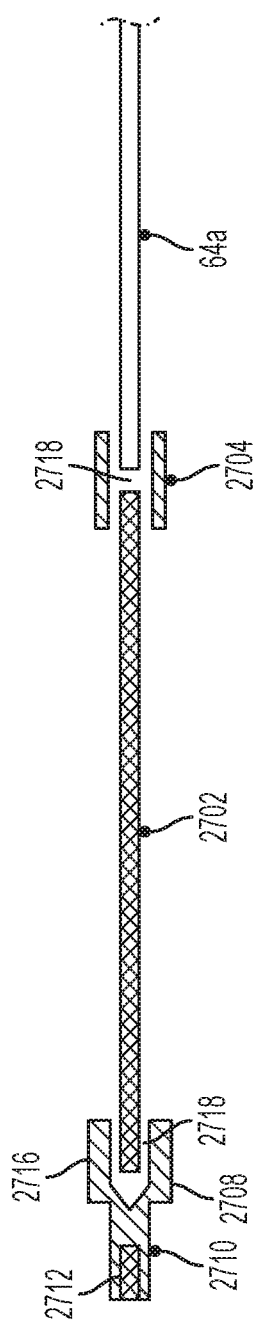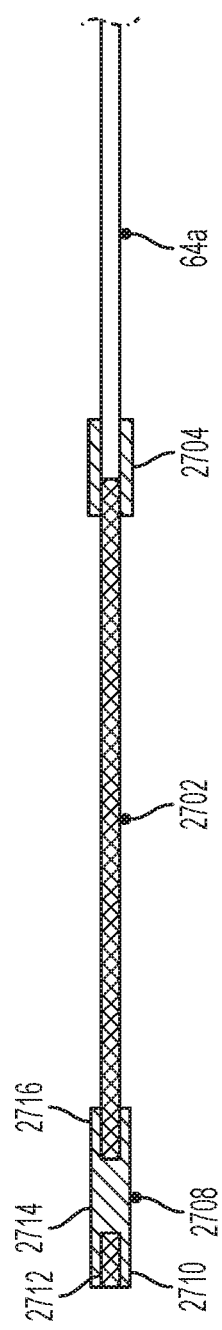

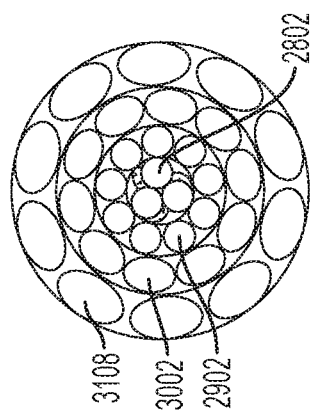
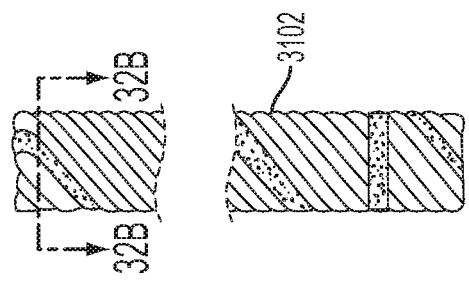
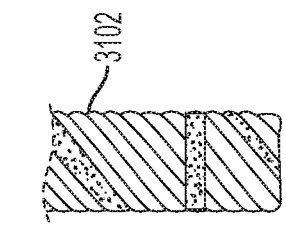
FIG. 32B
FIG. 32A
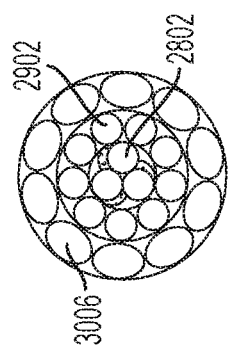
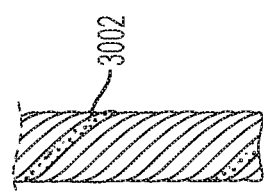
FIG. 31B
FIG. 31A
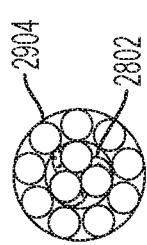
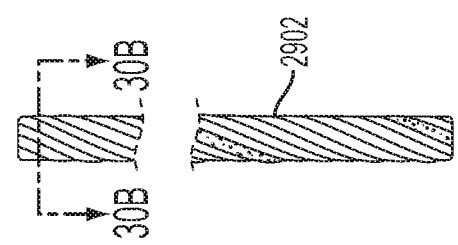
FIG. 30B
FIG. 30A
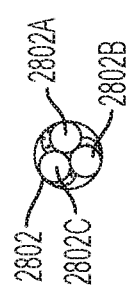
FIG. 29B
FIG. 29A

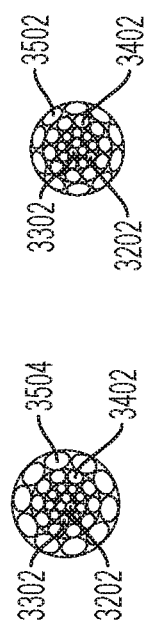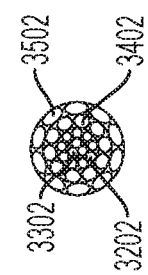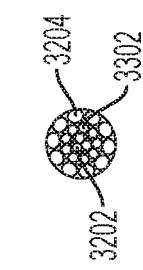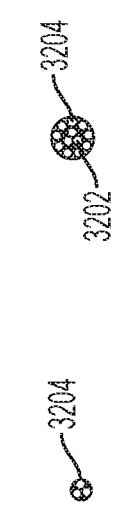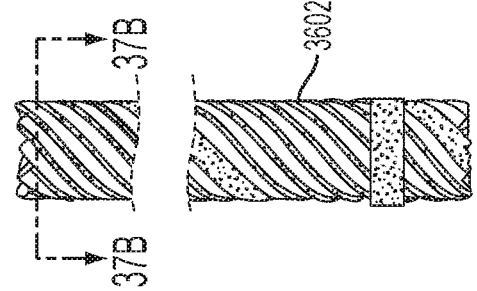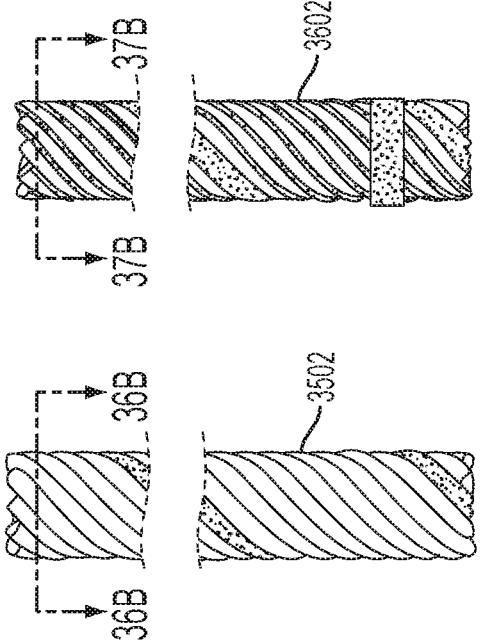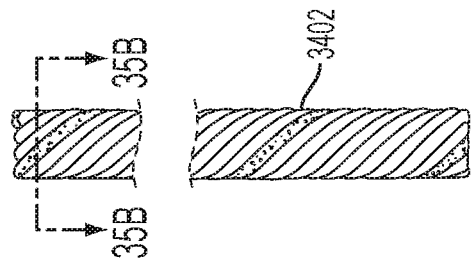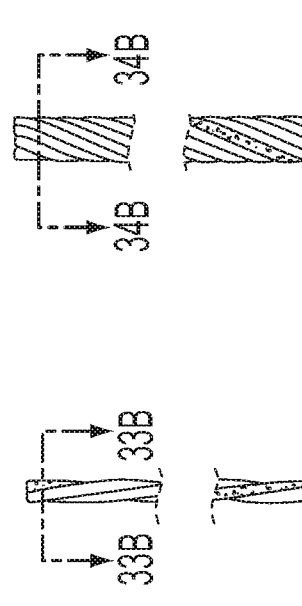

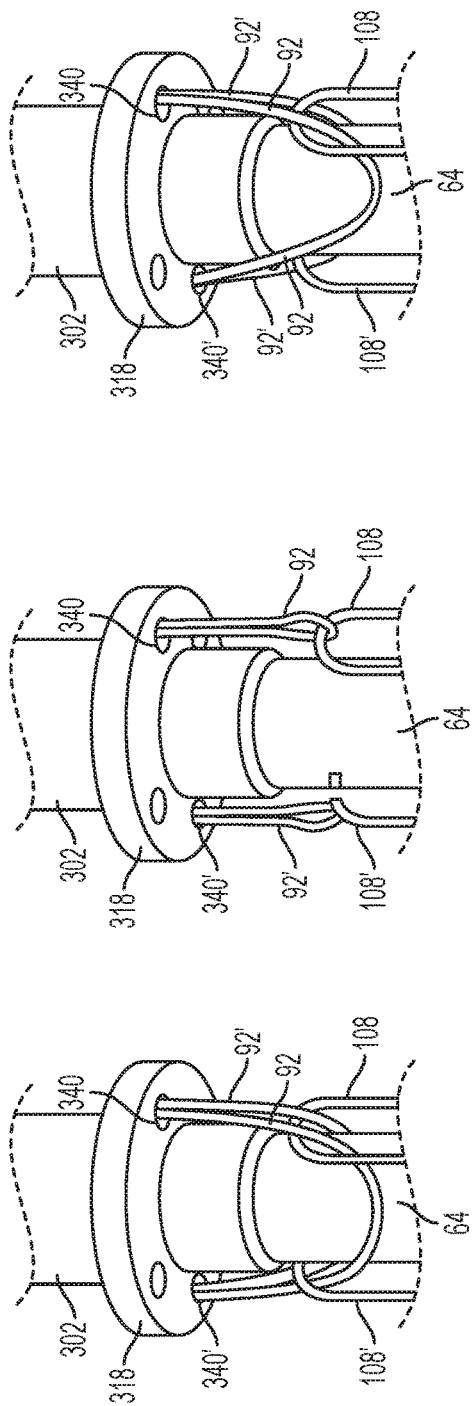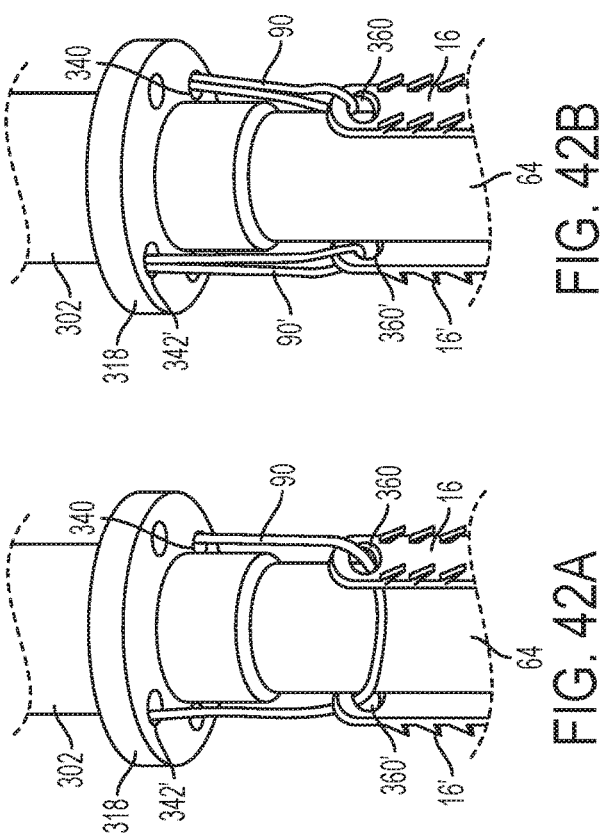

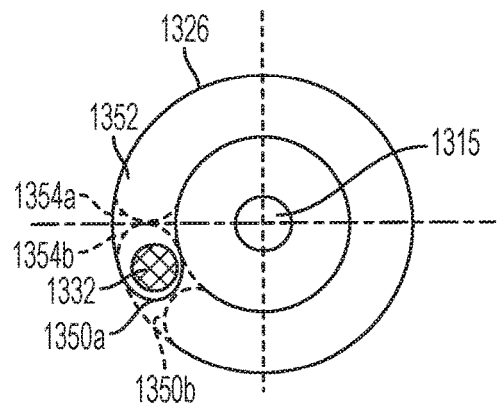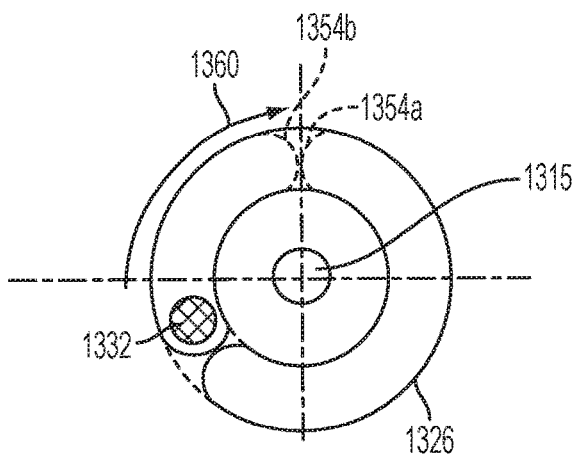
FIG. 62A  FIG. 62B
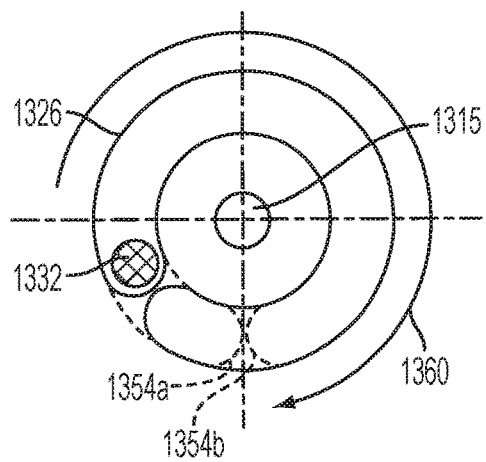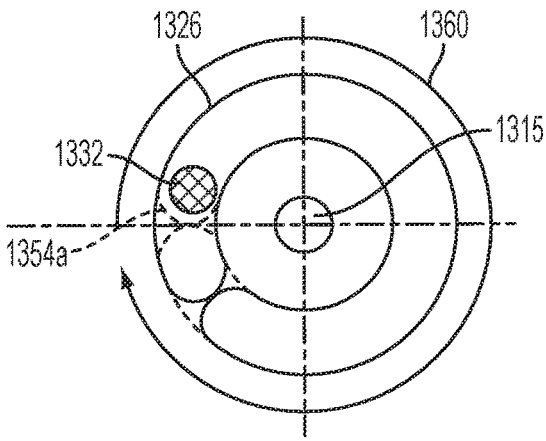
FIG. 62C  FIG. 62D
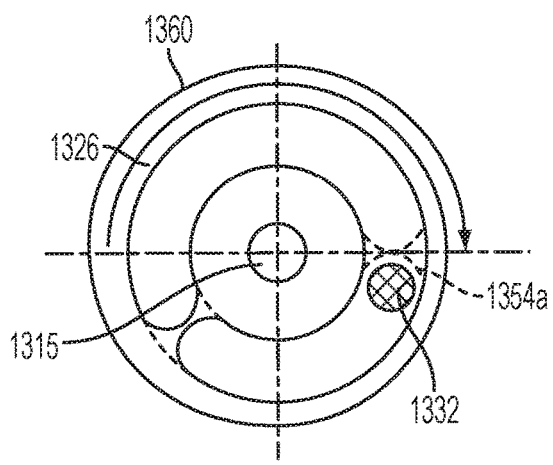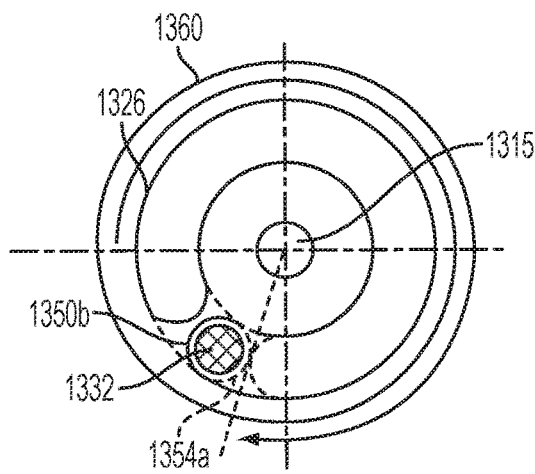
FIG. 62E  FIG. 62F

SYSTEM FOR FIXATION OF LEAFLETS OF A HEART VALVE

CROSS-REFERENCE TO RELATED APPLICATIONS

The present application is a continuation of U.S. patent application Ser. No. 16/540,285, filed Aug. 14, 2019, which is a continuation of U.S. patent application Ser. No. 14/575,024, filed Dec. 18, 2014, now U.S. Pat. No. 10,624,640, which is a continuation of U.S. patent application Ser. No. 13/231,586, filed Sep. 13, 2011, now U.S. Pat. No. 8,945,177, the entire contents of all of which are incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity. More recently, minimally invasive catheter based procedures have been developed to deliver implantable clips to the incompetent valve. These clips are used to fasten a portion of the valve leaflets together, thereby reducing the regurgitation. While the clips appear to be promising, delivery and deployment of the clip can be challenging. In some situations, it may be challenging to visualize the clip and valve leaflets using techniques such as fluoroscopy and echocardiography. Therefore, improved attachment mechanisms and attachment evaluation methods would be desirable.

For these reasons, it would be desirable to provide improved methods, devices, and systems for performing the repair of mitral and other cardiac valves. Such methods, devices, and systems should preferably not require open chest access and be capable of being performed either endovascularly, i.e., using devices which are advanced to the heart from a point in the patient's vasculature remote from the heart or by a minimally invasive approach. Further, such devices and systems should provide features which allow easier delivery of fixation devices, as well as repositioning and optional removal of the fixation device prior to fixation to ensure optimal placement. Still more preferably, the methods, devices, and systems would be useful for repair of tissues in the body other than heart valves. At least some of these objectives will be met by the inventions described hereinbelow.

2. Description of the Background Art

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759.

Maisano et al. (1998) *Eur. J. Cardiothorac. Surg.* 13:240-246; Fucci et al. (1995) *Eur. J. Cardiothorac. Surg.* 9:621-627; and Umana et al. (1998) *Ann. Thorac. Surg.* 66:1640-1646, describe open surgical procedures for performing "edge-to-edge" or "bow-tie" mitral valve repair where edges of the opposed valve leaflets are sutured together to lessen regurgitation. Dec and Fuster (1994) *N. Engl. J. Med.* 331:1564-1575 and Alvarez et al. (1996) *J. Thorac. Cardiovasc. Surg.* 112:238-247 are review articles discussing the nature of and treatments for dilated cardiomyopathy.

Mitral valve annuloplasty is described in the following publications. Bach and Bolling (1996) *Am. J. Cardiol.* 78:966-969; Kameda et al. (1996) *Ann. Thorac. Surg.* 61:1829-1832; Bach and Bolling (1995) *Am. Heart J.* 129:1165-1170; and Bolling et al. (1995) 109:676-683. Linear segmental annuloplasty for mitral valve repair is described in Ricchi et al. (1997) *Ann. Thorac. Surg.* 63:1805-1806. Tricuspid valve annuloplasty is described in McCarthy and Cosgrove (1997) *Ann. Thorac. Surg.* 64:267-268; Tager et al. (1998) *Am. J. Cardiol.* 81:1013-1016; and Abe et al. (1989) *Ann. Thorac. Surg.* 48:670-676.

Percutaneous transluminal cardiac repair procedures are described in Park et al. (1978) *Circulation* 58:600-608; Uchida et al. (1991) *Am. Heart J.* 121: 1221-1224; and Ali Khan et al. (1991) *Cathet. Cardiovasc. Diagn.* 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY OF THE INVENTION

The invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, where the instruments utilized must negotiate long, narrow, and tortuous pathways to the treatment site. In addition, many of the devices and systems of the invention are adapted to be reversible and removable from the patient at any point without interference with or trauma to internal tissues.

In preferred embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches. Using the devices, systems and methods of the invention, the mitral valve can be accessed from a remote surgical or vascular access point and the two valve leaflets may be coapted using endovascular or minimally invasive approaches. While less preferred, in some circumstances the invention may also find application in open surgical approaches as well. According to the invention, the mitral valve may be approached either from the atrial side (antegrade approach) or the ventricular side (retrograde approach), and either through blood vessels or through the heart wall.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

In a first aspect of the present invention, a system for fixing tissue comprises an implantable tissue fixation device comprising a pair of fixation elements each having a first end, a free end opposite the first end, and an engagement surface therebetween for engaging the tissue. The fixation device further comprises a pair of gripping elements. Each gripping element is moveable with respect to one of the fixation elements and is disposed in opposition to one of the engagement surfaces so as to capture tissue therebetween. The system also comprises a gripper pusher releasably coupled to the implantable fixation device adjacent the pair of gripping elements. The gripper pusher has an expanded configuration and a collapsed configuration. In the expanded configuration the gripper pusher engages the pair of gripping elements and advances the pair of gripping elements toward the engagement surfaces of the fixation elements. In the collapsed configuration the gripper pusher has a reduced radial profile relative to the gripper pusher radial profile in the expanded configuration thereby allowing the pair of gripping elements to move away from the engagement surfaces of the fixation elements.

The first ends of the fixation elements may be movably coupled together such that the fixation elements are moveable between a closed position and an inverted position. In the closed position, the engagement surfaces may face each other, and in the inverted position the engagement surfaces may face away from each other. Each fixation element may be at least partially concave such that each gripping element is separated from an opposing engagement surface in an undeployed configuration, and each gripping element may be at least partially recessed within a fixation element in a deployed configuration. The fixation elements may be further moveable to an open position between the closed position and the inverted position.

The gripping elements may be movable independently of the fixation elements. They may be biased toward the engagement surfaces. The gripping elements may be approximately parallel to each other in an undeployed configuration.

The gripper pusher may comprise a spring element that moves from the collapsed configuration to the expanded configuration when a compressive force is applied thereto. The spring element may comprise a longitudinal axis, and the compressive force may be applied in a direction substantially parallel thereto. The spring element may be resiliently biased to return to the collapsed configuration when the compressive force is released. The spring element may be resiliently biased to return to the expanded configuration. The gripper pusher may comprise two spring elements, or an elongate deflectable arm. The arm may comprise a plurality of peaks or bowed regions. The deflectable arm may be biased to return to the expanded configuration, and proximal retraction of the proximal elements may collapse the deflectable arm from the expanded configuration to the collapsed configuration.

The gripper pusher may comprise an attachment mechanism for releasably attaching a distal portion of the gripper pusher to the implantable fixation device. The attachment mechanism may comprise a notched region on a distal portion of the gripper pusher, and a boss adjacent a proximal end of the implantable fixation device. The notched region may be sized to accept the boss. The system may further comprise an elongate delivery shaft having a proximal portion and a distal portion. The distal portion of the elongate delivery shaft may be releasably coupled to a proximal portion of the gripper pusher. The gripper pusher may comprise an attachment ring or coupling ring that may be coupled to the proximal portion thereof, and the attachment ring may be slidably disposed over the delivery shaft.

The system may further comprise an actuation mechanism that may be coupled to the fixation elements, and that is adapted to move the fixation elements between the closed position and the inverted position. The system may also comprise a coupling member for detachably coupling the fixation device to an elongate delivery shaft. A covering may be disposed on the fixation elements that is adapted to promote tissue ingrowth. A coating may be disposed on the fixation elements that is adapted to deliver a therapeutic agent to the treatment tissue.

In another aspect of the invention, a system for fixing tissue may comprise an implantable tissue fixation device and a first gripper actuator. The implantable tissue fixation device comprises a pair of fixation elements and a pair of gripping elements. The pair of fixation elements comprises a first fixation element and a second fixation element. Each fixation element has a first end, a free end opposite the first end, and an engagement surface therebetween for engaging the tissue. The pair of gripping elements comprises a first gripping element and a second gripping element. The first gripping element is moveable with respect to the first fixation element. The first gripping element is also disposed in opposition to the engagement surface of the first fixation element so as to capture tissue therebetween. Similarly, the second gripping element is moveable with respect to the second fixation element and is disposed in opposition to the engagement surface of the second fixation element so as to capture tissue therebetween. The first gripper actuator is releasably coupled to the implantable fixation device adjacent to the first gripping element. The first gripper actuator has a first configuration and a second configuration. Actuating the first gripper actuator between the first configuration and the second configuration moves the first gripping element with respect to the first fixation element. Typically, the system further comprises a second gripper actuator. The second gripper actuator is releasably coupled to the implantable fixation device adjacent to the second gripping element. The second gripper actuator similarly has a first configuration and a second configuration. Actuating the second gripper actuator between the first configuration and the second configuration moves the second gripping element with respect to the second fixation element. The first gripper actuator and the second gripper actuator are actuatable between their first configurations and their second configurations independently of each other.

In many embodiments, the first ends are movably coupled together such that the fixation elements are moveable between a closed position and an inverted position. In the closed position, the first ends of the pair of fixation elements have their engagement surfaces facing each other. In the open position, the first ends of the pair of fixation elements have their engagement surfaces facing away from each other. The system may further comprise an actuation mechanism coupled to the fixation elements. The actuation mechanism is adapted to move the fixation elements between the closed position and the inverted position.

In many embodiments, each fixation element is at least partially concave. By being at least partially concave, each gripping element is separated from an opposing engagement surface in an undeployed configuration and may be at least partially recessed within the fixation element in a deployed configuration. The fixation elements may further be moveable to an open position between the closed position and the inverted position.

In addition to being independently moveable relative to one another, the gripping elements may be movable independently of the fixation elements. The gripping elements may be biased toward the engagement surfaces. The gripping elements may be approximately parallel to each other in an undeployed configuration.

In many embodiments, the system further comprises a gripper pusher as described above. The gripper pusher is releasably coupled to the implantable fixation device adjacent the pair of gripping elements. The gripper pusher has an expanded configuration and a collapsed configuration. In the expanded configuration, the gripper pusher engages one or more of the pair of gripping elements and advances one or more of the pair of gripping elements toward the engagement surfaces of the fixation elements. In the collapsed configuration, the gripper pusher has a reduced radial profile relative to the gripper pusher radial profile in the expanded configuration. This reduced radial profile allows the pair of gripping elements to move away from the engagement surfaces of the fixation elements.

In many embodiments, the first gripper actuator comprises a first wire and the second gripper actuator comprises a second wire. The first wire and the second wire may be substantially flat or have other profiles such as round, square, elliptical, etc. Preferably, the substantially flat sides of the first and second wire are positioned to engage the first and second gripping elements and are biased to bend or flex along the flat side. Thus, as the first and second wires are advanced, they will tend to deflect in the direction toward the first and second gripping elements.

In many embodiments, at least one of a distal end of the first gripper actuator or a distal end of the second gripper actuator is releasably coupled to the implantation fixation device by a suture knot.

In many embodiments, the system further comprises an elongate delivery shaft having a proximal portion and a distal portion. The distal portion of the elongate delivery shaft is releasably coupled to a proximal portion of the fixation device. Each of the first and second gripper actuators may comprise distal portions. The distal portions of the first and second gripper actuators may be releasably coupled to at least one of the distal portion of the elongate delivery shaft or the proximal portion of the fixation device. For example, the distal portions of the first gripper actuator and second gripper actuator may each comprise a closed loop or a coiled distal end disposed over at least one of the distal portion of the elongate delivery shaft or the proximal portion of the fixation device.

In many embodiments, the proximal portion of the fixation device comprises a channel having a pair of notches. The distal portion of the elongate delivery shaft comprises a pair of L-shaped ends resiliently biased to fit into the pair of notches. The distal portion of the elongate delivery shaft is releasably coupled to the proximal portion of the fixation device by placing the pair of L-shaped ends into channel of the fixation device and locking the pair of notches in the channel. The first and second gripper actuators each comprise distal ends. Placing the distal ends of the first and second gripper actuators and coupling the distal portion of the elongate delivery shaft to the proximal portion of the fixation device locks the distal ends of the first and second gripper actuators in place. The first and second gripper actuator may each comprise T-shaped distal ends. The system may further comprise a covering assembly coupled to and disposed over the distal portion of the elongate delivery shaft. The covering assembly comprises an outer slideable section and an inner section having a pair of T-shaped openings. The first and second gripper actuator are releasably coupled to the fixation device by sliding the T-shaped distal ends of the first and second gripper actuators into the pair of the T-shaped opening of the inner section of the covering assembly and sliding the outer slideable section to cover the T-shaped openings.

In many embodiments, the first and second gripper actuators are releasably coupled to the first and second gripping elements, respectively. The first and second gripping elements may each comprise portions extending radially outward. The system may further comprise first and second holding elements. The first holding element is coupled to the first gripper actuator and releasably coupled to the first gripping element at its portion extending radially outward. The second holding element is coupled to the second gripper actuator and releasably coupled to the second gripping element at its portion extending radially outward. The first and second holding element may comprises a first and second ring, respectively. The rings are disposed over the portions extending radially outward of their respective gripping elements. Alternatively, the first and second holding elements may comprise a first and second clip, respectively. The clips are releasably attached to the portion extending radially outward of their respective gripping elements. The first and second clips may each comprise a pair of legs disposed over the length of their respective gripping elements. The portions extending radially outward of the first and second gripping elements may each have apertures. The first and second gripper actuators may be threaded through the apertures of the radially outward portion of the first and second gripping elements, respectively. The first and second gripper actuators may each comprise an enlarged portion. The diameters of the enlarged portions of the first and second gripper actuator may be greater than that of the aperture of the portion extending radially outward of the first and second gripping elements, respectively, to facilitate moving the first and second gripping elements. The enlarged portions of the first and second gripper actuator may comprises a sleeve disposed over the first and second gripper actuators.

In many embodiments, the first and second gripper actuator and the second gripper actuator each comprise an actuation line and a release line. Each actuation line may comprise a loop while each release line may comprises a single release cable. The single release cable is threaded through the loop of the actuation line when a gripper actuator is coupled a gripping element. Pulling the single release cable out through the loop of the actuation line allows a gripper actuator to be released from a gripping element.

The system may further comprise a coupling member for detachably coupling the fixation device to an elongate delivery shaft, a covering on the fixation elements adapted for promoting tissue growth, and/or a coating on the fixation elements adapted for delivering a therapeutic agent.

Another aspect of the invention provides a method for fixing tissue. An implantable tissue fixation device is provided. The fixation device comprises a pair of fixation elements. Each fixation element has a first end, a free end opposite the first end, and an engagement surface therebetween for engaging the tissue. The fixation device further comprises a pair of gripping elements. Each gripping element is moveable with respect to one of the fixation elements and is disposed in apposition to one of the engagement surfaces so as to capture tissue therebetween. The fixation element is positioned relative to tissue so that the tissue is disposed between the pair of gripping elements and the engagement surfaces of the pair of fixation element. The pair of gripping elements is advanced toward the engagement surfaces of the fixation elements.

In many embodiments, a gripper pusher releasably coupled to the implantable fixation device adjacent the pair of gripping elements is provided, and the pair of gripping elements is advanced toward the engagement surfaces of the fixation elements by engaging the pair of gripping elements with the gripper pusher. Engaging the pair of gripping elements with the gripper pusher may comprise placing the gripper pusher into an expanded configuration from a collapsed configuration. The gripper pusher may comprise a spring element having a longitudinal axis, and the pair of gripping elements may be engaged with the gripper pusher by applying a compressive force to the spring element in a direction substantially parallel to the longitudinal axis to move the gripper pusher to the expanded configuration. The gripper pusher may be placed into the collapsed configuration from the expanded configuration to reduce the radial profile of the gripper pusher relative to the gripper pusher radial profile in the expanded configuration to allow the pair of gripping elements to move away from the engagement surfaces of the fixation elements.

In many embodiments, the first ends of the pair of the fixation elements is moved between a closed position to an inverted position. The engagement surfaces face each other when the fixation element is in the closed position and away from each other when the fixation element is in the inverted position. The fixation elements may be moved to an open position between the closed position and the inverted position.

Another aspect of the invention provides a method of fixing tissue. An implantable tissue fixation device is provided. The fixation device comprises a pair of fixation elements, which comprises a first fixation element and a second fixation element. Each fixation element has a first end, a free end opposite the first end, and an engagement surface therebetween for engaging the tissue. The fixation device further comprises a pair of gripping elements, which comprise a first gripping element and a second gripping element. The first gripping element is disposed in apposition to the engagement surface of the first fixation element. The second gripping element is likewise disposed in apposition to the engagement surface of the second fixation element. The fixation element is positioned relative to tissue so that the tissue is disposed between the first gripping element and the engagement surface of the first fixation element. The tissue is captured between the first gripping element and the engagement surface of the first fixation element by moving the first gripping element with respect to the first fixation element. The position of the second gripping element is maintained with respect to the second fixation element while the first gripping element is moved with respect to the first fixation element.

In many embodiments, a first gripping element actuator coupled to the first gripping element and a second gripping element actuator coupled to the second gripping element are provided. The tissue between the first gripping element and the engagement surface of the first fixation element may be captured by moving the first gripping element actuator to move the first gripping element. The position of the second gripping element with respect to the second fixation element may be maintained by holding the second gripping element actuator stationary relative to the second gripping element.

In many embodiments, the captured tissue between the first gripping element and the engagement surface of the first fixation element is released by moving the first gripping element away from the first fixation element. The fixation can then be repositioned relative to the tissue.

In many embodiments, the fixation element is positioned relative to tissue so that the tissue is disposed between the second gripping element and the engagement surface of the second fixation element. The tissue between the second gripping element and the engagement surface of the second fixation element may be captured by moving the second gripping element with respect to the second fixation element. In some embodiments, the captured tissue between the pair of gripping elements and the engagement surfaces of the pair of fixation elements can be released by moving the pair of gripping elements away from the engagement surfaces of the pair of fixation elements. The fixation can then be repositioned relative to the tissue.

Other aspects of the nature and advantages of the invention are set forth in the detailed description set forth below, taken in conjunction with the drawings.

BRIEF DESCRIPTION OF THE DRAWINGS

FIGS. 15W1-15AB7 illustrate various embodiments of coupling a proximal element line to a proximal element of the fixation device of FIG. 7.

FIGS. 15AC1-15AC4 illustrate various control mechanisms of the independently actuatable proximal element lines of the fixation device of FIGS. 15I-15V.

FIGS. 28A-28B illustrate an exemplary embodiment of an actuator rod assembly.

FIGS. 29A-29B, 30A-30B, 31A-31B, and 32A-32B illustrate layers of an exemplary cable used in the actuator rod of FIGS. 28A-28B.

FIGS. 33A-33B, 34A-34B, 35A-35B, 36A-36B, and 37A-37B illustrate layers in another exemplary cable used in the actuator rod of FIGS. 28A-28B.

FIG. 41A-41C illustrate various arrangements of lock lines engaging release harnesses of a locking mechanism.

FIGS. 42A-42B illustrate various arrangements of proximal element lines engaging proximal elements of a fixation device.

FIGS. 62A-62F illustrate a ball restricting rotation of a disk.

DETAILED DESCRIPTION OF THE INVENTION

I. Cardiac Physiology

Figure 1:
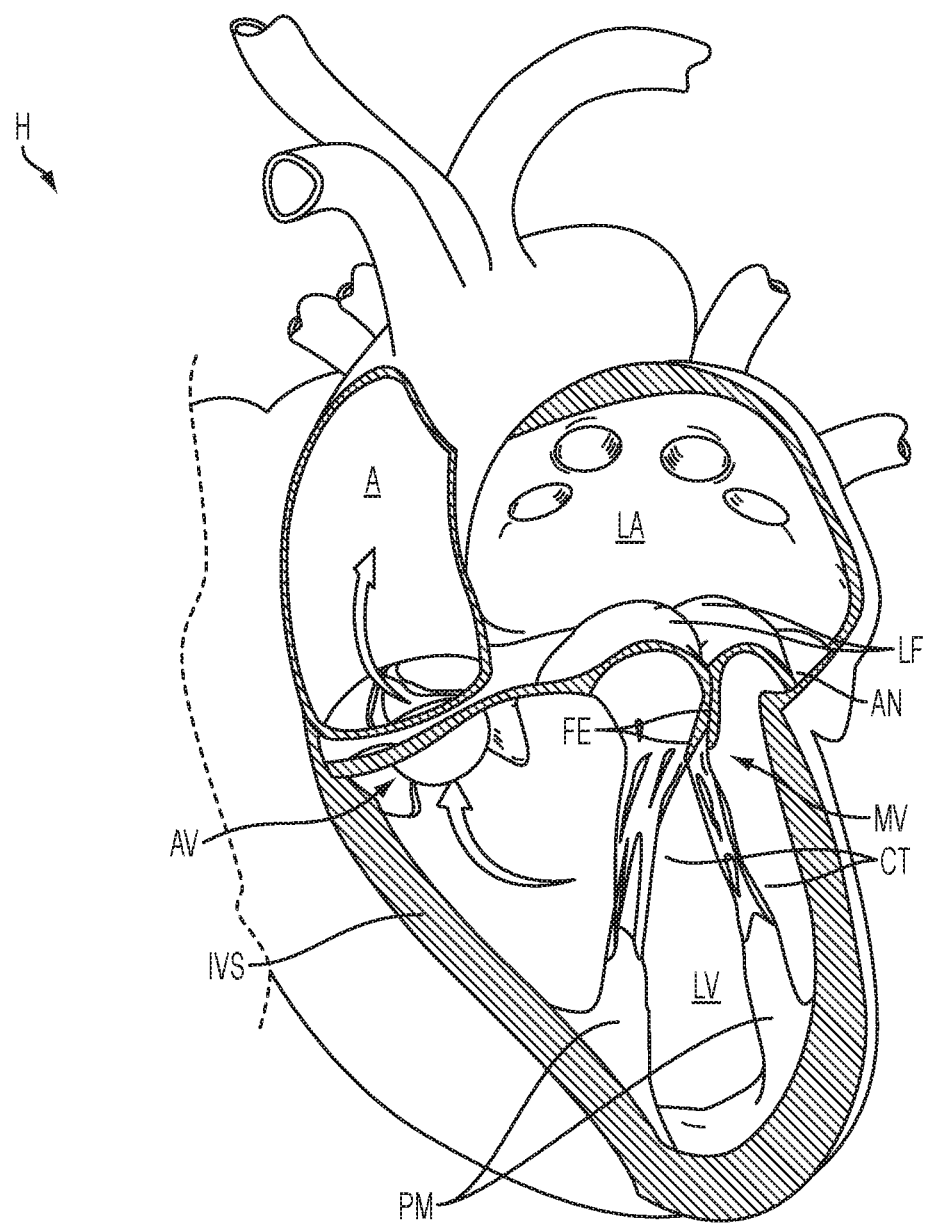
FIG. 1 illustrates the left ventricle and left atrium of the heart during systole.

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendinae CT (referred to hereinafter as the chordae) which include a plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figure 2A:
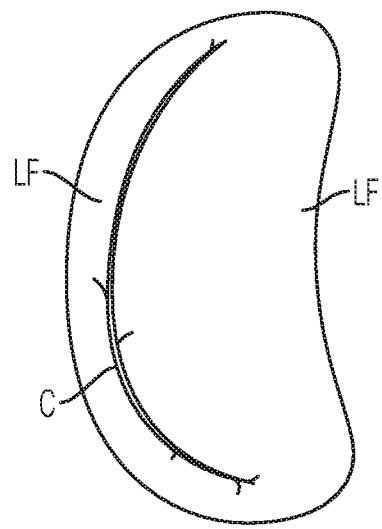
FIG. 2A illustrates free edges of leaflets in normal coaptation.
Figure 2B:
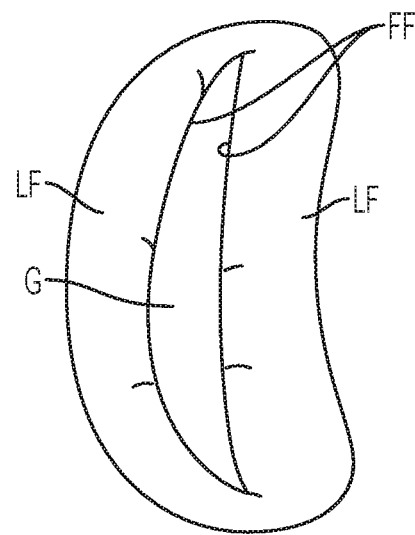
FIG. 2B illustrates the free edges in regurgitative coaptation.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation C. An example of a defect causing regurgitation is shown in FIG. 2B. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

The present invention provides methods and devices for grasping, approximating and fixating tissues such as valve leaflets to treat cardiac valve regurgitation, particularly mitral valve regurgitation. The present invention also provides features that allow repositioning and removal of the device if so desired, particularly in areas where removal may be hindered by anatomical features such as chordae CT. Such removal would allow the surgeon to reapproach the valve in a new manner if so desired.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic." This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

Figure 3A:
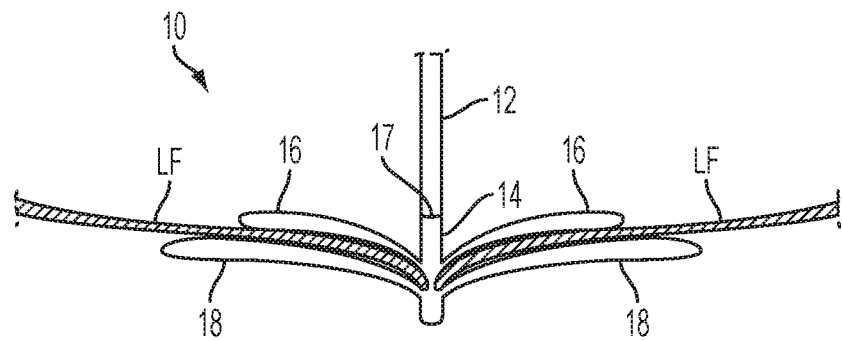
FIGS. 3A-3C illustrate grasping of the leaflets with a fixation device, inversion of the distal elements of the fixation device and removal of the fixation device, respectively.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve. Referring to FIG. 3A, an interventional tool 10, having a delivery device, such as a shaft 12, and a fixation device 14, is illustrated having approached the mitral valve MV from the atrial side and grasped the leaflets LF. The mitral valve may be accessed either surgically or by using endovascular techniques, and either by a retrograde approach through the ventricle or by an antegrade approach through the atrium, as described above. For illustration purposes, an antegrade approach is described.

The fixation device 14 is releasably attached to the shaft 12 of the interventional tool 10 at its distal end. When describing the devices of the invention herein, "proximal" shall mean the direction toward the end of the device to be manipulated by the user outside the patient's body, and "distal" shall mean the direction toward the working end of the device that is positioned at the treatment site and away from the user. With respect to the mitral valve, proximal shall refer to the atrial or upstream side of the valve leaflets and distal shall refer to the ventricular or downstream side of the valve leaflets.

The fixation device 14 typically comprises proximal elements 16 (or gripping elements) and distal elements 18 (or fixation elements) which protrude radially outward and are positionable on opposite sides of the leaflets LF as shown so as to capture or retain the leaflets therebetween. The proximal elements 16 are preferably comprised of cobalt chromium, nitinol or stainless steel, and the distal elements 18 are preferably comprised of cobalt chromium or stainless steel, however any suitable materials may be used. The fixation device 14 is coupleable to the shaft 12 by a coupling mechanism 17. The coupling mechanism 17 allows the fixation device 14 to detach and be left behind as an implant to hold the leaflets together in the coapted position.

Figure 3B:
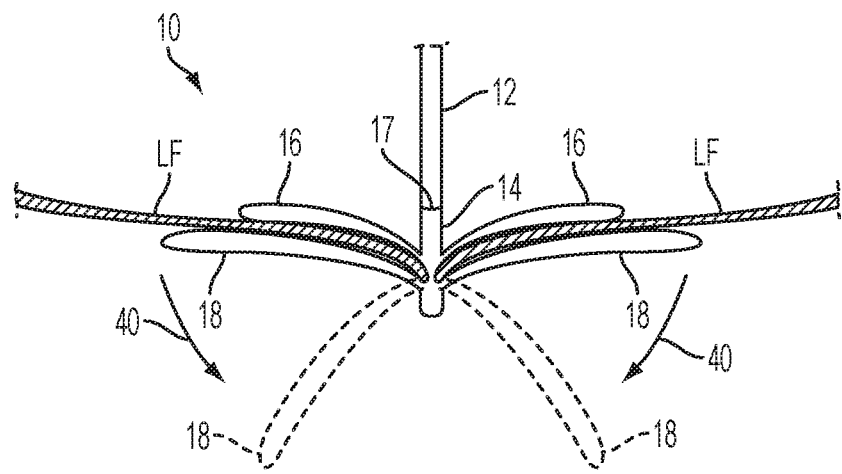
Figure 3C:
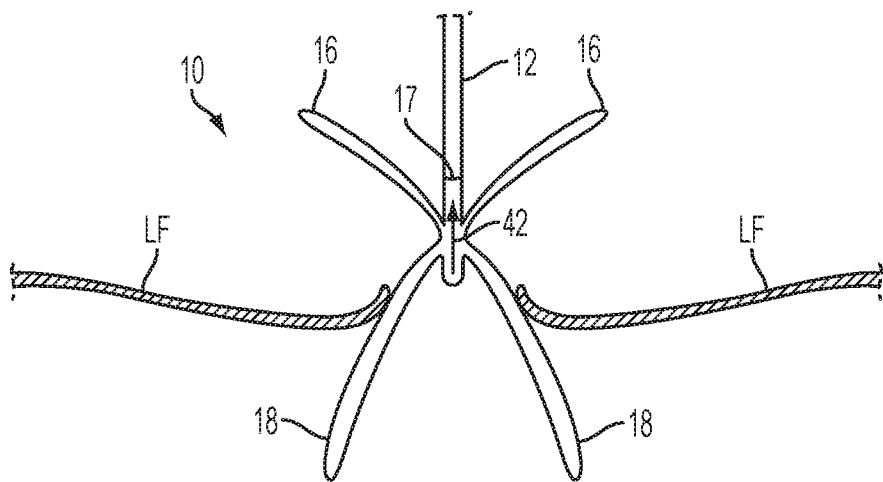

In some situations, it may be desired to reposition or remove the fixation device 14 after the proximal elements 16, distal elements 18, or both have been deployed to capture the leaflets LF. Such repositioning or removal may be desired for a variety of reasons, such as to reapproach the valve in an attempt to achieve better valve function, more optimal positioning of the device 14 on the leaflets, better purchase on the leaflets, to detangle the device 14 from surrounding tissue such as chordae, to exchange the device 14 with one having a different design, or to abort the fixation procedure, to name a few. To facilitate repositioning or removal of the fixation device 14 the distal elements 18 are releasable and optionally invertible to a configuration suitable for withdrawal of the device 14 from the valve without tangling or interfering with or damaging the chordae, leaflets or other tissue. FIG. 3B illustrates inversion wherein the distal elements 18 are moveable in the direction of arrows 40 to an inverted position. Likewise, the proximal elements 16 may be raised, if desired. In the inverted position, the device 14 may be repositioned to a desired orientation wherein the distal elements may then be reverted to a grasping position against the leaflets as in FIG. 3A. Alternatively, the fixation device 14 may be withdrawn (indicated by arrow 42) from the leaflets as shown in FIG. 3C. Such inversion reduces trauma to the leaflets and minimizes any entanglement of the device with surrounding tissues. Once the device 14 has been withdrawn through the valve leaflets, the proximal and distal elements may be moved to a closed position or configuration suitable for removal from the body or for reinsertion through the mitral valve.

Figure 4:
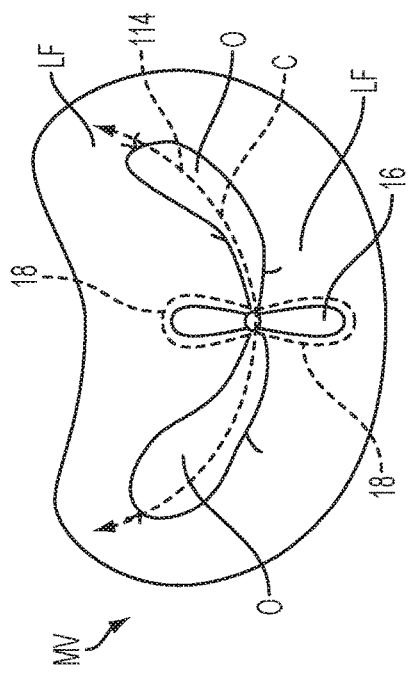
FIG. 4 illustrates the position of the fixation device in a desired orientation relative to the leaflets.

FIG. 4 illustrates the position of the fixation device 14 in a desired orientation in relation to the leaflets LF. This is a short-axis view of the mitral valve MV from the atrial side, therefore, the proximal elements 16 are shown in solid line and the distal elements 18 are shown in dashed line. The proximal and distal elements 16, 18 are positioned to be substantially perpendicular to the line of coaptation C. The device 14 may be moved roughly along the line of coaptation to the location of regurgitation. The leaflets LF are held in place so that during diastole, as shown in FIG. 4, the leaflets LF remain in position between the elements 16, 18 surrounded by openings O which result from the diastolic pressure gradient. Advantageously, leaflets LF are coapted such that their proximal or upstream surfaces are facing each other in a vertical orientation, parallel to the direction of blood flow through mitral valve MV. The upstream surfaces may be brought together so as to be in contact with one another or may be held slightly apart, but will preferably be maintained in the vertical orientation in which the upstream surfaces face each other at the point of coaptation. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation. If the resulting color Doppler image shows insufficient improvement in mitral regurgitation, the interventional tool 10 may be repositioned. This may be repeated until an optimal result is produced wherein the leaflets LF are held in place.

Figure 5B:
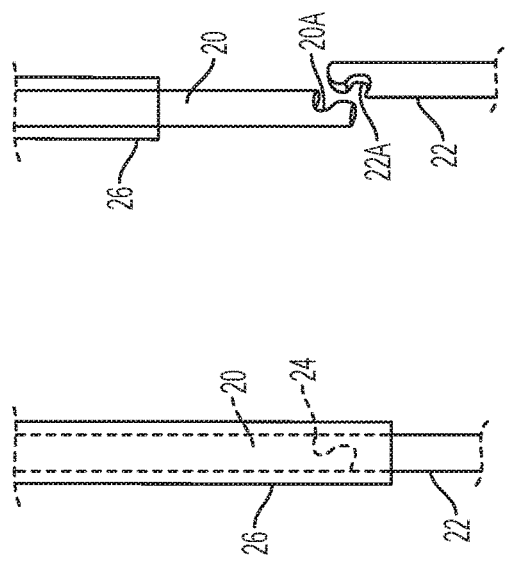
Figure 5A:
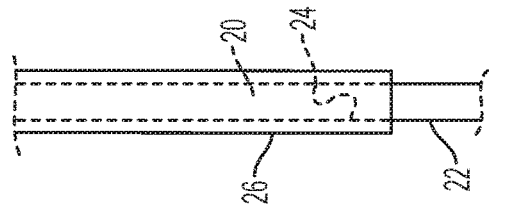

Once the leaflets are coapted in the desired arrangement, the fixation device 14 is then detached from the shaft 12 and left behind as an implant to hold the leaflets together in the coapted position. As mentioned previously, the fixation device 14 is coupled to the shaft 12 by a coupling mechanism 17. FIGS. 5A-5B, 6A-6B illustrate exemplary embodiments of such coupling mechanisms. FIG. 5A shows an upper shaft 20 and a detachable lower shaft 22 which are interlocked at a joining line or mating surface 24. The mating surface 24 may have any shape or curvature which will allow or facilitate interlocking and later detachment. A snuggly fitting outer sheath 26 is positioned over the shafts 20, 22 to cover the mating surface 24 as shown. FIG. 5B illustrates detachment of the lower shaft 22 from the upper shaft 20. This is achieved by retracting the outer sheath 26, so that the mating surface 24 is exposed, which allows the shafts 20, 22 to separate.

Figure 6B:
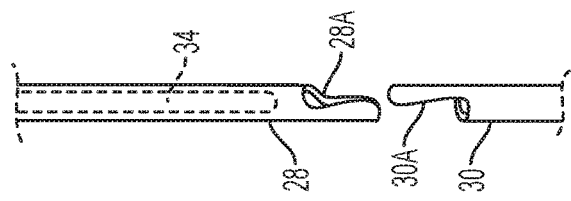
FIGS. 5A-5B and 6A-6B illustrate exemplary embodiments of coupling mechanisms of the instant application.
Figure 6A:
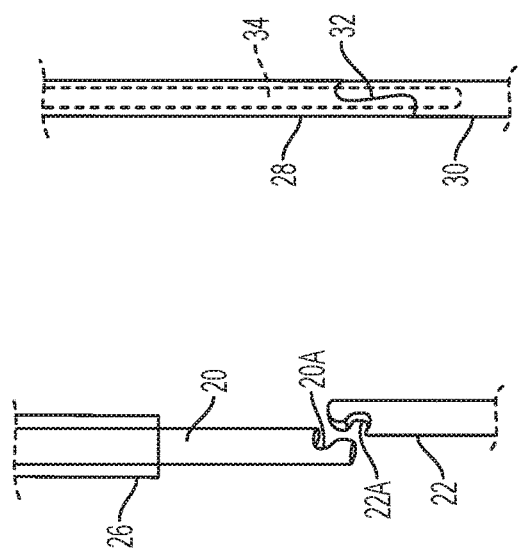

Similarly, FIG. 6A illustrates a tubular upper shaft 28 and a detachable tubular lower shaft 30 which are interlocked at a mating surface 32. Again, the mating surface 32 may have any shape or curvature which will allow or facilitate interlocking and later detachment. The tubular upper shaft 28 and tubular lower shaft 30 form an outer member having an axial channel. A snuggly fitting rod 34 or inner member is inserted through the tubular shafts 28, 30 to bridge the mating surface 32 as shown. The rod 34 may also be used to actuate the fixation device, such as actuator rod 64 seen in FIG. 26 or actuator rod 64a illustrated in FIGS. 28A-28B, described below. FIG. 6B illustrates detachment of the lower shaft 30 from the upper shaft 28. This is achieved by retracting the rod 34 to a position above the mating surface 32 which in turn allows the shafts 28, 30 to separate. Other examples of coupling mechanisms are described and illustrated in U.S. Pat. No. 6,752,813, and U.S. Patent Publication No. 2009/0163934, the entire contents of each of which are incorporated herein by reference for all purposes.

In a preferred embodiment, mating surface 24 (or mating surface 32) is a sigmoid curve defining a male element and female element on upper shaft 20 (or upper shaft 28) which interlock respectively with corresponding female and male elements on lower shaft 22 (or lower shaft 30). Typically, the lower shaft is the coupling mechanism 17 of the fixation device 14. Therefore, the shape of the mating surface selected will preferably provide at least some mating surfaces transverse to the axial axis of the a mechanism 19 to facilitate application of compressive and tensile forces through the coupling mechanism 17 to the fixation device 14, yet causing minimal interference when the fixation device 14 is to be released from the upper shaft.

III. Fixation Device

A. Introduction and Placement of Fixation Device

The fixation device 14 is delivered to the valve or the desired tissues with the use of a delivery device. The delivery device may be rigid or flexible depending on the application. For endovascular applications, the delivery device comprises a flexible delivery catheter which will be described in later sections. Typically, however, such a catheter comprises a shaft, having a proximal end and a distal end, and a fixation device releasably attached to its distal end. The shaft is usually elongate and flexible, suitable for intravascular introduction. Alternatively, the delivery device may comprise a shorter and less flexible interventional instrument which may be used for trans-thoracic surgical introduction through the wall of the heart, although some flexibility and a minimal profile will generally be desirable. A fixation device is releasably coupleable with the delivery device as illustrated in FIG. 3A. The fixation device may have a variety of forms, a few embodiments of which will be described herein.

Figure 7:
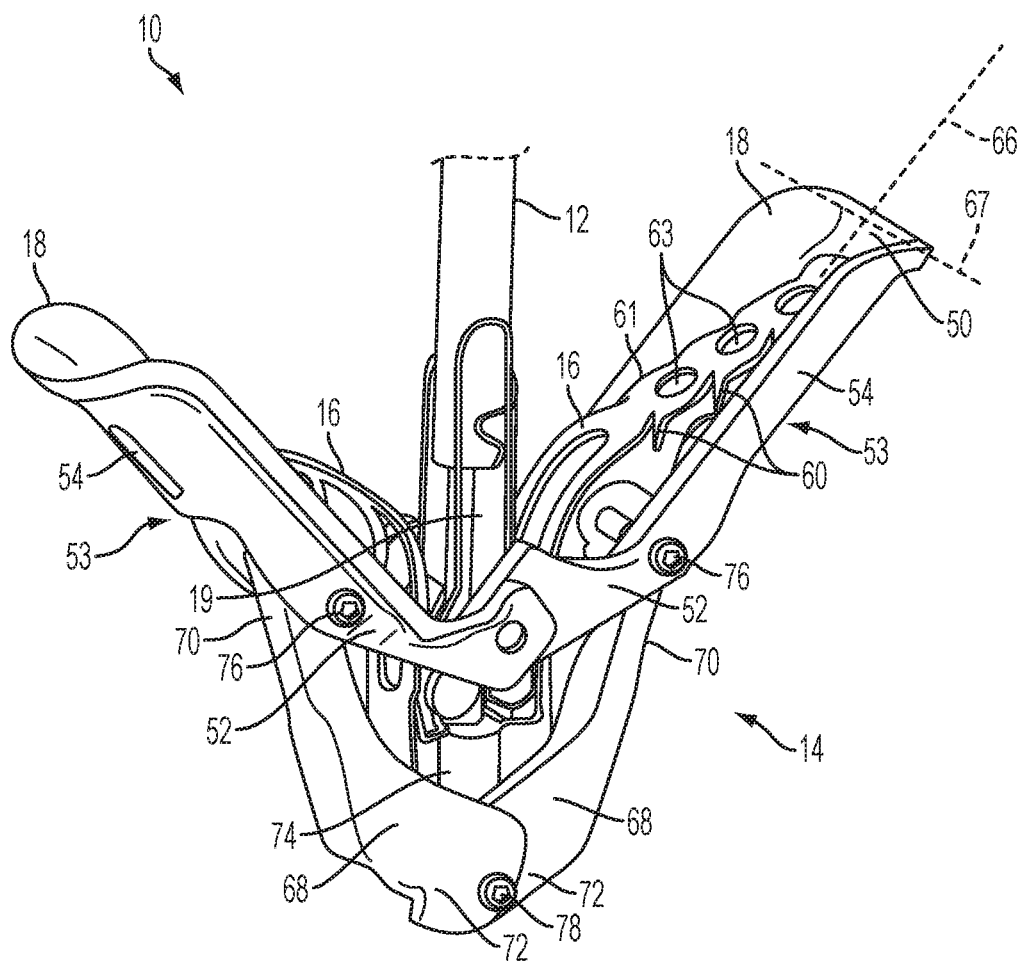
FIG. 7 illustrates an embodiment of the fixation device of the present invention.

FIG. 7 illustrates another embodiment of a fixation device 14. Here, the fixation device 14 is shown coupled to a shaft 12 to form an interventional tool 10. The fixation device 14 includes a coupling member 19 and a pair of opposed distal elements 18. The distal elements 18 comprise elongate arms 53, each arm having a proximal end 52 rotatably connected to the coupling member 19 and a free end 54. The free ends 54 have a rounded shape to minimize interference with and trauma to surrounding tissue structures. Preferably, each free end 54 defines a curvature about two axes, one being an axis 66 perpendicular to longitudinal axis of arms 53. Thus, the engagement surfaces 50 have a cupped or concave shape to surface area in contact with tissue and to assist in grasping and holding the valve leaflets. This further allows arms 53 to nest around the shaft 12 in the closed position to minimize the profile of the device. Preferably, arms 53 are at least partially cupped or curved inwardly about their longitudinal axes 66. Also, preferably, each free end 54 defines a curvature about an axis 67 perpendicular to axis 66 or the longitudinal axis of arms 53. This curvature is a reverse curvature along the most distal portion of the free end 54. Likewise, the longitudinal edges of the free ends 54 may flare outwardly. Both the reverse curvature and flaring minimize trauma to the tissue engaged therewith.

In a preferred embodiment suitable for mitral valve repair, the transverse width across engagement surfaces 50 (which determines the width of tissue engaged) is at least about 2 mm, usually 3-10 mm, and preferably about 4-6 mm. In some situations, a wider engagement is desired wherein the engagement surfaces 50 are larger, for example about 2 cm, or multiple fixation devices are used adjacent to each other. Arms 53 and engagement surfaces 50 are configured to engage a length of tissue of about 4-10 mm, and preferably about 6-8 mm along the longitudinal axis of arms 53. Arms 53 further include a plurality of openings to enhance grip and to promote tissue ingrowth following implantation.

The valve leaflets are grasped between the distal elements 18 and proximal elements 16. In some embodiments, the proximal elements 16 are flexible, resilient, and cantilevered from coupling member 19. The proximal elements are preferably resiliently biased toward the distal elements. Each proximal element 16 is shaped and positioned to be at least partially recessed within the concavity of the distal element 18 when no tissue is present. When the fixation device 14 is in the open position, the proximal elements 16 are shaped such that each proximal element 16 is separated from the engagement surface 50 near the proximal end 52 of arm 53 and slopes toward the engagement surface 50 near the free end 54 with the free end of the proximal element contacting engagement surface 50, as illustrated in FIG. 7. This shape of the proximal elements 16 accommodates valve leaflets or other tissues of varying thicknesses.

Proximal elements 16 include a plurality of openings 63 and scalloped side edges 61 to increase grip on tissue. The proximal elements 16 optionally include frictional accessories, frictional features or grip-enhancing elements to assist in grasping and/or holding the leaflets. In preferred embodiments, the frictional accessories comprise barbs 60 having tapering pointed tips extending toward engagement surfaces 50. It may be appreciated that any suitable frictional accessories may be used, such as prongs, windings, bands, barbs, grooves, channels, bumps, surface roughening, sintering, high-friction pads, coverings, coatings or a combination of these. Optionally, magnets may be present in the proximal and/or distal elements. It may be appreciated that the mating surfaces will be made from or will include material of opposite magnetic charge to cause attraction by magnetic force. For example, the proximal elements and distal elements may each include magnetic material of opposite charge so that tissue is held under constant compression between the proximal and distal elements to facilitate faster healing and ingrowth of tissue. Also, the magnetic force may be used to draw the proximal elements 16 toward the distal elements 18, in addition to or alternatively to biasing of the proximal elements toward the distal elements. This may assist in deployment of the proximal elements 16. In another example, the distal elements 18 each include magnetic material of opposite charge so that tissue positioned between the distal elements 18 is held therebetween by magnetic force. Actuation of the proximal elements may also be accomplished using one or more proximal element lines or actuators such as those described below.

The proximal elements 16 may be covered with a fabric or other flexible material as described below to enhance grip and tissue ingrowth following implantation. Preferably, when fabrics or coverings are used in combination with barbs or other frictional features, such features will protrude through such fabric or other covering so as to contact any tissue engaged by proximal elements 16.

In an exemplary embodiment, proximal elements 16 are formed from metallic sheet of a spring-like material using a stamping operation which creates openings 63, scalloped edges 61 and barbs 60. Alternatively, proximal elements 16 could be comprised of a spring-like material or molded from a biocompatible polymer. It should be noted that while some types of frictional accessories that can be used in the present invention may permanently alter or cause some trauma to the tissue engaged thereby, in a preferred embodiment, the frictional accessories will be atraumatic and will not injure or otherwise affect the tissue in a clinically significant way. For example, in the case of barbs 60, it has been demonstrated that following engagement of mitral valve leaflets by fixation device 14, should the device later be removed during the procedure barbs 60 leave no significant permanent scarring or other impairment of the leaflet tissue and are thus considered atraumatic.

The fixation device 14 also includes an actuation mechanism 58. In this embodiment, the actuation mechanism 58 comprises two link members or legs 68, each leg 68 having a first end 70 which is rotatably joined with one of the distal elements 18 at a riveted joint 76 and a second end 72 which is rotatably joined with a stud 74. The legs 68 are preferably comprised of a rigid or semi-rigid metal or polymer such as Elgiloy®, cobalt chromium or stainless steel, however any suitable material may be used. While in the embodiment illustrated both legs 68 are pinned to stud 74 by a single rivet 78, it may be appreciated, however, that each leg 68 may be individually attached to the stud 74 by a separate rivet or pin. The stud 74 is joinable with an actuator rod 64 (not shown) which extends through the shaft 12 and is axially extendable and retractable to move the stud 74 and therefore the legs 68 which rotate the distal elements 18 between closed, open and inverted positions. Likewise, immobilization of the stud 74 holds the legs 68 in place and therefore holds the distal elements 18 in a desired position. The stud 74 may also be locked in place by a locking feature which will be further described in later sections.

In any of the embodiments of fixation device 14 disclosed herein, it may be desirable to provide some mobility or flexibility in distal elements 18 and/or proximal elements 16 in the closed position to enable these elements to move or flex with the opening or closing of the valve leaflets. This provides shock absorption and thereby reduces force on the leaflets and minimizes the possibility for tearing or other trauma to the leaflets. Such mobility or flexibility may be provided by using a flexible, resilient metal or polymer of appropriate thickness to construct the distal elements 18. Also, the locking mechanism of the fixation device (described below) may be constructed of flexible materials to allow some slight movement of the proximal and distal elements even when locked. Further, the distal elements 18 can be connected to the coupling mechanism 19 or to actuation mechanism 58 by a mechanism that biases the distal element into the closed position (inwardly) but permits the arms to open slightly in response to forces exerted by the leaflets. For example, rather than being pinned at a single point, these components may be pinned through a slot that allowed a small amount of translation of the pin in response to forces against the arms. A spring is used to bias the pinned component toward one end of the slot.

Figure 8A:
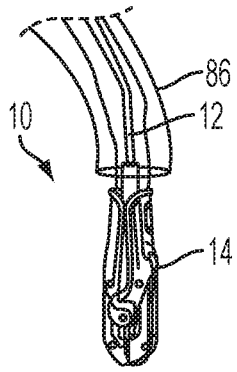
FIGS. 8A-8B, 9A-9B, 10A-10B, 11A-11B, and 12-14 illustrate the fixation device of FIG. 7 in various possible positions during introduction and placement of the device within the body to perform a therapeutic procedure.
Figure 8B:
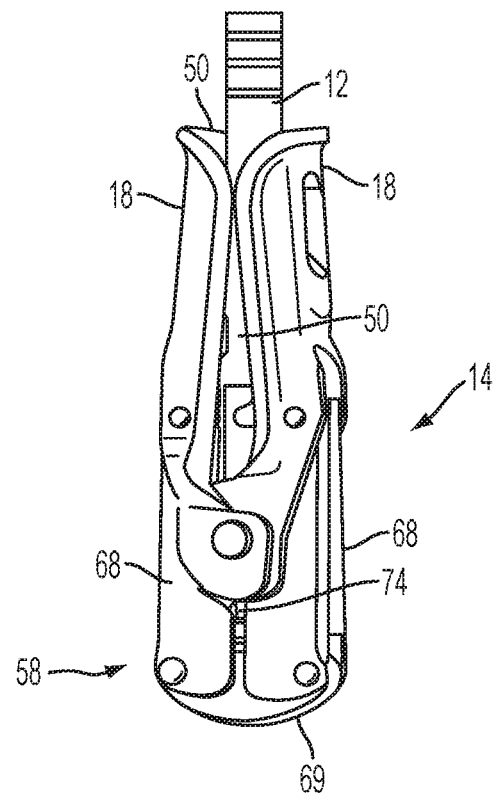

FIGS. 8A-8B, 9A-9B, 10A-10B, 11A-11B, and FIGS. 12-14 illustrate embodiments of the fixation device 14 of FIG. 7 in various possible positions during introduction and placement of the device 14 within the body to perform a therapeutic procedure. FIG. 8A illustrates an embodiment of an interventional tool 10 delivered through a catheter 86. It may be appreciated that the interventional tool 10 may take the form of a catheter, and likewise, the catheter 86 may take the form of a guide catheter or sheath. However, in this example the terms interventional tool 10 and catheter 86 will be used. The interventional tool 10 comprises a fixation device 14 coupled to a shaft 12 and the fixation device 14 is shown in the closed position. FIG. 8B illustrates a similar embodiment of the fixation device of FIG. 8A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12 and optionally contact each other on opposite sides of the shaft. This provides a low profile for the fixation device 14 which is readily passable through the catheter 86 and through any anatomical structures, such as the mitral valve. In addition, FIG. 8B further includes an actuation mechanism 58. In this embodiment, the actuation mechanism 58 comprises two legs 68 which are each movably coupled to a base 69. The base 69 is joined with an actuator rod 64 which extends through the shaft 12 and is used to manipulate the fixation device 14. In some embodiments, the actuator rod 64 attaches directly to the actuation mechanism 58, particularly the base 69. However, the actuator rod 64 may alternatively attach to a stud 74 which in turn is attached to the base 69. In some embodiments, the stud 74 is threaded so that the actuator rod 64 attaches to the stud 74 by a screw-type action. However, the rod 64 and stud 74 may be joined by any mechanism which is releasable to allow the fixation device 14 to be detached from shaft 12. Other aspects of the actuator rod and its coupling with the fixation device are disclosed below.

Figure 9A:
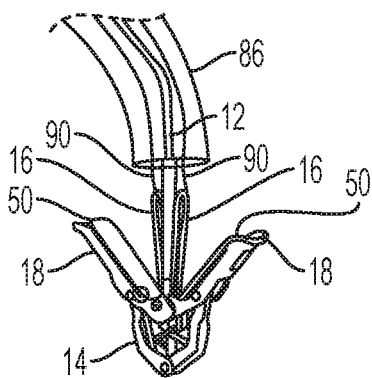
Figure 9B:
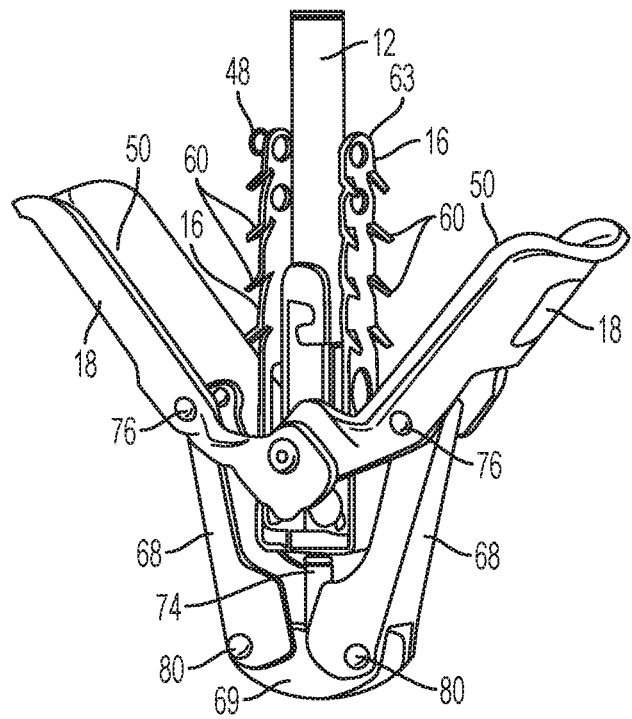

FIGS. 9A-9B illustrate the fixation device 14 in the open position. In the open position, the distal elements 18 are rotated so that the engagement surfaces 50 face a first direction. Distal advancement of the stud 74 relative to coupling member 19 by action of the actuator rod 64 applies force to the distal elements 18 which begin to rotate around joints 76 due to freedom of movement in this direction. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In one embodiment, in the open position the free ends 54 of arms 53 have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 may be connected with the proximal elements 16 by threading the lines 90 in a variety of ways. When the proximal elements 16 have a loop shape, as shown in FIG. 9A, the line 90 may pass through the loop and double back. When the proximal elements 16 have an elongate solid shape, as shown in FIG. 9B, the line 90 may pass through one or more of the openings 63 in the element 16. Further, a line loop 48 may be present on a proximal element 16, also illustrated in FIG. 9B, through which a proximal element line 90 may pass and double back. Such a line loop 48 may be useful to reduce friction on proximal element line 90 or when the proximal elements 16 are solid or devoid of other loops or openings through which the proximal element lines 90 may attach. A proximal element line 90 may attach to the proximal elements 16 by detachable means which would allow a single line 90 to be attached to a proximal element 16 without doubling back and would allow the single line 90 to be detached directly from the proximal element 16 when desired. Examples of such detachable means include hooks, snares, clips or breakable couplings, to name a few. By applying sufficient tension to the proximal element line 90, the detachable means may be detached from the proximal element 16 such as by breakage of the coupling. Other mechanisms for detachment may also be used. Similarly, a lock line 92 may be attached and detached from a locking mechanism by similar detachable means.

In the open position, the fixation device 14 can engage the tissue which is to be approximated or treated. The embodiment illustrated in FIGS. 7-9B is adapted for repair of the mitral valve using an antegrade approach from the left atrium. The interventional tool 10 is advanced through the mitral valve from the left atrium to the left ventricle. The distal elements 18 are oriented to be perpendicular to the line of coaptation and then positioned so that the engagement surfaces 50 contact the ventricular surface of the valve leaflets, thereby grasping the leaflets. The proximal elements 16 remain on the atrial side of the valve leaflets so that the leaflets lie between the proximal and distal elements. In this embodiment, the proximal elements 16 have frictional accessories, such as barbs 60 which are directed toward the distal elements 18. However, neither the proximal elements 16 nor the barbs 60 contact the leaflets at this time.

The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 10A:
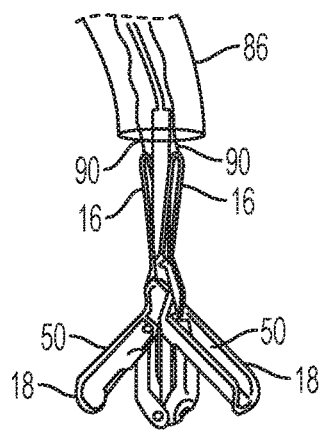
Figure 10B:
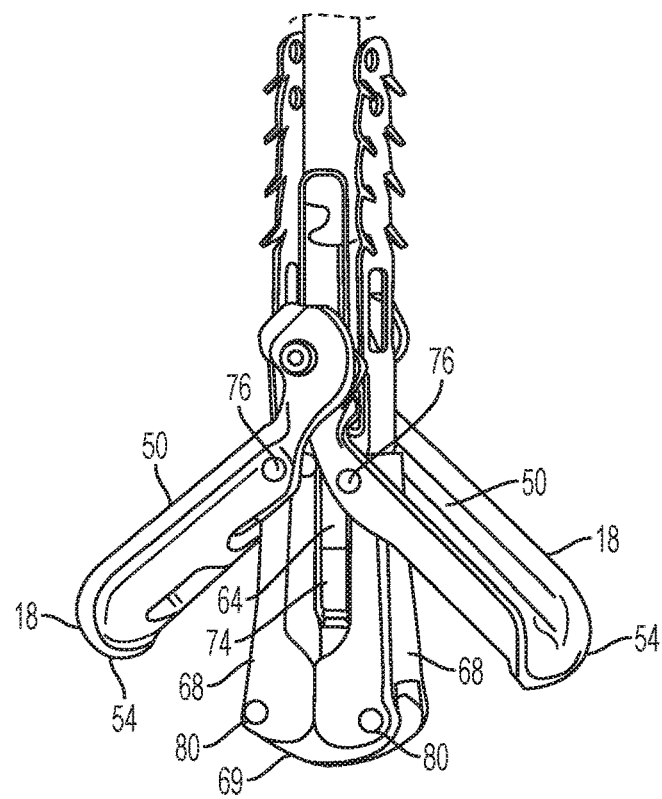

It may also be desired to invert the fixation device 14 to aid in repositioning or removal of the fixation device 14. FIGS. 10A-10B illustrate the fixation device 14 in the inverted position. By further advancement of stud 74 relative to coupling member 19, the distal elements 18 are further rotated so that the engagement surfaces 50 face outwardly and free ends 54 point distally, with each arm 53 forming an obtuse angle relative to shaft 12. The angle between arms 53 is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. In this illustration, the proximal elements 16 remain positioned against the shaft 12 by exerting tension on the proximal element lines 90. Thus, a relatively large space may be created between the elements 16, 18 for repositioning. In addition, the inverted position allows withdrawal of the fixation device 14 through the valve while minimizing trauma to the leaflets. Engagement surfaces 50 provide an atraumatic surface for deflecting tissue as the fixation device is retracted proximally. It should be further noted that barbs 60 are angled slightly in the distal direction (away from the free ends of the proximal elements 16), reducing the risk that the barbs will catch on or lacerate tissue as the fixation device is withdrawn.

Figure 11A:
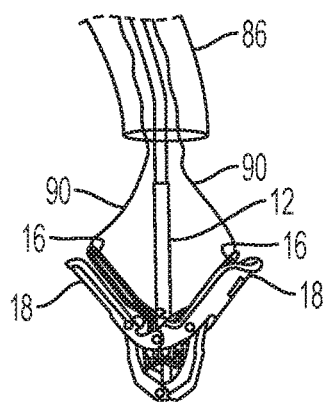
Figure 11B:
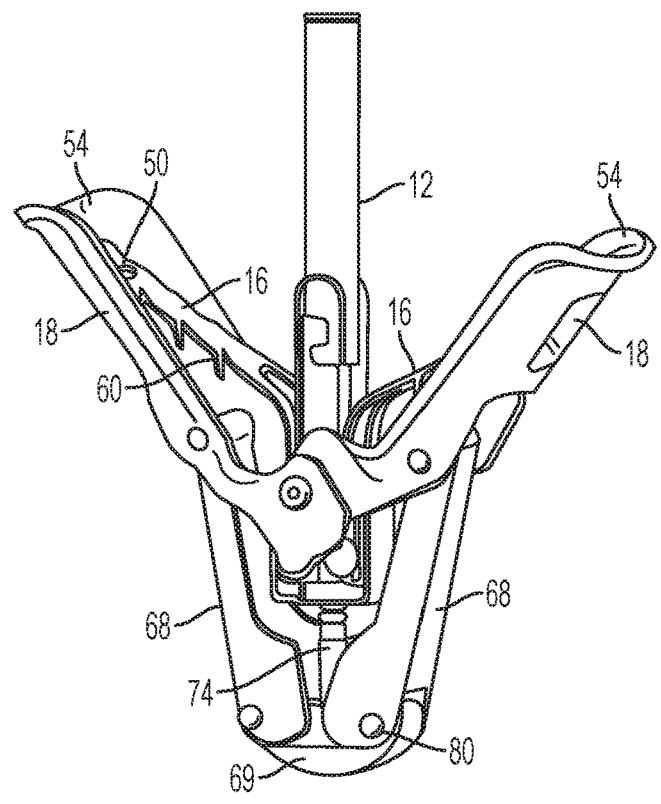

Once the fixation device 14 has been positioned in a desired location against the valve leaflets, the leaflets may then be captured between the proximal elements 16 and the distal elements 18. FIGS. 11A-11B illustrate the fixation device 14 in such a position. Here, the proximal elements 16 are lowered toward the engagement surfaces 50 so that the leaflets are held therebetween. In FIG. 11B, the proximal elements 16 are shown to include barbs 60 which may be used to provide atraumatic gripping of the leaflets. Alternatively, larger, more sharply pointed barbs or other penetration structures may be used to pierce the leaflets to more actively assist in holding them in place. This position is similar to the open position of FIGS. 9A-9B, however the proximal elements 16 are now lowered toward arms 53 by releasing tension on proximal element lines 90 to compress the leaflet tissue therebetween. At any time, the proximal elements 16 may be raised and the distal elements 18 adjusted or inverted to reposition the fixation device 14, if regurgitation is not sufficiently reduced.

Figure 12:
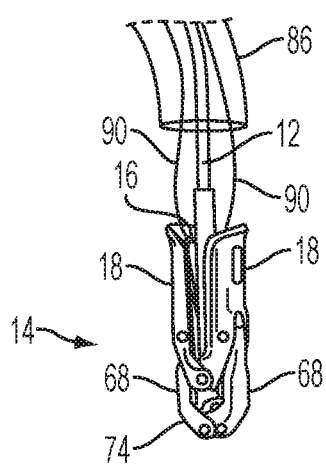

After the leaflets have been captured between the proximal and distal elements 16, 18 in a desired arrangement, the distal elements 18 may be locked to hold the leaflets in this position or the fixation device 14 may be returned to or toward a closed position. Such locking will be described in a later section. FIG. 12 illustrates the fixation device 14 in the closed position wherein the leaflets (not shown) are captured and coapted. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position as described below.

Figure 13:
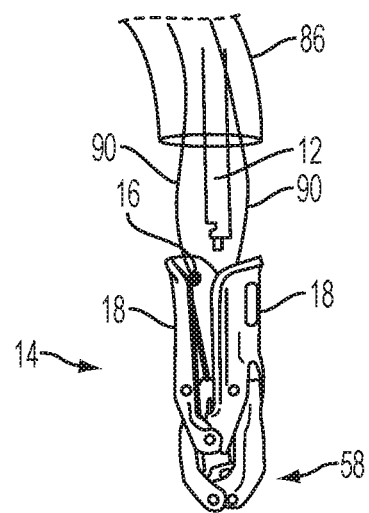

As shown in FIG. 13, the fixation device 14 may then be released from the shaft 12. As mentioned, the fixation device 14 is releasably coupleable to the shaft 12 by coupling member 19 (best seen in FIG. 17). FIG. 13 illustrates the coupling structure, a portion of the shaft 12 to which the coupling member 19 of the fixation device 14 attaches. As shown, the proximal element lines 90 may remain attached to the proximal elements 16 following detachment from shaft 12 to function as a tether to keep the fixation device 14 connected with the catheter 86. Optionally, a separate tether coupled between shaft 12 and fixation device 14 may be used expressly for this purpose while the proximal element lines 90 are removed. In any case, the repair of the leaflets or tissue may be observed by non-invasive visualization techniques, such as echocardiography, to ensure the desired outcome. If the repair is not desired, the fixation device 14 may be retrieved with the use of the tether or proximal element lines 90 so as to reconnect coupling member 19 with shaft 12.

In an exemplary embodiments, proximal element lines 90 are elongated flexible threads, wire, cable, sutures or lines extending through shaft 12, looped through proximal elements 16, and extending back through shaft 12 to its proximal end. When detachment is desired, one end of each line may be released at the proximal end of the shaft 12 and the other end pulled to draw the free end of the line distally through shaft 12 and through proximal element 16 thereby releasing the fixation device.

Figure 14:
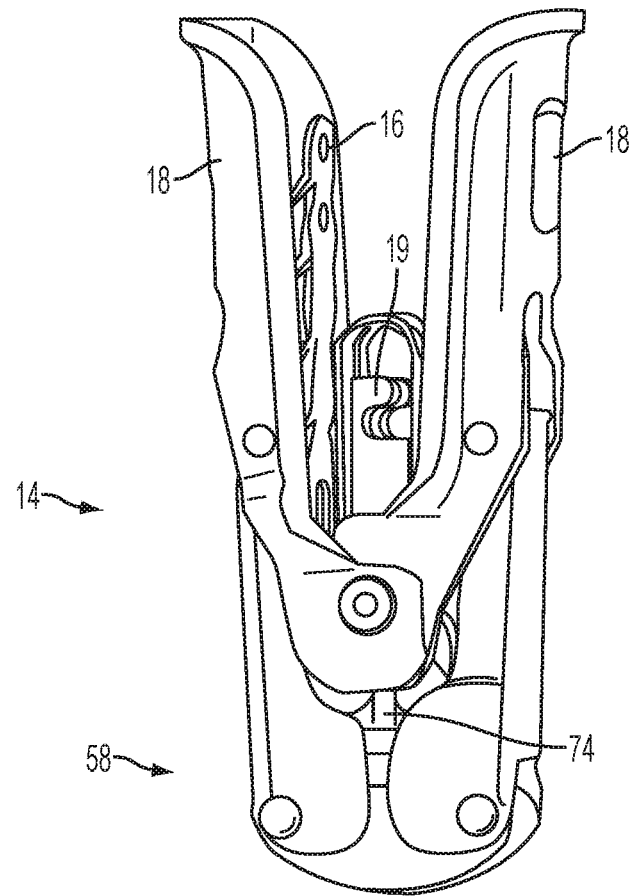

FIG. 14 illustrates a released fixation device 14 in a closed position. As shown, the coupling member 19 remains separated from the shaft 12 of the interventional tool 10 and the proximal elements 16 are deployed so that tissue (not shown) may reside between the proximal elements 16 and distal elements 18.

While the above described embodiments of the invention utilize a push-to-open, pull-to-close mechanism for opening and closing distal elements 18, it should be understood that a pull-to-open, push-to-close mechanism is equally possible. For example, distal elements 18 may be coupled at their proximal ends to stud 74 rather than to coupling member 19, and legs 68 may be coupled at their proximal ends to coupling member 19 rather than to stud 74. In this example, when stud 74 is pushed distally relative to coupling member 19, distal elements 18 would close, while pulling on stud 74 proximally toward coupling member 19 would open distal elements 18.

In some situations, the valve leaflets may fully or partially detach from the fixation device due to poor leaflet insertion between the proximal and distal elements. Evaluation of valve leaflet insertion in the fixation device is therefore performed using standard imaging technology such as echocardiography and fluoroscopy. However, depending on the angle and/or position of the proximal and distal elements relative to the delivery catheter, it can be challenging to assess the depth of valve leaflet insertion into the fixation device, or to differentiate between the leaflets and the proximal and distal elements of the fixation device. Visualization is therefore preferably performed with the distal elements in a more open configuration with the distal elements displaced from one another. However, since many current embodiments of the fixation device only permit the proximal elements to open up to an included angle of about 85°, the distal elements therefore must be closed up to an included angle of between about 45° and preferably 60° in order securely grasp the valve leaflets between the proximal and distal elements. While this configuration helps an operator visualize and differentiate between the valve leaflets and the fixation device, it is preferable to further open up the distal elements to an included angle of greater than 90°, and more preferably to 120° or more. Thus, it would be desirable to modify the proximal elements to open up further.

Figure 15A:
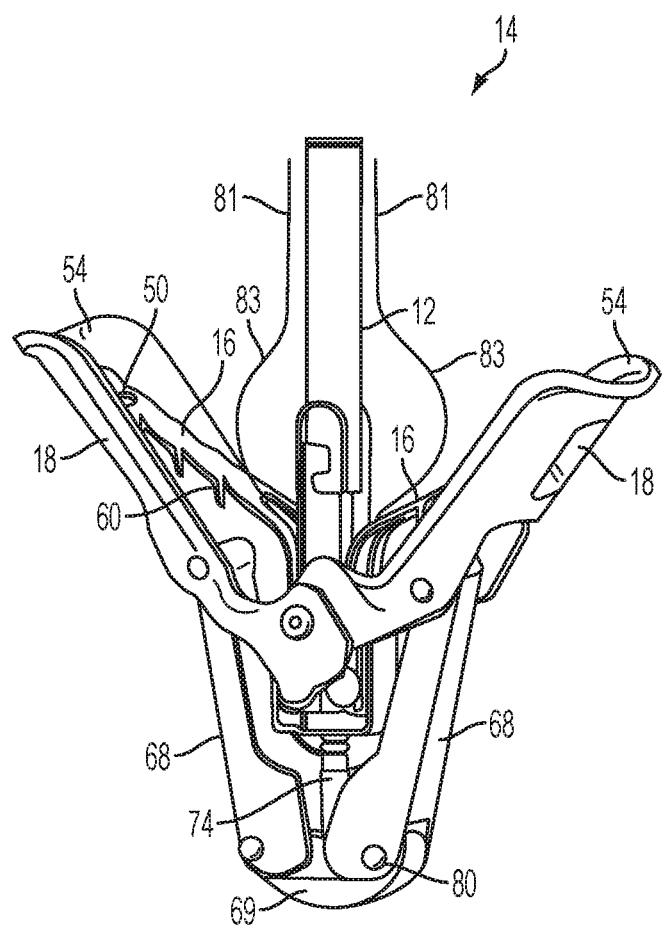
FIGS. 15A-15H illustrate the fixation device of FIG. 7 with a gripper pusher.

FIGS. 15A-15H illustrate an embodiment of a fixation device similar to the device of FIGS. 7A-14, with a major difference being that this embodiment includes a gripper pusher. FIG. 15A illustrates fixation device 14 that generally takes the same form as fixation device 14 previously described. In addition to the features previously described, fixation device 14 also includes a gripper pusher 81. The gripper pusher 81 deflects radially outward resulting in a bowed region 83 that expands outward until the bowed region 83 engages a superior surface of the proximal elements 16. As the bowed region 83 continues to deflect radially outward, it further pushes on the proximal elements 16 such that the proximal elements are deflected and rotated outward toward the engagement surface of the distal elements 18. Thus, the proximal elements 16 may be deflected outward further than they normally would, and therefore the valve leaflets may be captured between the proximal and distal elements when the distal elements are disposed in a more open position with a larger included angle therebetween. In preferred embodiments, the included angle between the distal elements is greater than about 90°, preferably greater than about 110°, and more preferably greater than about 120°. In the embodiment of FIG. 15A, the gripper pusher 81 includes two arms formed from a metal, polymer or other wire-like material. Exemplary materials include cobalt chromium alloy, stainless steel, nitinol, and the like. Polymers may also be used to fabricate the gripper pusher. The gripper pusher 81 may be actuated to bow outwards upon application of an axially oriented compressive force that is generally parallel to the longitudinal axis of the gripper pusher arms. During compression, the gripper pusher bows outward forming bowed region 83. In other embodiments, the gripper pusher may be a spring which is resiliently biased to bow outward forming bowed region 83. However, when proximal element lines (not illustrated here) are tensioned to lift the proximal elements 16, the gripper pusher springs will collapse to a reduced profile.

Figure 15B:
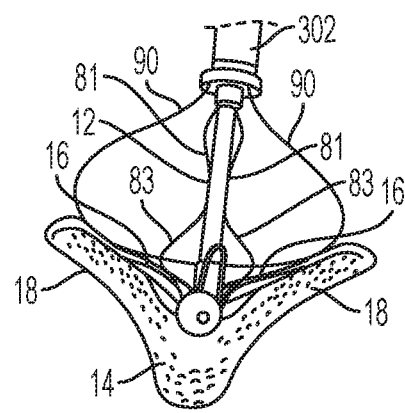
Figure 15C:
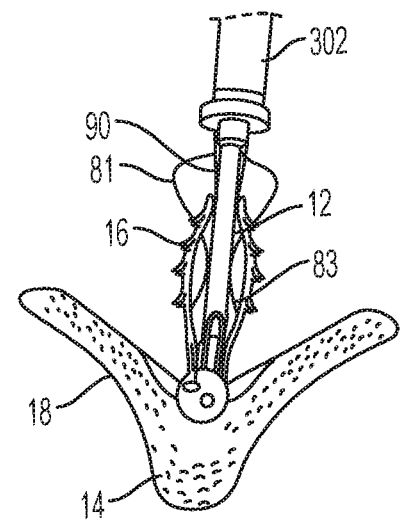

FIG. 15B illustrates the fixation device 14 having a covering for tissue ingrowth that is substantially the same as discussed in FIGS. 16A-16C below, and with the gripper pusher 81 expanded such that the proximal elements 16 (also referred to as gripping elements) are in engagement with the distal elements 18 (also referred to as fixation elements). The valve leaflets (not shown for convenience) are pinched therebetween. FIG. 15C illustrates the gripper pusher 81 in the collapsed configuration. The bowed region 83 collapses, allowing the proximal elements 16 to retract towards shaft 12, allowing the valve leaflets (not shown) to be released from the fixation device 14. The gripper pusher 83 is offset from the proximal elements 16 so that the proximal elements can retract without interfering with the gripper pusher 81.

Figure 15D:
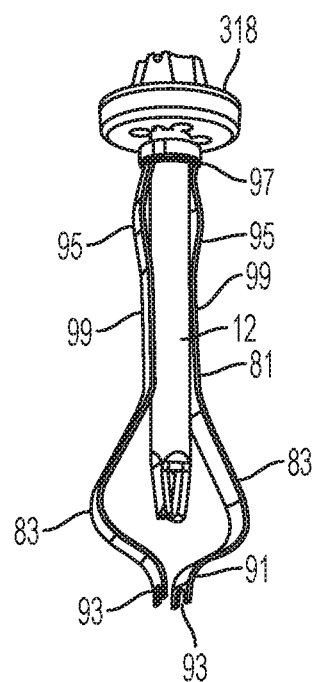
Figure 15E:
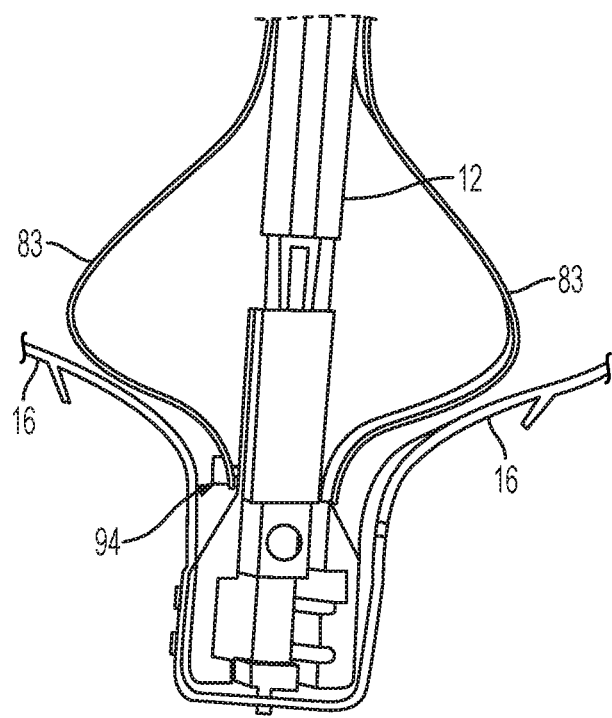

FIG. 15D highlights the gripper pusher 83 which preferably includes two spring arms 99. Each arm 99 is formed from wire or machined from a sheet or other stock material and in this embodiment has a rectangular cross-section, although other cross-sections are also contemplated. A distal portion 91 of each arm 99 has a notched region 93 forming a pair of fingers that can engage with a boss or other attachment mechanism on the fixation device. The notch may be released from the boss when the fixation device 14 is detached from the delivery catheter shaft 12. Additionally, each arm includes two bowed regions, or peaks, including a larger distal bowed region 83, and a smaller proximal bowed region 95. The larger bowed region 83 flares outwardly a greater distance so as to engage and push the proximal elements 16 into engagement with the distal elements 18. When the distal bowed region 83 relaxes and collapses away from the proximal elements 16, or when collapsed by retraction of the proximal elements, the smaller proximal bowed regions 95 expand radially outward. An attachment ring or coupling collar 97 is adjacent nose 318 (described in greater detail below) and is slidably disposed over the shaft 12 and allows coupling of the gripper arms 99 to the shaft 12. FIG. 15E illustrates the distal bowed region 83 in engagement with the proximal elements 16, and also illustrates engagement of the notch 93 on the distal portion of each arm 99 with a boss 94 on the fixation device 14.

Additional components may be provided to facilitate maintaining the alignment of the gripper pushers 83 relative to the delivery catheter shaft 12. FIG. 15E1 shows a cross-sectional view of the delivery catheter shaft 12 with the gripper pusher 83 and FIG. 15E2 shows a side view of the same. As shown in FIGS. 15E1 and 15E2, each arm 99 may have a slot 8112 and the delivery catheter shaft 12 may have one or more protrusions 1281 which the slots 8112 straddle to maintain the alignment of the gripper pusher 83 relative to the delivery catheter shaft 12. The region of the arm 99 having the slot 8112 is wider than the remainder of the arm 99 to accommodate the slot 8112. The greater width may also allow the arm 99 to be pushed to the side without becoming misaligned relative to the delivery catheter shaft 12. FIG. 15E3 shows a cross-sectional view of the delivery catheter shaft 12 and FIG. 15E4 shows a side view of the same. As shown in FIGS. 15E3 and 15E4, each arm 99 may have one or more inwardly bowed regions 8212 and the delivery catheter shaft 12 may have one or more troughs 1282 which accommodate the inwardly bowed regions 8212 to maintain the alignment of the gripper pusher 83 relative to the delivery catheter shaft 12.

Figure 15F:
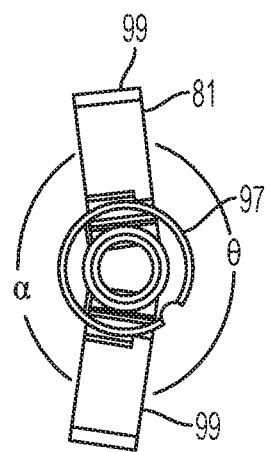
Figure 15G:
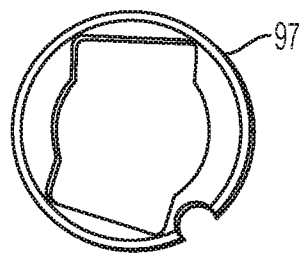
Figure 15H:
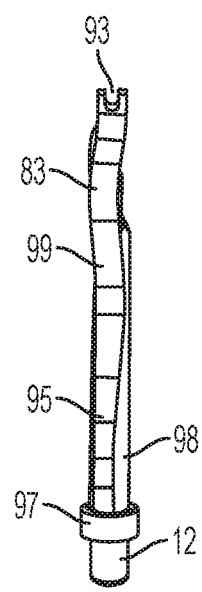

FIG. 15F illustrates a top view of the gripper pusher 81 having two arms 99. FIG. 15F illustrates that the two arms 99 are offset from one another such that in this exemplary embodiment, angle α is about 160° and angle θ is about 200°, as opposed to positioning the arms 180° apart from one another. Asymmetrically positioning the arms about the shaft creates a larger gap on one side, and allows the proximal elements 16 to avoid colliding with the gripper pusher arms 99 when the proximal elements retract against shaft 12. FIG. 15G is a top view of collar 97, and FIG. 15H is a side view of gripper pusher arm 99. A cutout 98 on one side of arm 99 creates additional room between arms 99, thereby also helping to prevent the proximal elements 16 from interfering with the gripper pusher 83 when the proximal elements 16 are retracted. The cutouts are on both arms 99 and face the larger gap represented by angle θ to maximize room for the proximal elements 16.

Figure 15J:
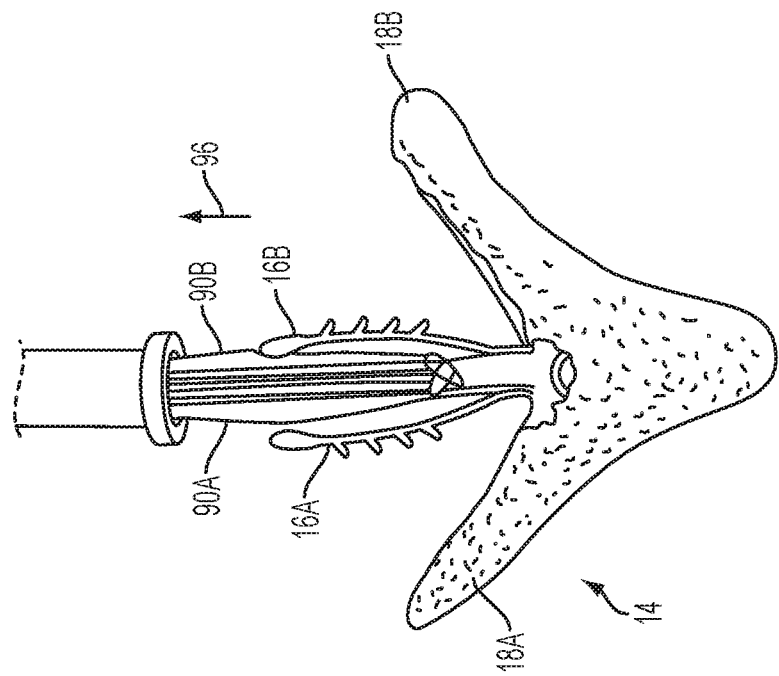
Figure 15I:
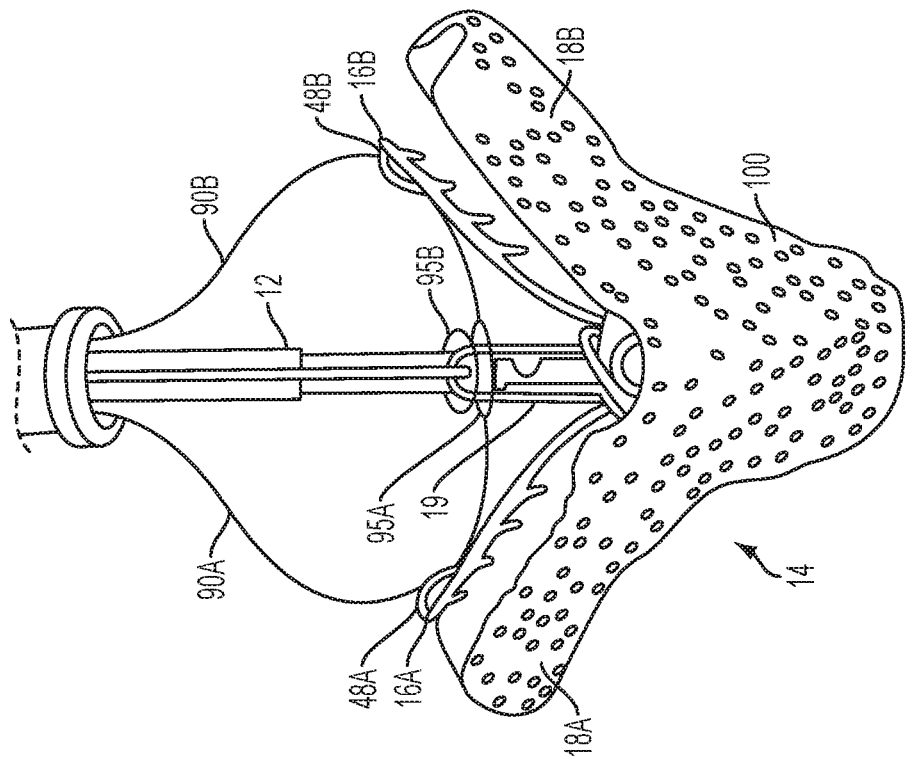
FIGS. 15I-15V illustrate the fixation device of FIG. 7 with independently actuatable proximal elements.

As described above, for example, with reference to FIGS. 9A and 9B, actuation of the proximal elements 16 may be accomplished by using one or more proximal element lines or actuators 90. Such actuation can be achieved in various ways. For example, as shown in FIG. 15I, the proximal element actuators 90A and 90B could be threaded through line loops 48A and 48B, which are disposed on the radially outward and proximal sides of the proximal elements 16A and 16B, respectively. The distal ends of proximal element actuators 90A and 90B may comprise closed loops 95A and 95B, which encircle the shaft 12 and the coupling member 19 shown in FIG. 15I as coupled together. As discussed above, the shaft 12 and the coupling member 19 can be releasably coupled together. To have the closed loops 95A and 95B surround shaft 12 and the coupling member 19, the closed loops 95A and 95B are placed over the shaft 12 and/or the coupling member 19 prior to the coupling shaft 12 and the coupling member 19 together. When the closed loops 95A and 95B encircle the shaft 12 and the coupling member 19, the closed loops 95A and 95B hold the distal ends of the proximal element actuators 90A and 90B in place relative to the shaft 12 and the coupling member 19 and restrict the degree to which the proximal element actuators 90A and 90B can be retracted. By being threaded through the line loops 48A and 48B, the proximal element actuators 90A and 90B are mechanically linked to the proximal elements 16A and 16B, respectively. Thus, as shown in FIG. 15J, when the proximal element actuators 90A and 90B are retracted proximally in a direction 96, they move the proximal elements 16A and 16B away from the distal elements 18A and 18B, respectively. Similarly, pushing the proximal element actuators 90A and 90B distally moves the proximal elements 16A and 16B toward the distal elements 18A and 18B.

Figure 15K:
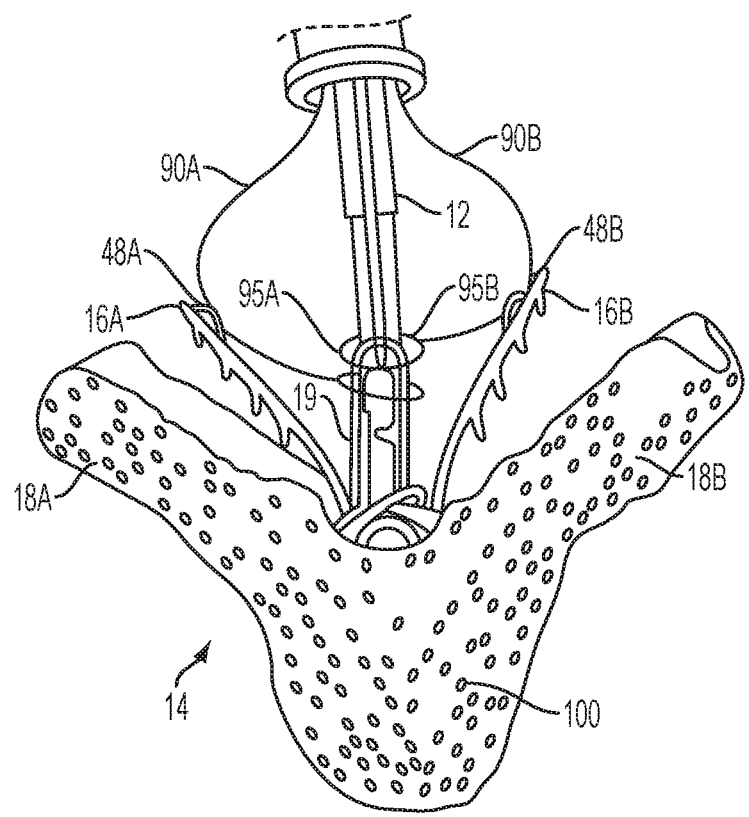
Figure 15L:
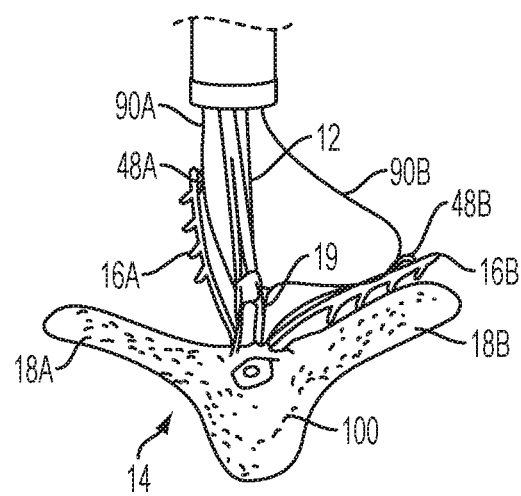
Figure 15N:
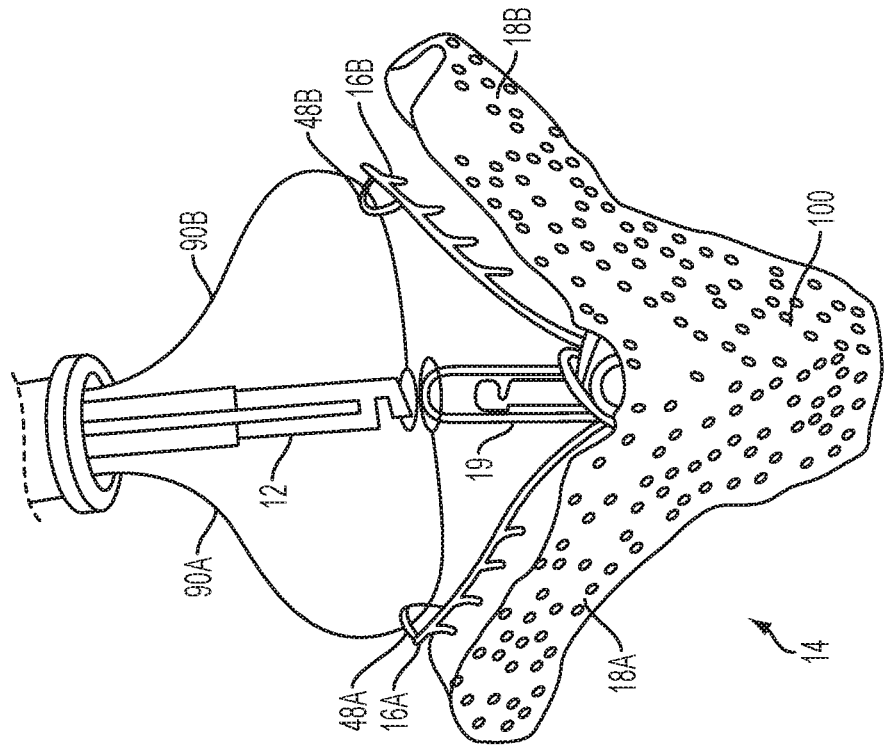

The proximal element actuators 90A and 90B may be moved so that the proximal elements 16A and 16B are moved at a variety of angles and distances from the distal elements 18A and 18B. And, the degree to which the proximal element actuators 90A and 90B are pushed or pulled can be maintained to keep the positions the proximal elements 16A and 16B have relative to the distal elements 18. For example, as shown in FIG. 15K, the proximal element actuators 90A and 90B are pulled proximally and maintained in the position shown so as to maintain the proximal elements 16A and 16B in an intermediate position relative to the distal elements 18. This intermediate position is between the position the proximal elements 16A and 16B are biased toward and that in which the proximal elements 16A and 16B are fully retracted as in FIG. 15J. As shown in FIG. 15N, once the proximal elements 16A and 16B are in a desired position, the shaft 12 and the coupling member 19 can be decoupled so that proximal retraction of the proximal element actuators 90A and/or 90B decouples the proximal element lines from the proximal elements 16. Thus, the fixation device 14 can be left in place while the shaft 12, the proximal element actuators 90A and 90B, and other parts can be removed from a site of operation. As shown in FIGS. 15I through 15O, the fixation device 14 typically includes a covering 100 substantially the same as discussed in FIGS. 16A-16C below.

Figure 15M:
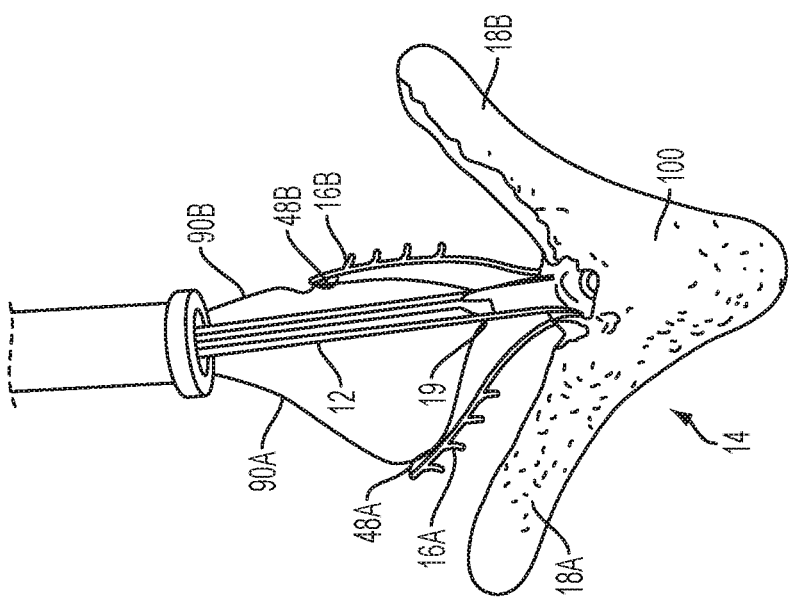

It may be desirable to provide for independent actuation of the proximal elements 16A and 16B. For example, as shown in FIG. 15L, the proximal element actuator 90A is proximally retracted and rotates the proximal element 16A away from the distal element 18A, while the proximal element actuator 90B is pushed distally and rotates the proximal element 16B toward the distal element 18B. Similarly, as shown in FIG. 15M, the proximal element actuator 90A is left alone, allowing the proximal element 16A to maintain the position it is biased toward, while the proximal element actuator 90B is proximally retracted, moving the proximal element 16B away from the distal element 18B. Providing for the independent actuation of the proximal elements 16A and 16B allows leaflets to be independently grasped by the proximal elements 16A and 16B and the distal elements 18A and 18B. Thus, the fixation device 14 can coapt leaflets more easily and at more optimal locations. For example, as opposed to grasping two leaflets simultaneously, a first leaflet can be grasped at a desired position and the fixation device 14 can then be repositioned so that a second leaflet can be grasped at a more optimal position. Alternatively, leaflets may be still be simultaneously grasped if desired as the independently actuatable proximal element actuators can still be moved simultaneously. Also, after leaflets are grasped, they can be released and the leaflets can be grasped again, for example, if the leaflets are malcoapted at the first grasp.

Figure 15O:
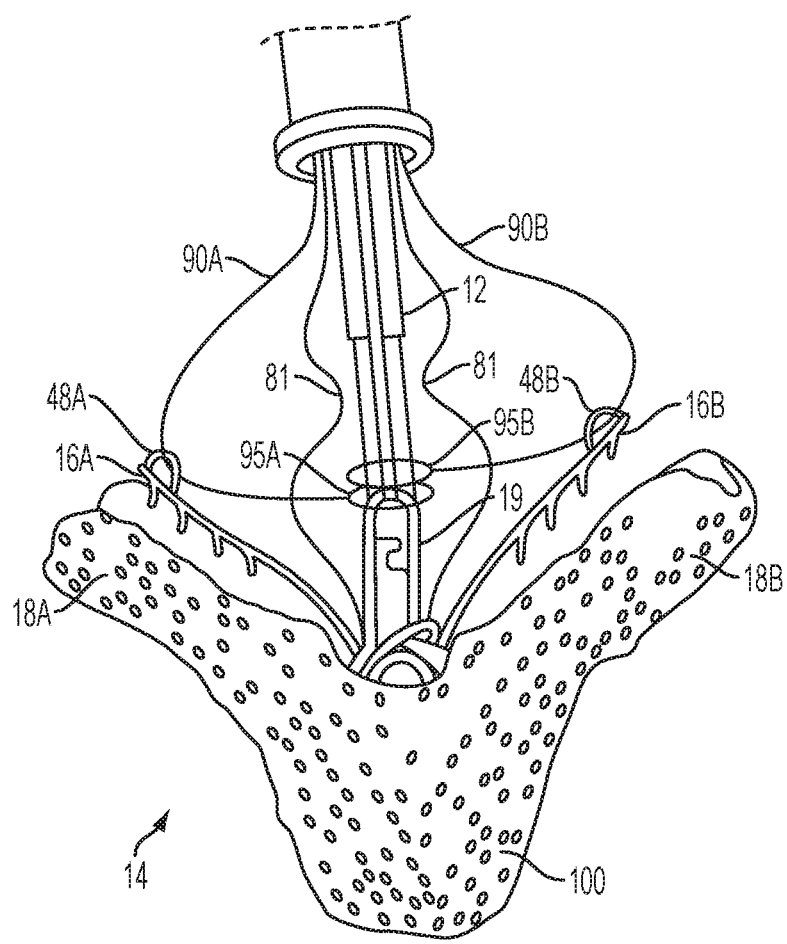

Embodiments of the fixation device similar to the devices described above may include both a gripper pusher 81 and independently actuatable proximal elements 16A and 16B, as shown for example in FIG. 15O. Having both a gripper pusher 81 and independently actuatable proximal elements 16A and 16B may allow the fixation device to have many of the advantages described above such as to more accurately and more strongly grasp leaflets.

Figure 15P:
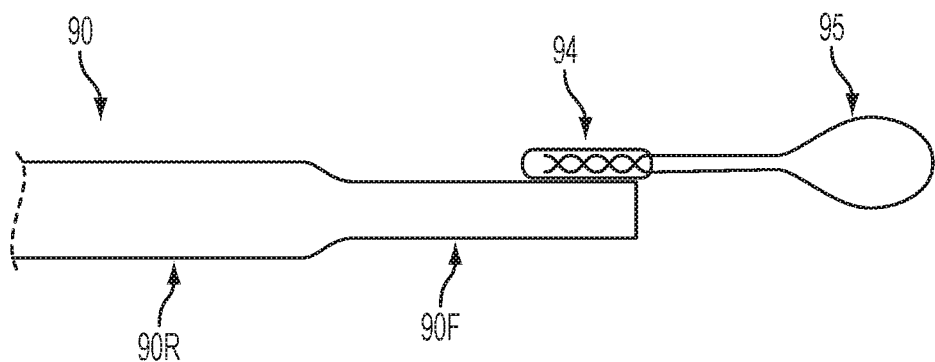

FIG. 15P shows the distal end of a proximal element actuator 90. The proximal element actuator 90 comprises a round section 90R and a flat section 90F distal of the round section 90R. When this proximal element actuator 90 is threaded through a proximal element 16 and coupled to a fixation device 14, the flatter portion of the flat section may be positioned so that it faces proximal element 16. As the proximal element actuator 90 is proximally advanced, it will therefore tend to deflect it in the direction toward the proximal element 16 instead of in other directions and push the proximal element. The proximal element actuator 90 further comprises a looped end 95. As shown in FIG. 15P, the looped end 95 may comprise a separate loop of wire attached with the distal end of the flat section 90F at its distal end, for example, with solder 94.

Figure 15Q:
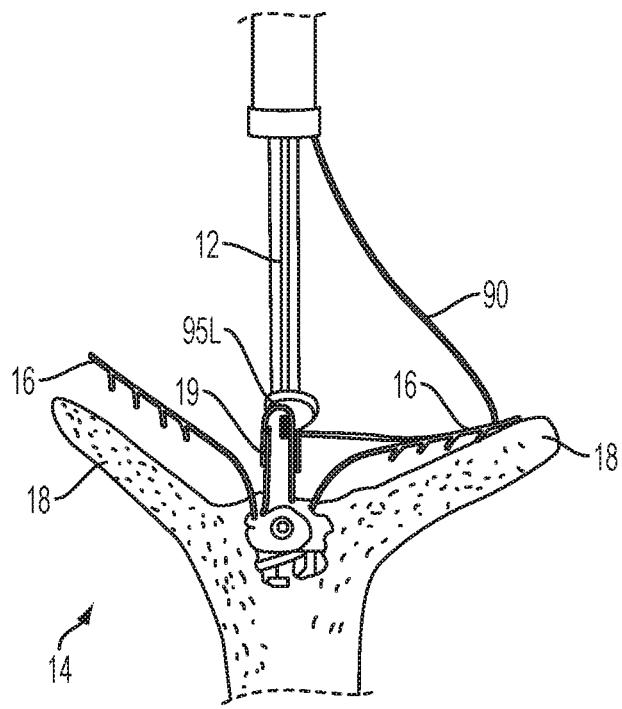
Figure 15R:
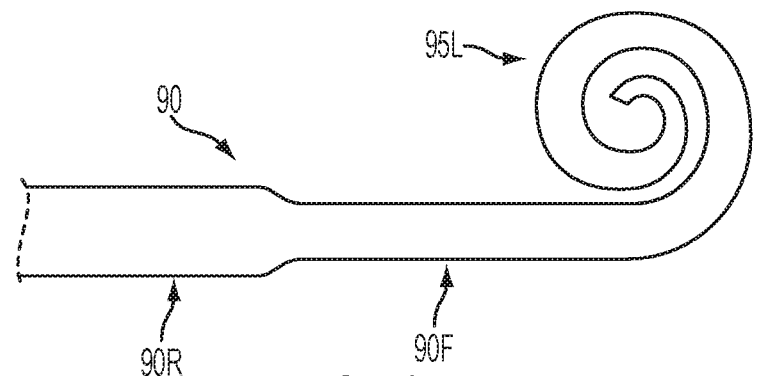

The proximal element actuator 90 may also be releasably coupled to the fixation device 14 in other ways. For example, as shown in FIGS. 15Q and 15R, the proximal element actuator 90 comprises a spiraled distal section 95L which is releasably coupled to the fixation device 14. The spiraled distal section 95L is wrapped about the shaft 12 and/or the coupling mechanism 19. Retracting the proximal element actuator 90 with sufficient force may deform the spiraled distal section 95L so that it is released from the fixation device 14. Alternatively or in combination, the spiraled distal section 95L may comprise a shape memory material such that the spiraled distal section 95L is straightened upon the application of a sufficient amount of heat, facilitating the proximal retraction of the proximal element actuator 90 away from the fixation device 14.

Figure 15S:
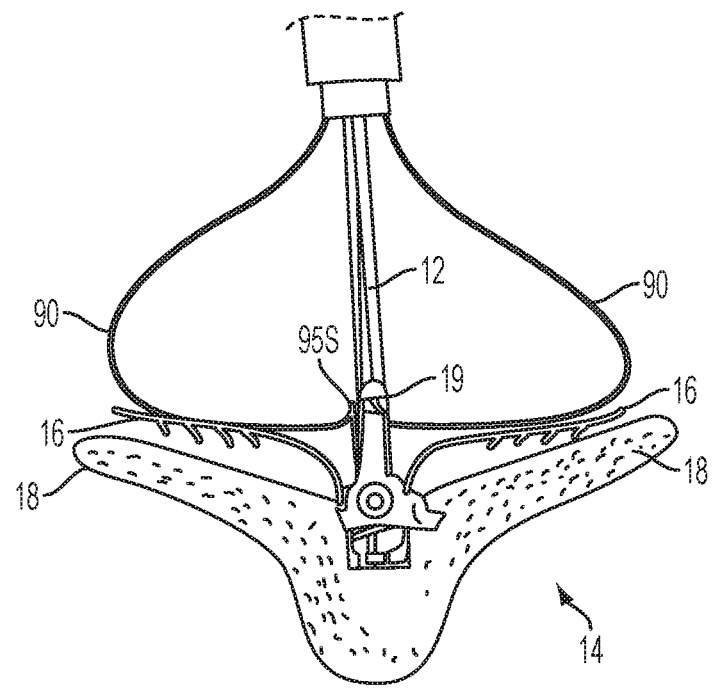
Figure 15T:
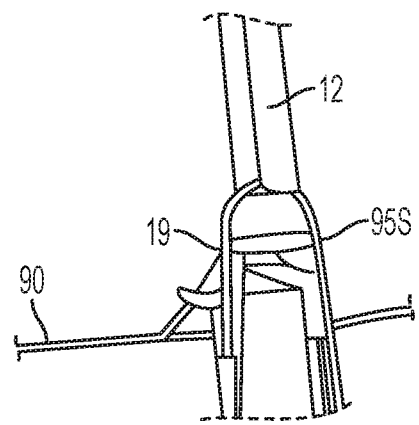

The proximal element actuator 90 may be releasably coupled to the fixation device 14 by suture. As shown in FIGS. 15S and 15T, a proximal element actuator 90 is releasably coupled to the fixation device 14 via a suture knot 95S. Each proximal actuator 90 may be coupled to the fixation device 14 by a separate suture knot 95S. Alternatively, a pair of proximal actuators 90 may be coupled to the fixation device 14 by a single suture knot.

Figure 15U:
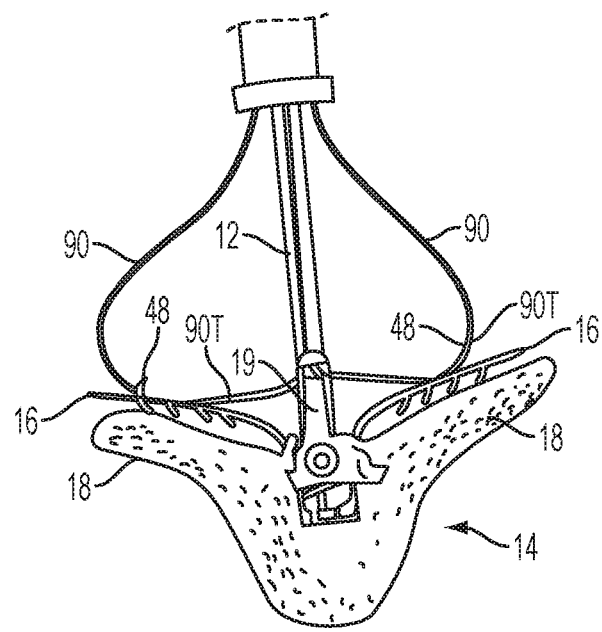
Figure 15V:
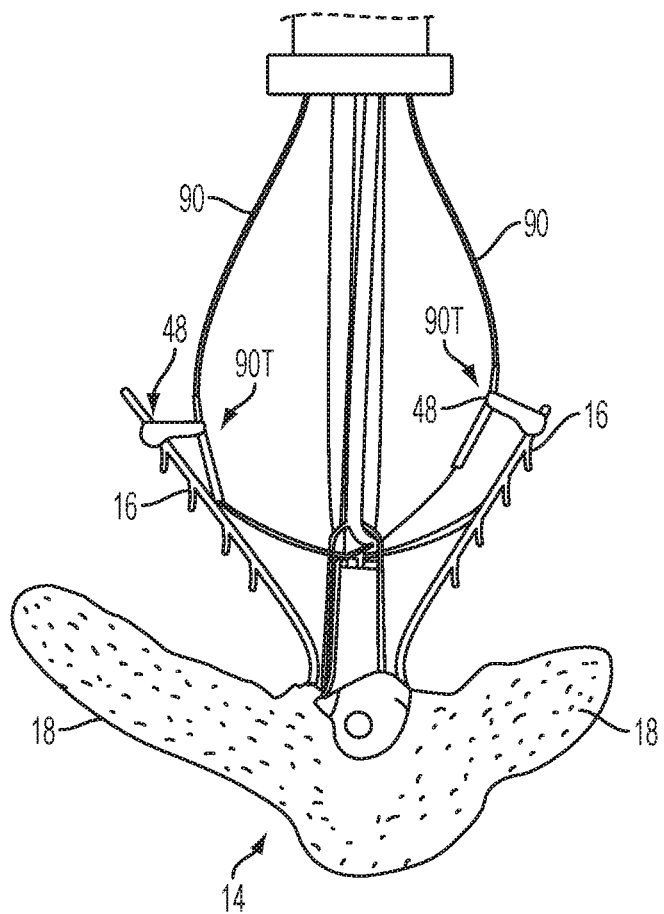

A proximal element actuator 90 may comprise an enlarged section 90T as shown in FIGS. 15U and 15V. The diameter of the enlarged section 90T exceeds the diameter of the opening of the loop line 48. As the proximal element actuator 90 is retracted, the loop line 48 restricts the proximal movement of the enlarged section 90T. Thus, a pulling force is exerted on the loop line 48 and proximal element 16, which facilitates the actuation of a proximal element 16. The enlarged section 90T may be a sleeve attached over the proximal element actuator 90.

The proximal element actuator 90 may be releasably coupled to the proximal element 16 at the radially outward ends of the proximal element 16 by an attachment device, for example, as shown in FIGS. 15W1 to 15W2. The attachment device may comprise a ring 90CR as shown in a perspective view in FIG. 15W1, a short clip 90CC as shown in a perspective view in FIG. 15W2, or a long clip 90CL as shown in FIGS. 15W3 to FIG. 15W5. FIG. 15W3 shows a perspective view of the long clip 90CL attaching the proximal element actuator 90 to a proximal element 16. FIGS. 15W4 and 15W5 show a front and side view of the same, respectively. The long clip 90CL may comprise a pair of legs 90CLL which traverse the length of the proximal element 16. As shown in FIG. 15W5, a leg 90CLL is disposed between two rows of barbs 60.

The above described attachment devices may be spring loaded to latch onto or sized to slip fit into the radially outward ends of the proximal element 16. As the proximal element actuator 90 is retracted, the attachment device continues to be attached to the proximal element 16. As the proximal element 16 is rotated to be substantially parallel to a shaft 19, however, further proximal retraction of the proximal element actuator 90 can release the attachment device from the outer end of the proximal element 16. A mechanical mechanism may be provided to limit the degree to which the proximal element actuator 90 can be proximally retracted so that the attachment device is not detached inadvertently. Instead, detachment will occur only upon retraction of the whole delivery device, including the proximal element actuators 90, from the fixation device 14.

The proximal element actuator 90 may comprise two lines: an actuation line 90AA and a release line 90RR, for example, as shown in FIGS. 15X1 to 15X3. FIG. 15X1 shows a perspective view of an radially outer end of a proximal element 16 having an aperture 48A. FIG. 15X2 shows a cross-sectional view of the same. The actuation line 90AA has a looped end 90AAL which is threaded through the aperture 48A to cross through proximal element 16. The release line 90RR is threaded through the portion of the looped end 90AAL. In FIG. 15X3, the actuation line 90AA and the release line 90RR are similarly positioned through loop line 48 of proximal element 16. While the actuation line 90AA and the release line 90RR are positioned in the arrangement shown in FIGS. 15X1 to 15X3, retracting the actuation line 90AA rotates the proximal element 16 relative to a distal element 18 similarly to the embodiments described above. Retracting the release line 90RR so that it no longer is threaded through the looped end 90AAL allows the actuation line to be retracted away from the proximal element 16.

In many embodiments, the shaft 12 and the coupling member 19 are releasably coupled together via an L-locking mechanism. For example, as shown in FIG. 15Y1, the proximal element actuator 90 may comprise a round T-shaped end 90T distal of the flat section 90F and the shaft 12 may comprise L-shaped ends 12L. As shown in the perspective view of FIG. 15Y2, the proximal element actuator 90 is releasably coupled to the coupling member 19 when it and shaft 12 are placed into the channel 19C of the coupling member 19. As the shaft 12 is placed through the channel 19C, the L-shaped ends 12L are forced inwardly until they reach apertures 19A. At that point, the L-shaped ends 12L expand outwardly to fit into the apertures 19A, thereby locking the shaft 12 in place relative to the coupling member 19, as shown in cross-sectional view of FIG. 15Y3. The round T-shaped distal end 90T will typically be placed in the channel 19C prior to the shaft 12. As shown in FIG. 15Y3, the round T-shaped distal end 90T then becomes trapped in the space 19CA between the channel 19C and a wider portion of the shaft 12 when the shaft is placed therein. Other L-locking or other locking mechanisms are described in commonly assigned U.S. patent application Ser. No. 12/393,452 entitled "Detachment Mechanism for Implantable Fixation Devices" and filed Feb. 26, 2009, the full contents of which are incorporated herein by reference.

The round T-shaped end 90T of the proximal element actuator 90 may also be used to facilitate releasably coupling the proximal element line 90 to the shaft 12 and coupling member 19 is many other ways. For example, as shown in FIG. 15Z1, the L-shaped end 12L of the shaft 12 may comprise at least one proximal element line slot 12S. As shown in FIGS. 15Z3 and 15Z4, the T-shape end 90T of the proximal element actuator 90 is slid into the proximal element line slot 12S. Then, the shaft 12 is placed into the coupling member 19, thereby also locking the proximal element line 90 in place. As shown in FIG. 15Z5, removing the shaft 12 from the coupling member 19 allows the proximal element line 90 to be slid out of the proximal element line slot 12S of L-shaped end 12L, thereby decoupling the proximal element actuator 90 from both the shaft 12 and the coupling device 19.

As shown in FIG. 15AA1, the proximal element actuator 90 may comprise a flat T-shaped end 90TF. The shaft 12 may further comprise an inner distal covering 1511 surrounding a distal portion of the shaft 12 and an outer distal covering 1521 surrounding the inner distal covering. The inner distal covering 1511 will typically be in a fixed position relative to the shaft 12 while the outer distal covering will be moveable relative to the shaft 12 at a range determined by tabs 1515 of inner distal covering 1511 placed through side channels 1525 of the outer distal covering 1521. To releasably couple the proximal element actuator 90 to the shaft 12 and coupling line 19, the T-shaped end 90TF is fit into a T-shaped cutout 1513 of inner distal covering 1511, and when the shaft 12 is placed into the coupling device 19, the coupling device 19 pushes the outer distal covering 1521 over the inner distal covering 1511 to cover the T-shaped cutout 1513 as well as the T-shaped end 90TF, as shown in FIG. 15AA2. In some embodiments, the outer distal covering 1521 may be spring loaded against the inner distal cover 1523 so that tend to maintain their relative positions shown in FIG. 15AA1.

Proximal element actuators 90 may be releasably coupled to the fixation device 14 in a variety of ways using variations of inner and outer distal collars over the distal portion of shaft 12, for example, as shown in FIGS. 15AB1 to 15AB7. FIG. 15AB1 shows an inner distal collar 1511A having a pair of T-shaped cutouts 1513 and a tab 1514. FIG. 15AB3 shows an outer distal collar 1521A having a channel 1524. The channel 1524 guides the inner distal collar 1511A via its tab 1514 as the inner distal collar 1511A is slid into the outer distal collar 1521A, for example as shown in FIGS. 15AB3 through 15AB5. As in the embodiment shown in FIGS. 15AA1 and 15AA2, to releasably couple the proximal element actuators 90 to the shaft 12 and coupling member 19, the T-shaped end 90TF is fit into a T-shaped cutout 1513 of inner distal collar 1511S. When the shaft 12 is placed into the coupling device 19, the coupling member 19 pushes the outer distal collar 1521S over the inner distal collar 1511S to cover the T-shaped cutout 1513 as well as the T-shaped end 90TF, as shown in FIGS. 15AB6 and 15AB7.

As described below, a delivery device or delivery catheter 300 may be used to introduce and position fixation devices as described above. In embodiments of the invention with independently actuatable proximal element lines, the handle 304 of the delivery catheter will typically include control mechanisms for the independently actuable proximal element lines. For example, a control mechanism may comprise a pair of independently actuable proximal element line handles 393A and 393B placed in parallel, as shown in FIG. 15AC1, or placed coaxially, as shown in FIG. 15AC2. The proximal element line handles 393A and 393B are coupled to proximal element lines 90A and 90B and may share a common or interconnecting lumens in the delivery device. Stop may be provided to limit the degree to which the proximal element line handles 393A and 393B can be retracted or advanced, thereby limiting the degree to which the proximal element actuators 90A and 90B can be retracted or advanced. In some embodiments, for example, as shown by FIGS. 15AC3 and 15AC4, a proximal element line handle 393 may be actuated by a rotatable switch 395 attached to it.

B. Covering on Fixation Device

The fixation device 14 may optionally include a covering. The covering may assist in grasping the tissue and may later provide a surface for tissue ingrowth. Ingrowth of the surrounding tissues, such as the valve leaflets, provides stability to the device 14 as it is further anchored in place and may cover the device with native tissue thus reducing the possibility of immunologic reactions. The covering may be comprised of any biocompatible material, such as polyethylene terepthalate, polyester, cotton, polyurethane, expanded polytetrafluoroethylene (ePTFE), silicon, or various polymers or fibers and have any suitable form, such as a fabric, mesh, textured weave, felt, looped or porous structure. Generally, the covering has a low profile so as not to interfere with delivery through an introducer sheath or with grasping and coaptation of leaflets or tissue.

Figure 16A:
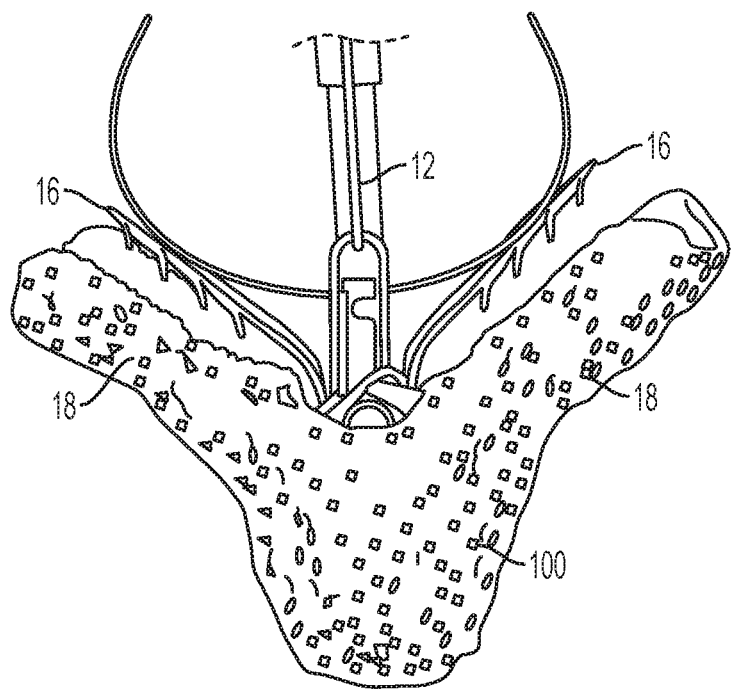
FIGS. 16A-16C illustrate a covering on the fixation device wherein the device is in various positions.
Figure 16B:
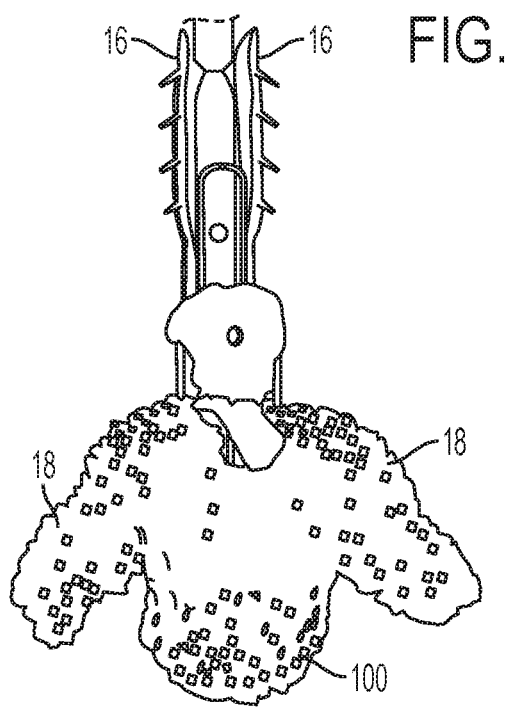
Figure 16C:
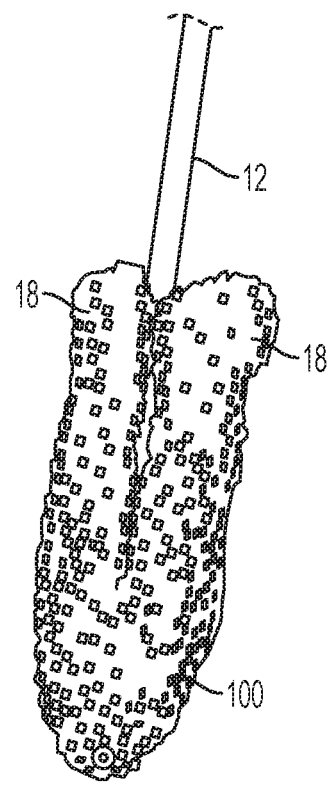

FIGS. 16A-16C illustrate a covering 100 on the fixation device 14 wherein the device 14 is in various positions. FIG. 16A shows the covering 100 encapsulating the distal elements 18 and the actuation mechanism 58 while the device 14 is in the open position. Thus, the engagement surfaces 50 are covered by the covering 100 which helps to minimize trauma on tissues and provides additional friction to assist in grasping and retaining tissues. FIG. 16B shows the device 14 of FIG. 16A in the inverted position. The covering 100 is loosely fitted and/or is flexible or elastic such that the device 14 can freely move to various positions and the covering 100 conforms to the contours of the device 14 and remains securely attached in all positions. FIG. 16C shows the device 14 in the closed position. Thus, when the fixation device 14 is left behind as an implant in the closed position, the exposed surfaces of the device 14 are substantially covered by the covering 100. It may be appreciated that the covering 100 may cover specific parts of the fixation device 14 while leaving other parts exposed. For example, the covering 100 may comprise sleeves that fit over the distal elements 18 and not the actuation mechanism 58, caps that fit over the distal ends 54 of the distal elements 18 or pads that cover the engagement surfaces 50, to name a few. It may be appreciated that, the covering 100 may allow any frictional accessories, such as barbs, to be exposed. Also, the covering 100 may cover the proximal elements 16 and/or any other surfaces of the fixation device 14. In any case, the covering 100 should be durable to withstand multiple introduction cycles and, when implanted within a heart, a lifetime of cardiac cycles.

The covering 100 may alternatively be comprised of a polymer or other suitable materials dipped, sprayed, coated or otherwise adhered to the surfaces of the fixation device 14. Optionally, the polymer coating may include pores or contours to assist in grasping the tissue and/or to promote tissue ingrowth.

Any of the coverings 100 may optionally include drugs, antibiotics, anti-thrombosis agents, or anti-platelet agents such as heparin, COUMADIN® (Warfarin Sodium), to name a few. These agents may, for example, be impregnated in or coated on the coverings 100. These agents may then be delivered to the grasped tissues surrounding tissues and/or bloodstream for therapeutic effects.

C. Fixation Device Locking Mechanisms

Figure 17:
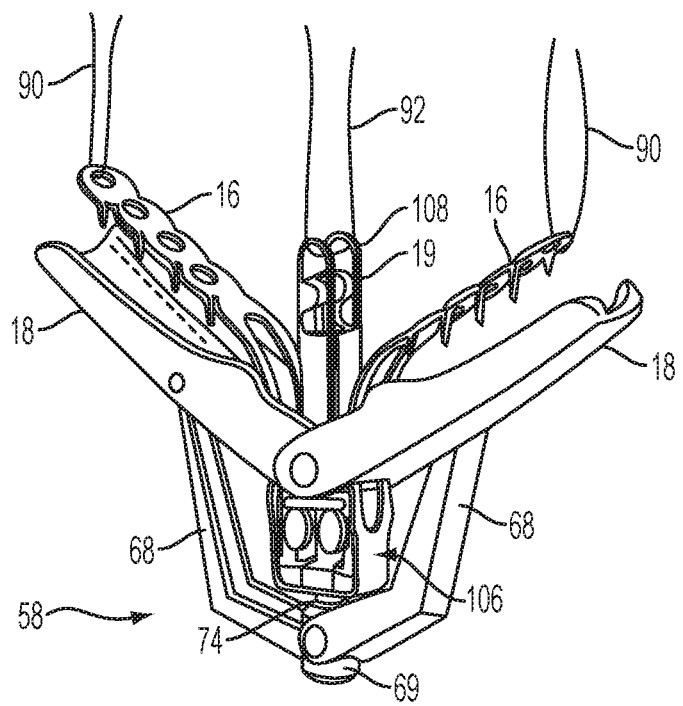
FIG. 17 illustrates an embodiment of the fixation device including proximal elements and a locking mechanism.

As mentioned previously, the fixation device 14 optionally includes a locking mechanism for locking the device 14 in a particular position, such as an open, closed or inverted position or any position therebetween. It may be appreciated that the locking mechanism includes an unlocking mechanism which allows the device to be both locked and unlocked. FIGS. 17-20 illustrate an embodiment of a locking mechanism 106. Referring to FIG. 17, in this embodiment, the locking mechanism 106 is disposed between the coupling member 19 and the base 69 of the actuation mechanism 58. The base 69 is fixedly attached to the stud 74 which extends through the locking mechanism 106. The stud 74 is releasably attached to the actuator rod 64 which passes through the coupling member 19 and the shaft 12 of the interventional tool 10. The base 69 is also connected to the legs 68 of the actuation mechanism 58 which are in turn connected to the distal elements 18.

FIG. 17 also illustrates the proximal elements 16, which in this embodiment straddle the locking mechanism and join beneath the locking mechanism 106. The proximal elements 16 are shown supported by proximal element lines 90. The proximal elements 16 are raised and lowered by manipulation of the proximal element lines 90. In addition, lock lines 92 are shown connected with a release harness 108 of the locking mechanism 106. The lock lines 92 are used to lock and unlock the locking mechanism 106 as will be described below. The proximal element lines 90 and lock lines 92 may be comprised of any suitable material, typically wire, nitinol wire, cable, suture or thread, to name a few. In addition, the proximal element lines 90 and/or lock lines 92 may include a coating, such as parylene. Parylene is a vapor deposited pinhole free protective film which is conformal and biocompatible. It is inert and protects against moisture, chemicals, and electrical charge.

Figure 18:
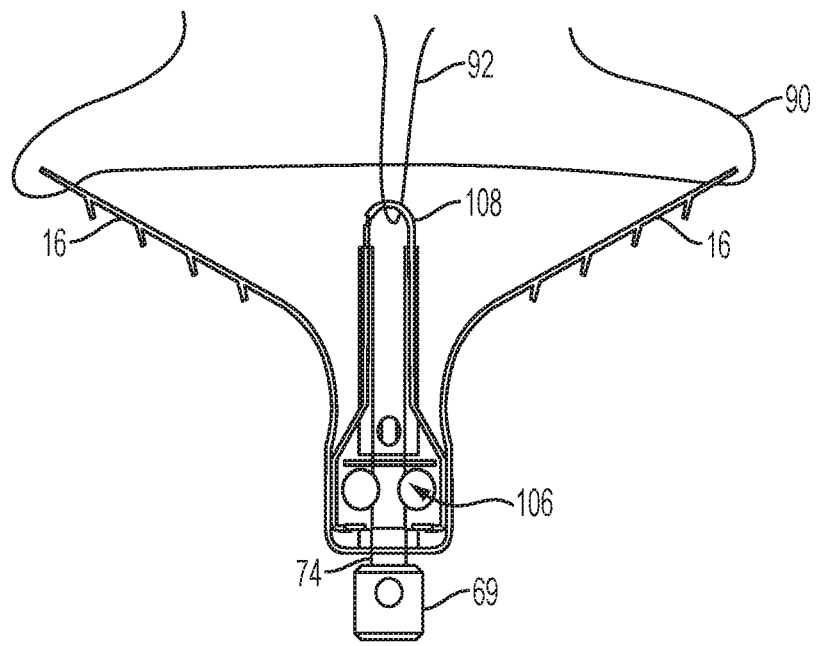
FIG. 18 provides a cross-sectional view of the locking mechanism of FIG. 17.

FIG. 18 provides a front view of the locking mechanism 106 of FIG. 17. However, here the proximal elements 16 are supported by a single proximal element line 90 which is through both of the proximal elements 16. In this arrangement both of the elements are raised and lowered simultaneously by action of a single proximal element line 90. Whether the proximal elements 16 are manipulated individually by separate proximal element lines 90 or jointly by a single proximal element line 90, the proximal element lines 90 may extend directly through openings in the proximal elements and/or through a layer or portion of a covering 100 on the proximal elements, or through a suture loop above or below a covering 100.

Figure 19:
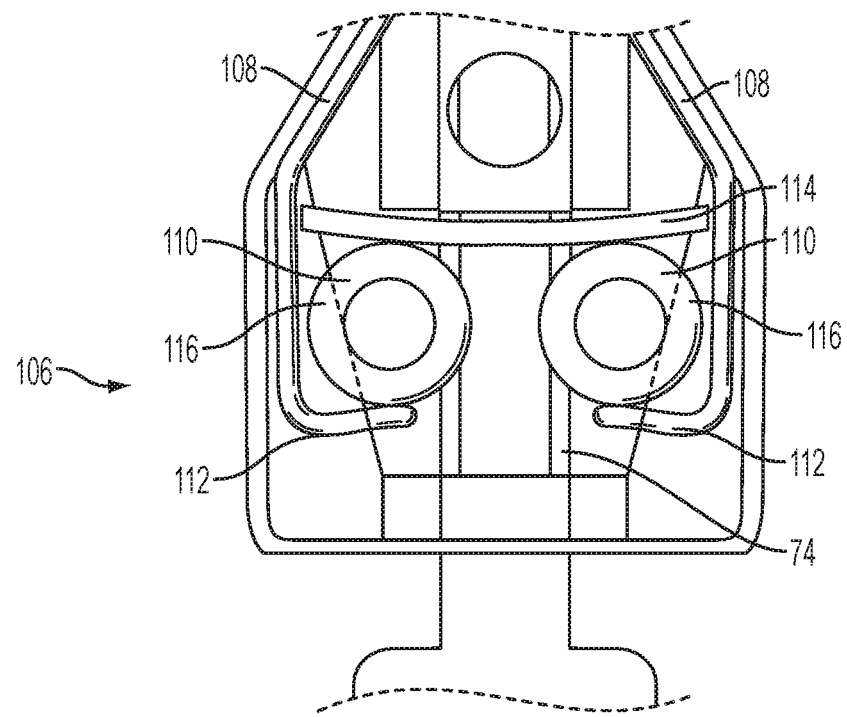
FIGS. 19-20 provide a cross-sectional view of the locking mechanism in the unlocked and locked positions respectively.
Figure 20:
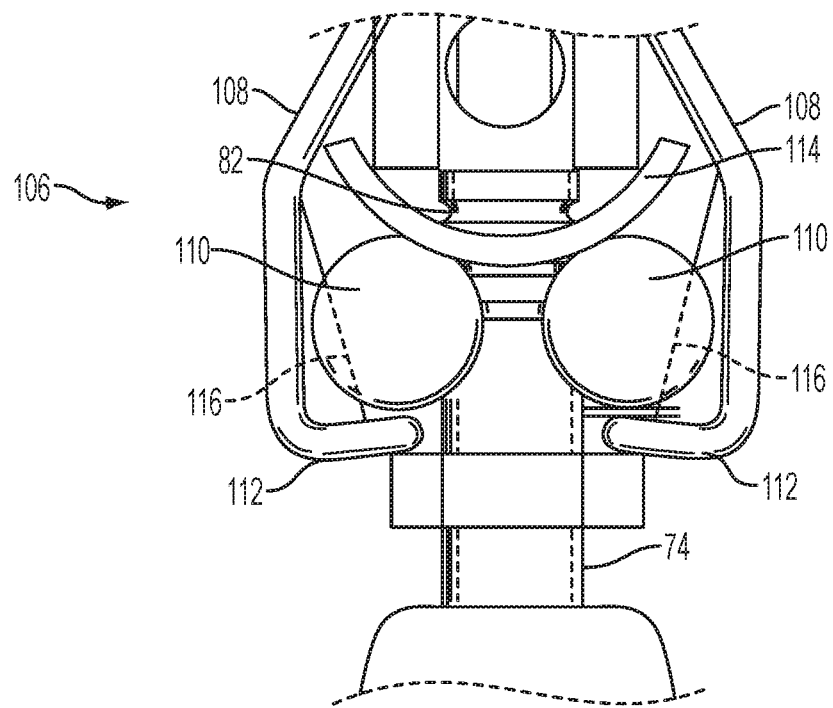

FIGS. 19-20 illustrate the locking mechanism 106 showing the locking mechanism 106 in the unlocked and locked positions respectively. Referring to FIG. 19, the locking mechanism 106 includes one or more wedging elements, such as rolling elements. In this embodiment, the rolling elements comprise a pair of barbells 110 disposed on opposite sides of the stud 74, each barbell having a pair of generally cylindrical caps and a shaft therebetween. The barbells 110 and the stud 74 are preferably comprised of cobalt chromium or stainless steel, however any suitable material may be used. The barbells 110 are manipulated by hooked ends 112 of the release harness 108. When an upwards force is applied to the harness 108 by the lock line 92 (illustrated in FIG. 17), the hooked ends 112 raise the barbells 110 against a spring 114, as shown in FIG. 19. This draws the barbells 110 up along a sidewall or sloping surface 116 which unwedges the barbells 110 from against the stud 74. In this position, the stud 74 is free to move. Thus, when the lock line 92 raises or lifts the harness 108, the locking mechanism 106 is in an unlocked position wherein the stud 74 is free to move the actuation mechanism 58 and therefore the distal elements 18 to any desired position. Release of the harness 108 by the lock line 92 transitions the locking mechanism 106 to a locked position, illustrated in FIG. 20. By releasing the upwards force on the barbells 110 by the hooked ends 112, the spring 114 forces the barbells 110 downwards and wedges the barbells 110 between the sloping surface 116 and the stud 74. This restricts motion of the stud 74, which in turn locks the actuation mechanism 58 and therefore distal elements 18 in place. In addition, the stud 74 may include one or more grooves 82 or indentations which receive the barbells 110. This may provide more rapid and positive locking by causing the barbells 110 to settle in a definite position, increase the stability of the locking feature by further preventing movement of the barbells 110, as well as tangible indication to the user that the barbell has reached a locking position. In addition, the grooves 82 may be used to indicate the relative position of the distal elements 18, particularly the distance between the distal elements 18. For example, each groove 82 may be positioned to correspond with a 0.5 or 1.0 mm decrease in distance between the distal elements 18. As the stud 74 is moved, the barbells 110 will contact the grooves 82; by counting the number of grooves 82 that are felt as the stud 74 is moved, the user can determine the distance between the distal elements 18 and can provide the desired degree of coaptation based upon leaflet thickness, geometry, spacing, blood flow dynamics and other factors. Thus, the grooves 82 may provide tactile feedback to the user.

The locking mechanism 106 allows the fixation device 14 to remain in an unlocked position when attached to the interventional tool 10 during grasping and repositioning and then maintain a locked position when left behind as an implant. It may be appreciated, however, that the locking mechanism 106 may be repeatedly locked and unlocked throughout the placement of the fixation device 14 if desired. Once the final placement is determined, the lock line 92 and proximal element lines 90 are removed and the fixation device is left behind.

Figure 21:
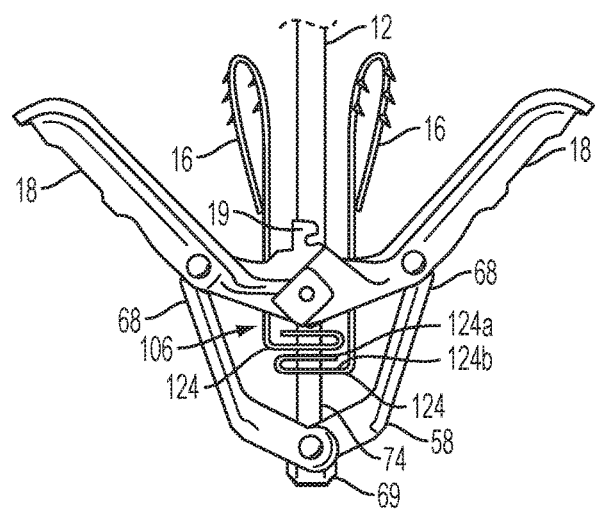
FIGS. 21 and 22A-22B illustrate another embodiment of a locking mechanism.
Figure 22A:
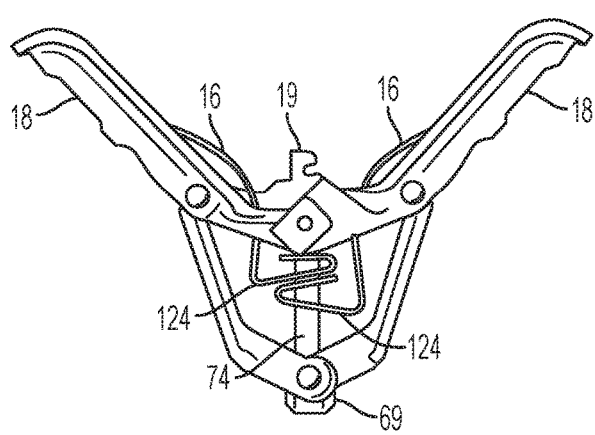
Figure 22B:
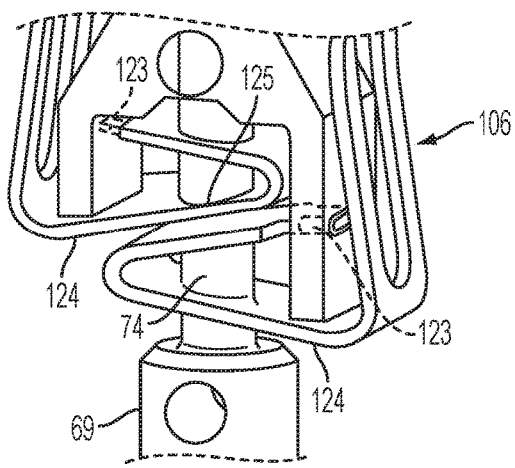

FIGS. 21, 22A-22B illustrate another embodiment of a locking mechanism 106. Referring to FIG. 21, in this embodiment, the locking mechanism 106 is again disposed between the coupling member 19 and the base 69 of the actuation mechanism 58. The base 69 is connected to the stud 74 which extends through the locking mechanism 106, and connects to an actuator rod which extends through the coupling member 19 and the shaft 12 of the interventional tool 10. The base 69 is also connected to the legs 68 of the actuation mechanism 58 which are in turn connected to the distal elements 18. FIG. 21 also illustrates the proximal elements 16 which manipulate the locking mechanism 106 in this embodiment. The locking mechanism 106 comprises folded leaf structures 124 having overlapping portions 124a, 124b, each folded structure 124 being attached to a proximal element 16. In FIG. 21 and FIG. 22A, the folded structures 124 are shown without the remainder of the locking mechanism 106 for clarity. Proximal elements 16 are flexible and resilient and are biased outwardly. The folded leaf structures 124 include holes 125 (FIG. 22B) in each overlapping portion 124a, 124b so that the stud 74 passes through the holes 125 of the portions 124a, 124b as shown. The locking mechanism includes slots into which ends 123 of the folded leaf structures 124 are fixed. When the proximal elements 16 are in an undeployed position, as in FIG. 21, the folded leaf structures 124 lie substantially perpendicular to the stud 74 so that the holes 125 in each overlapping portion are vertically aligned. This allows the stud 74 to pass freely through the holes and the locking mechanism 106 is considered to be in an unlocked position.

Deployment of the proximal elements 16, as shown in FIG. 22A, tilts the folded leaf structures 124 so as to be disposed in a non-perpendicular orientation relative to the stud 74 and the holes 125 are no longer vertically aligned with one another. In this arrangement, the stud 74 is not free to move due to friction against the holes of the folded leaf structure 124. FIG. 22B provides a larger perspective view of the folded structures 124 in this position. Thus, the locking mechanism 106 is considered to be in a locked position. This arrangement allows the fixation device 14 to maintain an unlocked position during grasping and repositioning and then maintain a locked position when the proximal elements 16 are deployed and the fixation device 14 is left behind as an implant. It may be appreciated, however, that the locking mechanism 106 may be repeatedly locked and unlocked throughout the placement of the fixation device 14 if desired.

Figure 23:
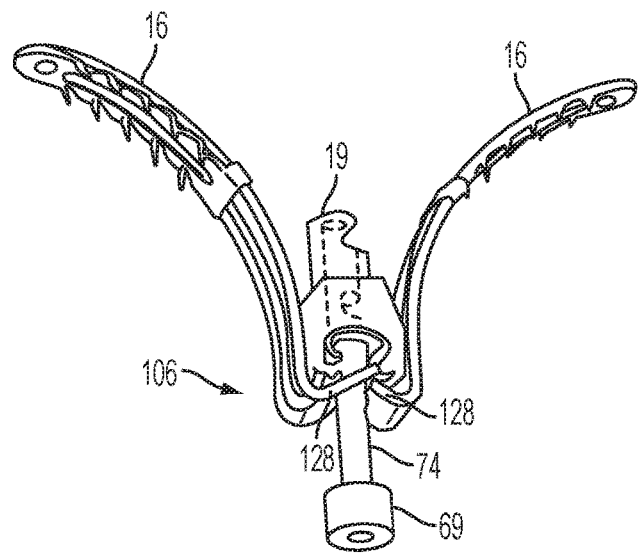
FIGS. 23 and 24A-24B illustrate yet another embodiment of a locking mechanism.
Figure 24A:
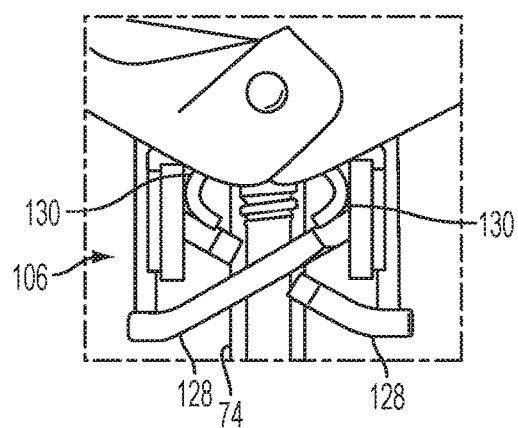
Figure 24B:
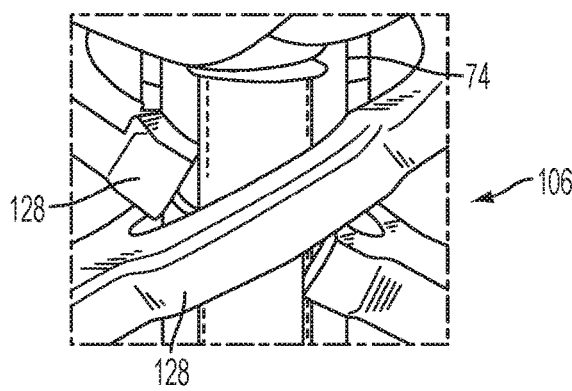

FIGS. 23, 24A-24B illustrate another embodiment of a locking mechanism 106. Referring to FIG. 22, in this embodiment, the locking mechanism 106 is again disposed between the coupling member 19 and the base 69 of the actuation mechanism 58. And, the base 69 is connected to the stud 74 which extends through the locking mechanism 106 and connects to an actuator rod which extends through the coupling member 19 and the shaft of the interventional tool 10. FIG. 22 illustrates the proximal elements 16 which manipulate the locking mechanism 106 in this embodiment. The locking mechanism 106 comprises C-shaped structures 128, each C-shaped structure 128 attached to a proximal element 16. The C-shaped structures 128 hook around the stud 74 so that the stud 74 passes through the "C" of each structure 128 as shown in FIGS. 24A-24B. As shown, the structures 128 cross each other and the "C" of each structure 128 faces each other. A spring 130 biases the C-shaped structures into engagement with one another. When the proximal elements are in an undeployed position, as in FIG. 24A, the C-shaped structures 128 are urged into an orientation more orthogonal to the axial direction defined by stud 74, thus bringing the "C" of each structure 128 into closer axial alignment. This allows the stud 74 to pass freely through the "C" of each structure 128. Deployment of the proximal elements 16 outwardly urges the C-shaped structures into a more angular, non-orthogonal orientation relative to stud 74 causing the sidewalls of the "C" of each structure 128 to engage stud 74 more forcefully. In this arrangement, the stud 74 is not free to move due to friction against the "C" shaped structures 128.

D. Additional Embodiments of Fixation Devices

In other embodiments, the proximal elements may be manipulated to enhance gripping. For example, the proximal elements may be lowered to grasp leaflets or tissue between the proximal and distal elements, and then the proximal elements may be moved to drag the leaflets or tissue into the fixation device. In another example, the proximal elements may be independently lowered to grasp the leaflets or tissue. This may be useful for sequential grasping. In sequential grasping, one proximal element is lowered to capture a leaflet or tissue portion between the proximal and distal elements. The fixation device is then moved, adjusted or maneuvered to a position for grasping another leaflet or tissue portion between another set of proximal and distal elements. In this position, the second proximal element is then lowered to grasp this other leaflet or tissue portion.

Other exemplary embodiments of fixation devices are disclosed in U.S. Pat. Nos. 7,563,267 and 7,226,467, the entire contents of each, fully incorporated herein by reference. One of skill in the art will appreciate that the various features of the disclosed fixation devices may be substituted with one another or used in combination with other disclosed features.

IV. Delivery Device

A. Overview of Delivery Device

Figure 25:
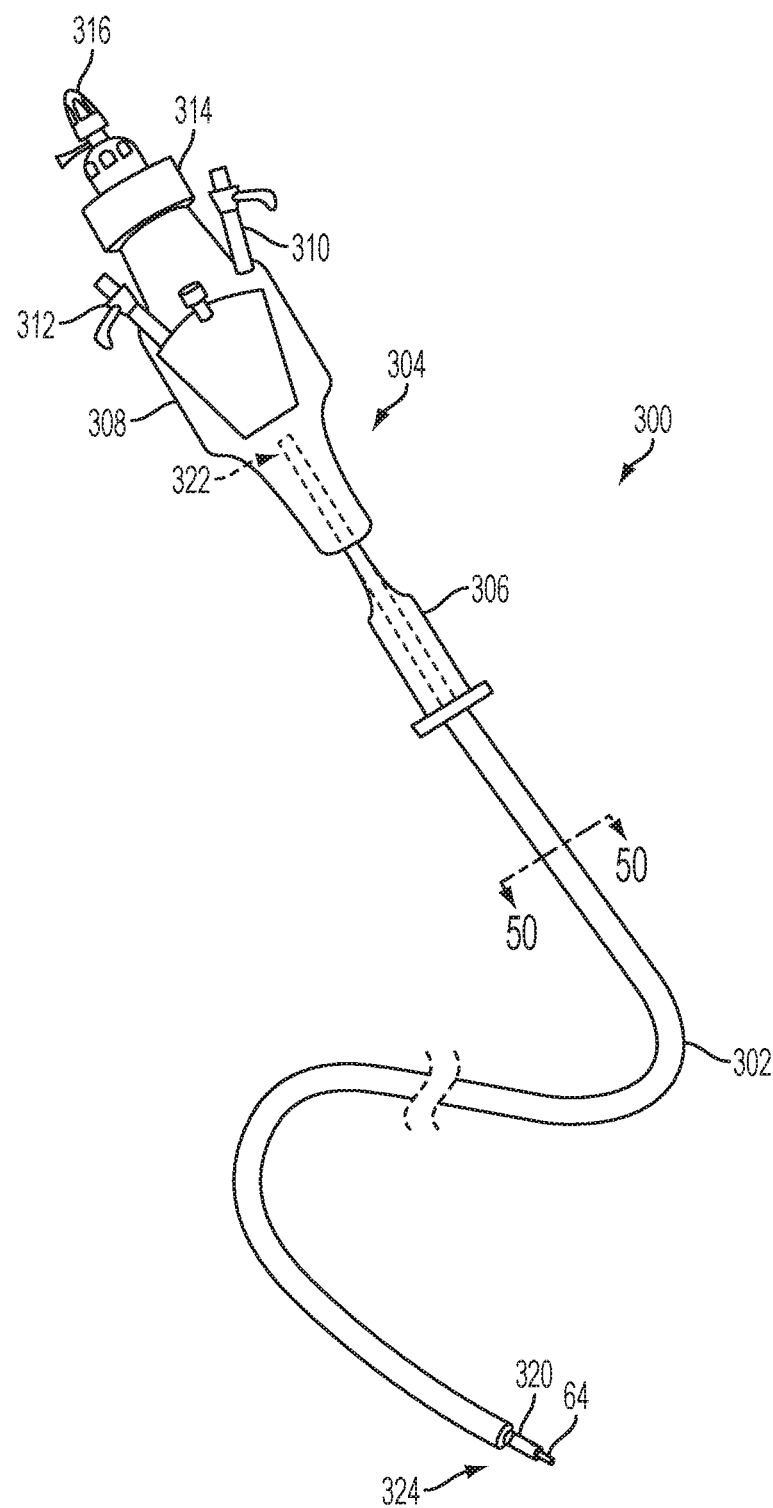
FIG. 25 is a perspective view of an embodiment of a delivery catheter for a fixation device.

FIG. 25 provides a perspective view of an embodiment of a delivery device or delivery catheter 300 which may be used to introduce and position a fixation device as described above. The delivery catheter 300 includes a shaft 302, having a proximal end 322 and a distal end 324, and a handle 304 attached to the proximal end 322. A fixation device (not shown) is removably coupleable to the distal end 324 for delivery to a site within the body, typically for endovascular delivery to the mitral valve. Thus, extending from the distal end 324 is a coupling structure 320 for coupling with a fixation device. Also extending from the distal end 324 is an actuator rod 64. The actuator rod 64 is connectable with the fixation device and acts to manipulate the fixation device, typically opening and closing the distal elements. Such coupling to a fixation device is illustrated in FIG. 26.

Figure 26:
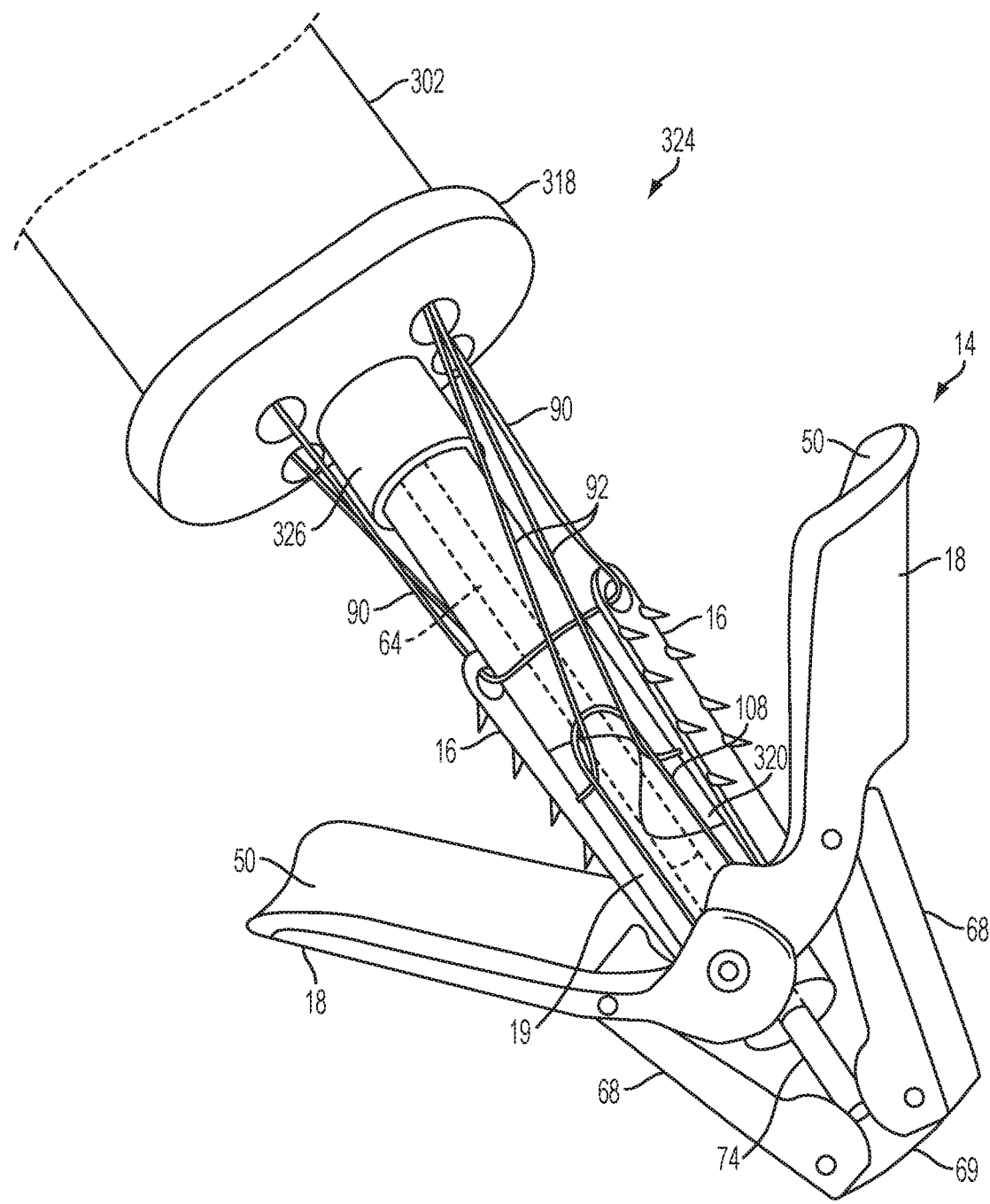
FIG. 26 illustrates an embodiment of a fixation device coupled to the distal end of a delivery catheter.

FIG. 26 illustrates an embodiment of a fixation device 14 coupled to the distal end 324 of the delivery catheter 300. The shaft 302 is shown having a nose 318 near its distal end 324. In this embodiment, the nose 318 has a flanged shape. Such a flanged shape prevents the nose 318 from being retracted into a guiding catheter or introducer as will be discussed in later sections. However, it may be appreciated that the nose 318 may have any shape including bullet, rounded, blunt or pointed, to name a few. Extending from the nose 318 is a compression coil 326 through which the coupling structure 320 and actuator rod 64 pass. The actuator rod 64 is coupleable, as shown, with the stud 74 of the fixation device 14. Such coupling is illustrated in FIG. 27.

Figure 27:
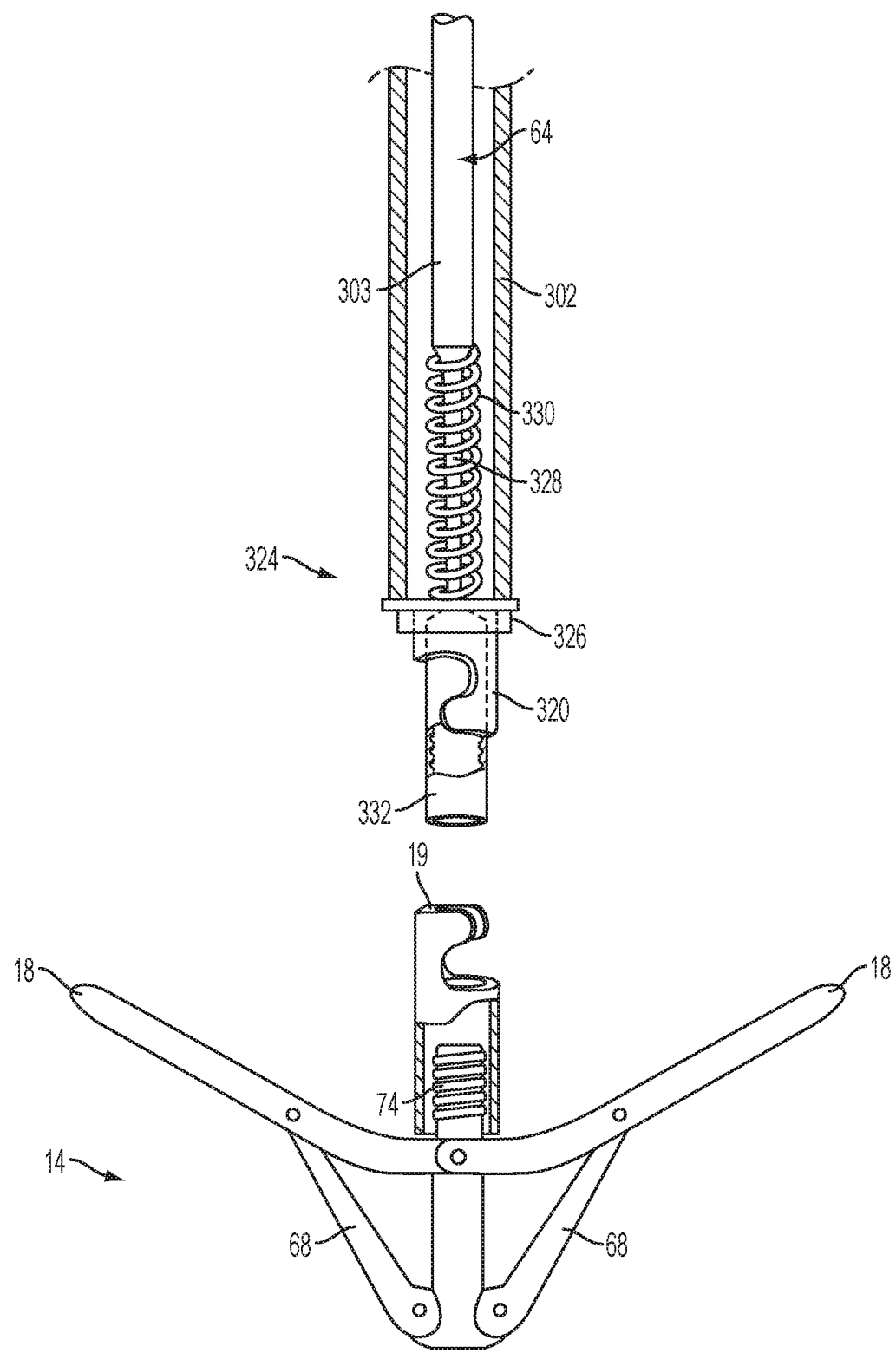
FIG. 27 illustrates a portion of the shaft of a delivery catheter and a fixation device which is coupleable with the catheter.

FIG. 27 illustrates a portion of the shaft 302 of the delivery catheter 300 and a fixation device 14 which is coupleable with the catheter 300. Passing through the shaft 302 is the actuator rod 64. In this embodiment, the actuator rod 64 comprises a proximal extremity 303 and a distal extremity 328, the distal extremity 328 of which is surrounded by a coil 330. The proximal extremity 303 is typically comprised of stainless steel, nitinol, or Elgiloy®, to name a few, and may have a diameter in the range of 0.010 in. to 0.040 in., preferably 0.020 in. to 0.030 in., more preferably 0.025 in., and a length in the range of 48 to 72 in. The distal extremity 328 may be tapered, is typically comprised of stainless steel, nitinol, or Elgiloy®, to name a few, and may have a diameter in the range of 0.011 to 0.025 in and a length in the range of 4 to 12 in. Such narrowing increases flexibility of the distal end 324 of the actuator rod 64. The actuator rod 64 further comprises a joiner 332 which is attached to the distal extremity 328. The joiner 332 is removably attachable with stud 74 of the fixation device 14. In this embodiment, the joiner 332 has internal threads which mate with external threads on the stud 74 of the fixation device 14. As described previously, the stud 74 is connected with the distal elements 18 so that advancement and retraction of the stud 74, by means of the actuator rod 64, manipulates the distal elements. Likewise, the coupling member 19 of the fixation device 14 mates with the coupling structure 320 of the catheter 300. Thus, the coupling member 19 and coupling structure 320 function as previously described in relation to FIGS. 6A-6B.

Referring back to FIG. 26, the fixation device 14 may also include a locking mechanism which includes a release harness 108, as previously described in relation to FIGS. 17-20. Lock lines 92 are connected with the release harness 108 to lock and unlock the locking mechanism 106 as previously described. The lock lines 92 extend through the shaft 302 of the delivery catheter 300 and may connect with the release harness 108 in various arrangements as will be illustrated in later sections. Similarly, proximal element lines 90 extend through the shaft 302 of the delivery catheter 300 and connect with the proximal elements 16. The proximal elements 16 are raised and lowered by manipulation of the proximal element lines 90 as previously described. The proximal element lines 90 may connect with the proximal elements 16 in various arrangements as will be illustrated in later sections.

Referring back to FIG. 25, the handle 304 attached to the proximal end 322 of the shaft 302 is used to manipulate the coupled fixation device 14 and to optionally decouple the fixation device 14 for permanent implantation. As described, the fixation device 14 is primarily manipulated by the actuator rod 64, proximal element lines 90 and lock lines 92. The actuator rod 64 manipulates the distal elements 18, the proximal element lines 90 manipulate the proximal elements 16 and the lock lines 92 manipulate the locking mechanism. In this embodiment, the actuator rod 64 may be translated (extended or retracted) to manipulate the distal elements 18. This is achieved with the use of the actuator rod control 314 which will be described in later sections. The actuator rod 64 may also be rotated to engage or disengage the threaded joiner with the threaded stud 74. This is achieved with the use of the actuator rod handle 316 which will also be described in later sections. Further, the proximal element lines 90 may be extended, retracted, loaded with various amounts of tension or removed with the use of the proximal element line handle 312. And, the lock lines 92 may be may be extended, retracted, loaded with various amounts of tension or removed with the use of the lock line handle 310. Both of these handles 310, 312 will be described in more detail in later sections. The actuator rod handle 316, actuator rod control 314, proximal element line handle 312 and lock line handle 310 are all joined with a main body 308 within which the actuator rod 64, proximal element lines 90 and lock lines 92 are guided into the shaft 302. The handle 304 further includes a support base 306 connected with the main body 308. The main body 308 is slideable along the support base 306 to provide translation of the shaft 302. Further, the main body 308 is rotatable around the support base 306 to rotate the shaft.

While the embodiment of FIG. 27 is promising, in certain situations, the actuator rod 64 may deform, especially along the thinner distal extremity region 328, during delivery of fixation device 14, thereby making it more challenging to properly deliver and attach the fixation device to the valve leaflets. For example, when tracking tortuous vessels, or when steering the distal portion of the delivery device through large angles, e.g. 90° or more, the distal tapered extremity 328 of the actuator rod 64 may take a permanent set and thus may fail to return to a substantially straight configuration after being deflected. FIGS. 28A-28B illustrate an alternative embodiment of the actuator rod illustrated in FIG. 27. In this embodiment, the distal tapered extremity 328 has been replaced with a flexible cable. Actuator rod 64a is a long shaft or mandrel that generally takes the same form as actuator rod 64 in FIG. 27. A flexible cable 2702 is disposed between a distal end of the actuator rod 64a, and a proximal end of coupler or joiner 2708. The flexible cable 2702 allows torque, tension, and compression to be transmitted to the coupler 2708, while allowing bending and flexing without resulting in the flexible cable taking a set. In this exemplary embodiment, a distal portion of actuator rod 64a is joined to a proximal end of the flexible cable 2702 with a sleeve 2704. The sleeve 2704 has a central channel 2718 extending therethrough for receiving the flexible cable and the actuator rod. The sleeve 2704 may then be crimped, swaged, or otherwise reduced in diameter in order to fixedly attach the two ends together. In alternative embodiments, adhesives, welds, soldering joints, etc. may also be used to join the two ends together. Similarly, a proximal end of the coupler 2708 may include a central channel 2718 that is sized to receive a distal portion of the flexible cable 2702. In this exemplary embodiment, the coupler is cylindrically shaped with a proximal portion 2716 having a larger diameter than the distal portion 2710. After the proximal portion 2716 has been crimped or swaged onto the flexible cable, the diameters of the proximal and distal portions of the coupler may be the same, as illustrated in FIG. 28B. The distal portion of the coupler may include a threaded channel 2712 which may be threadably attached to the fixation device 14, such as previously described above in FIGS. 7 and 27. FIG. 28B illustrates the actuator rod 64a after it has been coupled with the flexible cable and the coupler by swaging.

The flexible cable is preferably resiliently biased to return to a substantially straight or linear configuration, even after being bent or deflected by 90° or more. In preferred embodiments, the flexible cable is 25 cm or shorter, preferably 10 cm to 20 cm long, and more preferably 15 to 20 cm long. The flexible cable also has an outer diameter preferably 0.015" to 0.035" and more preferably is 0.020" to 0.030" and nominally is 0.025" although one of skill in the art will appreciate that other dimensions may also be used. The actuator rod 64a generally takes the same form as actuator rod 64 in FIG. 27. The actuator rod 64a and flexible cable 2702 are configured to transmit at least 0.74 inch-ounces of torque with a substantially 1:1 torque transmission ratio from the proximal end of the actuator mandrel to the distal end of the flexible cable. This torque is required to threadably disengage the coupler 2708 from the fixation device after the valve has been satisfactorily repaired. Additionally, the actuator rod 64a and the flexible cable 2702 are also designed to transmit at least 2.5 pounds of compressive force distally to the fixation device in order to actuate the distal elements thereof. Also, the actuator rod and flexible cable can withstand at least 14.7 pounds of tensile force without substantial stretching or elongation. This force is experienced when actuating the fixation device to close the distal elements. Various metals, polymers, and other materials may be used for the actuator rod, flexible cable, sleeve, and coupler. However, in preferred embodiments, the coupler is fabricated from 17-4 H1150 stainless steel, while the cable comprises 304V stainless steel, and the mandrel is 304 stainless steel with an ultraspring wire temper.

Various configurations of the flexible cable may be used, such as the cable illustrated in FIGS. 29A-32B. The flexible cable of FIG. 29A-32B is a stranded cable with a reverse wind designed to have a high torque transmission ratio in the counterclockwise direction. This cable includes four layers of wires. The innermost layer 2802 is seen in FIG. 29A and includes three wires 2802a, 2802b, 2802c helically wound together. FIG. 29B illustrates a cross-section of cable 2802 taken along the line A-A. The next layer 2902 comprises nine additional strands of wire 2904 wrapped around the innermost layer 2802 as illustrated in FIG. 30A. FIG. 30B is a cross-section taken along the line B-B. The next layer 3002 is illustrated in FIG. 31A, and comprises ten additional strands of wire 3006 wrapped around layer 2902, and a cross-section taken along line D-D is shown in FIG. 31B. Finally, the outermost layer 3102 comprises ten more wires 3108 wrapped around layer 3002 as seen in FIG. 32A, with cross-sectional taken along line D-D in FIG. 32B. One of skill in the art will appreciate the various strand material characteristics (e.g. diameter, tensile strength, etc.) and winding patterns that may be used.

An alternative embodiment is illustrated in FIGS. 33A-37B. This embodiment is similar to that previously described above, with the major difference being that after the cable has been wound, it is drawn thereby altering the surface finish and some of the mechanical characteristics. FIG. 33A illustrates the innermost layer 3202 which includes three wires 3204 wound together, as seen in the cross-section of FIG. 33B taken along the line A-A. FIG. 34A shows the next layer 3302 which includes nine wires 3304 wrapped around the innermost layer 3202. FIG. 34B shows a cross-section taken along line B-B. The next layer 3402 of wires are shown in FIG. 35A having ten wires 3404 wrapped around the previous layer 3302, as illustrated in the cross-section of FIG. 35B taken along line C-C. The outermost layer 3502 is shown in FIG. 36A and includes another ten wires 3504 wrapped around the previous layer 3402, with cross-section taken along line D-D in FIG. 36B. The assembly of four layers of wire are then drawn in order to alter the surface finish of the cable and to alter material properties of the finished cable assembly to a desired value. FIG. 37A illustrates the finished cable assembly 3602 with cross-section taken along line E-E in FIG. 37B. One of skill in the art will appreciate that other cable configurations may be used, and that these are only exemplary embodiments.

B. Delivery Catheter Shaft

Figure 38:
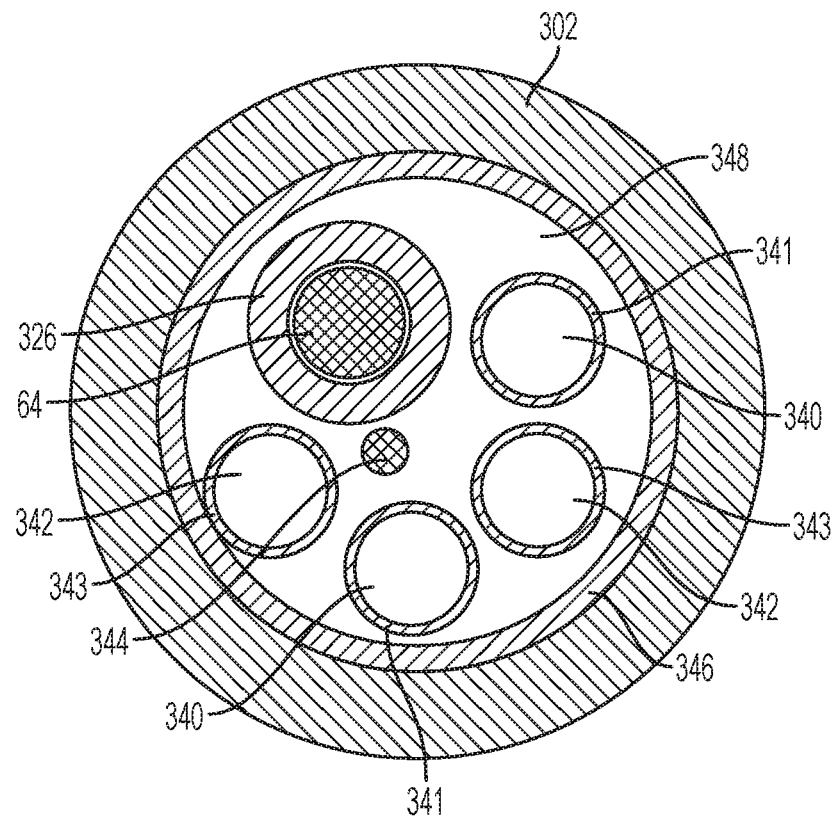
FIGS. 38-40 are cross-sectional views of embodiments of the shaft of the delivery catheter.

FIG. 38 illustrates a cross-sectional view of the delivery catheter shaft 302 of FIG. 25. In this embodiment, the shaft 302 has a tubular shape with inner lumen 348 and is comprised of a material which provides hoop strength while maintaining flexibility and kink resistance, such as a braided laminated material. Such material may include stainless steel braided or coiled wire embedded in a polymer such as polyurethane, polyester, Pebax, Grilamid TR55, and AESNO to name a few. To provide further support and hoop strength, a support coil 346 is disposed within the lumen 348 of shaft 302 as illustrated in FIG. 38.

Passing through the support coil 346 are a variety of elongated bodies, including tubular guides and cylindrical rods. For example, one type of tubular guide is a compression coil 326 extending through lumen 348 from the proximal end 322 to the distal end 324 of the shaft 302, and the actuator rod 64 extends through the compression coil 326. Therefore, the compression coil typically has a length in the range of 48 to 60 in. and an inner diameter in the range of 0.020 to 0.035 in. to allow passage of the actuator rod 64 therethrough. The actuator rod 64 is manipulable to rotate and translate within and relative to the compression coil 326. The compression coil 326 allows lateral flexibility of the actuator rod 64 and therefore the shaft 302 while resisting buckling and providing column strength under compression. The compression coil may be comprised of 304V stainless steel to provide these properties.

To provide additional tensile strength for the shaft 302 and to minimize elongation, a tension cable 344 may also pass through the support coil 346. The tension cable 344 extends through lumen 348 from the proximal end 322 to the distal end 324 of the shaft 302. Therefore, the tension cable 344 typically has a diameter in the range of 0.005 in. to 0.010 in. and a length in the range of 48 to 60 in. In preferred embodiments, the tension cable 344 is comprised of 304V stainless steel.

In addition, at least one lock line shaft 341 having a tubular shape may be present having a lock line lumen 340 through which lock lines 92 pass between the lock line handle 310 and the locking mechanism 106. The lock line shaft 341 extends through lumen 348 from the proximal end 322 to the distal end 324 of the shaft 302. Therefore, the lock line shaft 341 typically has a length in the range of 48 to 60 in., an inner diameter in the range of 0.016 to 0.030 in., and an outer diameter in the range of 0.018 to 0.034 in. In preferred embodiments, the lock line shaft 341 is comprised of a 304V stainless steel coil however other structures or materials may be used which provide kink resistance and compression strength.

Similarly, at least one proximal element line shaft 343 having a tubular shape may be present having a proximal element line lumen 342. Proximal element lines 90 pass through this lumen 342 between the proximal element line handle 312 and the proximal elements 16. Thus, the proximal element line shaft 343 extends through lumen 348 from the proximal end 322 to the distal end 324 of the shaft 302. Therefore, the proximal element line shaft 343 typically has a length in the range of 48 to 60 in., an inner diameter in the range of 0.016 to 0.030 in., and an outer diameter in the range of 0.018 to 0.034 in. In preferred embodiments, the proximal element line shaft 343 is comprised of a 304V stainless steel coil however other structures or materials may be used which provide kink resistance and compression strength.

In this embodiment, the elongated bodies (compression coil 326 enclosed actuator rod 64, tension cable 344, lock line shaft 342, proximal element line shaft 343) each "float" freely in inner lumen 348 within the support coil 346 and are fixed only at the proximal end 322 and distal end 324 of shaft 302. The lumen 348 is typically filled and flushed with heparinized saline during use. Alternatively or in addition, the lumen 348 may be filled with one or more fillers, such as flexible rods, beads, extruded sections, gels or other fluids. Preferably the fillers allow for some lateral movement or deflection of the elongated bodies within lumen 348 but in some cases may restrict such movement. Typically, the elongated bodies are fixed at the proximal and distal ends of the shaft and are free to move laterally and rotationally therebetween. Such freedom of movement of the elongated bodies provides the shaft 302 with an increased flexibility as the elongated bodies self-adjust and reposition during bending and/or torqueing of the shaft 302. It may be appreciated that the elongated bodies may not be fixed at the proximal and distal ends. The elongated bodies are simply unconstrained relative to the shaft 302 in at least one location so as to be laterally moveable within the lumen 348. Preferably the elongated bodies are unrestrained in at least a distal portion of the catheter, e.g. 5-15 cm from the distal end 324, so as to provide maximum flexibility in the distal portion.

Figure 39:
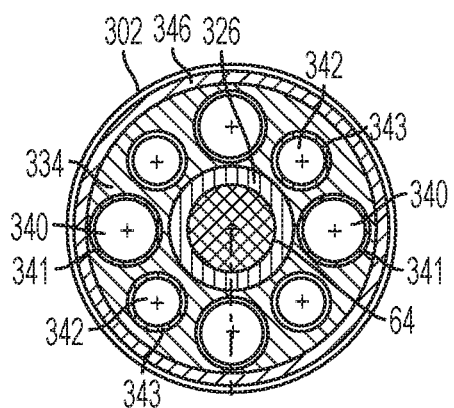

It may be appreciated, however, that alternate shaft 302 designs may also be used. For example, referring to FIG. 39, in this embodiment the shaft 302 again has a tubular shape with an inner lumen 348 and a support coil 346 disposed within the lumen 348 of shaft 302. Filling the inner lumen 348 within the support coil 346 is an extrusion 334 having lumens through which pass a variety of elongated bodies, including the compression coil 326 enclosed actuator rod 64, tension cable 344, lock line shafts 342, and proximal element line shafts 343, as shown. The support coil 346 and elongated bodies may have the same geometries and be comprised of the same materials as described above in relation to FIG. 38.

Figure 40:
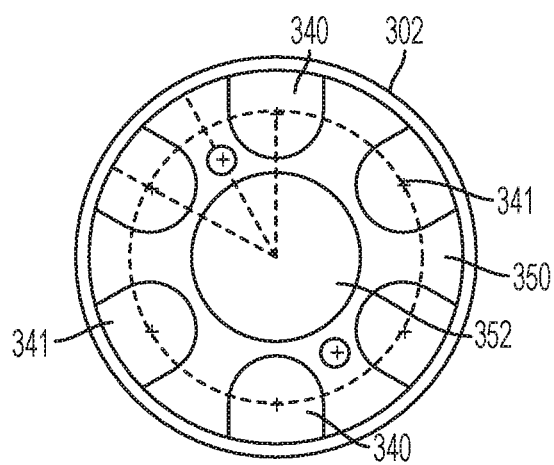

Alternatively, as shown in FIG. 40, the shaft 302 may include an internal partition 350 to create multiple lumens within the shaft 302. For example, the partition 350 may have a central lumen 352 for passage of the actuator rod 64, optionally surrounded by the compression coil 326. In addition, the partition 350 may also create at least one lock line lumen 340 for passage of a lock line 92 and at least one proximal element line lumen 341 for passage of a proximal element line 90. Optionally, each of the lumens defined by partition 350 may be lined with a kink-resistant element, such as a coil as in previous embodiments.

Figure 40A:
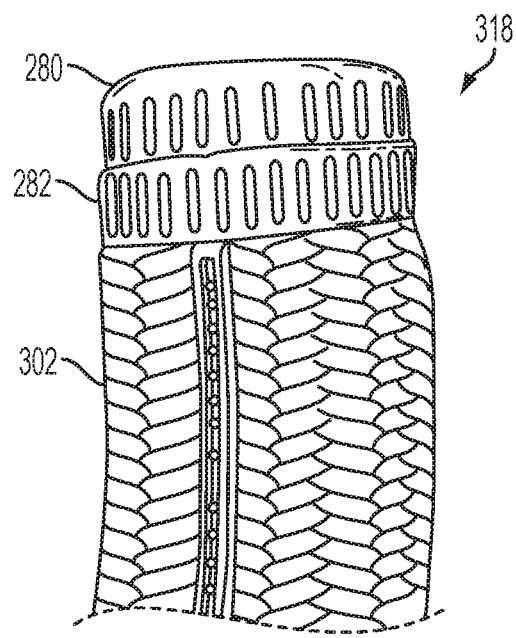
FIGS. 40A-40B illustrate embodiments of the nose of the shaft of the delivery catheter.
Figure 40B:
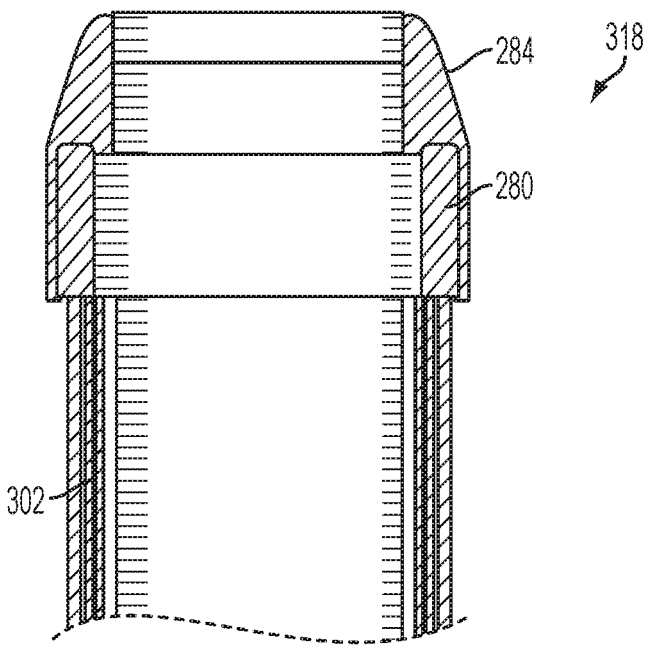

FIGS. 40A-40B illustrate embodiments of the nose 318 of the shaft 302. In FIG. 40A, the nose 318 comprises a tip ring 280 and a lock ring 282. In preferred embodiments, Epoxy and PEBAX are deposited between the tip ring 280 and the lock ring 282 to bond them together. The lock ring 282 has a geometry to mate with the tip ring 280 to maintain relative alignment between the two. FIG. 40B illustrates another embodiment of the nose 318 of the shaft 302. Here, the tip ring 280 is covered by a soft tip 284 to provide a more atraumatic tip and a smoother transition to the shaft.

C. Lock Line Arrangements

As mentioned previously, when lock lines 92 are present, the lines 92 pass through at least one lock line lumen 340 between the lock line handle 310 and the locking mechanism 106. The lock lines 92 engage the release harnesses 108 of the locking mechanism 106 to lock and unlock the locking mechanism 106 as previously described. The lock lines 92 may engage the release harnesses 108 in various arrangements, examples of which are illustrated in FIGS. 41A-41C. In each embodiment, two lock line lumens 340 are present within the shaft 302 of the delivery catheter 300 terminating at the nose 318. The lumens 340 are disposed on alternate sides of the actuator rod 64 so that each lumen 340 is directed toward a release harness 108.

FIG. 41A illustrates an embodiment wherein two lock lines 92, 92' pass through a single lock line lumen 340 and are threaded through a release harness 108 on one side of the actuator rod 64 (the actuator rod 64 is shown without surrounding housing such as coupling structure, for clarity). The lock lines 92, 92' are then separated so that each lock line passes on an opposite side of the actuator rod 64. The lock lines 92, 92' then pass through the release harness 108' on the opposite side of the actuator rod 64 and continue together passing through a another single lock line lumen 340'. This lock line arrangement is the same arrangement illustrated in FIG. 26.

FIG. 41B illustrates an embodiment wherein one lock line 92 passes through a single lock line lumen 340, is threaded through a release harness 108 on one side of the actuator rod 64, and is returned to the lock line lumen 340. Similarly, another lock line 92' passes through another single lock line lumen 340', is threaded through a different release harness 108' located on the opposite side of the actuator rod 64, and is returned to the another single lock line lumen 340'.

FIG. 41C illustrates an embodiment wherein both lock lines 92, 92' pass through a single lock line lumen 340. One lock line 92 is threaded through a release harness 108 on one side of the actuator rod 64 and is then passed through another lock line lumen 340' on the opposite side of the actuator rod 64. The other lock line 92' is threaded through another release harness 108' on the other side of the actuator rod 64' and is then passed through the another lock line lumen 340' with the previous lock line 92.

It may be appreciated that a variety of lock line arrangements may be used and are not limited to the arrangements illustrated and described above. The various arrangements allow the harnesses 108 to be manipulated independently or jointly, allow various amounts of tension to be applied and vary the force required for removal of the lock lines when the fixation device is to be left behind. For example, a single lock line passing through one or two lumens may be connected to both release harnesses for simultaneous application of tension.

D. Proximal Element Line Arrangements

As mentioned previously, when proximal element lines 90 are present, the lines 90 pass through at least one proximal element line lumen 342 between the proximal element line handle 312 and at least one proximal element 16. The proximal element lines 90 engage the proximal elements 16 to raise or lower the element 16 as previously described. The proximal element lines 90 may engage the proximal elements 16 in various arrangements, examples of which are illustrated in FIGS. 42A-42B. In each embodiment, two proximal element line lumens 342 are present within the shaft 302 of the delivery catheter 300 terminating at the nose 318. The lumens 342 are disposed on alternate sides of the actuator rod 64 (the actuator rod 64 is shown without surrounding housing such as coupling structure, for clarity) so that each lumen 342 is directed toward a proximal element 16.

FIG. 42A illustrates an embodiment wherein one proximal element line 90 passes through a single proximal element line lumen 342. The proximal element line 90 is threaded through an eyelet 360 of a proximal element 16 on one side of the actuator rod 64, passes over the actuator rod 64 and is threaded through an eyelet 360' of another proximal element 16' on the other side of the actuator rod 64. The proximal element line 90 then passes through another single proximal element line lumen 342'. This proximal element line arrangement is the same arrangement illustrated in FIG. 26.

FIG. 42B illustrates an embodiment wherein one proximal element line 90 passes through a single proximal element line lumen 342, is threaded through an eyelet 360 of a proximal element 16 on one side of the actuator rod 64, and is returned to the proximal element line lumen 342. Similarly, another proximal element line 90' passes through another single proximal element line lumen 342' on the opposite side of the actuator rod 64, and is returned to the another single proximal element line lumen 342'.

It may be appreciated that a variety of proximal element line arrangements may be used and are not limited to the arrangements illustrated and described above. The various arrangements allow the proximal elements to be manipulated independently or jointly, allow various amounts of tension to be applied and vary the force required for removal of the proximal element lines when the fixation device is to be left behind. For example, a single proximal element line passing through one or two lumens in shaft 302 may be used for simultaneous actuation of both proximal elements.

E. Main Body of Handle

Figure 43:
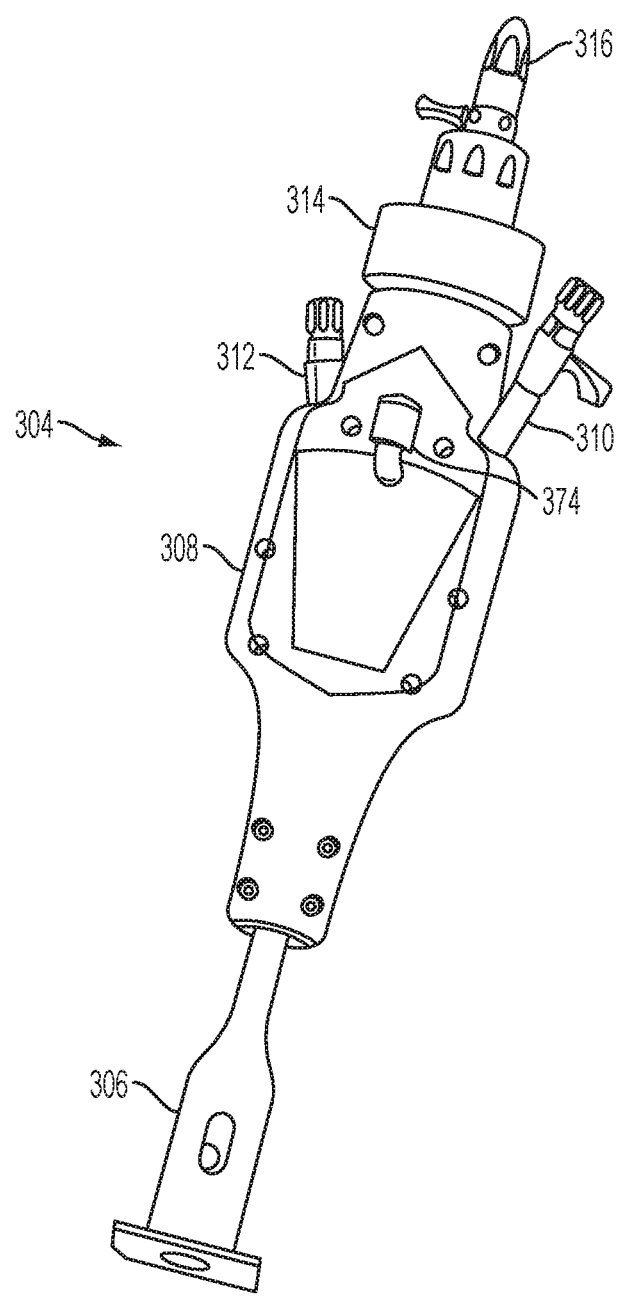
FIG. 43 illustrates an embodiment of the handle of the delivery catheter.

FIG. 43 illustrates an embodiment of the handle 304 of the delivery catheter 300. As mentioned previously, the actuator rod handle 316, actuator rod control 314, proximal element line handle 312 and lock line handle 310 are all joined with the main body 318. The handle 304 further includes a support base 306 connected with the main body 308. The main body 308 is slideable along the support base 306 to provide translation of the shaft 302 and the main body 308 is rotatable around the support base 306 to rotate the shaft.

Figure 44:
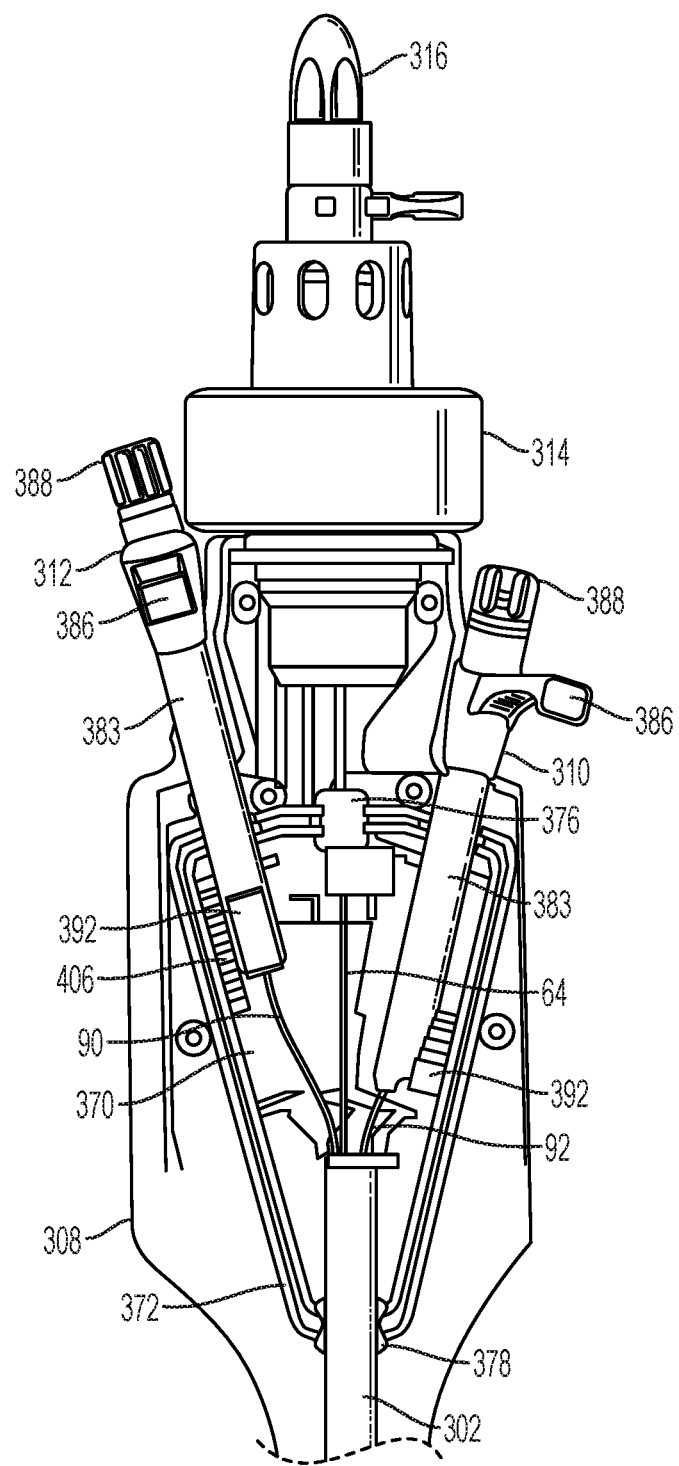
FIG. 44 is a cross-sectional view of the main body of the handle.

FIG. 44 provides a partial cross-sectional view of the main body 308 of the handle 304 depicted in FIG. 43. As shown, the main body 308 includes a sealed chamber 370 within which the actuator rod 64, proximal element lines 90 and lock lines 92 are guided into the shaft 302. The sealed chamber 370 is in fluid communication with the inner lumen 348 of shaft 302 and is typically filled with saline and flushed with heparin or heparinized saline. The sealed chamber 370 has a seal 372 along its perimeter to prevent leakage and the introduction of air to the chamber 370. Any air in the chamber 370 may be bled from the chamber 370 by one or more luers 374 which pass through the main body 308 into the chamber 370 as illustrated in FIG. 43. In this embodiment, the handle 304 includes two such luers 374, one on each side of the main body 308 (second luer symmetrically positioned on backside of main body 308 in FIG. 43, hidden from view). Referring now to FIG. 44, the sealed chamber 370 also has various additional seals, such as an actuator rod seal 376 which surrounds the actuator rod 64 where the actuator rod 64 enters the sealed chamber 370, and a shaft seal 378 which surrounds the shaft 302 where the shaft 302 enters the sealed chamber 370.

F. Lock Line Handle and Proximal Element Line Handle

As mentioned previously, the lock lines 92 may be may be extended, retracted, loaded with various amounts of tension or removed using the lock line handle 310. Likewise, the proximal element lines 90 may be extended, retracted, loaded with various amounts of tension or removed using the proximal element line handle 312. Both of these handles 310, 312 may be similarly designed to manipulate the appropriate lines 90, 92 passing therethrough.

Figure 45:
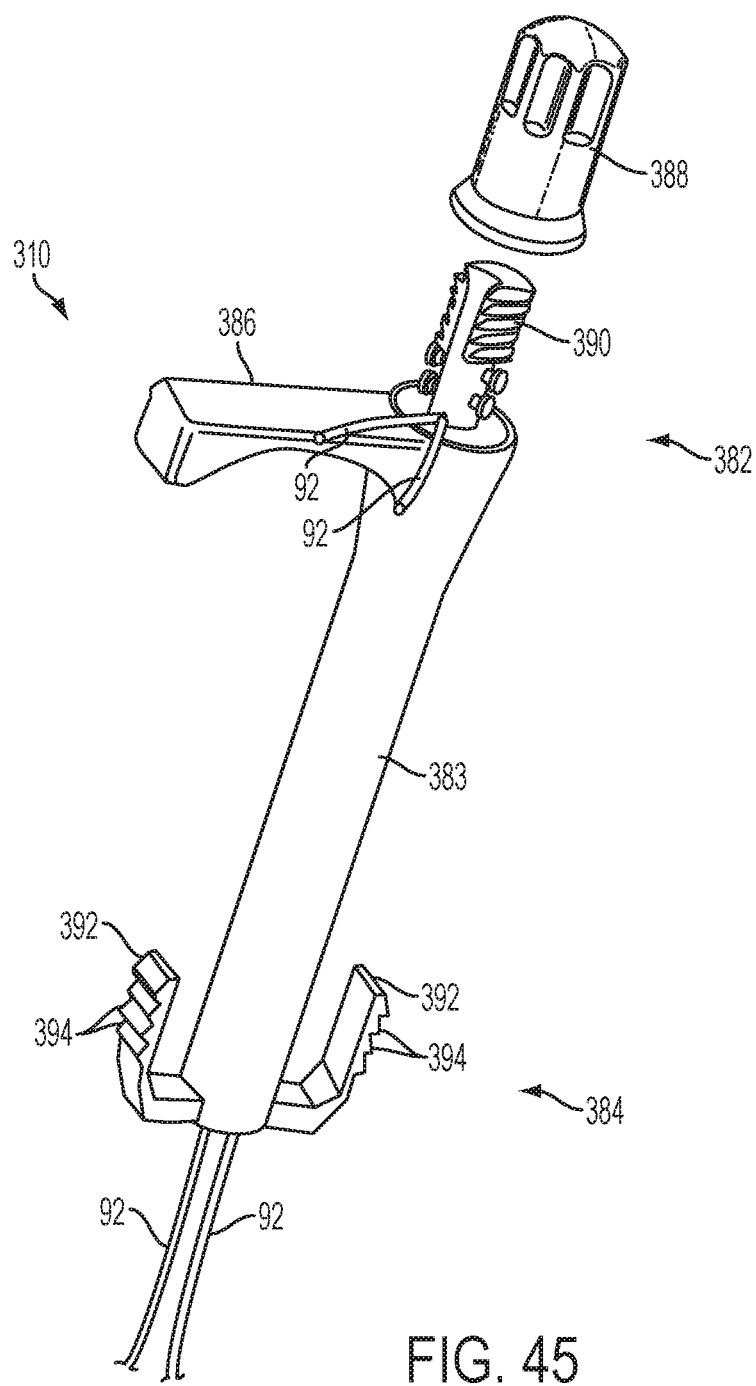
FIG. 45 illustrates an embodiment of a lock line handle.

FIG. 45 illustrates an embodiment of a lock line handle 310 having lock lines 92 passing therethrough. The lock line handle 310 has a distal end 384, a proximal end 382 and an elongate shaft 383 therebetween. The distal end 382 is positionable within the sealed chamber 370 so that the proximal end 382 extends out of the chamber 370, beyond the main body 308. The free ends of the lock lines 92 are disposed near the proximal end 382, passing through the wall of the handle 310 near a threaded nub 390. The handle 310 further includes a cap 388 which is positionable on the nub 309. Internal threading with the cap 388 mates with the threading on the threaded nub 390 so that the cap 388 holds the free ends of the lock lines 92 between the cap 388 and the nub 390 and/or other portions of the handle 310 by friction. The lock lines 92 pass through a central lumen (not shown) of the elongate shaft 383, extend through the sealed chamber 370 (as shown in FIG. 44) and extend through the shaft 302 to the locking mechanism 106.

Disposed near the distal end 384 of the handle 310 is at least one wing 392. In the embodiment of FIG. 45, two wings 392 are present, each wing 392 disposed on opposite sides of the elongate shaft 383. The wings 392 extend radially outwardly and curve proximally so that a portion is parallel to the elongate shaft 383, as shown. It may be appreciated that the wings 392 may alternatively have the shape of solid or continuous protrusions which extend radially and have a portion which is parallel to the elongate shaft 383. The wings 392 are used to hold the lock line handle 310 in a desired position which in turn holds the lock under a desired load of tension, as will be described further below. The handle 310 also includes a finger grip 386 near the proximal end 382 which extends radially outwardly in alignment with the radial extension of the at least one wing 392. Thus, the user may determine the orientation of the wings 392 within the sealed chamber 370 from the orientation of the finger grip 386 outside of the main body 308. The finger grip 386 may also serve an ergonomic purpose to assist in manipulating the handle 310.

Figure 45A:
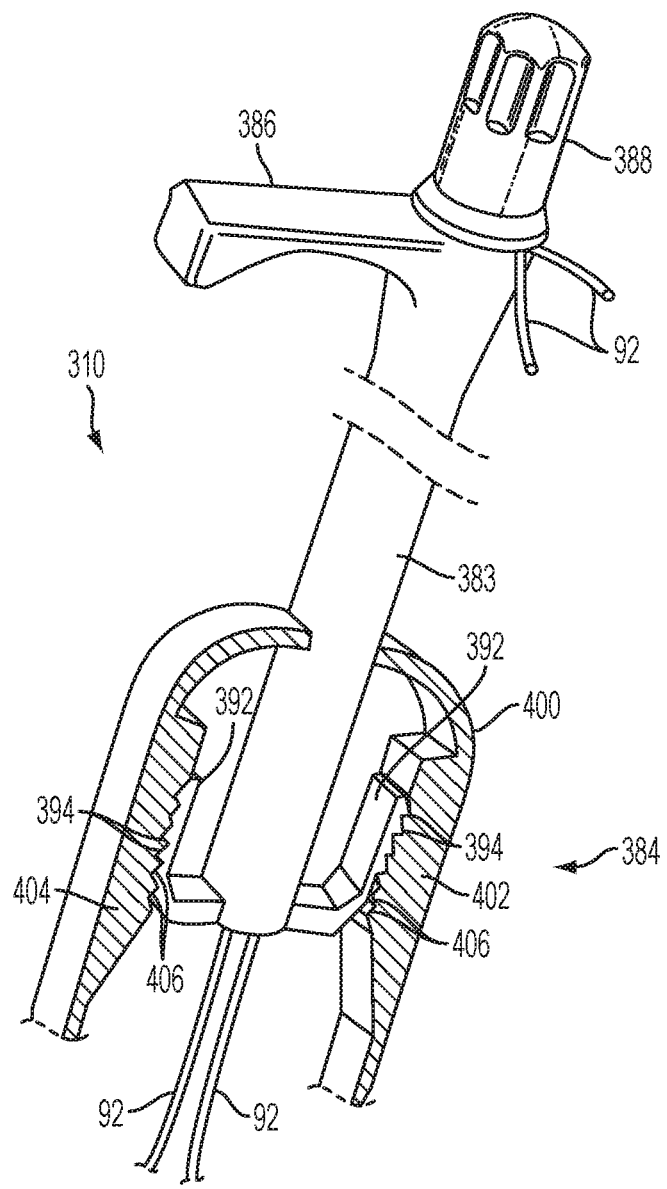
FIG. 45A illustrates the lock line handle of FIG. 45 positioned within a semi-tube which is disposed within the sealed chamber.

The portion of the wings 392 parallel to the elongate shaft 383 have grooves or serrations 394. The serrations 394 are used to apply tension to the lock lines 92. As shown in FIG. 45A, the lock line handle 310 is positioned within a semi-tube 400 which is disposed within the sealed chamber 370.

Figure 46A:
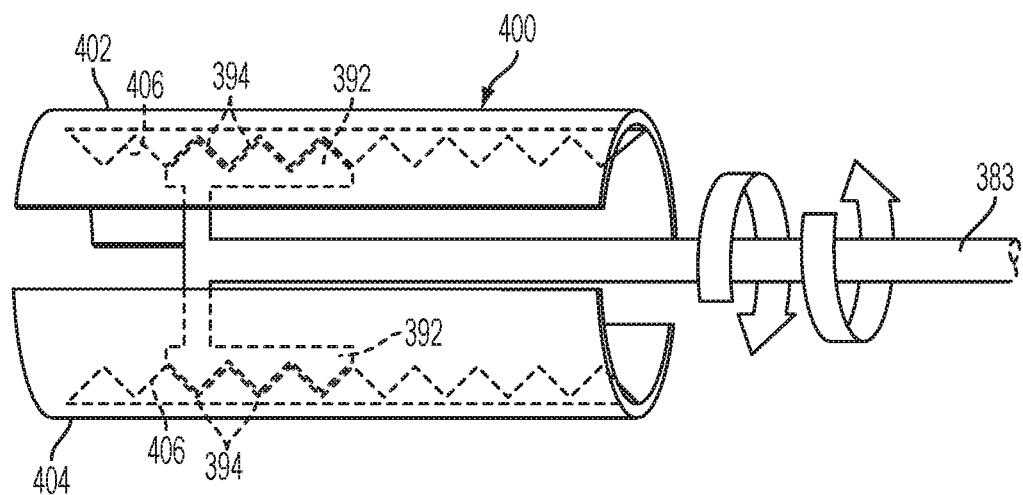
FIGS. 46A-46B illustrate a mechanism for applying tension to lock lines.
Figure 46B:
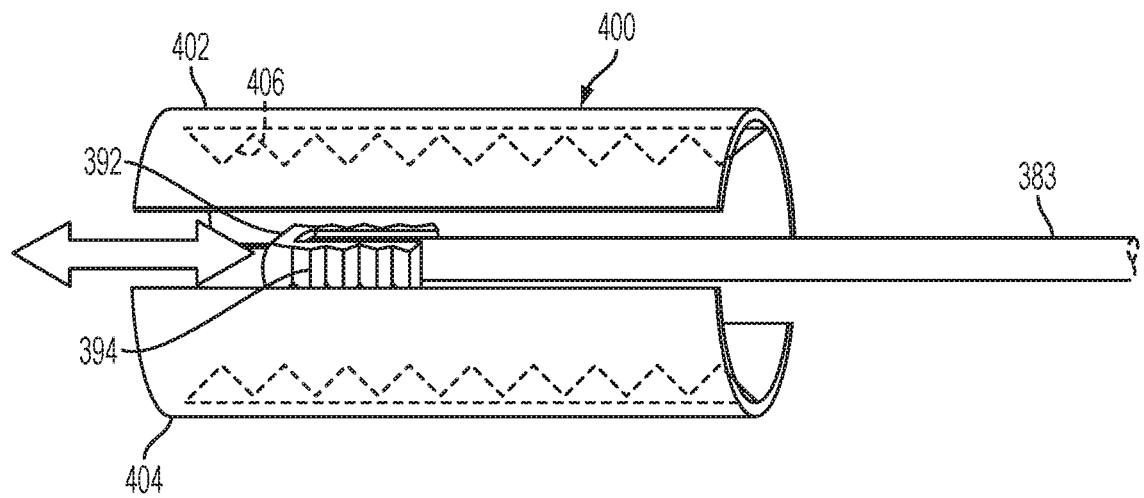

The semi-tube 400 comprises a top half 402 and a bottom half 404, each half 402, 404 having grooves or serrations 406 which mate with the serrations 394 of the wings 392. Thus, when the wings 392 are rotated to mate the serrations 394, 406, as shown in FIG. 46A, the elongate shaft 383 is held in place. Likewise, the wings 392 may be rotated, as shown in FIG. 46B, so that the wings 392 are disposed between the halves 402, 404 and the serrations 394, 406 are disengaged. In this position, the shaft 383 may be translated to apply or release tension in the lock lines 92. Thus, tension in the lines 92 may be adjusted by rotating the shaft 383 to disengage the serrations 394, 406, translating the shaft 383 and then rotating the shaft 383 back to reengage the serrations 394, 406. Alternatively, the finger grip 386 may be pulled to apply tension to the lock lines 92. Pulling the finger grip 386 translates the lock line handle 310 within the semi-tube 400. Such translation is achievable due to angling of the serrations 394, 406 and flexibility of wings 382. However, the angling of the serrations 394, 406 prevents translation in the opposite direction, i.e. by pushing the finger grip 386. Therefore, to release tension from the lock lines 92, the shaft 383 is rotated to disengage the serrations 394, 406, allowing translation of the shaft 383, and then the shaft 383 is rotated back to reengage the serrations 394, 406.

To remove the lock lines 92, the cap 388 is removed from the threaded nub 390 exposing the free ends of the lock lines 92. If one lock line 92 is present having two free ends, continuous pulling on one of the free ends draws the entire length of lock line 92 out of the catheter 300. If more than one lock line 92 is present, each lock line 92 will have two free ends. Continuous pulling on one of the free ends of each lock line 92 draws the entire length of each lock line 92 out of the catheter 300.

It may be appreciated that the proximal element line handle 312 has corresponding features to the lock line handle 310 and operates in the same manner as illustrated in FIGS. 45A, 46A-46B. It may also be appreciated that other mechanisms may be used for manipulating the lock lines 92 and proximal element lines 90, such as including buttons, springs, levers and knobs.

G. Actuator Rod Control and Handle

Figure 47:
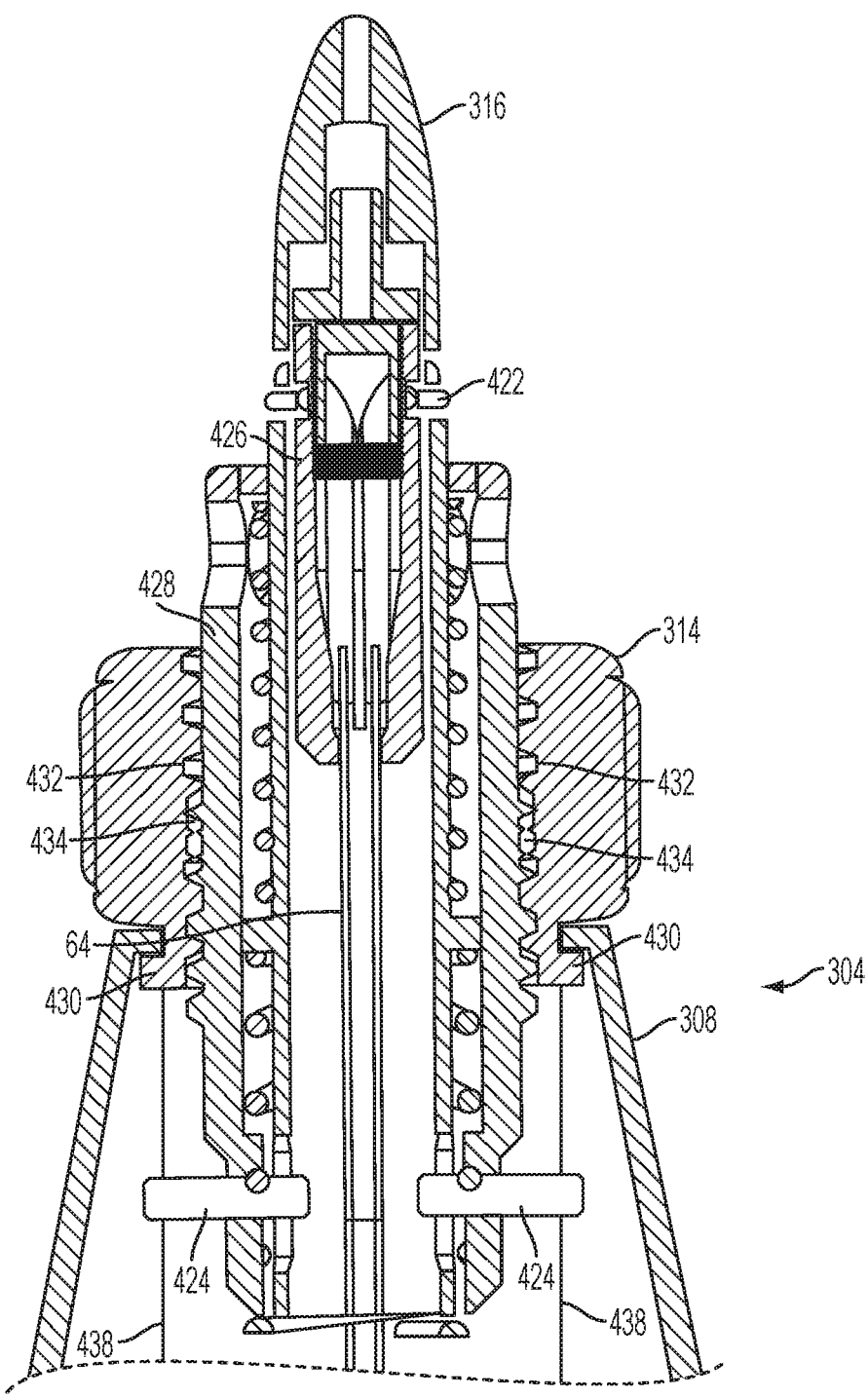
FIGS. 47 and 47A-47B illustrate features of the actuator rod control and handle.

The actuator rod 64 may be manipulated using the actuator rod control 314 and the actuator rod handle 316. FIG. 47 provides a cross-sectional view of a portion of the handle 304 which includes the actuator rod control 314 and the actuator rod handle 316. The actuator rod handle 316 is located at the proximal end of the handle 314. The actuator rod handle 316 is fixedly attached to the proximal end of the actuator rod 64. The actuator rod 64 is inserted through a collet 426 which is disposed within a holder 428 as shown. The holder 428 has external threads 434 which mate with internal threads 432 of the actuator rod control 314. Thus, rotation of the actuator rod control 314 causes the holder 428 to translate along the actuator rod control 314 by action of the threading, as will be described in more detail below. The actuator rod control 314 is rotatably coupled with the main body 308 of the handle 304 and is held in place by a lip 430.

Figure 47A:
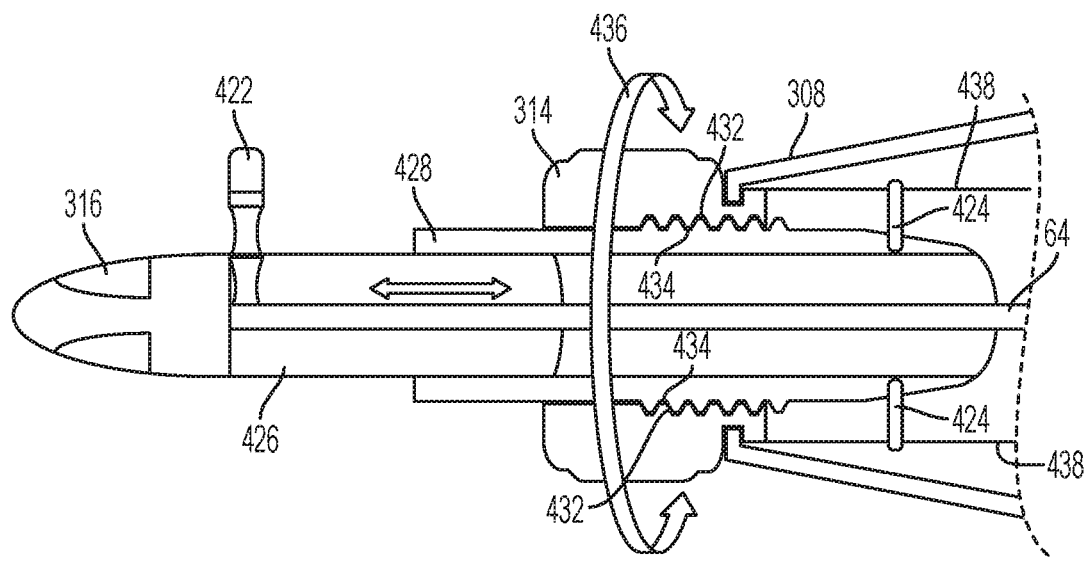

Referring to FIG. 47A, the actuator rod control 314 may be manually rotated in a clockwise or counter clockwise direction, as indicated by arrow 436. Rotation of the actuator rod control 314 translates (extends or retracts) the actuator rod 64 to manipulate the distal elements 18 of the fixation device 14. Specifically, rotation of the actuator rod control 314 causes the external threads 434 of the adjacent holder 428 to translate along the mated internal threads 432 of the actuator rod control 314. Rotation of the holder 428 itself is prevented by holding pins 424 which protrude from the holder 428 and nest into grooves 438 in the main body 308 of the handle 304. As the holder 428 translates, each holding pin 424 translates along its corresponding groove 438. Since the collet 426 is attached to the holder 428, the collet 426 translates along with the holder 428. To simultaneously translate the actuator rod 64, the actuator rod 64 is removably attached to the collet 426 by a pin 422. The pin 422 may have any suitable form, including a clip-shape which partially wraps around the collet 426 as illustrated in FIG. 47. Thus, rotation of the actuator rod control 314 provides fine control of translation of the actuator rod 64 and therefore fine control of positioning the distal elements 18.

Figure 47B:
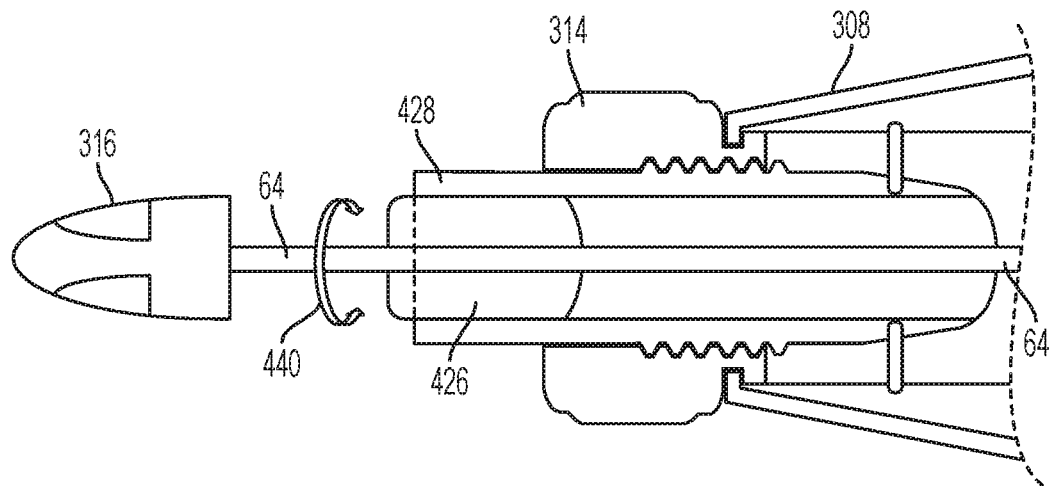

Referring to FIG. 47B, removal of the pin 422, as shown, allows disengagement of the actuator rod handle 316 and fixedly attached actuator rod 64 from the collet 426. Once disengaged, the actuator rod 64 may be rotated, as indicated by arrow 440, by manually rotating the actuator rod handle 316. As described previously, rotation of the actuator rod 64 engages or disengages the threaded joiner 332 of the delivery catheter 300 from the threaded stud 74 of the fixation device 14. This is used to attach or detach the fixation device 14 from the delivery catheter 300. In addition, when the actuator rod 64 is in the disengaged state, the actuator rod 64 may optionally be retracted and optionally removed from the catheter 300 by pulling the actuator rod handle 316 and withdrawing the actuator rod 64 from the handle 304.

Depending on the application, the location of the target site, and the approach selected, the devices of the invention may be modified in ways well known to those of skill in the art or used in conjunction with other devices that are known in the art. For example, the delivery catheter may be modified in length, stiffness, shape and steerability for a desired application. Likewise, the orientation of the fixation device relative to the delivery catheter may be reversed or otherwise changed. The actuation mechanisms may be changed to be driven in alternate directions (push to open, pull to close, or pull to open, push to close). Materials and designs may be changed to be, for example, more flexible or more rigid. And the fixation device components may be altered to those of different size or shape. Further, the delivery catheter of the present invention may be used to deliver other types of devices, particularly endovascular and minimally invasive surgical devices used in angioplasty, atherectomy, stent-delivery, embolic filtration and removal, septal defect repair, tissue approximation and repair, vascular clamping and ligation, suturing, aneurysm repair, vascular occlusion, and electrophysiological mapping and ablation, to name a few. Thus, the delivery catheter of the present invention may be used for applications in which a highly flexible, kink-resistant device is desirable with high compressive, tensile and torsional strength.

H. Pusher Handle Design

Figure 70:
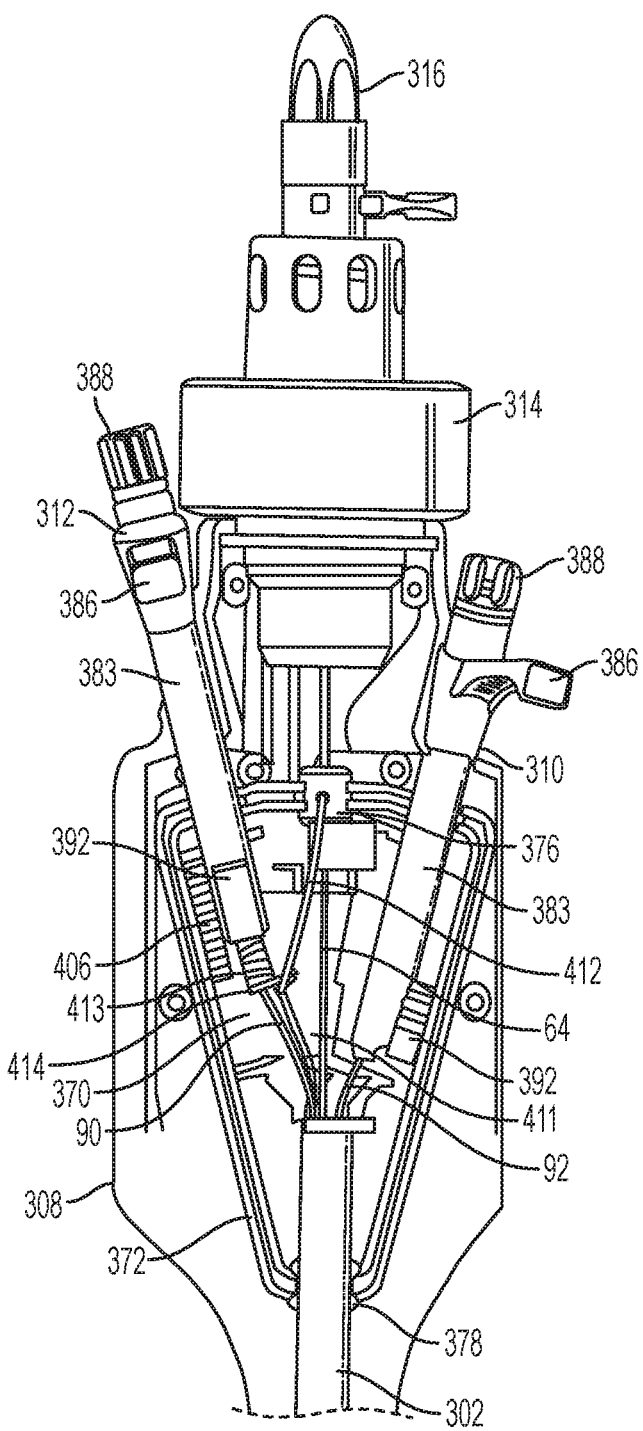
FIG. 70 illustrates a handle in accordance with an exemplary embodiment.

After engaging successfully grasping the leaflets, usually at an angle between 120 and 180 degrees, the actuator rod 64 is manually rotated to manipulate the distal elements of the fixation device. This moves the distal elements proximally to an angle, such as 60 degrees as shown in FIG. 11B. However, with reference to FIG. 15B, the gripper pusher 81 and the proximal element actuators 90 also need to be retracted as angle between the distal elements 18 is reduced. FIG. 70 shows an embodiment of a handle that coordinates these movements. As shown in the figure, the proximal element line handle 312 of FIG. 44 is fitted with a spring loaded pusher attachment 414 that is connected to a gripper pusher actuator 411 that extends to the gripper pusher 81 of the fixation device. This spring loaded pusher attachment 414 surrounds, but moves independently of the proximal element line 90. The spring 413 functions to provide a tension on the proximal element line 90 by exerting a small force on the gripper pusher 81 relative to the gripper pusher actuator. Further, a gripper pusher actuator wire 412 is coupled to the actuator rod 64 so that when the actuator rod 64 is actuated to close the distal elements 18, the gripper pusher 81 is retracted. As shown in FIG. 70, the pusher actuator wire 412 interacts with the spring loaded pusher attachment 414 to retract the spring loaded pusher attachment 414 when the distal elements 18 are closed. On the other hand, the distal end of the pusher actuator wire 412 is configured to slide distally with respect to the spring loaded pusher attachment 414 so that the distal movement of the gripper pusher 81 is independent of the movement of the distal elements 18. This permits separation between the proximal elements 16 and the distal elements 18 to aid in grasping leaflets. Lastly, due to the spring coupling between the spring loaded pusher attachment 414 and the proximal element line handle 312, the proximal element actuator 90 is also retracted in combination with the retracting of the gripper pusher actuator 411. Notably, due to the spring coupling via the spring 413, the proximal element actuator 90 is permitted further travel than the gripper pusher actuator 411. This additional travel is permitted via expansion of the spring 413 and functions to remove slack in the proximal element actuator as the angle between the proximal elements 16 and the distal elements 18 is reduced.

V. Multi-Catheter Guiding System

A. Overview of Guiding System

Figure 48:
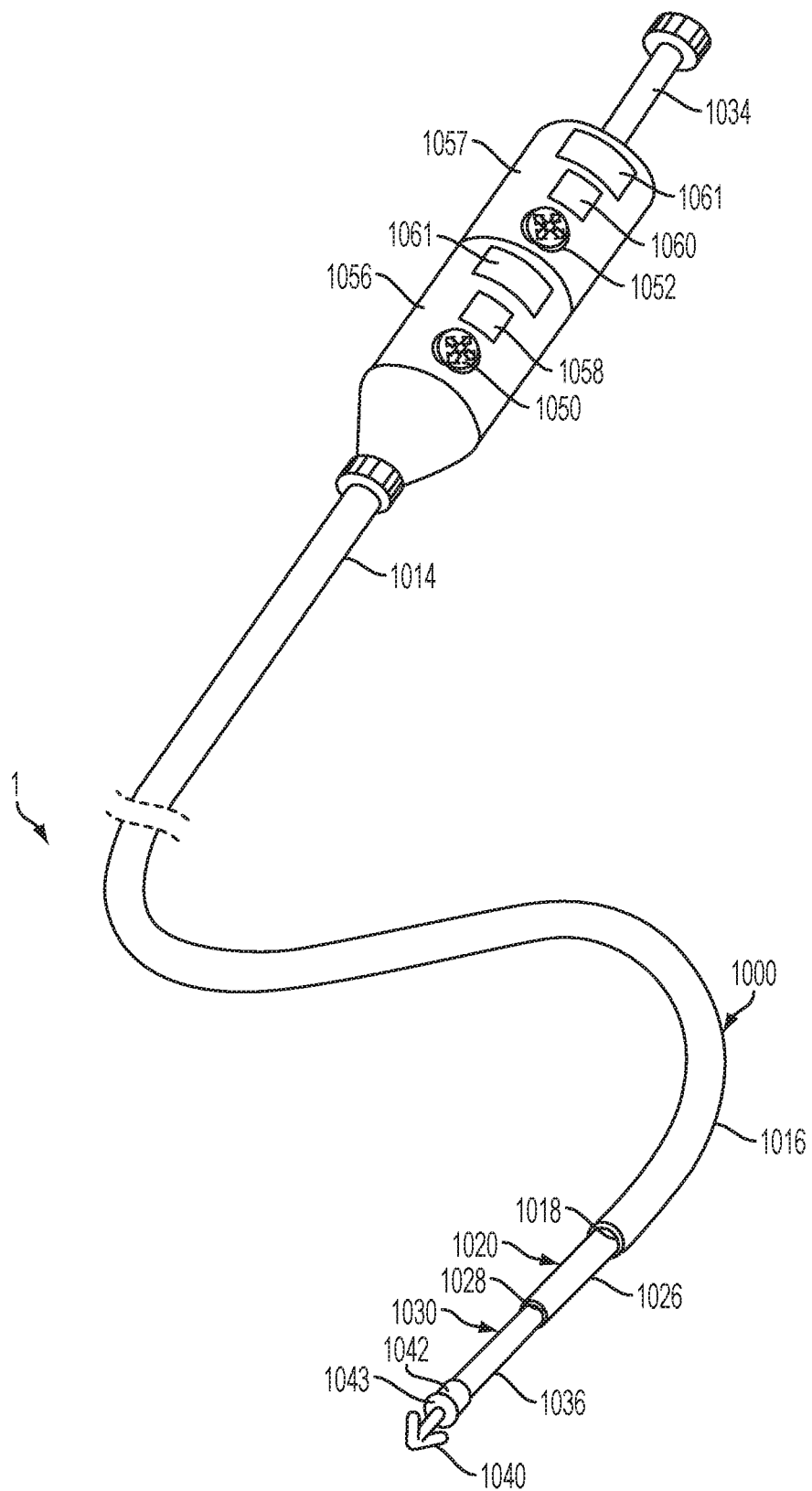
FIG. 48 is a perspective view of an embodiment of a multi-catheter guiding system of the present invention, and an interventional catheter positioned therethrough.

Referring to FIG. 48, an embodiment of a multi-catheter guiding system 1 of the present invention is illustrated. The system 1 comprises an outer guide catheter 1000, having a proximal end 1014, a distal end 1016, and a central lumen 1018 therethrough, and an inner guide catheter 1020, having a proximal end 1024, distal end 1026 and central lumen 1028 therethrough, wherein the inner guide catheter 1020 is positioned coaxially within the central lumen 1018 of the outer guide catheter 1000, as shown. The distal ends 1016, 1026 of catheters 1000, 1020, respectively, are sized to be passable to a body cavity, typically through a body lumen such as a vascular lumen. Thus, the distal end 1016 preferably has an outer diameter in the range of approximately 0.040 in. to 0.500 in., more preferably in the range of 0.130 in. to 0.320 in. The central lumen 1018 is sized for the passage of the inner guide catheter 1020; the distal end 1026 preferably has an outer diameter in the range of approximately 0.035 in. to 0.280 in., more preferably 0.120 in to 0.200 in. The central lumen 1028 is sized for the passage of a variety of devices therethrough. Therefore, the central lumen 1028 preferably has an inner diameter in the range of approximately 0.026 in. to 0.450 in., more preferably in the range of 0.100 in. to 0.180 in.

FIG. 48 illustrates an interventional catheter 1030 positioned within the inner guide catheter 1020 which may optionally be included in system 1, however other interventional devices may be used. The interventional catheter 1030 has a proximal end 1034 and a distal end 1036, wherein an interventional tool 1040 is positioned at the distal end 1036. In this embodiment, the interventional tool 1040 comprises a detachable fixation device or clip. Optionally, the interventional catheter 1030 may also include a nosepiece 1042 having a stop 1043, as shown. The stop 1043 prevents the interventional tool 1040 from entering the central lumen 1028 of the inner guide catheter 1020. Thus, the interventional catheter 1030 may be advanced and retracted until the stop 1043 contacts the distal end 1026 of the inner guiding catheter 1020 preventing further retraction. This may provide certain advantages during some procedures. It may be appreciated that in embodiments which include such a stop 1043, the interventional catheter 1030 would be pre-loaded within the inner guide catheter 1020 for advancement through the outer guiding catheter 1000 or both the interventional catheter 1030 and the inner guiding catheter 1020 would be pre-loaded into the outer guiding catheter 1000 for advancement to the target tissue. This is because the stop 1043 prevents advancement of the interventional catheter 1030 through the inner guiding catheter 1020.

The outer guide catheter 1000 and/or the inner guide catheter 1020 are precurved and/or have steering mechanisms, embodiments of which will be described later in detail, to position the distal ends 1016, 1026 in desired directions. Precurvature or steering of the outer guide catheter 1000 directs the distal end 1016 in a first direction to create a primary curve while precurvature and/or steering of the inner guide catheter 1020 directs distal end 1026 in a second direction, differing from the first, to create a secondary curve. Together, the primary and secondary curves form a compound curve. Advancement of the interventional catheter 1030 through the coaxial guide catheters 1000, 1020 guides the interventional catheter 1030 through the compound curve toward a desired direction, usually in a direction which will allow the interventional catheter 1030 to reach its target.

Steering of the outer guide catheter 1000 and inner guide catheter 1020 may be achieved by actuation of one or more steering mechanisms. Actuation of the steering mechanisms is achieved with the use of actuators which are typically located on handles connected with each of the catheters 1000, 1020. As illustrated in FIG. 48, handle 1056 is connected to the proximal end 1014 of the outer guide catheter 1000 and remains outside of the patient's body during use. Handle 1056 includes steering actuator 1050 which may be used to bend, arc or reshape the outer guide catheter 1000, such as to form a primary curve. Handle 1057 is connected to the proximal end (not shown) of the inner guide catheter 1020 and may optionally join with handle 1056 to form one larger handle, as shown. Handle 1057 includes steering actuator 1052 which may be used to bend, arc or reshape the inner guide catheter 1020, such as to form a secondary curve and move the distal end 1026 of the inner guide catheter 1020 through an angle theta, as will be described in a later section.

In addition, locking actuators 1058, 1060 may be used to actuate locking mechanisms to lock the catheters 1000, 1020 in a particular position. Actuators 1050, 1052, 1058, 1060 are illustrated as buttons, however it may be appreciated that these and any additional actuators located on the handles 1056, 1057 may have any suitable form including knobs, thumbwheels, levers, switches, toggles, sensors or other devices. Other embodiments of the handles will be described in detail in a later section.

In addition, the handle 1056 may include a numerical or graphical display 1061 of information such as data indicating the position the catheters 1000, 1020, or force on actuators. It may also be appreciated that actuators 1050, 1052, 1058, 1060 and any other buttons or screens may be disposed on a single handle which connects with both the catheters 1000, 1020.

B. Example Positions

Figure 49A:
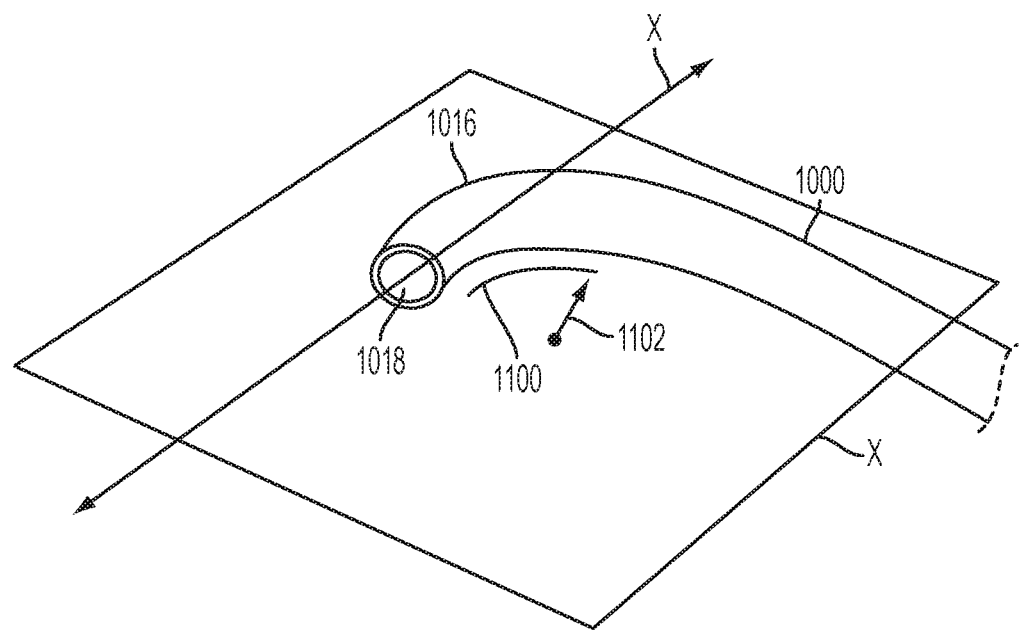
FIG. 49A illustrates a primary curvature in an outer guide catheter.

FIGS. 49A-49D illustrate examples of positions that the catheters 1000, 1020 may hold. Referring to FIG. 49A, the outer guide catheter 1000 may be precurved and/or steered into a position which includes a primary curve 1100. The primary curve 1100 typically has a radius of curvature 1102 in the range of approximately 0.125 in. to 1.000 in., preferably in the range of approximately 0.250 in. to 0.500 in. or forms a curve in the range of approximately 0° to 120°. As shown, when the position includes only a primary curve 1100, the distal end 16 lies in a single plane X. An axis x, transversing through the center of the central lumen 18 at the distal end 16, lies within plane X.

Figure 49B:
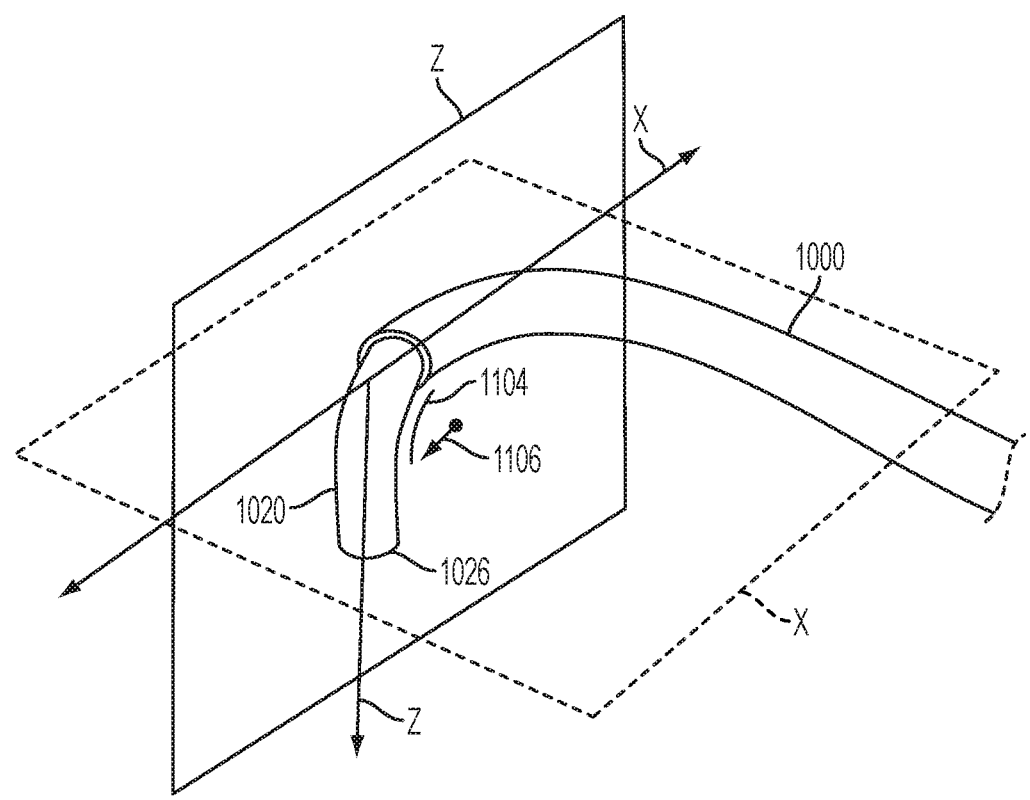
FIG. 49B illustrates a secondary curvature in an inner guide catheter.

Referring to FIG. 49B, the inner guide catheter 1020 extends through the central lumen 1018 of the outer guide catheter 1000. The inner guide catheter 1020 may be precurved and/or steered into a position which includes a secondary curve 1104. The secondary curve 1104 typically has a radius of curvature 10600 in the range of approximately 0.050 in. to 0.750 in., preferably in the range of approximately 0.125 in. to 0.250 in. or forms a curve in the range of approximately 0° to 180°. The secondary curve 1104 can lie in the same plane as the primary curve 1100, plane X, or it can lie in a different plane, such as plane Z as shown. In this example, plane Z is substantially orthogonal to plane X. Axis z, transversing through the center of the central lumen 1028 of the inner guide catheter 1020 at the distal end 1026, lies within plane Z. In this example, axis x and axis z are at substantially 90 degree angles to each other; however, it may be appreciated that axis x and axis z may be at any angle in relation to each other. Also, although in this example the primary curve 1100 and the secondary curve 1104 lie in different planes, particularly in substantially orthogonal planes, the curves 1100, 1104 may alternatively lie in the same plane.

Figure 49C:
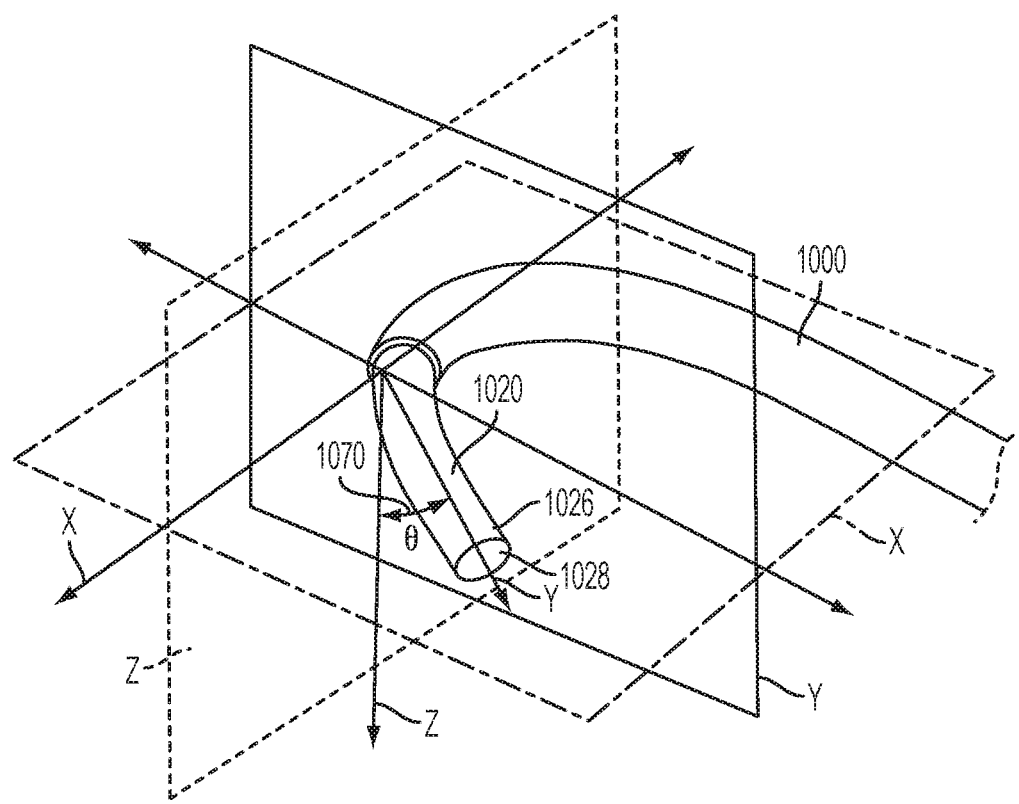
FIGS. 49C-49D illustrate example movement of an inner guide catheter through angle thetas.

Referring now to FIG. 49C, the inner guide catheter 1020 may be further manipulated to allow the distal end 1026 to move through an angle theta 1070. The angle theta 1070 is in the range of approximately −180° to +180°, typically in the range of −90° to +90°, possibly in the range of −60° to +60°, −45° to +45°, −30° to +30° or less. As shown, the angle theta 1070 lies within a plane Y. In particular, axis y, which runs through the center of the central lumen 1028 at the distal end 1026, forms the angle theta 1070 with axis z. In this example, plane Y is orthogonal to both plane X and plane Z. Axes x, y, z all intercept at a point within the central lumen 1028 which also coincides with the intersection of planes X, Y, Z.

Figure 49D:
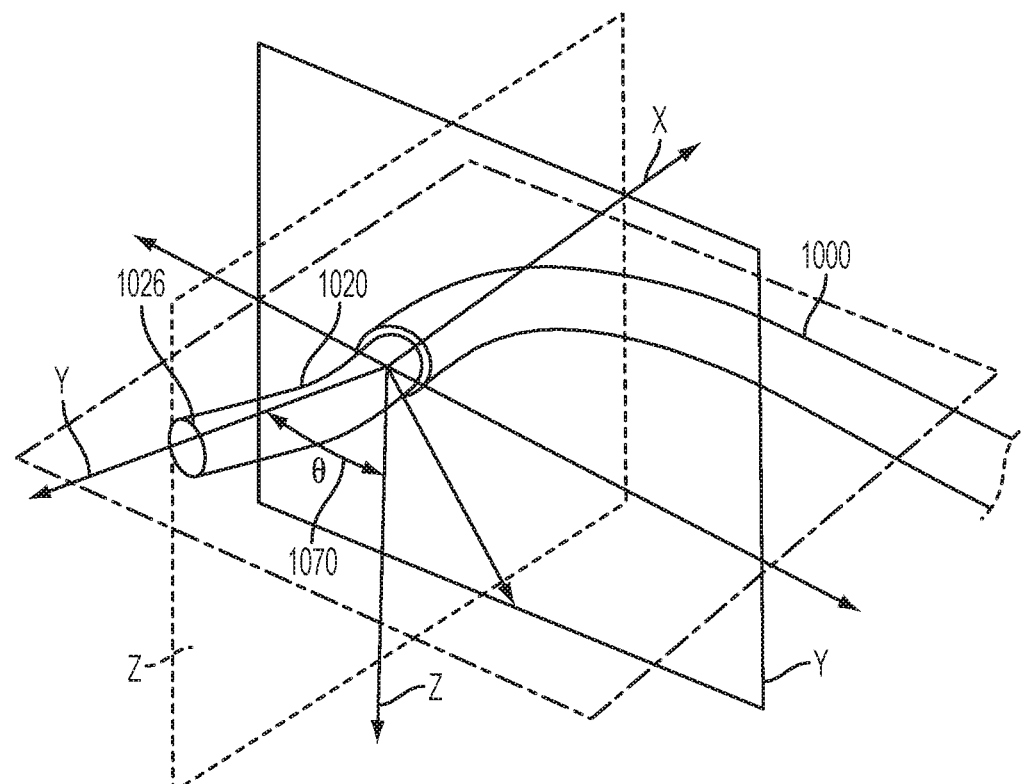

Similarly, FIG. 49D illustrates movement of the distal end 1026 through an angle theta 1070 on the opposite side of axis z. Again, the angle theta 1070 is measured from the axis z to the axis y, which runs through the center of the central lumen 1016 at the distal end 1026. As shown, the angle theta 1070 lies in plane Y. Thus, the primary curve 1100, secondary curve 1104, and angle theta 1070 can all lie in different planes, and optionally in orthogonal planes. However, it may be appreciated that the planes within which the primary curve 1100, secondary curve 1104 and angle theta 1070 lie may be mutually dependent and therefore would allow the possibility that some of these lie within the same plane.

Figure 50A:
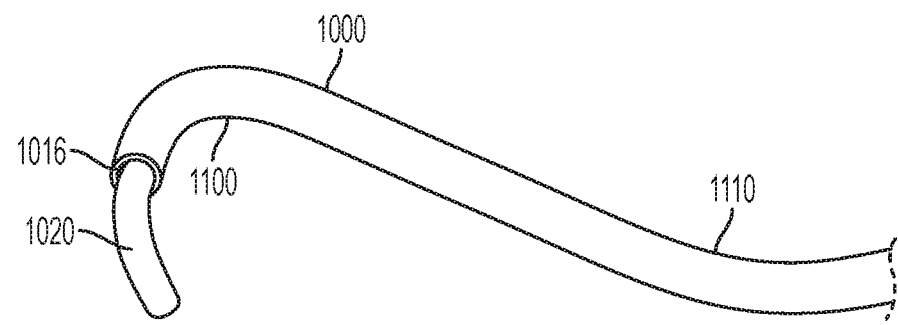
FIG. 50A is a perspective side view of a multi-catheter guiding system having an additional curve in the outer guide catheter.
Figure 50B:
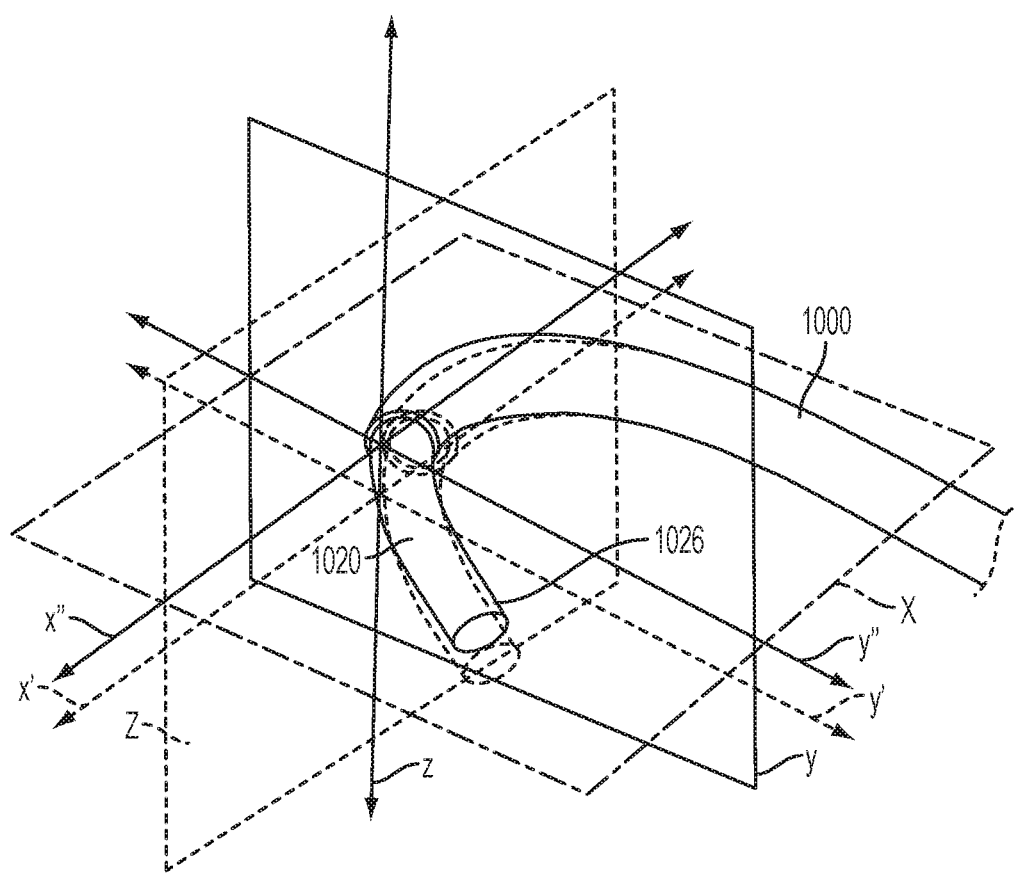
FIG. 50B illustrates lifting of the outer guide catheter due to the additional curve of FIG. 49A.

In addition, the outer guide catheter 1000 may be preformed and/or steerable to provide additional curves or shapes. For example, as illustrated in FIG. 50A, an additional curve 1110 may be formed by the outer guide catheter 1000 proximal to the primary curve 1100. In this example, the curve 1110 provides lift or raises the distal end 1016 of the outer guide catheter 1000, which in turn raises the distal end 1026 of the inner guide catheter 1020. Such lifting is illustrated in FIG. 50B. Here, the system 1 is shown prior to lifting in dashed line wherein the axis y' passes through the intersection of axis z and axis x'. After application of curve 1110, the distal portion of the system 1 is lifted in the direction of axis z so that axis x' is raised to axis x" and axis y' is raised to axis y". This raises distal end 1026 to a desired height.

Figure 51A:
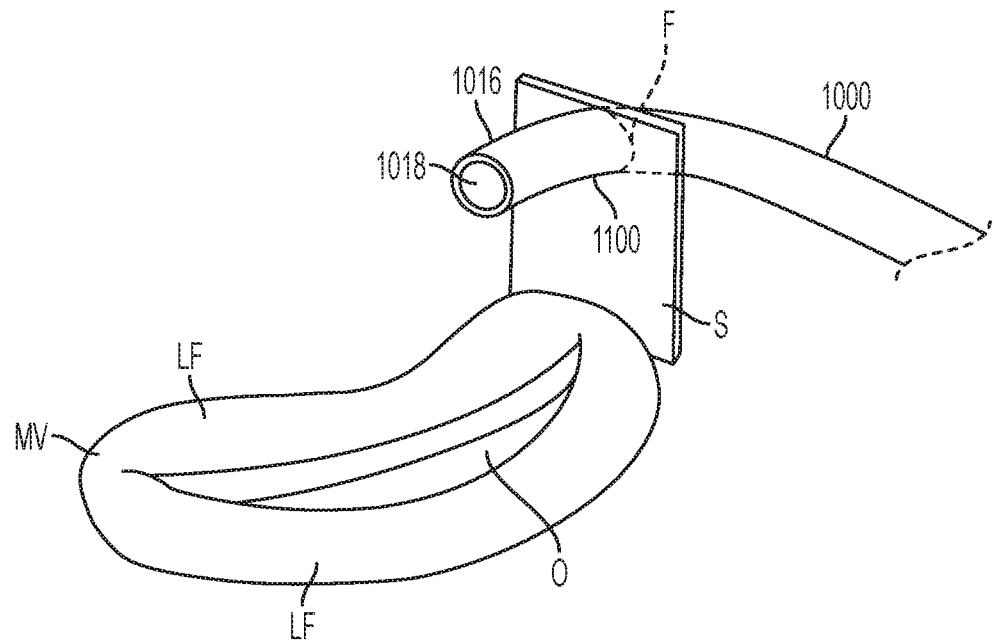
FIGS. 51A-51D illustrate a method of using the multi-catheter guiding system for accessing the mitral valve.

The articulated position of the multi-catheter guiding system 1 illustrated in FIGS. 49A-49D and FIGS. 50A-50B is particularly useful for accessing the mitral valve. FIGS. 51A-51D illustrate a method of using the system 1 for accessing the mitral valve MV. To gain access to the mitral valve, the outer guide catheter 1000 may be tracked over a dilator and guidewire from a puncture in the femoral vein, through the inferior vena cava and into the right atrium. As shown in FIG. 51A, the outer guide catheter 1000 may be punctured through a fossa F in the interatrial septum S. The outer guide catheter 1000 is then advanced through the fossa F and curved by the primary curve 1100 so that the distal end 1016 is directed over the mitral valve MV. Again, it may be appreciated that this approach serves merely as an example and other approaches may be used, such as through the jugular vein, femoral artery, port access or direct access, to name a few. Positioning of the distal end 1016 over the mitral valve MV may be accomplished by precurvature of the outer guide catheter 1000, wherein the catheter 1000 assumes this position when the dilator and guidewire are retracted, and/or by steering of the outer guide catheter 1000 to the desired position. In this example, formation of the primary curve 1100 moves the distal end 1016 within a primary plane, corresponding to previous plane X, substantially parallel to the valve surface. This moves the distal end 1016 laterally along the short axis of the mitral valve MV, and allows the distal end 1016 to be centered over the opening O between the leaflets LF.

Figure 51B:
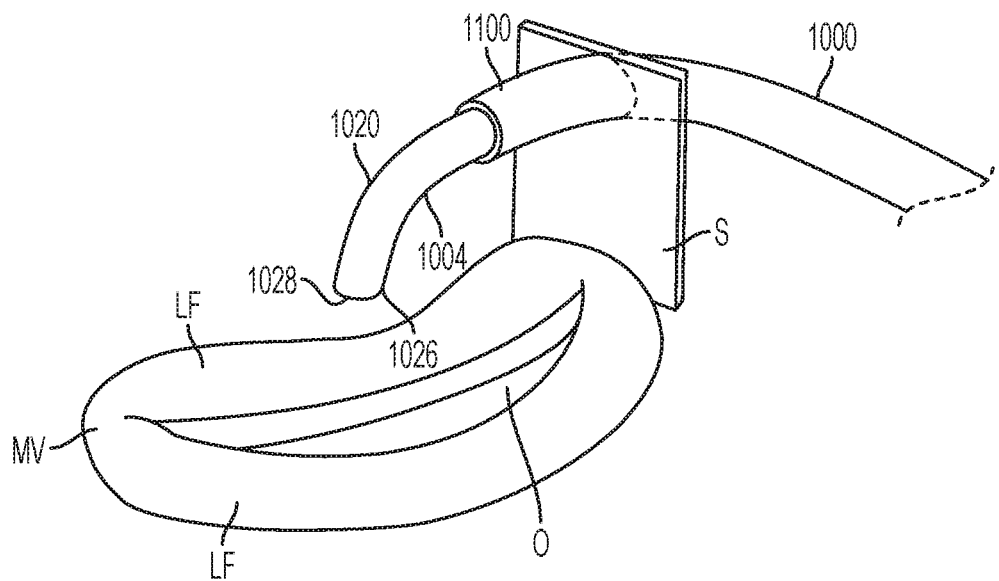

Referring to FIG. 51B, the inner guide catheter 1020 is advanced through the central lumen 1018 of the outer guide catheter 1000 and the distal end 1026 is positioned so that the central lumen 1028 is directed toward the target tissue, the mitral valve MV. In particular, the central lumen 1028 is to be directed toward a specific area of the mitral valve MV, such as toward the opening O between the valve leaflets LF, so that a particular interventional procedure may be performed. In FIG. 51B, the inner guide catheter 1020 is shown in a position which includes a secondary curve 1104 in a secondary plane, corresponding to previous plane Z. Formation of the secondary curve 1104 moves the distal end 1026 vertically and angularly between the commissures C, directing the central lumen 1028 toward the mitral valve MV. In this position an interventional device or catheter 1030 which is passed through the central lumen 1028 would be directed toward and/or through the opening O. Although the primary curve 1100 and the secondary curve 1104 may be varied to accommodate different anatomical variations of the valve MV and different surgical procedures, further adjustment may be desired beyond these two curvatures for proper positioning of the system 1.

Figure 51C:
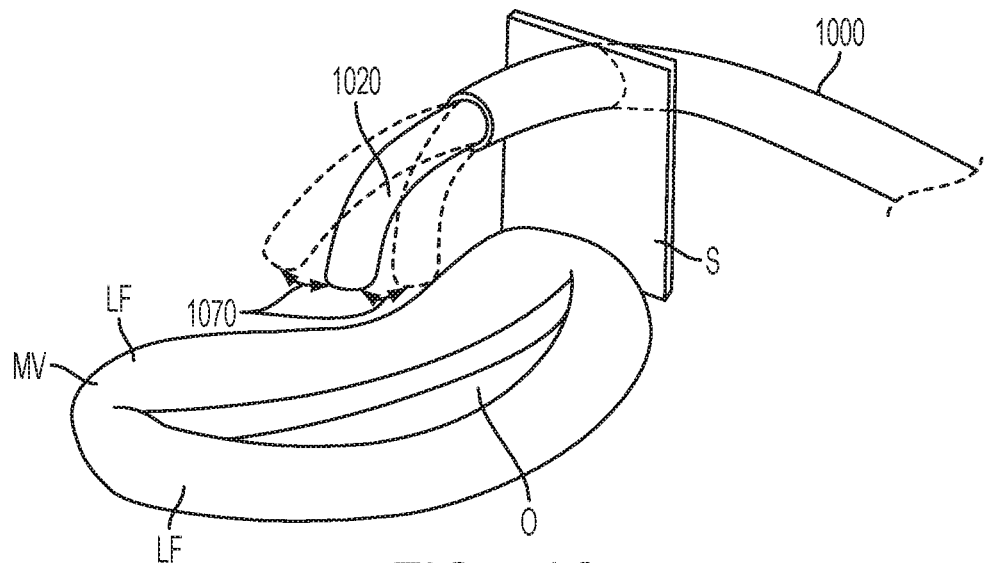

Referring to FIG. 51C, the distal end 1026 of the inner guide catheter 1020 may be positioned through an angle theta 1070. This moves the distal end 1026 vertically and angularly through a theta plane, corresponding to previous plane Y. Movement of the distal end 1026 through the angle theta 1070 in either direction is shown in dashed line in FIG. 51C. Such movement can be achieved by precurvature and/or by steering of the catheter 1020. Consequently, the central lumen 1028 can be directed toward the mitral valve MV within a plane which differs from the secondary plane. After such movements, the inner guide catheter 1020 will be in a position so that the opening of the central lumen 1028 at the end 1016 faces the desired direction. In this case, the desired direction is toward the center of and orthogonal to the mitral valve.

In some instances, it is desired to raise or lower the distal end 1026 so that it is at a desired height in relation to the mitral valve MV. This may be accomplished by precurvature and/or by steering of the outer guide catheter 1000 to form additional curve 1110. Generally this is used to lift the distal end 1026 above the mitral MV wherein such lifting was illustrated in FIG. 50B.

Figure 51D:
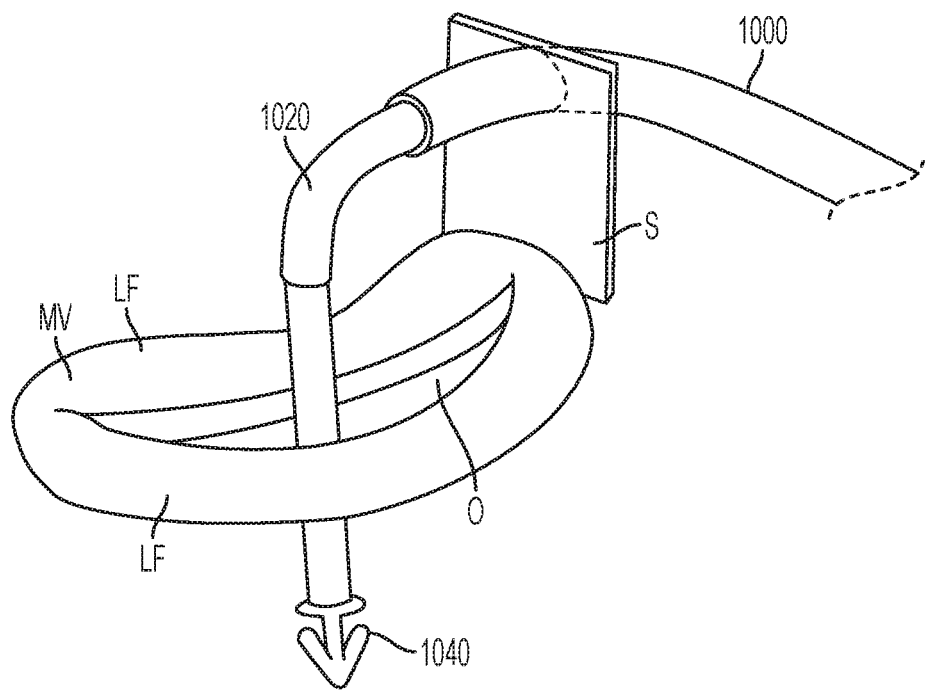

When the curvatures in the catheters 1000, 1020 are formed by steering mechanisms, the steering mechanisms may be locked in place by a locking feature. Locking can provide additional stiffness and stability in the guiding system 1 for the passage of interventional devices or catheters 1030 therethrough, as illustrated in FIG. 48. The interventional catheter 1030 can be passed through the central lumen 1028 toward the target tissue, in this case the mitral valve MV. Positioning of the distal end 1026 over the opening O, as described above, allows the catheter 1030 to pass through the opening O between the leaflets LF if desired, as shown in FIG. 51D. At this point, any desired procedure may be applied to the mitral valve for correction of regurgitation or any other disorder.

C. Steering Mechanisms

As described previously, the curvatures may be formed in the catheters 1000, 1020 by precurving, steering or any suitable means. Precurving involves setting a specific curvature in the catheter prior to usage, such as by heat setting a polymer or by utilizing a shape-memory alloy. Since the catheters are generally flexible, loading of the catheter on a guidewire, dilator obturator or other introductory device straightens the catheter throughout the curved region. Once the catheter is positioned in the anatomy, the introductory device is removed and the catheter is allowed to relax back into the precurved setting.

Figure 52A:
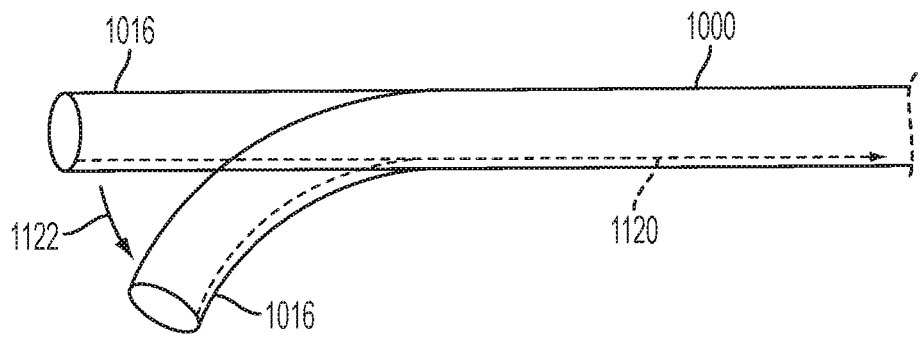
FIGS. 52A-52D illustrate curvature of a guide catheter of the present invention by the actuation of one or more pullwires.
Figure 52B:
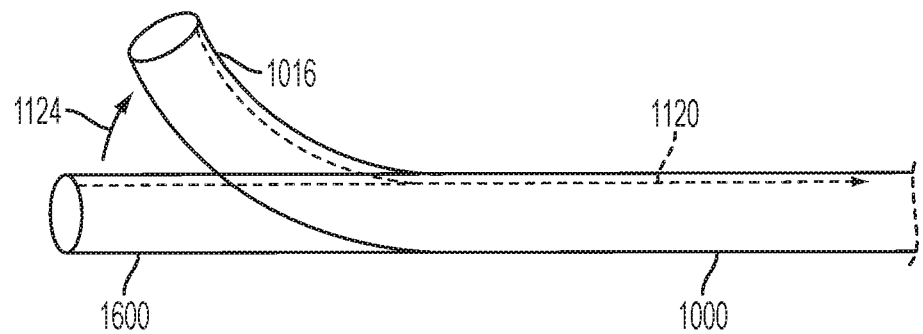
Figure 52C:
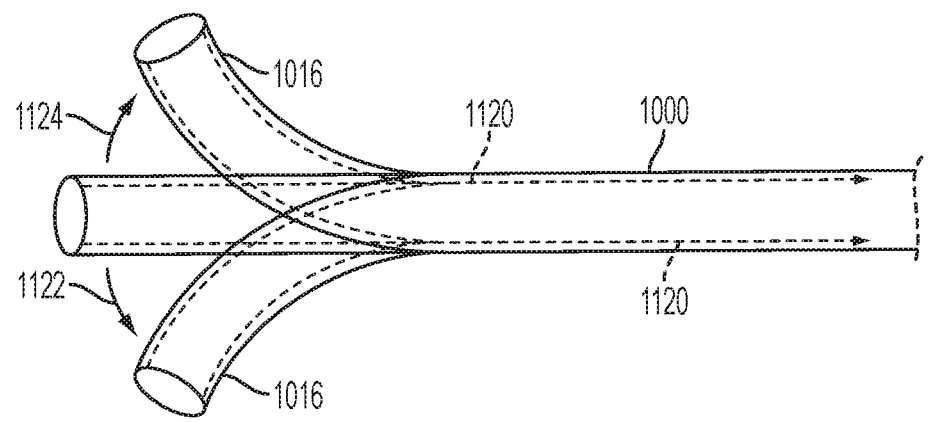
Figure 52D:
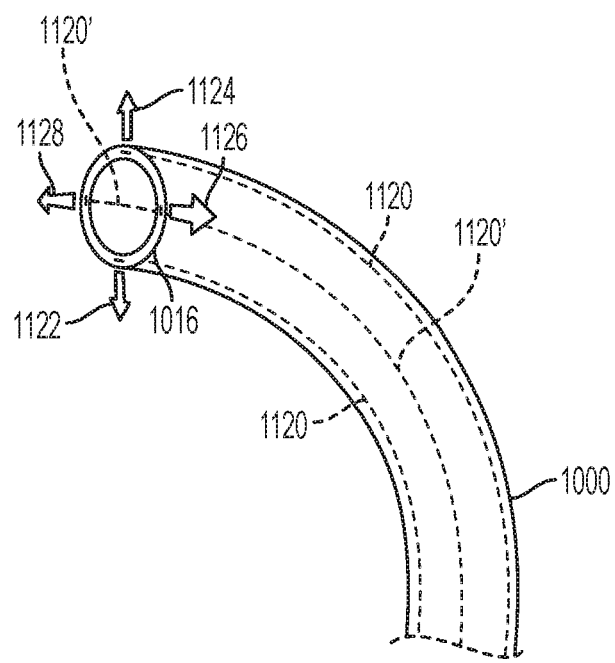

To provide a higher degree of control and variety of possible curvatures, steering mechanisms may be used to create the curvatures and position the catheters. In some embodiments, the steering mechanisms comprise cables or pullwires within the wall of the catheter. As shown in FIG. 52A, the outer guide catheter 1000 may include a pullwire 1120 slidably disposed in lumens within the wall of the catheter 1000 extending to the distal end 1016. By applying tension to the pullwire 1120 in the proximal direction, the distal end 1016 curves in the direction of the pullwire 1120 as illustrated by arrow 1122. Likewise, as shown in FIG. 52B, placement of the pullwire 1120 along the opposite side of the catheter 1000 will allow the distal end 1016 to curve in the opposite direction, as illustrated by arrow 1124, when tension is applied to the pullwire 1120. Thus, referring to FIG. 52C, diametrically opposing placement of pullwires 1120 within the walls of the catheter 1000 allows the distal end 1016 to be steered in opposite directions. This provides a means of correcting or adjusting a curvature. For example, if tension is applied to one pullwire to create a curvature, the curvature may be lessened by applying tension to the diametrically opposite pullwire. Referring now to FIG. 52D, an additional set of opposing pullwires 1120' may extend within the wall of the catheter 1000 as shown. This combination of pullwires 1120, 1120' allows curvature of the distal end in at least four directions illustrated by arrows 1122, 1124, 1126, 1128. In this example, pullwires 1120 create the primary curve 1100 of the outer guide catheter 1000 and the pullwires 1120' create the lift. It may be appreciated that FIGS. 52A-52D also pertain to the inner guide catheter 1020. For example, in FIG. 52D, pullwires 1120 may create the secondary curve 1104 of the inner guide catheter 1020 and the pullwires 1120' create the angle theta 1070.

Figure 52E:
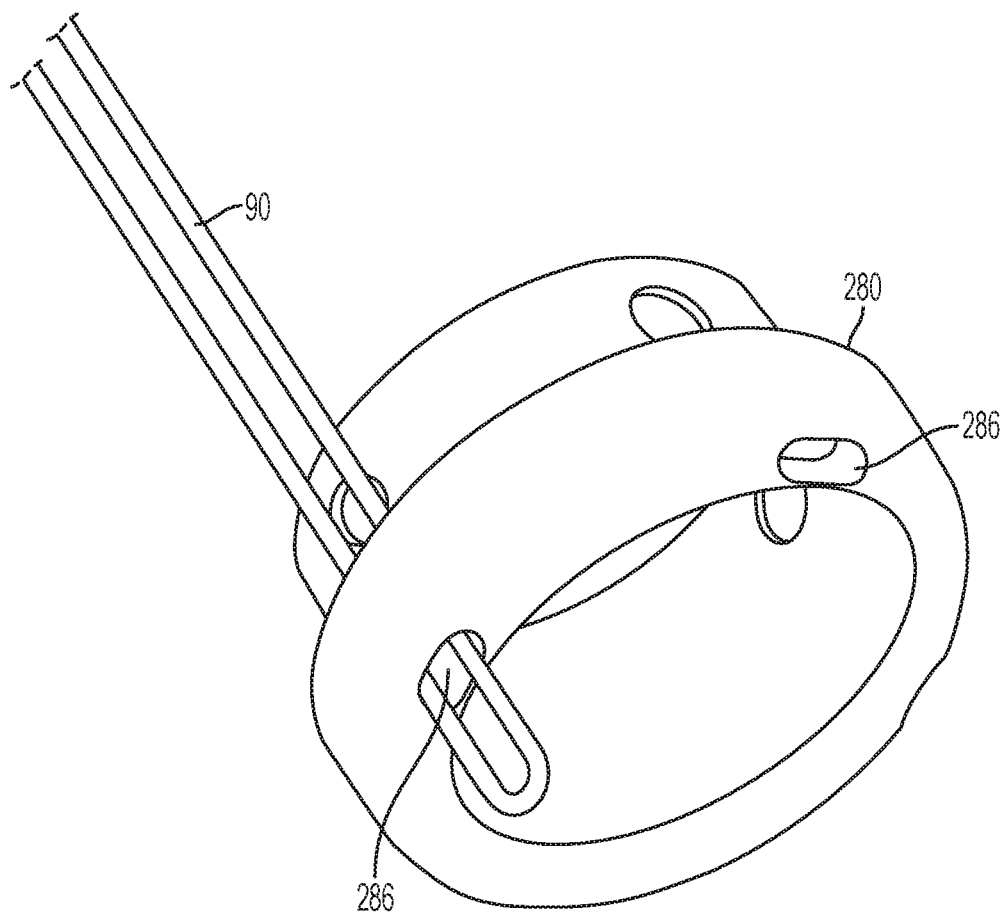
FIG. 52E illustrates attachment of a pullwire to a tip ring.

Such pullwires 1120 and/or pullwires 1120' and associated lumens may be placed in any arrangement, singly or in pairs, symmetrically or nonsymmetrically and any number of pullwires may be present. This may allow curvature in any direction and about various axes. The pullwires 1120, 1120' may be fixed at any location along the length of the catheter by any suitable method, such as gluing, tying, soldering, or potting, to name a few. When tension is applied to the pullwire, the curvature forms from the point of attachment of the pullwire toward the proximal direction. Therefore, curvatures may be formed throughout the length of the catheter depending upon the locations of the points of attachment of the pullwires. Typically, however, the pullwires will be attached near the distal end of the catheter, optionally to an embedded tip ring 280, illustrated in FIG. 52E. As shown, the pullwire 1120 passes through an orifice 286 in the tip ring 280, forms a loop shape and then passes back through the orifice 286 and travels back up through the catheter wall (not shown). In addition, the lumens which house the pullwires may be straight, as shown in FIGS. 52A-52D, or may be curved.

D. Catheter Construction

The outer guide catheter 1000 and inner guide catheter 1020 may have the same or different construction which may include any suitable material or combination of materials to create the above described curvatures. For clarity, the examples provided will be in reference to the outer guide catheter 1000, however it may be appreciated that such examples may also apply to the inner guide catheter 1020.

In embodiments in which the catheter is precurved rather than steerable or in addition to being steerable, the catheter 1000 may be comprised of a polymer or copolymer which is able to be set in a desired curvature, such as by heat setting. Likewise, the catheter 1000 may be comprised of a shape-memory alloy.

In embodiments in which the catheter is steerable, the catheter 1000 may be comprised of one or more of a variety of materials, either along the length of the catheter 1000 or in various segments. Example materials include polyurethane, Pebax, nylon, polyester, polyethylene, polyimide, polyethylenetelephthalate (PET), polyetheretherketone (PEEK). In addition, the walls of the catheter 1000 may be reinforced with a variety of structures, such as metal braids or coils. Such reinforcements may be along the length of the catheter 1000 or in various segments.

Figure 53A:
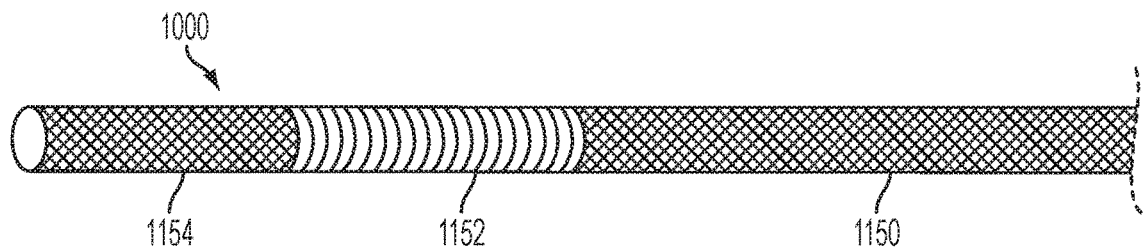
FIGS. 53A-53I illustrate embodiments of the present invention comprising sections constructed with the inclusion of braiding or a coil.
Figure 53B:
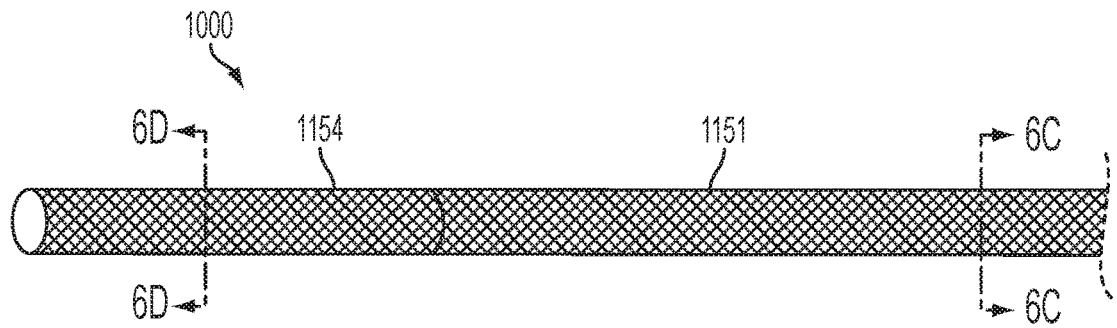
Figure 53C:
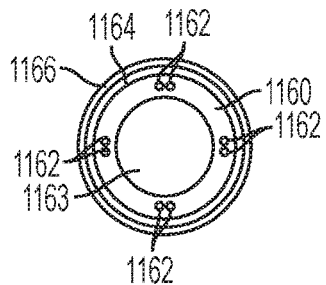
Figure 53D:
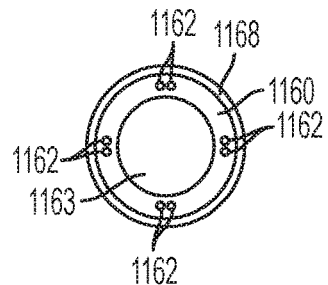
Figure 53F:
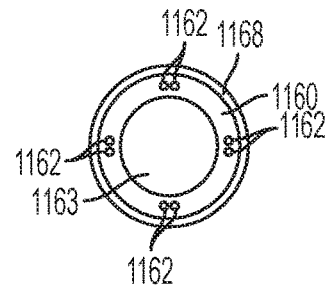
Figure 53E:
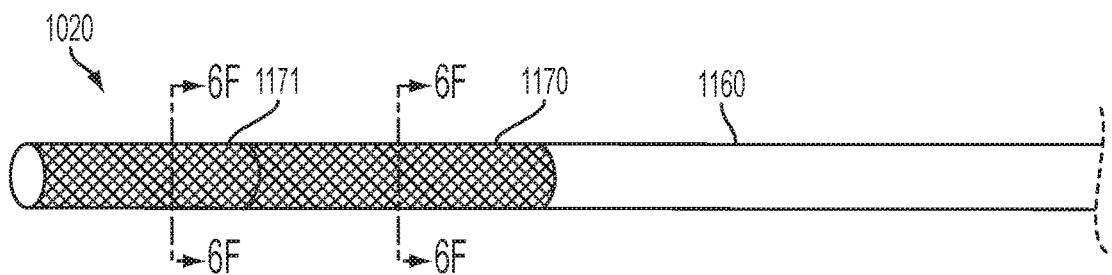

For example, referring to FIG. 53A, the catheter 1000 may have a proximal braided segment 1150, a coiled segment 1152 and distal braided segment 1154. The proximal braided segment 1150 provides increased column strength and torque transmission. The coiled segment 1152 provides increased steerability. The distal braided segment 1154 provides a blend of steerability and torque/column strength. In another example, referring to FIG. 53B, the outer guiding catheter 1000 has a proximal double-layer braided segment 1151 and a distal braided segment 1154. Thus, the proximal double-layer segment 1151 comprises a multi-lumen tube 1160 (having steering lumens 1162 for pullwires, distal ends of the steering lumens 1162 optionally embedded with stainless steel coils for reinforcement, and a central lumen 1163), an inner braided layer 1164, and an outer braided layer 1166, as illustrated in the cross-sectional view of FIG. 53C. Similarly, FIG. 53D provides a cross-sectional view of the distal braided segment 1154 comprising the multi-lumen tube 1160 and a single braided layer 1168. In a further example, referring to FIG. 53E, the inner guiding catheter 1020 comprises a multi-lumen tube 1160 without reinforcement at its proximal end, a single braided layer middle segment 1170 and a single braided layer distal segment 1171. Each of the single braided layer segments 1170, 1171 have a multi-lumen tube 1160 and a single layer of braiding 1168, as illustrated in cross-sectional view FIG. 53F. However, the segments 1170, 1171 are comprised of polymers of differing durometers, typically decreasing toward the distal end.

Figure 53G:
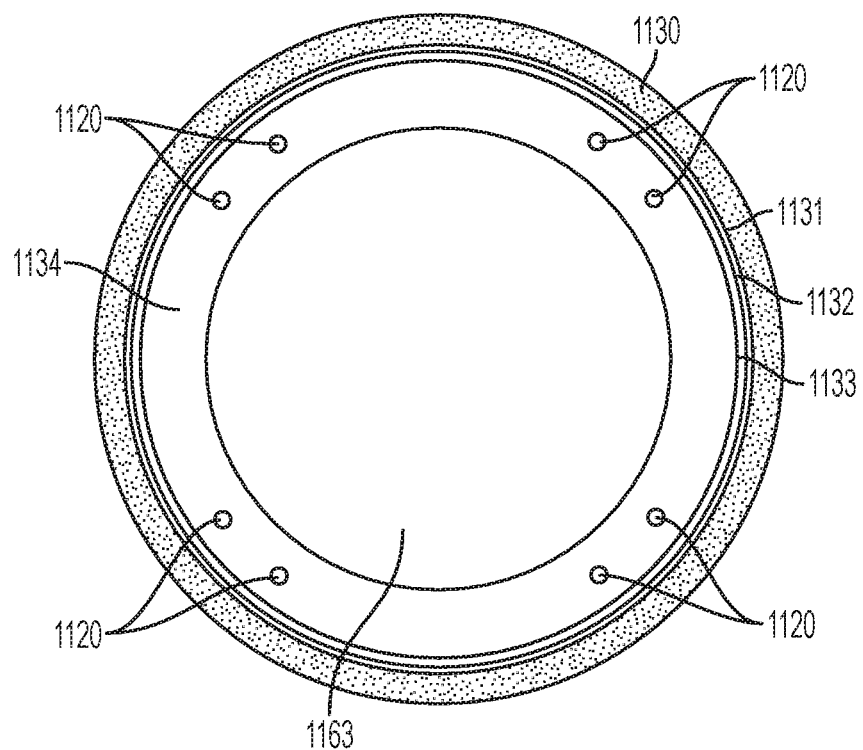

FIG. 53G illustrates an other example of a cross-section of a distal section of an outer guiding catheter 1000. Here, layer 1130 comprises 55D Pebax and has a thickness of approximately 0.0125 in. Layer 1131 comprises a 30 ppi braid and has a thickness of approximately 0.002 in. by 0.0065 in. Layer 1132 comprises 55D Pebax and has a thickness of approximately 0.006 in. Layer 1133 comprises 30 ppi braid and has a thickness of approximately 0.002 in by 0.0065 in. And finally, layer 1134 comprises Nylon 11 and includes steering lumens for approximately 0.0105 in. diameter pullwires 1120. Central lumen 1163 is of sufficient size for passage of devices.

Figure 53H:
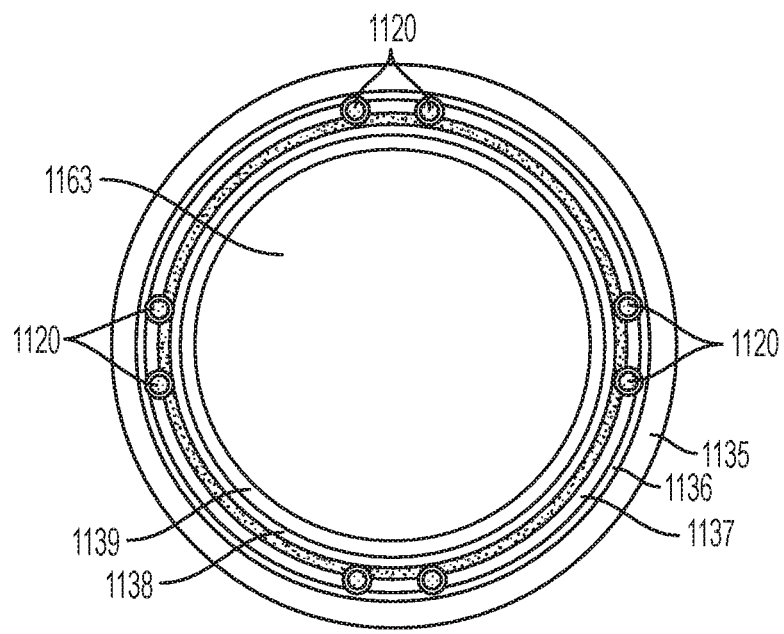
Figure 53I:
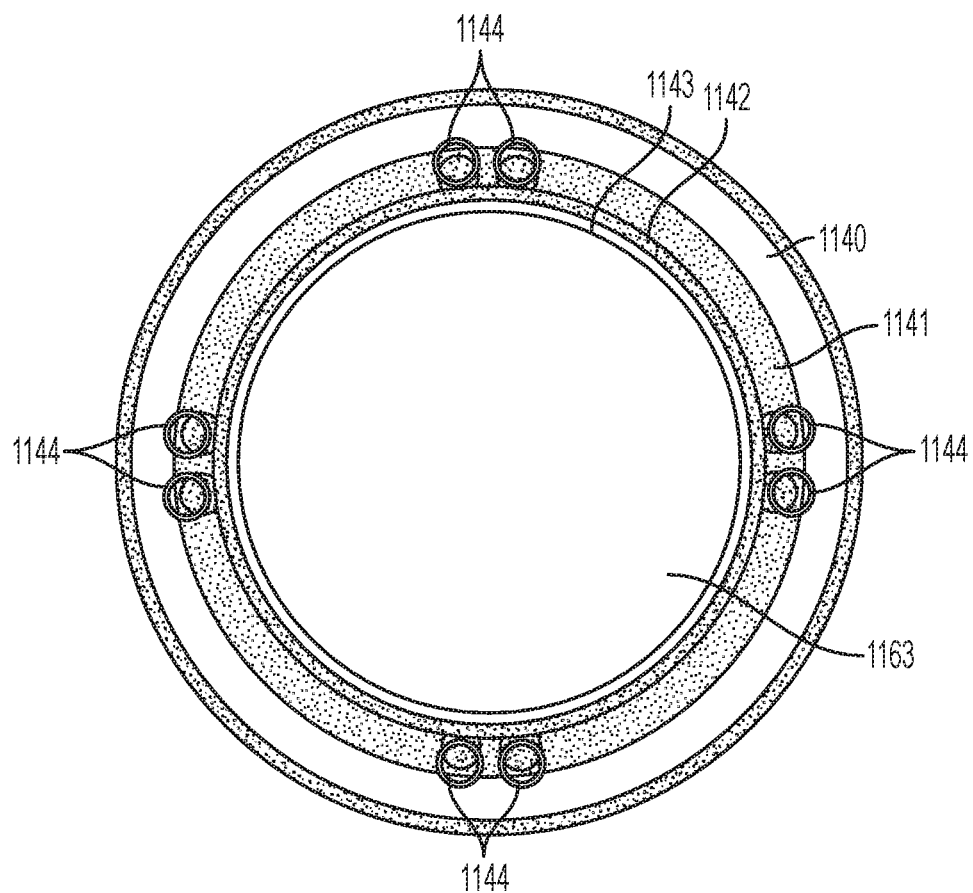

FIGS. 53H-53I illustrate additional examples of cross-sections of an inner guiding catheter 1020, FIG. 53I illustrating a cross-section of a portion of the distal end and FIG. 53I illustrating a cross-section of a more distal portion of the distal end. Referring to FIG. 53H, layer 1135 comprises 40D polymer and has a thickness of approximately 0.0125 in. Layer 1136 comprises a 30 ppi braid and has a thickness of approximately 0.002 in. by 0.0065 in. Layer 1137 comprises 40D polymer and has a thickness of approximately 0.006 in. Layer 1138 comprises a 40 D polymer layer and has a thickness of approximately 0.0035 in. And finally, layer 1139 comprises a 55D liner. In addition, coiled steering lumens are included for approximately 0.0105 in. diameter pullwires 1120. And, central lumen 1163 is of sufficient size for passage of devices. Referring to FIG. 53I, layer 1140 comprises a 40D polymer, layer 1141 comprises a 35D polymer, layer 1142 comprises a braid and layer 1143 comprises a liner. In addition, coiled steering lumens 1144 are included for pullwires. And, central lumen 1163 is of sufficient size for passage of devices.

Figure 54A:
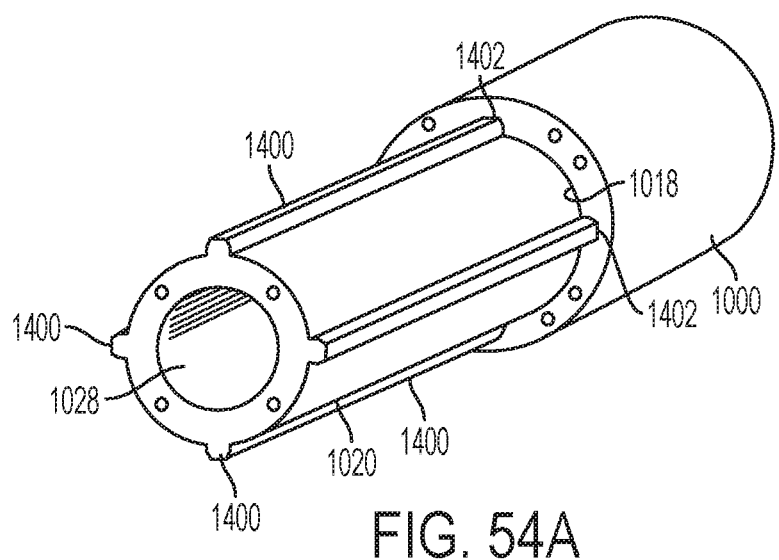
FIGS. 54A-54C illustrate a keying feature of the present invention.
Figure 54B:
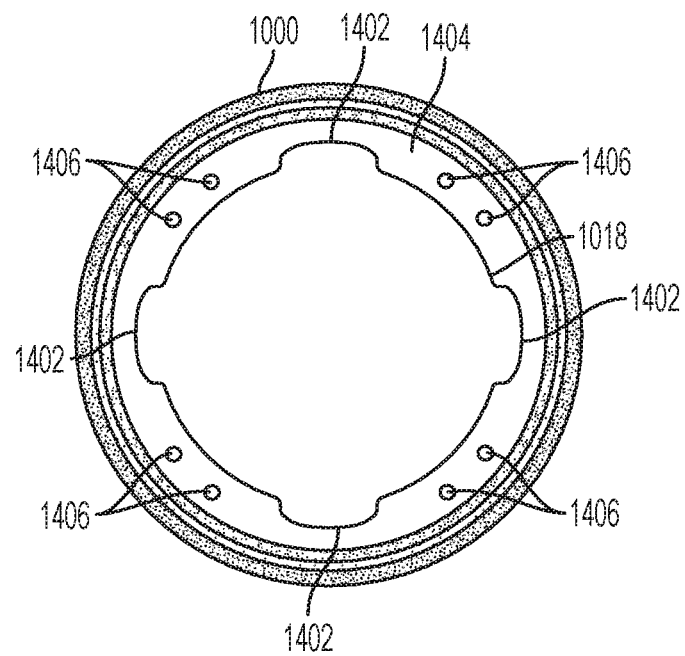
Figure 54C:
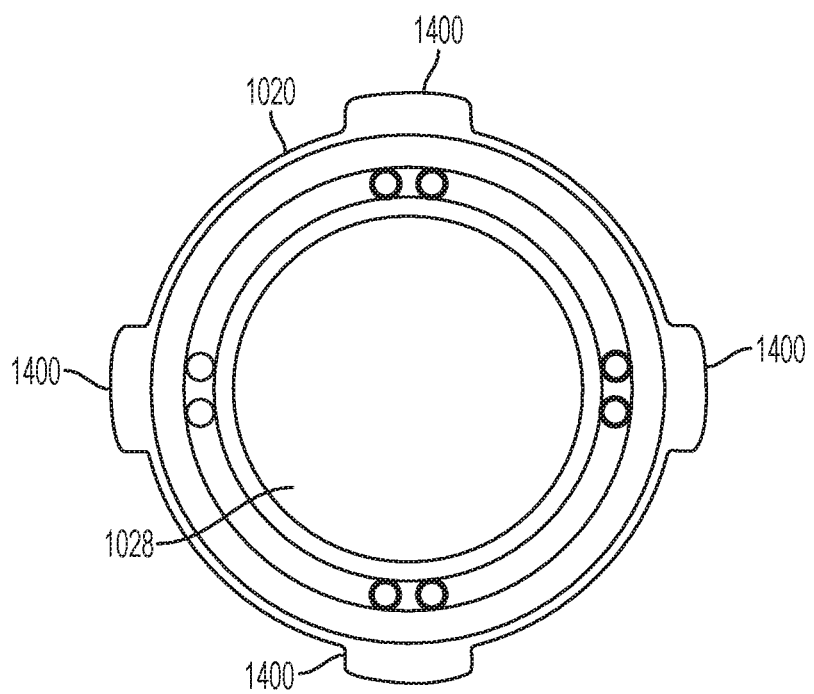

FIGS. 54A-54C illustrate an embodiment of a keying feature which may be incorporated into the catheter shafts. The keying feature is used to maintain relationship between the inner and outer guide catheters to assist in steering capabilities. As shown in FIG. 54A, the inner guide catheter 1020 includes one or more protrusions 1400 which extend radially outwardly. In this example, four protrusions 1400 are present, equally spaced around the exterior of the catheter 1020. Likewise, the outer guide catheter 1000 includes corresponding notches 1402 which align with the protrusions 1400. Thus, in this example, the catheter 1000 includes four notches equally spaced around its central lumen 1018. Thus, the inner guide catheter 1020 is able to be translated within the outer guide catheter 1000, however rotation of the inner guide catheter 1020 within the outer guide catheter 1000 is prevented by the keying feature, i.e. the interlocking protrusions 1400 and notches 1402. Such keying helps maintain a known correlation of position between the inner guide catheter 1020 and outer guide catheter 1000. Since the inner and outer guide catheters 1020, 1000 form curvatures in different directions, such keying is beneficial to ensure that the compound curvature formed by the separate curvatures in the inner and outer guide catheters 1020, 1000 is the compound curvature that is anticipated. Keying may also increase stability wherein the curvatures remain in position reducing the possibility of compensating for each other.

FIG. 54B illustrates a cross-sectional view of the outer guiding catheter 1000 of FIG. 54A. Here, the catheter 1000 includes a notched layer 1404 along the inner surface of central lumen 1018. The notched layer 1404 includes notches 1402 in any size, shape, arrangement and number. Optionally, the notched layer 1404 may include lumens 1406, typically for passage of pullwires 1120. However, the lumens 1406 may alternatively or in addition be used for other uses. It may also be appreciated that the notched layer 1404 may be incorporated into the wall of the catheter 1000, such as by extrusion, or may be a separate layer positioned within the catheter 1000. Further, it may be appreciated that the notched layer 1404 may extend the entire length of the catheter 1000 or one or more portions of the length of the catheter 1000, including simply a small strip at a designated location along the length of the catheter 1000.

FIG. 54C illustrates a cross-sectional view of the inner guiding catheter 1020 of FIG. 54A. Here, the catheter 1020 includes protrusions 1400 along the outer surface of the catheter 1020. The protrusions 1400 may be of any size, shape, arrangement and number. It may be appreciated that the protrusions 1400 may be incorporated into the wall of the catheter 1020, such as by extrusion, may be included in a separate cylindrical layer on the outer surface of the catheter 1020, or the protrusions 1400 may be individually adhered to the outer surface of the catheter 1020. Further, it may be appreciated that the protrusions 1400 may extend the entire length of the catheter 1000 or one or more portions of the length of the catheter 1020, including simply a small strip at a designated location along the length of the catheter 1020.

Thus, the keying feature may be present along one or more specific portions of the catheters 1000, 1020 or may extend along the entire length of the catheters 1000, 1020. Likewise, the notches 1402 may extend along the entire length of the outer guiding catheter 1020 while the protrusions 1400 extend along discrete portions of the inner guiding catheter 1000 and vice versa. It may further be appreciated that the protrusions 1400 may be present on the inner surface of the outer guiding catheter 1000 while the notches 1402 are present along the outer surface of the inner guiding catheter 1020.

Figure 55A:
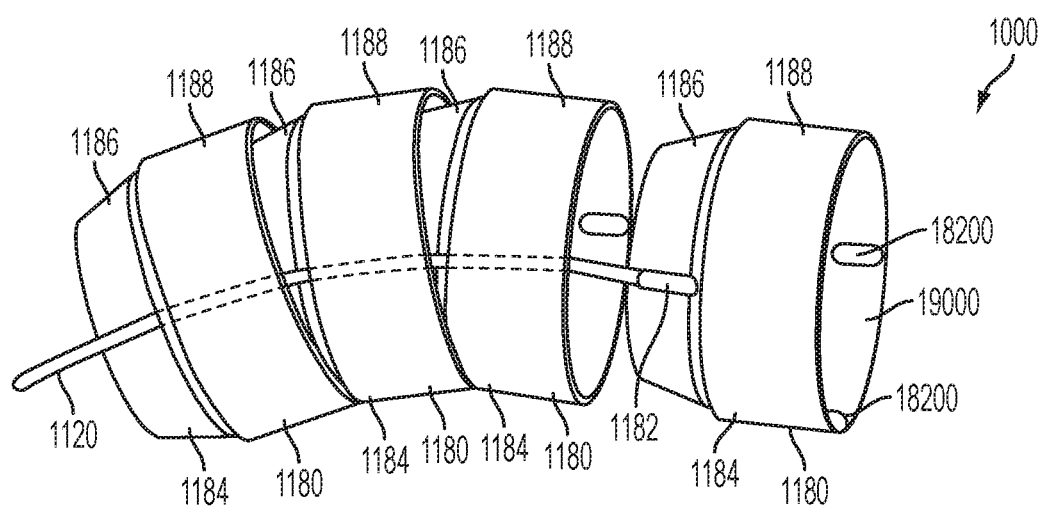
FIGS. 55A-55B are perspective views of a guide catheter including a series of articulating members.
Figure 55B:
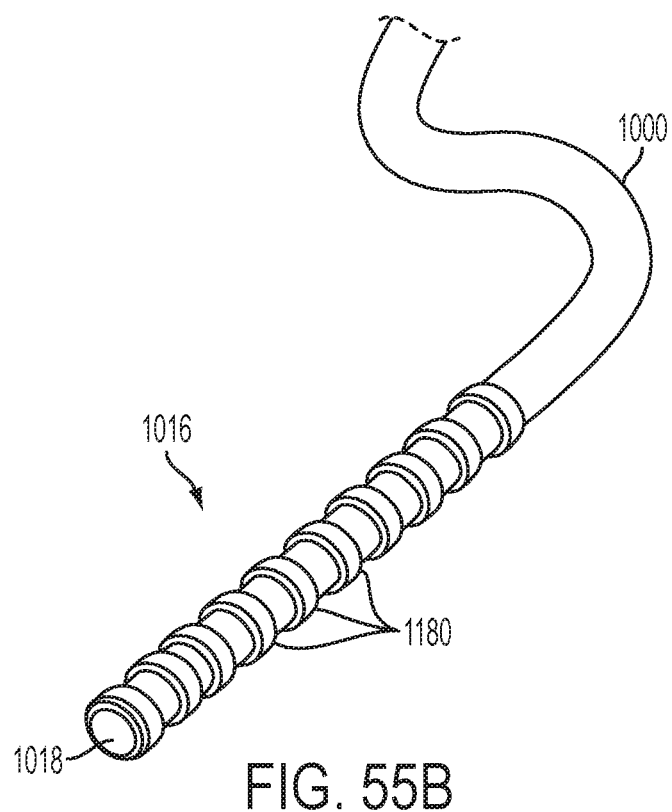

Alternatively or in addition, one or more steerable portions of the catheter 1000 may comprise a series of articulating members 1180 as illustrated in FIG. 55A. Exemplary embodiments of steerable portions of catheters comprising such articulating members 1180 are described in U.S. Pat. No. 7,682,319 incorporated herein by reference for all purposes. FIG. 55B illustrates the outer guide catheter 1000 having a steerable portion comprising articulating members 1180 at its distal end 1016.

Briefly, referring to FIG. 55A, each articulating member 1180 may have any shape, particularly a shape which allows interfitting or nesting as shown. In addition, it is desired that each member 1180 have the capability of independently rotating against an adjacent articulating member 1180. In this embodiment, the articulating members 1180 comprise interfitting domed rings 1184. The domed rings 1184 each include a base 1188 and a dome 1186. The base 1188 and dome 1186 have a hollow interior which, when the domed rings 1184 are interfit in a series, forms a central lumen 1190. In addition, the dome 1186 allows each articulating member 1180 to mate against an inner surface of an adjacent domed ring 1184.

The interfitting domed rings 1184 are connected by at least one pullwire 1120. Such pullwires typically extend through the length of the catheter 1000 and at least one of the interfitting domed rings 1184 to a fixation point where the pullwire 1120 is fixedly attached. By applying tension to the pullwire 1120, the pullwire 1120 arcs the series of interfitting domed rings 1184 proximal to the attachment point to form a curve. Thus, pulling or applying tension on at least one pullwire, steers or deflects the catheter 1000 in the direction of that pullwire 1120. By positioning various pullwires 1120 throughout the circumference of the domed rings 1184, the catheter 1000 may be directed in any number of directions.

Also shown in FIG. 55A, each interfitting domed ring 1184 may comprise one or more pullwire lumens 1182 through which the pullwires 1120 are threaded. Alternatively, the pullwires 1120 may be threaded through the central lumen 1190. In any case, the pullwires are attached to the catheter 1000 at a position where a desired curve is to be formed. The pullwires 1120 may be fixed in place by any suitable method, such as soldering, gluing, tying, welding or potting, to name a few. Such fixation method is typically dependent upon the materials used. The articulating members 1180 may be comprised of any suitable material including stainless steel, various metals, various polymers or co-polymers. Likewise the pullwires 1120 may be comprised of any suitable material such as fibers, sutures, metal wires, metal braids, or polymer braids.

E. Handles

Figure 56:
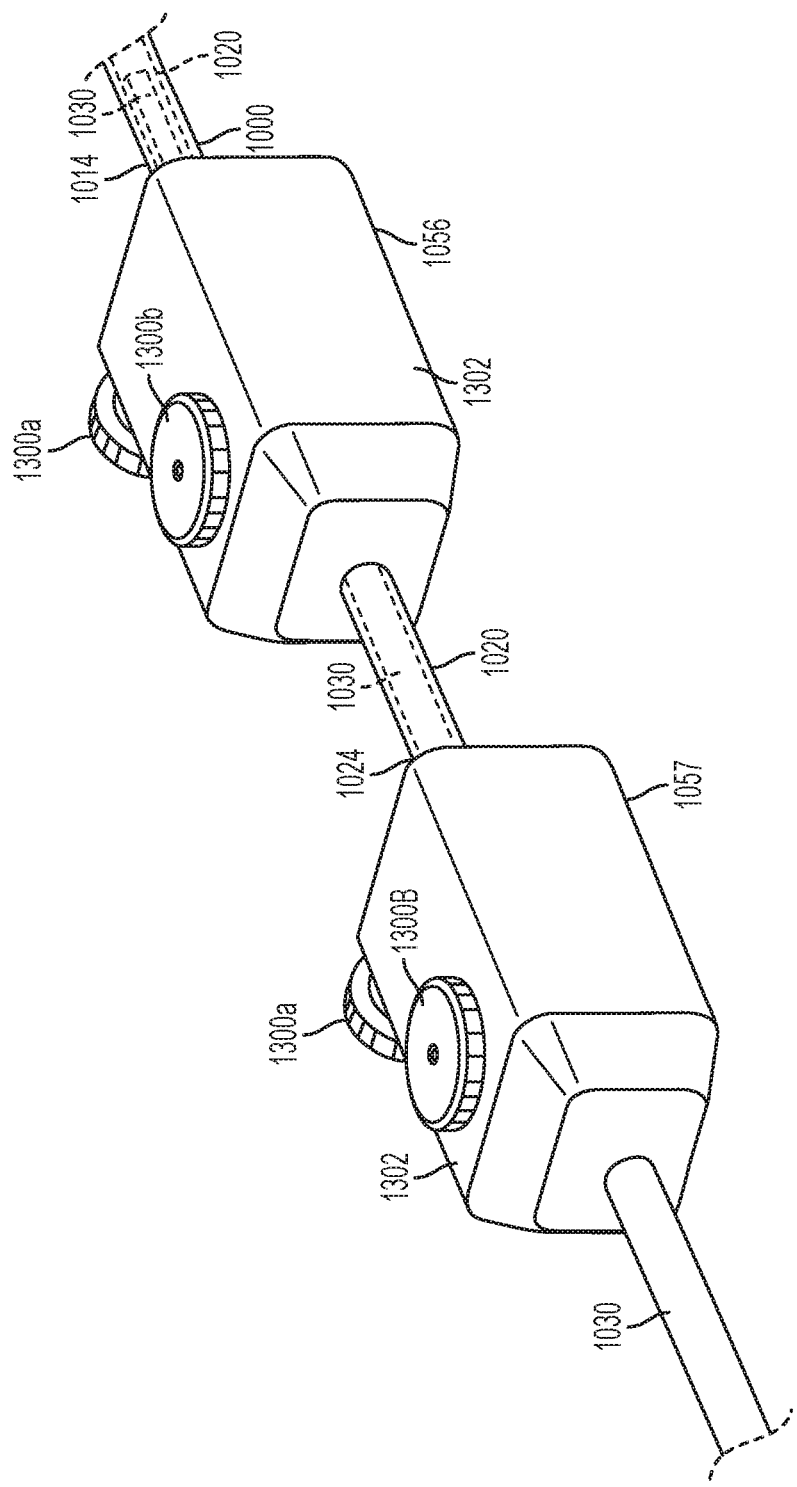
FIG. 56 illustrates embodiments of the handles.

As mentioned previously, manipulation of the guide catheters 1000, 1020 is achieved with the use of handles 1056, 1057 attached to the proximal ends of the catheters 1000, 1020. FIG. 56 illustrates a preferred embodiment of handles 1056, 1057. As shown, handle 1056 is attached to the proximal end 1014 of outer guide catheter 1000 and handle 1057 is attached to the proximal end 1024 of inner guide catheter 1020. Inner guide catheter 1020 is inserted through handle 1056 and is positioned coaxially within outer guide catheter 1000. In this embodiment, the handles 1056, 1057 are not linked together as shown in the embodiment illustrated in FIG. 48. It may be appreciated that such handles 1056, 1057 may alternatively be connected by external connecting rods, bars or plates or by an additional external stabilizing base. An embodiment of a stabilizing base will be described in a later section. Referring back to FIG. 56, interventional catheter is inserted through handle 1057 and is positioned coaxially within inner guide catheter 1020 and outer guide catheter 1000.

Each handle 1056, 1057 includes two steering knobs 1300a, 1300b emerging from a handle housing 1302 for manipulation by a user. Steering knobs 1300a are disposed on a side of the housing 1302 and steering knobs 1300b are disposed on a face of the housing 1302. However, it may be appreciated that such placement may vary based on a variety of factors including type of steering mechanism, size and shape of handle, type and arrangement of parts within handle, and ergonomics to name a few.

Figure 57:
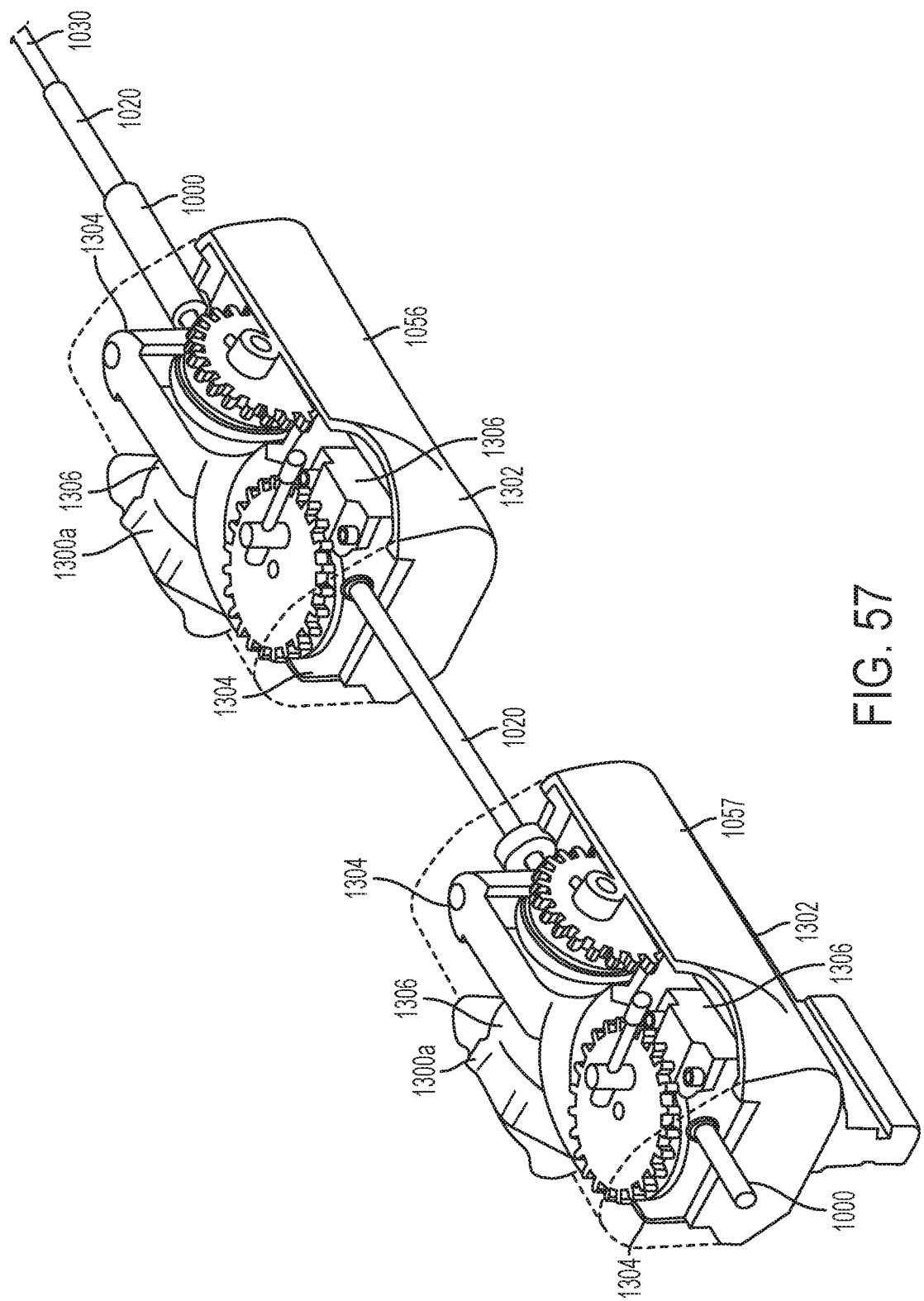
FIG. 57 illustrates the handles of FIG. 56 with a portion of the housing removed.

FIG. 57 illustrates the handles 1056, 1057 of FIG. 56 with a portion of the housing 1302 removed to reveal the assemblies of the handles. Each knob 1300a, 1300b controls a steering mechanism which is used to form a curvature in the attached catheter. Each steering mechanism includes a hard stop gear assembly 1304 and a friction assembly 1306. Tension is applied to one or more pullwires by action of the hard stop gear assembly to form a curve in a catheter. Tension is maintained by the friction assembly. When tension is released from the one or more pullwires the catheter returns to a straightened position.

Figure 58:
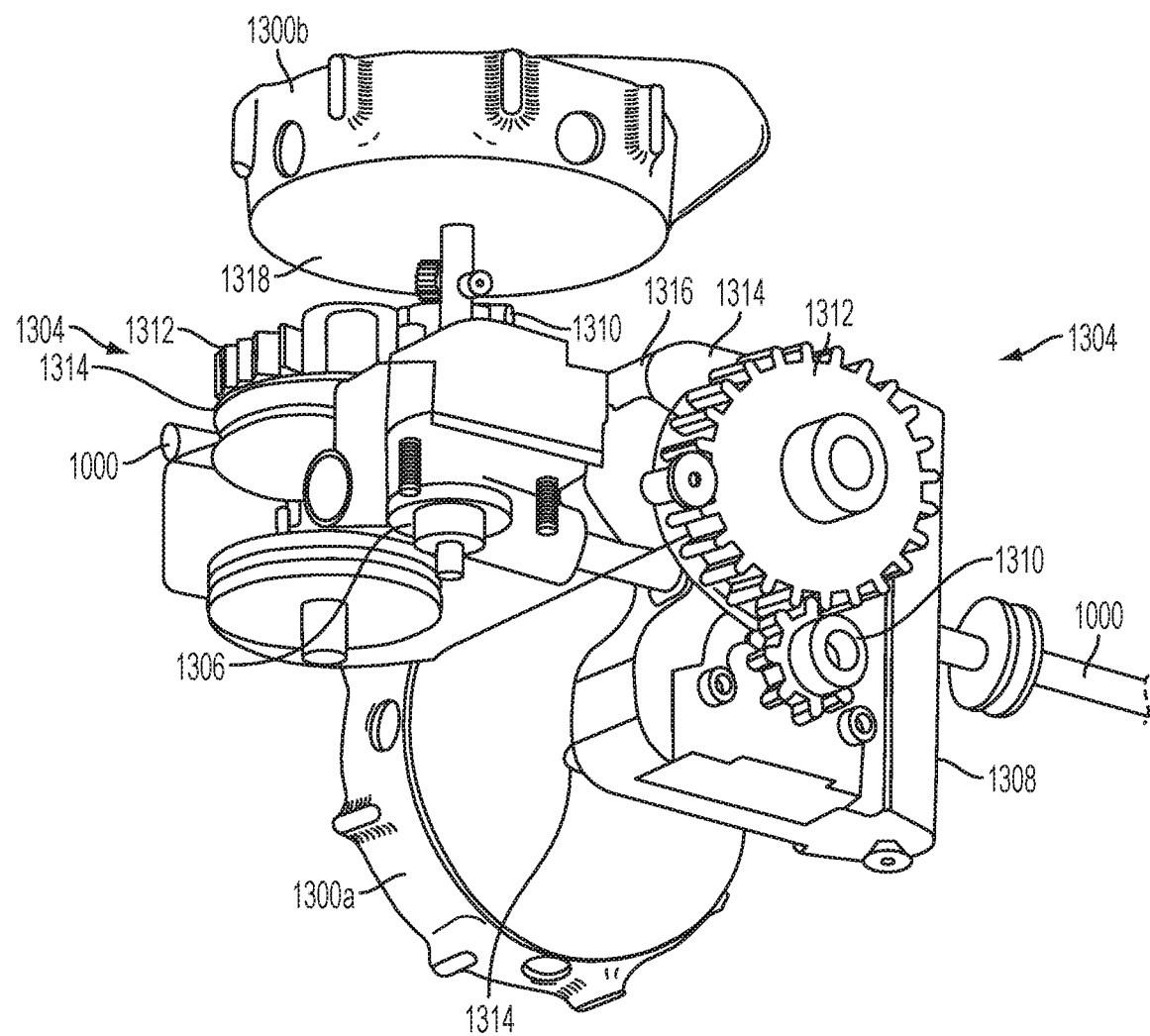
FIG. 58 illustrates steering mechanisms within a handle.

FIG. 58 illustrates steering mechanisms within a handle wherein the housing 1302 is removed for clarity. Here, steering knob 1300a is attached to a hard stop gear assembly 1304 and a friction assembly (not in view) and steering knob 1300b is attached to a separate hard stop gear assembly 1304 and friction assembly 1306. Steering knob 1300a is attached to a knob post 1318 which passes through a base 1308, terminating in a knob gear wheel 1310. The knob gear wheel 1310 actuates the hard stop gear assembly 1304, thereby applying tension to one or more pullwires 1120.

Figure 59:
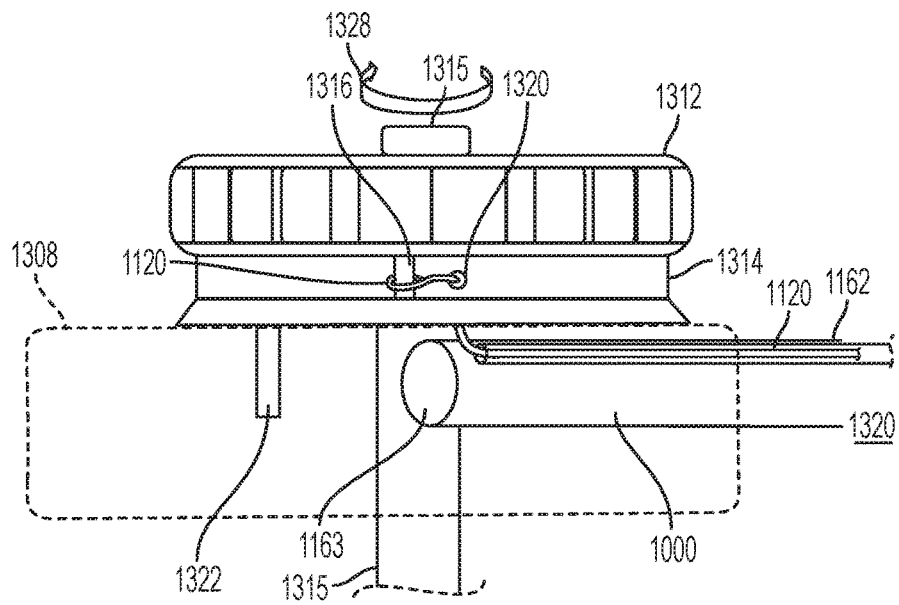
FIG. 59 illustrates attachment of a pullwire to a disk.

The knob gear wheel 1310 is a toothed wheel that engages a disk gear wheel 1312. Rotation of the steering knob 1300a rotates the knob post 1318 and knob gear wheel 1310 which in turn rotates the disk gear wheel 1312. Rotation of the disk gear wheel 1312 applies tension to one or more pullwires extending through the attached catheter, in this example the outer guiding catheter 1000. As shown, the outer guiding catheter 1000 passes through the base 1308, wherein one or more pullwires 1120 extending through the catheter 1000 are attached to the disk 1314. Such attachment is schematically illustrated in FIG. 59. Catheter 1000 is shown passing through base 1308. A pullwire 1120 passing through a steering lumen 1162 in the catheter 1000 emerges from the wall of the catheter 1000, passes through an aperture 1320 in the disk 1314 and is attached to an anchor peg 1316 on the disk 1314. Rotation of the disk 1314 (indicated by arrow 1328) around disk post 1315 by action of the disk gear wheel 1312, applies tension to the pullwire 1120 by drawing the pullwire 1120 through the aperture 1320 and wrapping the pullwire 1120 around the disk 1314 as it rotates. Additional rotation of the disk 1314 applies increasing tension to the pullwire 1120. To limit the amount of tension applied to the pullwire 1120, to limit curvature of the catheter and/or to avoid possible breakage of the pullwire 1120, the rotation of the disk 1314 may be restricted by hard stop peg 1322 which is attached to the disk 1314 and extends into the base 1308.

Figure 60A:
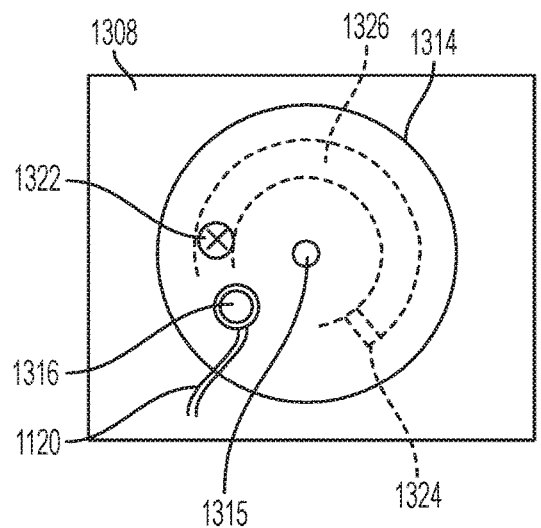
FIGS. 60A-60B illustrate a hard stop peg restricting rotation of a disk.
Figure 60B:
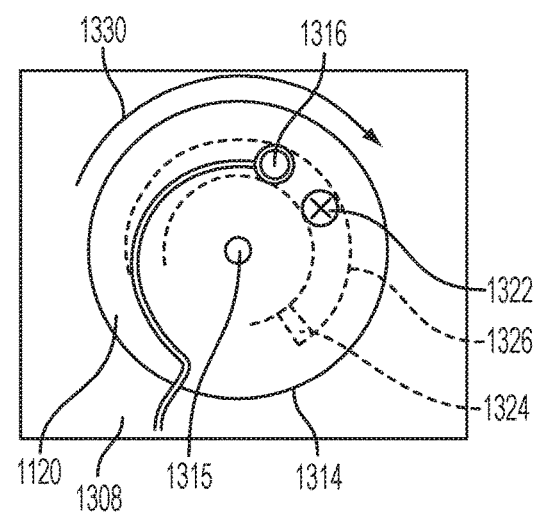

FIGS. 60A-60B illustrate how the hard stop peg 1322 is used to restrict rotation of disk 1314. FIGS. 60A-59B provide a top view, wherein the disk 1314 is disposed on the base 1308. The anchor peg 1316 is shown with the pullwire 1120 there attached. A groove 1326 is formed in the base 1308 beneath the disk 1314 and forms an arc shape. The hard stop peg 1322 extends from the disk 1314 into the groove 1326 in the base 1308. Referring now to FIG. 60B, rotation of the disk 1314 around knob post 1318, indicated by arrow 1330, draws the pullwire 1120 through the aperture 1320 as previously described, wrapping the pullwire 1120 around the disk 1314. As the disk 1314 rotates, the hard stop peg 1322 follows along the groove 1326, as shown. The disk 1314 continues rotating until the hard stop peg 1322 reaches a hard stop 1324. The hard stop 1324 is positioned in the groove 1326 and prevents further passage of the hard stop peg 1322. Thus, disk 1314 rotation may be restricted to any degree of rotation less than or equal to 360 degrees by positioning of the hard stop 1324.

Figure 61A:
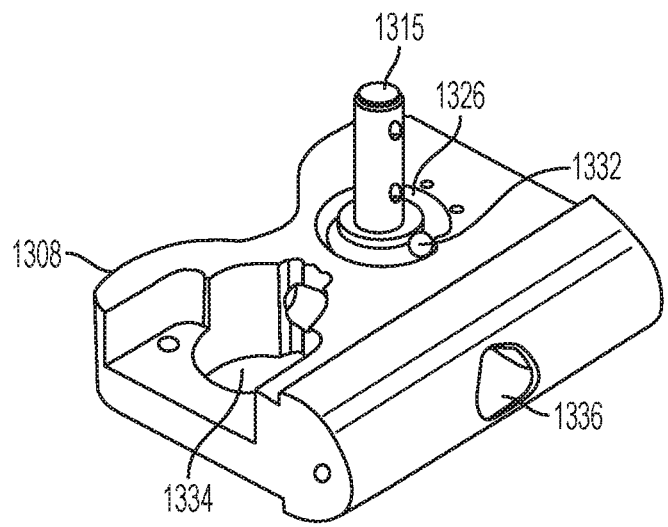
FIGS. 61A-61C illustrates a portion of a hard stop gear assembly.
Figure 61B:
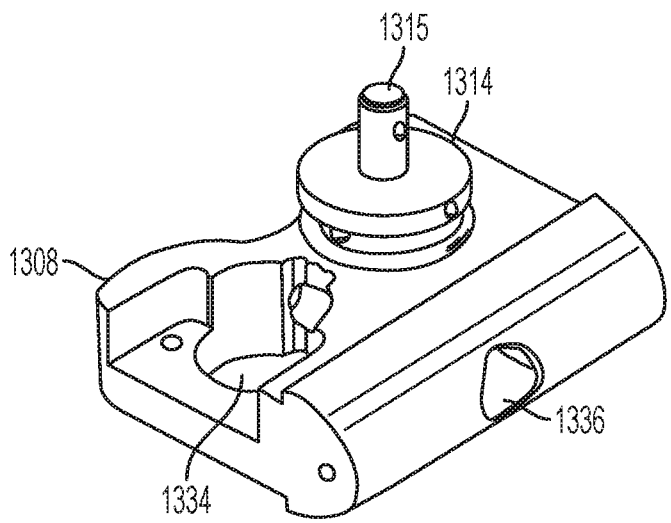
Figure 61C:
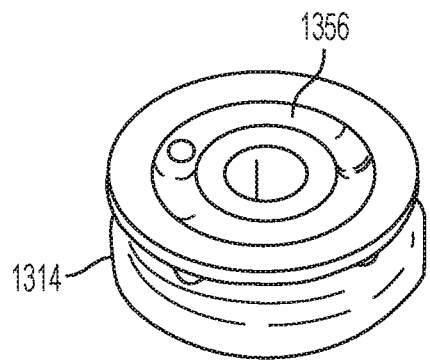

In some instances, it is desired to restrict rotation of the disk 1314 to a degree of rotation which is more than 360 degrees. This may be achieved with another embodiment of the hard stop gear assembly 1304. Referring now to FIGS. 61A-61B, a portion of such a hard stop gear assembly 1304 is shown. FIG. 61A illustrates the base 1308 and the disk post 1315 positioned therethrough. Also shown in the base 1308 is an aperture 1334 through which the knob post 1318, knob gear wheel 1310 and friction assembly 1306 pass, and a passageway 1336 through which the catheter 1000 passes. In this embodiment of the hard stop gear assembly 1304, a groove 1326 is also present in an arc shape around the disk post 1315, however a ball 1332 is positioned in the groove 1326 rather than a hard stop peg 1322. Disk 1314 is positioned over the groove 1326 and the ball 1332 as shown in FIG. 61B. The disk 1314, illustrated in FIG. 61C, has a groove 1356 in its surface which is positioned adjacent to the base 1308, the groove 1356 having an arc shape similar to the groove 1326 in the base 1308. The ball 1332 is not fixedly attached to the base 1308 or the disk 1314 and is therefore free to move along the channel formed by the groove 1326 in the base 1308 and the groove in the disk 1314.

FIGS. 62A-62F illustrate how rotation of the disk 1314 may be restricted by the ball 1332 to a degree of rotation which is more than 360 degrees. FIGS. 62A-62F illustrate the groove 1326 in the base 1308 wherein the groove 1326 has an arc shape around disk post 1315. The groove 1326 does not form a complete circle; a first groove end 1350a and a second groove end 1350b form a wall which prevent passage of the ball 1332. It may be appreciated that the groove ends 1350a, 1350b may be any distance apart, shortening the length of the groove 1326 by any amount, and allowing the ball 1332 movement, and hence catheter deflection, to be adjusted to any desired amount. To begin, referring to FIG. 62A, the ball 1332 is positioned within the groove 1326 near the first groove end 1350a. The disk 1314 has a matching groove 1352 (shape illustrated in dashed line) including a first groove end 1354a and a second groove end 1354b. The disk 1314 is positioned over the ball 1332 so that the ball 1332 is near the second groove end 1354b.

Referring now to FIG. 62B, the disk 1314 may be rotated while the ball 1332 remains in place. Here, the disk 1314 has rotated 90 degrees, as indicated by arrow 36000 and the position of the groove ends 1354a, 1354b. Referring now to FIG. 62C, the disk 1314 may be further rotated while the ball 1332 remains in place. Here, the disk 1314 has rotated 270 degrees, as indicated by arrow 36000 and the position of the groove ends 1354a, 1354b. The disk 1314 may continue rotating to 360 degrees, as shown in FIG. 62D, indicated by arrow 36000. Here, the first groove end 1354a in the disk 1314 has contacted the ball 1332 and pushes the ball 1332 along groove 1326 in the base. Referring now to FIG. 62E, the disk 1314 may be further rotated while the ball 1332 is pushed along the groove 1326 in the base 1308 by the first groove end 1354a in the disk 1314. Here, the disk 1314 is shown to have rotated 540 degrees. Referring to FIG. 62F, the disk 1314 rotates until the ball 1332 reaches the second groove end 1350b of the base 1308, providing a hard stop. In this position, the ball 1332 is held between the first groove end 1354a of the disk 1314 and the second groove end 1350b of the base 1308 and further rotation of the disk 1314 is prevented. Thus, the disk 1314 was rotated approximately 660 degrees in this example. Any maximum degree of rotation may be set by positioning of groove ends 1350a, 1350b and/or groove ends 1354a, 1354b. Additionally, in some embodiments, rotation can be limited by adding more than one ball 1332 to the groove 1326, for example, two, three, four, five, six, seven, eight, nine, ten or more balls may be used to limit travel and hence curvature.

It may be appreciated that one or more pullwires 1120 are attached to the disk 1314 in a manner similar to that illustrated in FIG. 59. Therefore, as the disk 1314 rotates, around disk post 1315 by action of the disk gear wheel 1312, tension is applied to the pullwire 1120 by drawing the pullwire 1120 through the aperture 1320 and wrapping the pullwire 1120 around the disk 1314 as it rotates. Additional rotation of the disk 1314 applies increasing tension to the pullwire 1120. Restriction of rotation as described above limits the amount of tension applied to the pullwire 1120, to limit curvature of the catheter and/or to avoid possible breakage of the pullwire 1120.

Figure 63:
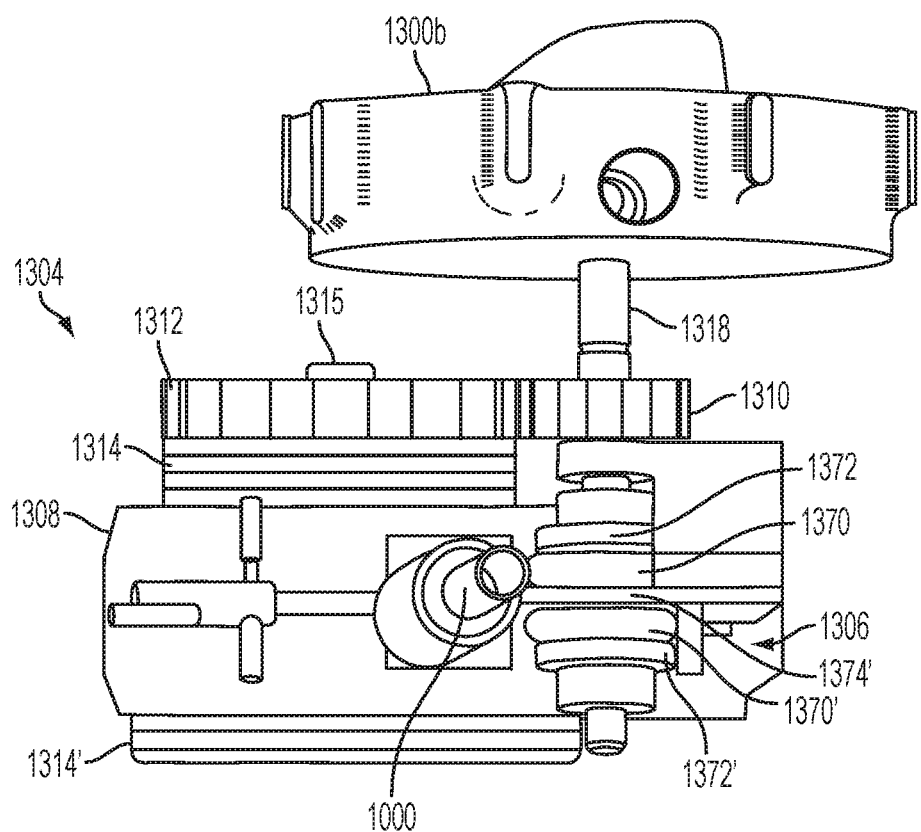
FIG. 63 illustrates an embodiment of a friction assembly.

As mentioned, each steering mechanism includes at least a hard stop gear assembly 1304 and a friction assembly 1306. As described above, tension is applied to one or more pullwires by action of the hard stop gear assembly to form a curve in a catheter. Tension is maintained by the friction assembly. FIG. 63 illustrates an embodiment of a friction assembly 1306. The friction assembly 1306 essentially holds a steering knob, in this example steering knob 1300b, and the associated knob post 1318 in a rotated position. Here, rotation of the knob 1300b and post 1318 rotates attached knob gear wheel 1310. The knob gear wheel 1310 actuates the hard stop gear assembly 1304, thereby applying tension to one or more pullwires 1120. The knob gear wheel 1310 is a toothed wheel that engages a disk gear wheel 1312. Rotation of the steering knob 1300b rotates the knob post 1318 and knob gear wheel 1310 which in turn rotates the disk gear wheel 1312. Rotation of the disk gear wheel 1312 applies tension to one or more pullwires extending through the attached catheter, in this example the outer guiding catheter 1000.

The steering knob 1300b and knob post 1318 are held in a rotated position by friction provided by a frictional pad 1370. The frictional pad 1370 is positioned between ring 1372 attached to the knob post 1318 and a plate 1374 attached to the base 1308. The knob post 1318 extends from the knob 1300b through the ring 1372, the frictional pad 1370 and then the plate 1374. The plate 1374 has internal threads which mate with threads on the knob post 1318. As the knob post 1318 rotates, the threads on the post 1318 advance through the threads on the plate 1374. This draws the ring 1372 closer to the plate 1374, compressing the frictional pad 1370 therebetween. Frictional pad 1370 may be comprised of any O-ring or sheet material with desirable frictional and compressibility characteristics, such as silicone rubber, natural rubber or synthetic rubbers, to name a few. In preferred embodiments, an EPDM rubber O-ring is used. Reverse rotation of the knob post 1318 is resisted by friction of the frictional pad 1370 against the ring 1372. The higher the compression of the frictional pad 1370 the stronger the frictional hold. Therefore, as the steering knob 1300b is rotated and increasing amounts of tension are applied to the pullwires 1120, increasing amounts of friction are applied to the ring 1372 to hold the knob 1300b in place.

Manual reverse rotation of the steering knob 1300b releases tension on the pullwires 1120 and draws the ring 1372 away from the plate 1374 thereby reducing the frictional load. When tension is released from the pullwires 1120 the catheter 1000 returns toward a straightened position.

It may be appreciated that each handle 1056, 1057 includes a steering mechanism for each curve to be formed in the attached catheter. Thus, as shown in FIG. 57, handle 1056 includes a steering mechanism to form the primary curve 1100 in outer guiding catheter 1000 and a steering mechanism to form the additional curve 1110. Likewise, handle 1057 includes a steering mechanism to form the secondary curve 1104 in inner guiding catheter 1020 and a steering mechanism to form the angle theta 1070.

Some curves, such as the primary curve 1100, secondary curve 1104 and additional curve 1110 each typically vary in curvature between a straight configuration and a curved configuration in a single direction. Such movement may be achieved with single set of a hard stop gear assembly 1304 and a friction assembly 1306. However, other curves, such as the angle theta 1070, may be formed in two directions as shown in FIGS. 49C-49D. Such movement is achieved with two sets of the hard stop gear assembly 1304 and the friction assembly 1306, each set controlling curvature in a single direction.

FIG. 63 illustrates the presence of an additional set of the friction assembly 1306'. One or more pullwires 1120', such as an opposing set as illustrated in FIG. 52D, extending within the wall of the catheter 1000 are attached to the disk 1314' in the same manner as pullwires 1120 are attached to disk 1314. The disks 1314, 1314' are arranged so that rotation of steering knob 1300b in one direction applies tension to the pullwires 1120 via disk 1314 and rotation of steering knob 1300b in the opposite direction applies tension to the pullwires 1120' via disk 1314'. Likewise, the additional friction assembly 1306' is shown having a ring 1372' attached to the knob post 1318 and a frictional pad 1370' disposed between the ring 1372' and the opposite side of the plate 1374. Therefore, as rotation of the steering knob 1300b in the opposite direction applies tension to the pullwires 1120' via disk 1314', the frictional pad 1370' applies tension to the ring 1372' holding the knob post 1318' in place.

It may be appreciated that various other mechanisms may be used for tensioning and holding pullwires 1120 in place. Example mechanisms that may alternatively be used include clutches, ratchets, levers, knobs, rack and pinions, and deformable handles, to name a few.

F. Interventional System

Figure 64:
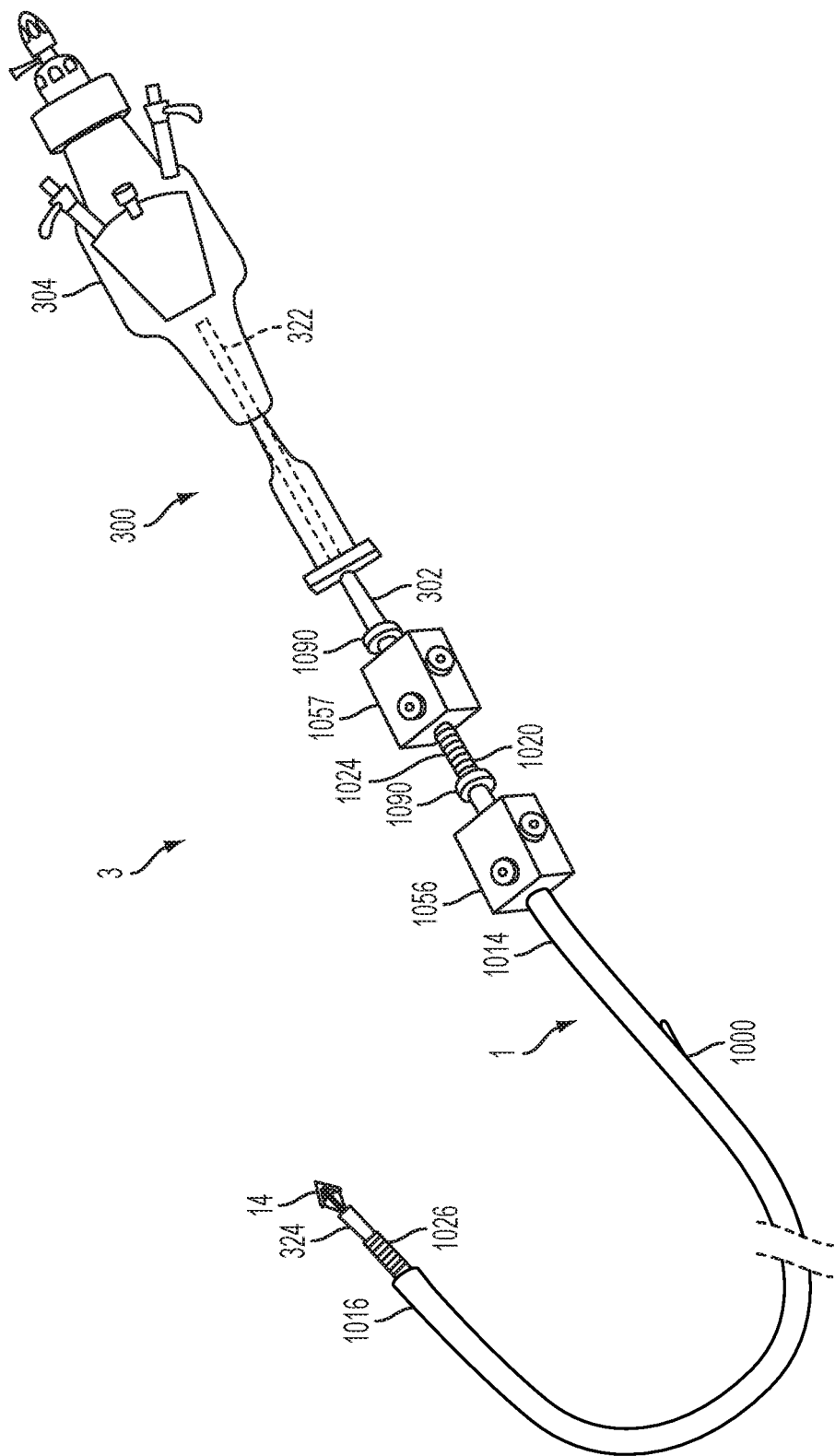
FIG. 64 illustrates an embodiment of an interventional system of the present invention.
Figure 64A:
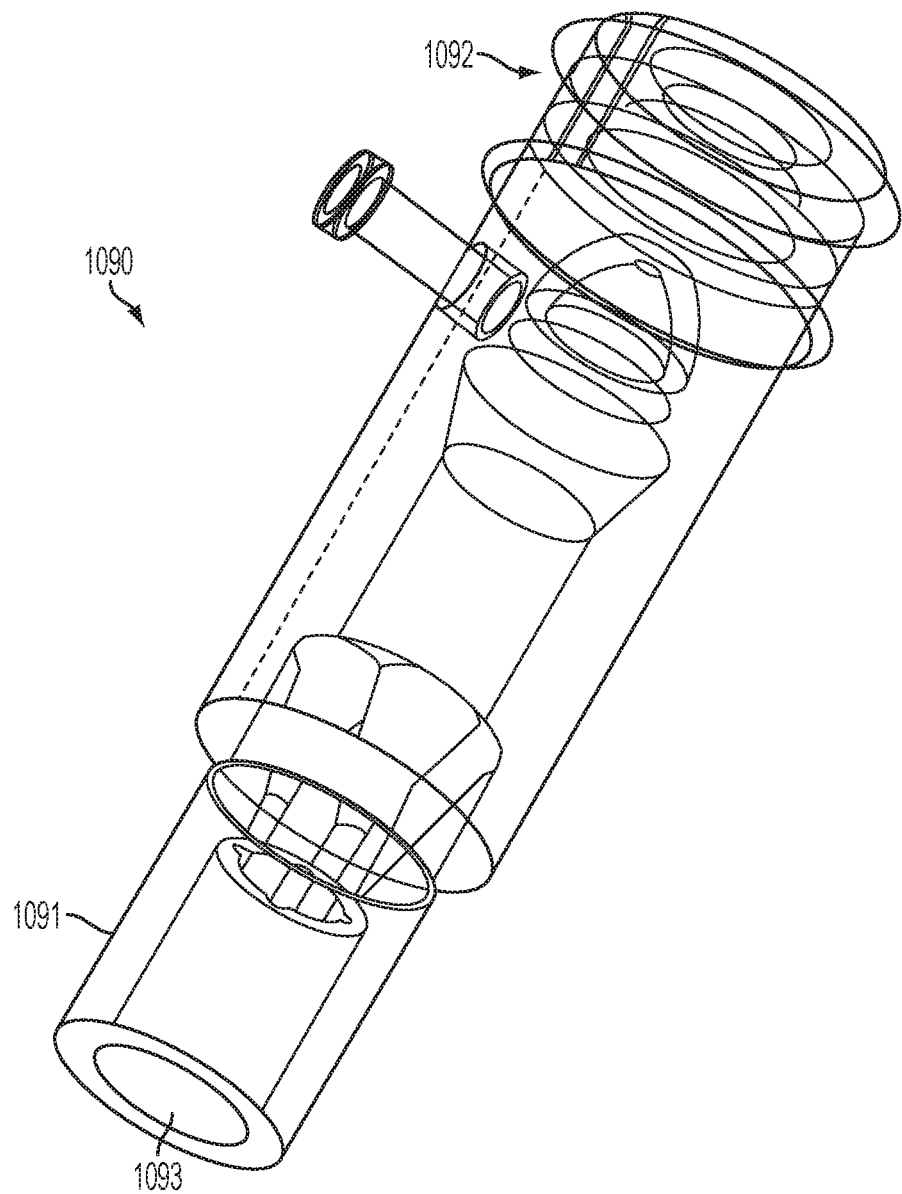
FIG. 64A illustrates an embodiment of a hemostatic valve for use with the present invention.

FIG. 64 illustrates an embodiment of an interventional system 3 of the present invention. An embodiment of the multi-catheter guiding system 1 of the present invention is shown comprising an outer guide catheter 1000, having a proximal end 1014 and a distal end 1016, and an inner guide catheter 1020, having a proximal end 1024 and a distal end 1026, wherein the inner guide catheter 1020 is positioned coaxially within the outer guide catheter 1000, as shown. In addition, a hemostatic valve 1090 is disposed within handle 1056 or external to handle 1056 as shown to provide leak-free sealing with or without the inner guide catheter 1020 in place. The valve 1090 also prevents back bleeding and reduces the possibility of air introduction when inserting the inner guide catheter 1020 through the outer guide catheter 1000. An example of a hemostatic valve 1090 is illustrated in FIG. 64A, however any suitable valve or hemostatic valve may be used to provide similar functions. In FIG. 64A, the valve 1090 has a first end 1091, a second end 1092 and a lumen 1093 therethrough. The inner wall of lumen 1093 is preferably tapered toward end 1091 and may further include a plurality of tapered axial channels configured to receive the protrusions 1400 on the inner guide catheter 1020. The first end 1091 is attached to the outer guide catheter 1000 and the second end 1092 is free. Referring now back to FIG. 64, the distal ends 1016, 1026 of catheters 1000, 1020, respectively, are sized to be passable to a body cavity, typically through a body lumen such as a vascular lumen.

Figure 64B:
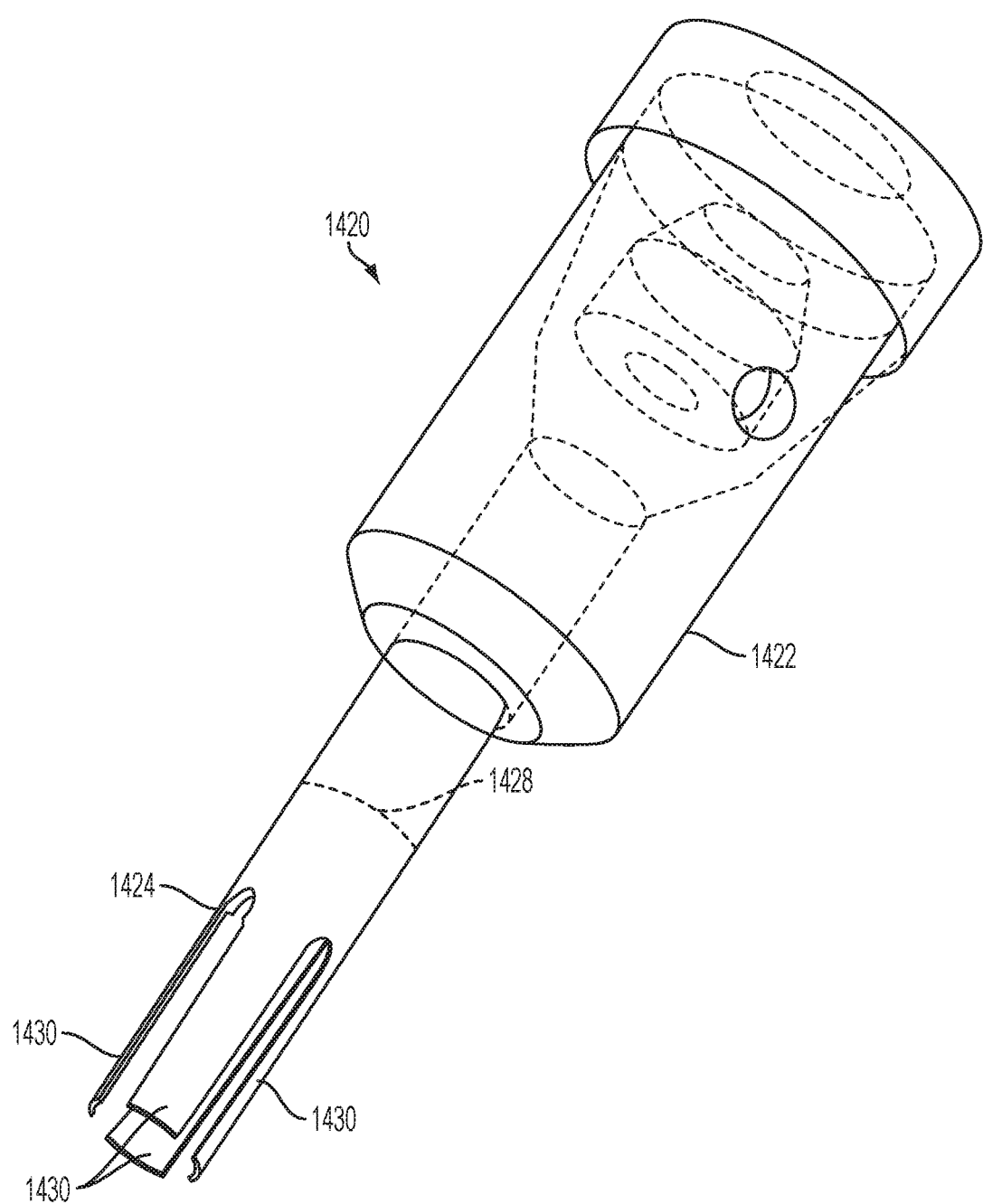
FIG. 64B illustrates an embodiment of a fixation device introducer.

To assist in inserting the fixation device 14 through a hemostatic valve 1090, a fixation device introducer may be used. For example, when the fixation device 14 is loaded on a delivery catheter 300 and an inner guide catheter 1020, insertion of the fixation device 14, delivery catheter 300 and inner guide catheter 1020 through an outer guide catheter 1000 involves passing the fixation device 14 through a hemostatic valve 1090 on the outer guide catheter 1000. To reduce any trauma to the fixation device 14 by the hemostatic valve 1090, a fixation device introducer may be used. An embodiment of a fixation device introducer 1420 is illustrated in FIG. 64B. The introducer 1420 includes a loading body 1422 and an insertion endpiece 1424. The fixation device 14 is loaded into the loading body 1422 and into the insertion endpiece 1424 to approximately the dashed line 1428. The insertion endpiece 1424 has a split end creating individual split sections 1430, in this embodiment, four split sections 1430. By compressing the split sections 1430, the endpiece 1424 forms a taper. Such a taper is then inserted through a hemostatic valve 1090, so that the insertion endpiece 1424 creates a smooth passageway through the valve for the fixation device 14. Once the insertion endpiece 1424 is inserted through the valve 1090, the fixation device 14, and attached delivery catheter 300 and inner guide catheter 1020, may then be advanced through the fixation device introducer 1420. The fixation device introducer 1420 also includes a hemostatic valve within the loading body 1422 to prevent any backbleeding or leakage through the introducer 1420.

Manipulation of the guide catheters 1000, 1020 is achieved with the use of handles 1056, 1057 attached to the proximal ends of the catheters 1000, 1020. As shown, handle 1056 is attached to the proximal end 1014 of outer guide catheter 1000 and handle 1057 is attached to the proximal end 1024 of inner guide catheter 1020. Inner guide catheter 1020 is inserted through handle 1056 and is positioned coaxially within outer guide catheter 1000.

An embodiment of the delivery catheter 300 of the present invention is inserted through handle 1057 and is positioned coaxially within inner guide catheter 1020 and outer guide catheter 1000. Therefore, a hemostatic valve 1090 is disposed within handle 1057 or external to handle 1057 as shown to provide leak-free sealing with or without the delivery catheter 300 in place. The valve 1090 functions as described above. The delivery catheter 300 includes a shaft 302, having a proximal end 322 and a distal end 324, and a handle 304 attached to the proximal end 322. A fixation device 14 is removably coupled to the distal end 324 for delivery to a site within the body.

The outer guide catheter 1000 and/or the inner guide catheter 1020 are precurved and/or have steering mechanisms to position the distal ends 1016, 1026 in desired directions. Precurvature or steering of the outer guide catheter 1000 directs the distal end 1016 in a first direction to create a primary curve while precurvature and/or steering of the inner guide catheter 1020 directs distal end 1026 in a second direction, differing from the first, to create a secondary curve. Together, the primary and secondary curves form a compound curve. Advancement of the delivery catheter 300 through the coaxial guide catheters 1000, 1020 guides the delivery catheter 300 through the compound curve toward a desired direction, usually in a direction which will position the fixation device 14 in a desired location within the body.

Figure 65:
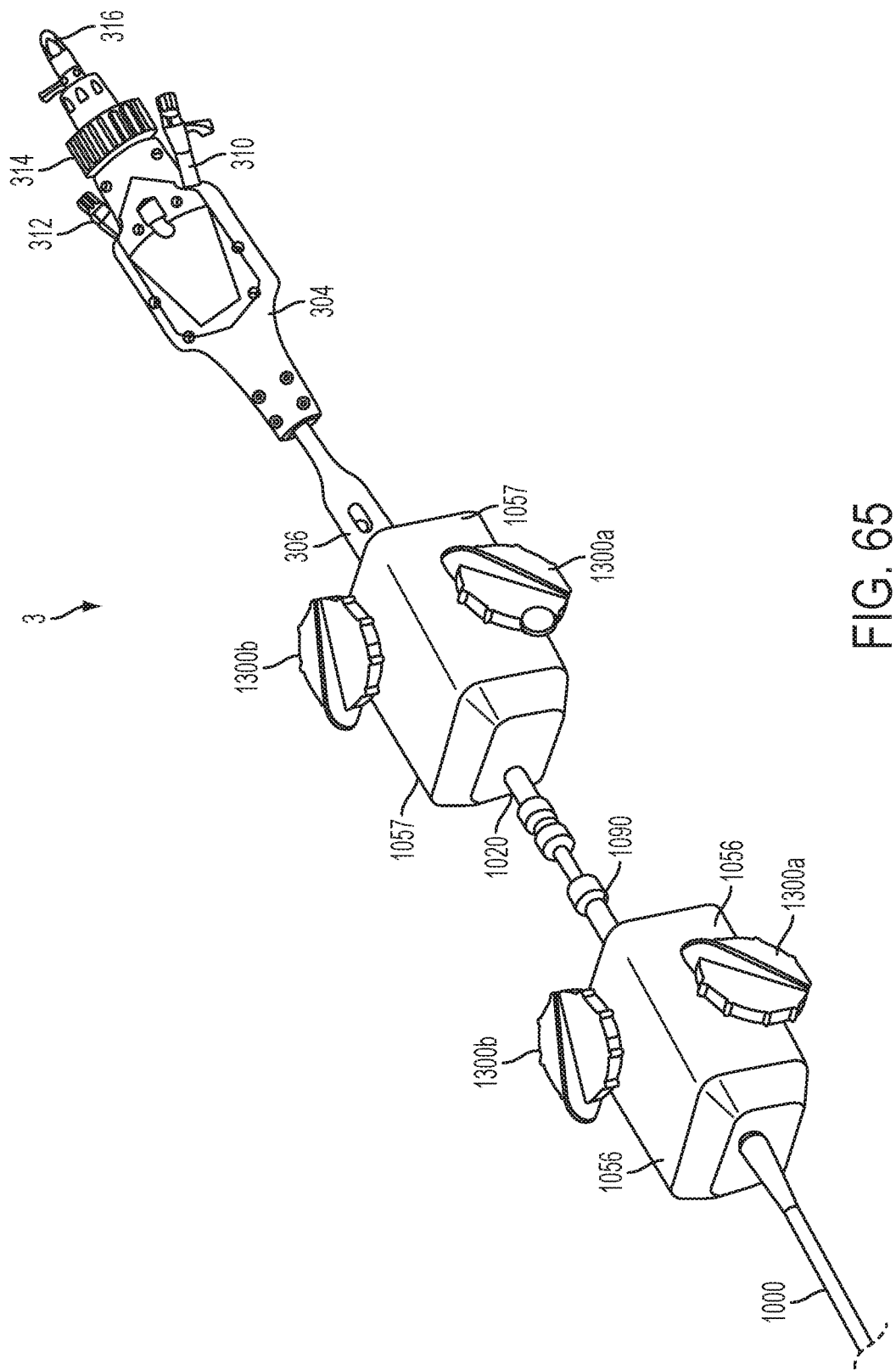
FIG. 65 illustrates another embodiment of an interventional system of the present invention.

FIG. 65 illustrates portions of another embodiment of an interventional system 3 of the present invention. Handles 1056, 1057 of the multi-catheter guiding system 1 of the present invention are shown. Each handle 1056, 1057 includes a set of steering knobs 1300a, 1300b, as shown. Manipulation of the guide catheters 1000, 1020 is achieved with the use of the steering knobs 1300a, 1300b attached to the proximal ends of the catheters 1000, 1020. Handle 304 of the delivery catheter 300 is also shown, including the proximal element line handle 312, the lock line handle 310, the actuator rod control 314 and the actuator rod handle 316, among other features. The handle 304 is supported by the support base 306 which is connected to the handle 1057.

It may be appreciated the above described systems 3 are not intended to limit the scope of the present invention. The systems 3 may include any or all of the components of the described invention. In addition, the multi-catheter guiding system 1 of the present invention may be used to introduce other delivery catheters, interventional catheters or other devices. Likewise, the delivery catheter 300 may be introduced through other introducers or guiding systems. Also, the delivery catheter 300 may be used to deliver other types of devices to a target location within the body, including endoscopic staplers, devices for electrophysiology mapping or ablation, septal defect repair devices, heart valves, annuloplasty rings and others.

In addition, many of the components of the system 3 may include one or more hydrophilic coatings. Hydrophilic coatings become slippery when wet, eliminate the need for separate lubricants. Thus, such coatings may be present on the multi-catheter guiding system, delivery catheter, and fixation device, including the proximal elements and distal elements, to name a few.

Figure 66:
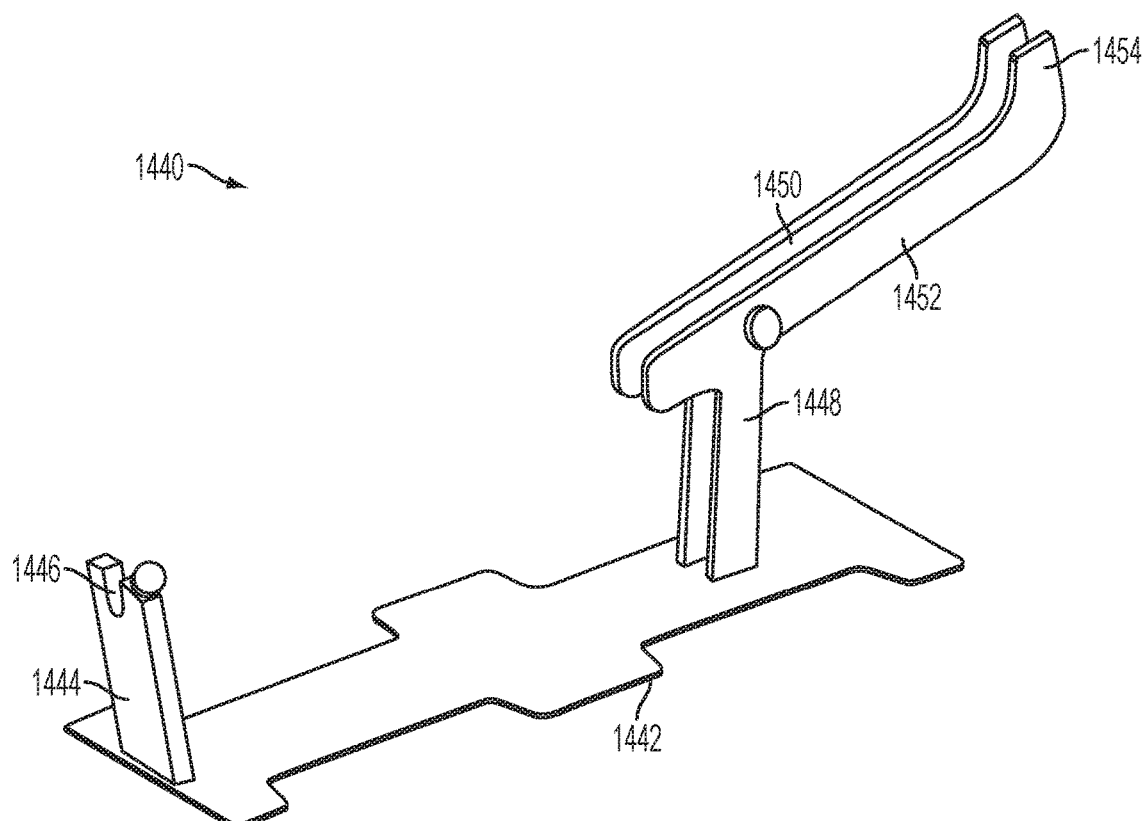
FIGS. 66-68 illustrate an embodiment of a stabilizer base for use with the present invention.
Figure 67:
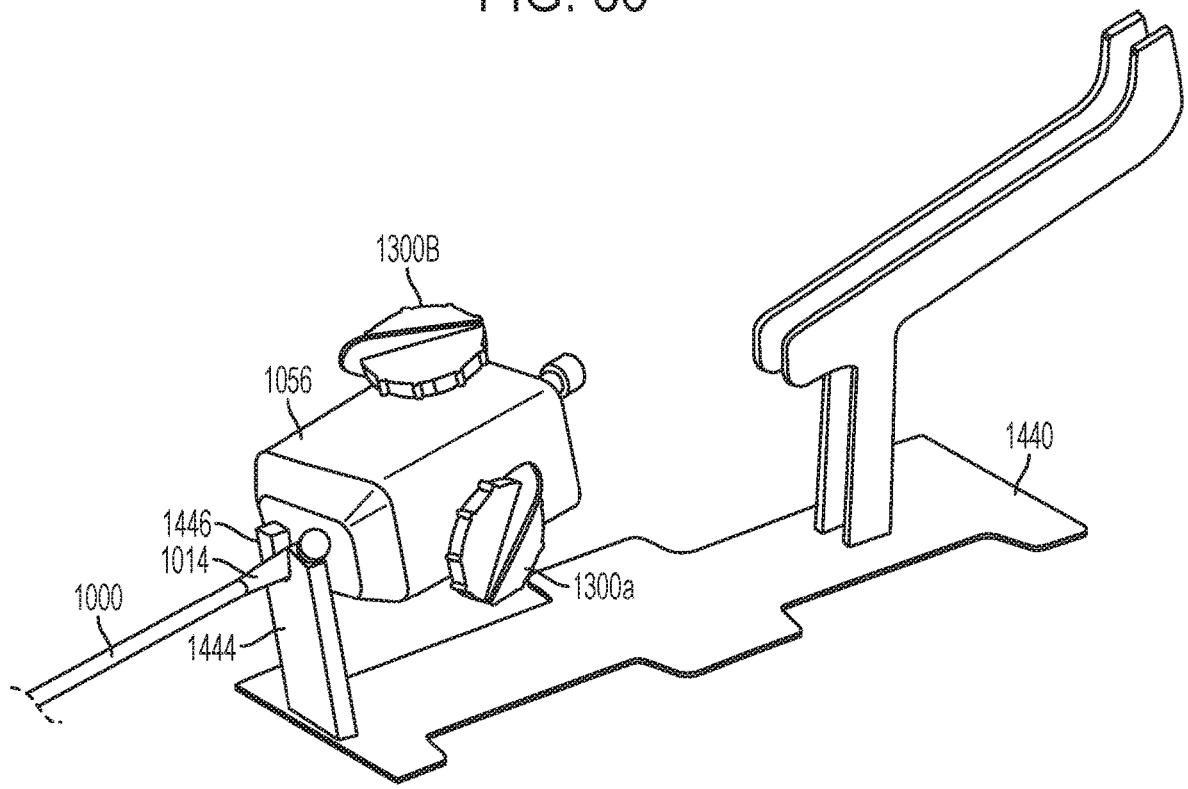
Figure 68:
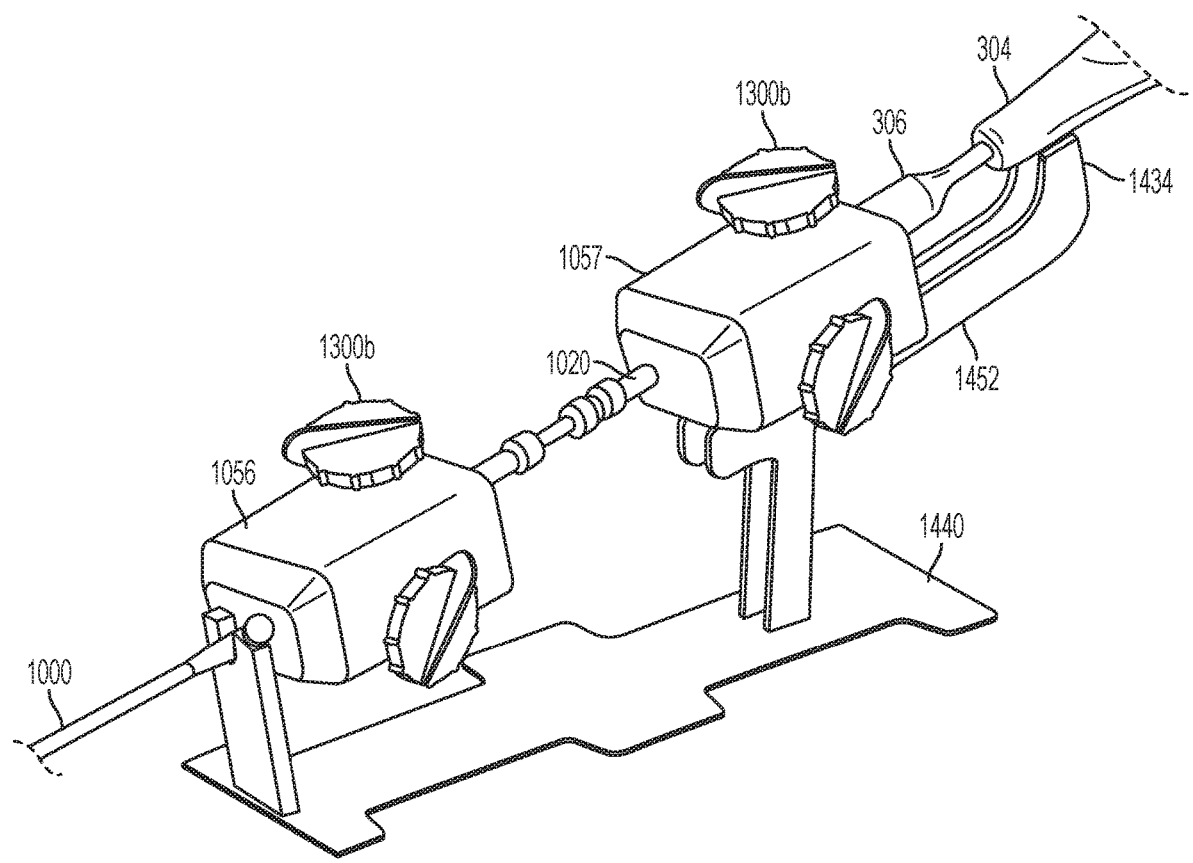

Further, the system 3 may be supported by an external stabilizer base 1440, an embodiment of which is illustrated in FIG. 66. Stabilizer base 1440 maintains the relative positions of the outer guide, inner guide and delivery catheter during a procedure. In this embodiment, the base 1440 comprises a platform 1442 having a planar shape for positioning on or against a flat surface, such as a table or benchtop. The base 1440 further includes a pair of handle holders 1444, 1448, each attached to the platform 1442 and extending upwardly from the platform 1442, either angularly or perpendicularly. Handle holder 1444 includes a notch 1446 for holding the outer guiding catheter 1000, as illustrated in FIG. 67, thereby supporting the handle 1056. FIG. 67 shows the handle 1056 attached to the outer guiding catheter 1000 positioned so that the proximal end 1014 of the outer guiding catheter 1000 rests in the notch 1446. Referring back to FIG. 66, handle holder 1448 includes an elongate portion 1452 having a trough 1450 and a hooked end 1454. As shown in FIG. 68, handle 1057 rests on the elongate portion 1452 and the handle 304 rests on hooked end 1454 so that the inner guiding catheter 1020 extends from the handle 1057 to the handle 1056 and continues on within outer guiding catheter 1000. The handle 304 is additionally supported by support base 306, as shown.

It may be appreciated that the stabilizer base 1440 may take a variety of forms and may include differences in structural design to accommodate various types, shapes, arrangements and numbers of handles.

G. Kits

Figure 69:
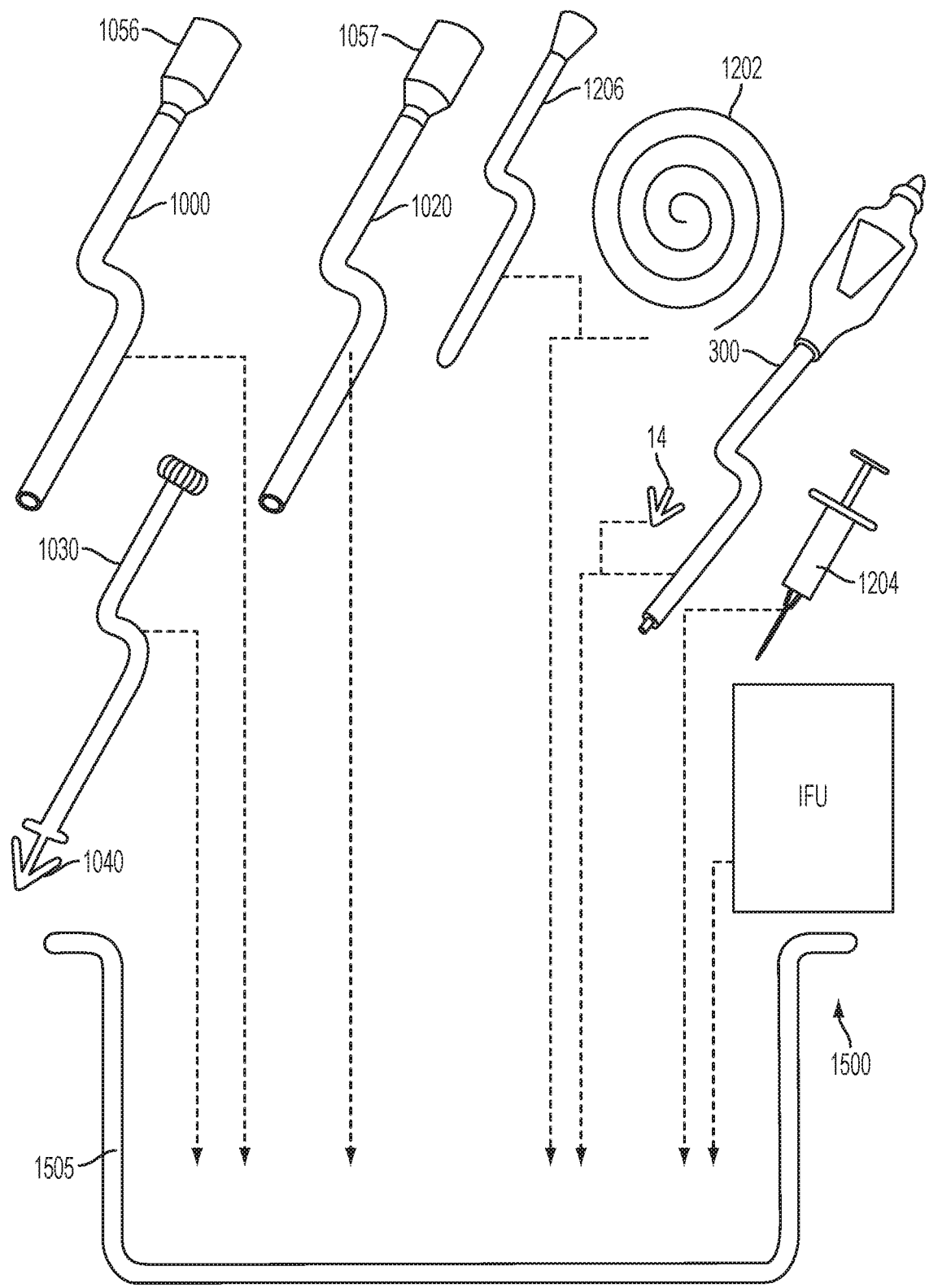
FIG. 69 illustrates a kit constructed in accordance with the principles of the present invention.

Referring now to FIG. 69, kits 1500 according to the present invention comprise any of the components described in relation to the present invention. The kits 1500 may include any of the components described above, such as the outer guide catheter 1000 including handle 1056, the inner guide catheter 1020 including handle 1057, the delivery catheter 300 and the fixation device 14 and instructions for use IFU. Optionally, any of the kits may further include any other system components described above, such as various interventional tools 1040, or components associated with positioning a device in a body lumen, such as a guidewire 1202, dilator 1206 or needle 1204. The instructions for use IFU will set forth any of the methods as described above, and all kit components will usually be packaged together in a pouch 1505 or other conventional medical device packaging. Usually, those kit components which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

While the foregoing is a complete description of the preferred embodiments of the invention, various alternatives, substitutions, additions, modifications, and equivalents are possible without departing from the scope of the invention. For example, in many of the above-described embodiments, the invention is described in the context of approaching a valve structure from the upstream side—that is, the atrial side in the case of a mitral valve. It should be understood that any of the foregoing embodiments may be utilized in other approaches as well, including from the ventricular or downstream side of the valve, as well as using surgical approaches through a wall of the heart. Moreover, the invention may be used in the treatment of a variety of other tissue structures besides heart valves, and will find usefulness in a variety of tissue approximation, attachment, closure, clamping and ligation applications, some endovascular, some endoscopic, and some open surgical.

Again, although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A fixation device for fixation of leaflets of a heart valve, comprising:
    an implantable fixation device comprising
        a first arm and a second arm,
        a first proximal element moveable relative the first arm between a first position and a second position, and
        a second proximal element moveable relative to the second arm between a first position and a second position; and
    a delivery device comprising
        a delivery catheter having a proximal end portion and a distal end portion, the delivery catheter defining at least one lumen extending between the proximal end portion and the distal end portion,
        an actuator rod extending through the at least one lumen and being operably coupled to the first and second arms so as to move the first and second arms between a first position and a second position,
        a first proximal element line extending through the at least one lumen, the first proximal element line releasably coupled to the first proximal element and actuatable to move the first proximal element between the first position and the second position,
        a second proximal element line extending through the at least one lumen, the second proximal element line releasably coupled to the second proximal element and actuatable to move the second proximal element between the first position and the second position, and
    a handle having
        a first proximal element line handle coupled to and actuatable to deploy the first proximal element line to move the first proximal element between the first position and the second position,
        a second proximal element line handle coupled to and actuatable to deploy the second proximal element line to move the second proximal element between the first position and the second position, wherein the first proximal element line handle and the second proximal element line handle are aligned in parallel and independently actuatable for independent movement of the first proximal element and the second proximal element.

2. The fixation system of claim 1, wherein the first and second proximal element line handles are adjacent each other.

3. The fixation system of claim 1, wherein the at least one lumen includes at least a first proximal element line lumen and a second proximal element line lumen.

4. The fixation system of claim 1, wherein the first proximal element line comprises one of suture, wire, nitinol wire, rod, cable, and polymeric line.

5. The fixation system of claim 4, wherein the second proximal element line comprises one of suture, wire, nitinol wire, rod, cable, and polymeric line.

6. The fixation system of claim 1, wherein the first proximal element line comprises a first end portion, a second end portion, and an intermediate portion between the first end portion and the second end portion, and wherein the first proximal element line is coupled to the first proximal element at the intermediate portion of the first proximal element line.

7. The fixation system of claim 6, wherein the second proximal element line comprises a first end portion, a second end portion, and an intermediate portion between the first end portion and the second end portion, and wherein the second proximal element line is coupled to the second proximal element at the intermediate portion of the second proximal element line.

8. The fixation system of claim 1, wherein the first proximal element comprises nitinol and the second proximal element comprises nitinol.

9. The fixation system of claim 1, wherein the delivery device further comprises a first guide catheter having a proximal end portion and a distal end portion, the first guide catheter defining at least one lumen extending between the proximal end portion and the distal end portion, and wherein the delivery catheter extends within the lumen of the first guide catheter.

10. The fixation system of claim 9, wherein the delivery device further comprises a second guide catheter having a proximal end portion and a distal end portion, the second guide catheter defining at least one lumen extending between the proximal end portion and the distal end portion, and wherein the first guide catheter extends within the lumen of the second guide catheter.

11. The fixation system of claim 10, wherein the first guide catheter is a steerable guide catheter.

12. The fixation system of claim 11, wherein the first guide catheter comprises a first guide catheter handle coupled to the proximal end portion of the first guide catheter and actuatable to deflect the distal end portion of the first guide catheter.

13. The fixation system of claim 12, wherein the first guide catheter handle comprises at least one first guide catheter steering knob, wherein the first guide catheter handle is actuated by rotating the at least one first guide catheter steering knob.

14. The fixation system of claim 10, wherein the first guide catheter and the second guide catheter form a guiding catheter system.

15. The fixation system of claim 10, wherein the distal end portion of the second guide catheter has an outer diameter of less than about 0.500 in.

16. The fixation system of claim 1, wherein the first proximal element is biased toward the first arm; and the second proximal element is biased toward the second arm.

17. The fixation system of claim 16, wherein the second guide catheter is a steerable guide catheter.

18. The fixation system of claim 17, wherein the second guide catheter comprises a second guide catheter handle coupled to the proximal end portion of the second guide catheter and actuatable to deflect the distal end portion of the second guide catheter.

19. The fixation system of claim 18, wherein the second guide catheter handle comprises at least one second guide catheter steering knob, wherein the second guide catheter handle is actuated by rotating the at least one second guide catheter steering knob.

20. The fixation system of claim 1, wherein the first proximal element line handle includes a first finger grip and the second proximal element line handle includes a second finger grip.

21. The fixation system of claim 20, wherein the first finger grip comprises a first contoured surface and the second finger grip comprises a second contoured surface.

22. The fixation system of claim 20, where the first finger grip comprises a first plurality of ridges and the second finger grip comprises a second plurality of ridges.

23. The fixation system of claim 1, wherein the first proximal element line handle and the second proximal element line handle are disposed on a first side of the handle.

24. The fixation system of claim 1, wherein the handle of the delivery device further includes an actuator rod control operably coupled to the actuator rod so as to move the actuator rod in a proximal-distal direction, the actuator rod being coupled to a stud of the implantable fixation device, and the first and second arms being coupled to the stud.

25. The fixation system of claim 1, wherein the handle of the delivery device further includes:
a first stop to limit a distance in which each of the first proximal element line handle and the second proximal element line handle can be moved in a first direction, and a second stop to limit a distance in which each of the first proximal element line handle and the second proximal element line handle can be moved in a second direction.

26. A fixation device for fixation of leaflets of a heart valve, comprising:
an implantable fixation device comprising
a proximal portion,
a first arm and a second arm,
a first proximal element moveable relative the first arm between a first position and a second position, and
a second proximal element moveable relative to the second arm between a first position and a second position; and
a delivery device comprising
a delivery catheter having a proximal end portion and a distal end portion, the delivery catheter defining at least one lumen extending between the proximal end portion and the distal end portion,
an elongate delivery shaft having a proximal portion and distal portion, the distal portion of the elongate delivery shaft being releasably coupled to the proximal portion of the implantable fixation device,
a first proximal element line extending through the at least one lumen, the first proximal element line releasably coupled to the first proximal element and actuatable to move the first proximal element between the first position and the second position, the first proximal element line having a distal portion releasably coupled to at least one of the distal portion of the elongate delivery shaft and the proximal portion of the implantable fixation device, a second proximal element line extending through the at least one lumen, the second proximal element line releasably coupled to the second proximal element and actuatable to move the second proximal element between the first position and the second position, the second proximal element line having a distal portion releasably coupled to at least one of the distal portion of the elongate delivery shaft and the proximal portion of the implantable fixation device, and a handle having a first proximal element line handle coupled to and actuatable to deploy the first proximal element line to move the first proximal element between the first position and the second position, a second proximal element line handle coupled to and actuatable to deploy the second proximal element line to move the second proximal element between the first position and the second position, wherein the first proximal element line handle and the second proximal element line handle are aligned in parallel and independently actuatable for independent movement of the first proximal element and the second proximal element.

* * * * *